(12) United States Patent
Isalan

(10) Patent No.: US 12,397,065 B2
(45) Date of Patent: Aug. 26, 2025

(54) NUCLEIC ACIDS, PEPTIDES AND METHODS

(71) Applicant: IMPERIAL COLLEGE INNOVATIONS LIMITED, London (GB)

(72) Inventor: Mark Isalan, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 191 days.

(21) Appl. No.: 15/773,779

(22) PCT Filed: Nov. 4, 2016

(86) PCT No.: PCT/GB2016/053454
§ 371 (c)(1),
(2) Date: May 4, 2018

(87) PCT Pub. No.: WO2017/077329
PCT Pub. Date: May 11, 2017

(65) Prior Publication Data
US 2019/0247519 A1  Aug. 15, 2019

(30) Foreign Application Priority Data
Nov. 5, 2015 (GB) ..................... 1519584

(51) Int. Cl.
| | | |
|---|---|---|
| *A61K 48/00* | (2006.01) | |
| *A61K 47/64* | (2017.01) | |
| *A61P 25/14* | (2006.01) | |
| *A61P 25/28* | (2006.01) | |
| *C07K 7/04* | (2006.01) | |
| *C07K 14/00* | (2006.01) | |
| *C07K 14/47* | (2006.01) | |
| *C12N 7/00* | (2006.01) | |
| *C12N 15/113* | (2010.01) | |
| *C12N 15/86* | (2006.01) | |
| *C12N 15/864* | (2006.01) | |
| *A61K 38/00* | (2006.01) | |

(52) U.S. Cl.
CPC .......... *A61K 48/0066* (2013.01); *A61K 47/64* (2017.08); *A61K 48/0025* (2013.01); *A61K 48/0075* (2013.01); *A61P 25/14* (2018.01); *A61P 25/28* (2018.01); *C07K 14/4702* (2013.01); *C12N 7/00* (2013.01); *C12N 15/113* (2013.01); *C12N 15/86* (2013.01); *A61K 38/00* (2013.01)

(58) Field of Classification Search
None
See application file for complete search history.

(56) References Cited

U.S. PATENT DOCUMENTS

| 9,096,682 B2 * | 8/2015 | Isalan et al. ....... C07K 14/4703 |
| 9,732,129 B2 * | 8/2017 | Isalan et al. ....... C07K 14/4703 |

FOREIGN PATENT DOCUMENTS

| WO | 2011/016840 A2 | 2/2011 | |
| WO | WO2012049332 A1 * | 4/2012 | ............. C07K 14/47 |

OTHER PUBLICATIONS

Agustín-Pavón et al. (Sep. 2016) "Deimmunization for gene therapy: host matching of synthetic zinc finger constructs enables long-term mutant Huntingtin repression in mice" Molecular neurodegeneration, 11(1), 1-16. (Year: 2016).*
Garriga-Canut et al., "Synthetic zinc finger repressors reduce mutant huntingtin expression in the brain of R6/2 mice." PNAS 109(45):E3136-E3145 (2012).
Ziegler et al., "AAV2 vector harboring a liver-restricted promoter facilitates sustained expression of therapeutic levels of α-galactosidase A and the induction of immune tolerance in Fabry mice." Molecular Therapy 9(2):231-240 (2004).
Agustín-Pavón et al., "Deimmunization for gene therapy: host matching of synthetic zinc finger constructs enables long-term mutant Huntingtin repression in mice." Molecular Neurodegeneration 11(1):64 (Sep. 6, 2016).
Garton et al., "A structural approach reveals how neighbouring C2H2 zinc fingers influence DNA binding specificity." Nucleic Acids Research 43(19):9147-9157 (Sep. 17, 2015).
Persikov et al., "A systematic survey of the Cys2His2 zinc finger DNA-binding landscape." Nucleic Acids Research 43(3):1965-1984 (Jan. 15, 2015).

* cited by examiner

*Primary Examiner* — Maria Marvich
(74) *Attorney, Agent, or Firm* — NIXON PEABODY LLP; David S. Resnick; Jeanne N. Jodoin

(57) ABSTRACT

Disclosed herein are novel nucleic acid molecules which encode novel polypeptides for use in treating polyglutamine diseases such as Huntington's disease. The polypeptides of the invention exhibit reduced immunotoxicity in vivo and may have utility in sustained (mid- or long-term) expression in vivo. Also disclosed are methods for the treatment of polyglutamine diseases, such as Huntington's disease and the use of nucleic acids and polypeptides of the invention in medical therapy. Gene therapy methods and compositions, such as AAV vectors for use in gene therapy methods are also disclosed.

18 Claims, 25 Drawing Sheets
Specification includes a Sequence Listing.

NUCLEIC ACIDS, PEPTIDES AND METHODS

CROSS-REFERENCE TO RELATED APPLICATIONS

This application is a 35 U.S.C. § 371 National Phase Entry Application of International Application No. PCT/GB2016/053454 filed Nov. 4, 2016, which designates the U.S., and claims benefit under 35 U.S.C. § 119(b) of G.B. Application No. 1519584.5, filed Nov. 5, 2015, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Aug. 31, 2022, is named 2022-08-31 P37016USA Sequence-listing-051039-092140USPX.txt and is 182,963 bytes in size.

FIELD OF THE INVENTION

This invention relates to novel zinc finger peptide and nucleic acid constructs having desirable properties, and to methods for manufacturing and using such constructs, in particular, for repression of target gene expression. The invention also relates to novel promoter/enhancer sequences for prolonged transgene expression. More particularly, the invention relates to zinc finger transcriptional repressor proteins and their encoding nucleic acid sequences that have host compatible sequences for prolonged transgene expression in therapeutic applications, such as in the treatment of neurological disorders.

BACKGROUND OF THE INVENTION

The development of increasingly safe gene therapy vectors, with reduced immunogenicity (Basner-Tschakarjan et al. (2014) *Frontiers in Immunology*), low insertional capabilities (Papayannakos & Daniel (2012) *Gene Ther.* 20: 581-8), and new and more effective delivery strategies (Sillay et al. (2013) *Stereotact Funct Neurosurg.* 91: 153-161; Yin et al. (2013) *Cancer Gene Ther.* 20: 336-41), has led to several successful clinical trials. Examples include a therapy against metachromatic leukodystrophy (inserting the functional enzyme arylsulfatase A in hematopoietic cells) (Biffi et al. (2013) *Science.* 341: 1233158), and a breakthrough in AIDS treatment that promises a 'functional cure' for HIV (Tebas et al. (2014) *N. Engl. J. Med.* 370: 901-910). The latter study employed the technology of synthetic zinc finger nucleases (Isalan M. (2011) *Nat. Methods.* 9: 32-34), targeted to knock-out the CCR5 receptor in CD4 T cells, ex vivo. Nuclease-modified cells were autologously transplanted back into patients, achieving drug-free reduction of viraemia. Site-specific nuclease technology is highly scaleable and, with the advent of vectorisable RNA programmable nucleases such as CRISPR/Cas9 lentiviruses (Shalem et al. (2014) *Science.* 343: 84-87), a revolution in genome editing is underway.

Despite this progress, it is becoming clear that the host immune system is a major barrier to successful long term therapies. In some cases, including some of the above examples, cells can be treated ex vivo, or with a single short intervention. However, in many diseases this is not possible; rather, it is necessary to modify the expression of disease genes in vivo. In this regard, the CRISPR/Cas systems have bacterial origins and so immunogenicity issues may significantly limit their effectiveness in mammalian therapies—especially those that require repetitive or sustained dosage regimes. Even zinc finger nucleases use bacterial nuclease domains (Fokl (Bibikova et al. (2001) *Mol. Cell Biol.* 21: 289-297)) and so it is unclear how they would be tolerated in vivo.

Immunological effects are particularly relevant when considering gene therapies for neurological diseases, i.e. those that affect the central nervous system (brain and spinal cord), the peripheral nervous system (peripheral nerves and cranial nerves), and the autonomic nervous system (parts of which are located in both central and peripheral nervous systems).

More than 600 neurological diseases have been identified in humans, which together affect all functions of the body, including coordination, communication, memory, learning, eating, and in some cases mortality. Although many tissues and organs in animals are capable of self-repair, generally the neurological system is not. Therefore, neurological disorders are often neurodegenerative, characterised by a progressive worsening of symptoms, beginning with minor problems that allow detection and diagnosis, but becoming steadily more severe until, in some cases, the death of the patient.

For some of these diseases treatments are available which may alleviate symptoms and/or prolong survival. However, despite intense research efforts, for most neurological disorders, and particularly for the most serious diseases, there are still no cures.

In this regard, most neurodegenerative diseases require the correction of mutation(s) in vivo, directly in the affected tissue, or the sustained expression of therapeutic factors (Agustín-Pavón & Isalan (2014) *BioEssays* 36: 979-990), e.g. to alter gene expression levels. Since the brain has limited regenerative capacity and complex connectivity, the tissue cannot simply be removed, repaired and re-implanted.

Furthermore, a collection of recent articles has demonstrated delayed immune responses when injecting foreign proteins from AAV vectors into the brain parenchyma (Ciesielska et al. (2013) *Mol. Ther.* 21: 158-166; Hadaczek et al. (2009) *Hum. Gene Ther.* 20: 225-237; Samaranch et al. (2014) *Mol. Ther.* 22: 329-337). Strikingly, despite the immune-privileged environment of the brain, even GFP has been found to induce a strong inflammatory and immune response in both rats and monkeys (Ciesielska et al. (2013) *Mol. Ther.* 21: 158-166; Hadaczek et al. (2009) *Hum. Gene Ther.* 20: 225-237). Similarly, a human enzyme with potential use in Parkinson's disease therapy has unwanted effects in rats (Ciesielska et al. (2013) *Mol. Ther.* 21: 158-166). In this case, using the vector AAV9, which is capable of infecting both neurons and glial cells, neuronal death started as early as 3 weeks after injection. Therefore, even though a range of new generation synthetic biology tools are being developed for (neuro)degenerative diseases (Agustín-Pavón & Isalan (2014) *BioEssays* 36: 979-990), the brain still remains a challenging target for gene therapy. There is thus a clear need for improved therapeutic agents and methods for treating neurological diseases.

Current knowledge of neurological disorders shows that they can be caused by many different factors, including (but not limited to): inherited genetic abnormalities, problems in the immune system, injury to the brain or nervous system, or diabetes. One known cause of neurological disorder is a genetic abnormality leading to the pathological expansion of CAG repeats on certain genes, which results in extended polyglutamine (polyQ) tracts in the expressed mutated gene products (Walker (2007) *Lancet* 369(9557): 218-228). The resulting proteins are thought to aggregate and cause toxic gain-of-function diseases, including spinocerebellar ataxias, spinobulbar muscular atrophy and Huntington's disease (Orr & Zoghbi (2007) *Annu. Rev. Neurosci.* 30: 575-621; Cha (2007) *Prog. Neurobiol.* 83(4): 228-248).

Huntington's disease (HD) neuropathology is associated with selective neuronal cell death, primarily of medium spiny neurons of the caudate and putamen and, to a lesser extent, cortical neurons, leading to cognitive dysfunction and chorea (Walker (2007) *Lancet* 369(9557): 218-228; and Kumar et al. *Pharmacol. Rep.* 62(1): 1-14). Since the discovery, in 1993, that the htt gene causes HD (The-Huntington's-Disease-Collaborative-Research-Group (1993) *Cell* 72(6): 971-983), much attention has focused on how the CAG-repeat number associated with the htt gene may affect the pathology and progression of this disease. Normally, the number of CAG repeats in the wild-type htt gene ranges from 10 to 29 (with a median of 18), whereas in HD patients it is typically in the range of 36 to 121 (with a median of 44). Furthermore, it has also been shown that the age of onset of HD disease is correlated to CAG repeat number (Walker (2007) *Lancet* 369(9557): 218-228; and Kumar et al. *Pharmacol. Rep.* 62(1): 1-14).

Although there has been a great deal of research into cures for HD, currently available therapeutics treat only the symptoms of the disease, and so there is still no way of stopping or delaying the onset or progression of HD (Walker (2007) *Lancet* 369(9557): 218-228; and Kumar et al. *Pharmacol. Rep.* 62(1): 1-14). For this reason it would be extremely desirable to have a treatment for HD that addresses the cause rather than the symptoms of the disease.

RNA interference (RNAi) has been shown to reduce expression of mutant htt (van Bilsen et al. (2008) *Hum. Gene Ther.* 19(7): 710-719; Zhang et al. (2009) *J. Neurochem.* 108(1): 82-90; Pfister et al. (2009) *Curr. Biol.* 19(9): 774-778). However, although RNAi has been shown to be a very powerful tool, the success of this technique depends on targeting single nucleotide or deletion polymorphisms that differentiate between mutant and wt alleles, and these often differ from patient to patient. The apparent requirement for personalised siRNA designs currently raises challenges for clinical trials and approved use in humans.

In a more general approach, Hu et al. used peptide nucleic acid (PNA) and locked nucleic acid (LNA) antisense oligomers, to target expanded CAG repeats of the ataxin-3 and htt genes (Hu et al. (2009) *Nat. Biotechnol.* 27(5): 478-484; Hu et al. (2009) *Ann. NY Acad. Sci.* 1175: 24-31). They reported selective inhibition of the mutant allele with peptide nucleic acids (PNAs) for up to 22 days. Although these results were promising, PNAs cannot be delivered to the central nervous system. Therefore, the authors also tried locked nucleic acids (LNAs), which are perhaps more suitable for use in vivo. Although selective inhibition of the mutant allele was observed, only up to 30% inhibition of wt htt was seen at the highest and most effective concentration of LNA used.

We have previously reported the design and synthesis of custom zinc finger transcription inhibitor peptides (WO 2012/049332), which selectively bind to expanded CAG repeat motifs and effectively inhibit the expression of the htt protein in vitro and in vivo. However, prolonged inhibition of htt expression in vivo has proved problematic. In addition, there appear to be many cells types in addition to neuronal cells, in the brain and in other organs/tissues, which may play a role in the development and/or progression of HD.

It would be desirable to have alternative and/or more effective therapeutic molecules and treatments for HD and related disorders, such as those caused by expanded CAG repeats. It would also be desirable to have the ability to therapeutically target cell types other than neuronal cells. It would be particularly desirable to be able to target such alternative cell types in a ubiquitous manner.

Accordingly, the present invention seeks to overcome or at least alleviate one or more of the problems found in the prior art.

SUMMARY OF THE INVENTION

In general terms, the present invention provides new zinc finger peptides and encoding nucleic acid molecules that can be used for the modulation of gene expression in vitro and/or in vivo. The new zinc finger peptides of the invention may be particularly useful in the modulation of target genes associated with expanded CAG trinucleotide repeats, and more specifically the repression of such genes. As a consequence, the possibility of more specific gene targeting is envisaged, which may be particularly useful for the modulation of gene expression within the genome and/or for distinguishing between similar nucleic acid sequences of differing lengths. In some embodiments, the new zinc finger peptides of the invention beneficially bind to expanded CAG trinucleotide repeats associated with mutated pathogenic genes with greater specificity and affinity than to wild-type trinucleotide repeat sequences associated with non-pathogenic, normal genes.

Furthermore, the invention relates to therapeutic molecules and compositions for use in treating polyglutamine-associated diseases, such as neurological diseases, and particularly Huntington's disease (HD). In some aspects and embodiments, the invention is directed to methods and therapeutic treatment regimes for treating patients affected by or diagnosed with HD and other polyglutamine diseases. For example, the therapeutic molecules of the invention may be used in medical treatments, such as gene therapy, for delaying the onset of symptoms, and/or for treating or alleviating the symptoms of the disease, and/or for reducing the severity of or preventing the progression of the disease.

In particular, the invention is directed towards novel zinc finger peptides (ZFP) that may exhibit prolonged, mid- to long-term, expression in target organisms in vivo, so as to be useful in medical treatments that may require long-term activity of the therapeutic agent. The zinc finger peptide sequences of the invention are adapted/optimised to closely match endogenous/wild-type peptide sequences expressed in the target organism so as to have reduced toxicity and immunogenicity. Cells expressing the zinc finger peptides of the invention may therefore be protected from the immune response of the target organism so as to prolong expression of the heterologous peptide in these cells.

In one aspect, therefore, the invention provides a polynucleotide molecule encoding a polypeptide, the polypeptide comprising a zinc finger peptide having from 8 to 32 zinc finger domains and wherein the zinc finger peptide comprising the sequence:

N'-[(Formula 4)-L$_3$]$_{n0}$-{[(Formula 6)-L$_2$-(Formula 6)-L$_3$]$_{n1}$-[(Formula 6)-L$_2$-(Formula 6)-X$_L$]}$_{n2}$-[(Formula 4)-L$_2$-(Formula 6)-L$_3$]$_{n3}$-[(Formula 6)-L$_2$-(Formula 6)]-[L$_3$-(Formula 6)]$_{n4}$-C', wherein n0 is 0 or 1, n1 is from 1 to 4, n2 is 1 or 2, n3 is from 1 to 4, n4 is 0 or 1, $L_2$ is the linker sequence -TGE/QK/RP-(SEQ ID NO: 7), $L_3$ is the linker sequence -TGG/S E/QK/RP-(SEQ ID NO: 8), and $X_L$ is a linker sequence of between 8 and 50 amino acids;

Formula 4 is a zinc finger domain of the sequence $X_2$ C $X_{2,4}$ C $X_5$ $X^{-1}$ $X^{+1}$ $X^{+2}$ $X^{+3}$ $X^{+4}$ $X^{+5}$ $X^{+6}$ H $X_{3,4,5}$ H/C and Formula 6 is a zinc finger domain of the sequence $X_2$ C $X_{2,4}$ C $X_5$ $X^{-1}$ $X^{+1}$ $X^{+2}$ $X^{+3}$ $X^{+4}$ $X^{+5}$ $X^{+6}$ H $X_3$ H, wherein X is any amino acid, the numbers in subscript indicate the possible numbers of residues represented by X at that position, and the number in superscript indicates the position of the amino acid in the recognition sequence of the zinc finger domain;

and wherein at least 8 adjacent zinc finger domains have a recognition sequence $X^{-1}$ $X^{+1}$ $X^{+2}$ $X^{+3}$ $X^{+4}$ $X^{+5}$ $X^{+6}$ according to SEQ ID NO: 1. In some embodiments, all zinc finger domains of the zinc finger peptide have the recognition sequence defined according to SEQ ID NO: 1. Advantageous recognition sequences of SEQ ID NO: 1 are SEQ ID Nos: 2 to 5. Any combination of the recognition sequences of SEQ ID Nos: 2 to 5 may be used within a zinc finger peptide of the invention to bind the target trinucleotide repeat sequence with suitable affinity and/or specificity. However, in some embodiments the zinc finger peptides of the invention have recognition sequences that are selected only from the group consisting of SEQ ID NOs: 2 and 5; or only from the group consisting of SEQ ID Nos: 3 and 4. In some embodiments all zinc finger domains of the peptide have the same recognition sequence.

In any of the embodiments of the invention, $L_2$ may be selected from the group consisting of -TGEKP-(SEQ ID NO: 6) and -TGQKP-(SEQ ID NO: 65). Similarly, in any embodiments of the invention, $L_3$ may be selected from the group consisting of -TGSERP-(SEQ ID NO: 10) and -TGSQKP-(SEQ ID NO: 16).

In some embodiments of the invention all of the zinc finger domains of the peptide are defined according to Formula 6. However, in other embodiments zinc finger domain structures selected from any of Formulas 1 to 6 may be used.

Beneficially the zinc finger peptide has from 8 to 32, 8 to 24 or 8 to 18 zinc finger domains; such as from 10 to 18 or from 11 to 18 zinc finger domains; for example, 10, 11, 12 or 18 zinc finger domains. Preferred zinc finger peptides of the invention have 11 or 12 zinc finger domains and a most preferred peptide has 11 zinc finger domains.

In one embodiment, the zinc finger peptide of the invention has 10, 11 or 12 zinc finger domains, $L_2$ is -TGEKP-(SEQ ID NO: 6), $L_3$ is -TGSERP-(SEQ ID NO: 10) or -TGSQKP-(SEQ ID NO: 16), XL is between 20 and 30 amino acids, and SEQ ID NO: 1 is selected from the group consisting of SEQ ID Nos: 2 and 5. In another embodiment, the zinc finger peptide of the invention has 10, 11 or 12 zinc finger domains, $L_2$ is -TGEKP-(SEQ ID NO: 6), $L_3$ is -TGSERP-(SEQ ID NO: 10) or -TGSQKP-(SEQ ID NO: 16), $X_L$ is between 20 and 30 amino acids, and SEQ ID NO: 1 is selected from the group consisting of SEQ ID Nos: 3 and 4. Preferred zinc finger peptides of these embodiments have 11 zinc finger domains.

In any of the embodiments of the invention $X_L$ may be selected from the group consisting of SEQ ID Nos: 21, 22, 23 and 24.

Suitably, the polypeptides of the invention comprise the human KRAB repressor domain from Kox-1 according to SEQ ID NO: 39 for expression in humans, or the mouse KRAB repressor domain from ZF87 according to SEQ ID NO: 40 for expression in mouse. Such repressor sequences are generally attached C-terminal to the zinc finger peptide. Conveniently the linker sequence is selected from the peptide sequences of SEQ ID NO: 42 or SEQ ID NO: 43.

A nuclear localisation signal sequence may also be incorporated into the polypeptides of the invention to allow targeting to the nucleus of cells in which they are expressed. A preferred nuclear localisation sequence for use in humans is SEQ ID NO: 37. A preferred nuclear localisation sequence for use in mouse is SEQ ID NO: 38. In some embodiments, however, the sequence of SEQ ID NO: 36 may alternatively be used for nuclear localisation.

Preferred zinc finger peptide sequences of the invention are selected from the group consisting of SEQ ID Nos: 29, 31, 33 and 35. Preferred polypeptide modulators of the invention comprise a sequence selected from SEQ ID NOs: 49, 50, 51, 52, 53, 54, 55, 56, 59, 61 and 63. Polypeptides of the invention may comprise sequences having at least 90%, at least 91%, at least 92%, at least 93%, at least 94%, at least 95%, at least 96%, at least 97%, at least 98%, or at least 99% identity to any of the polypeptides of SEQ ID NOs: 29, 31, 33, 35, 49, 50, 51, 52, 53, 54, 55, 56, 59, 61 and 63.

As indicated above, the invention is directed to polynucleotide (or nucleic acid) molecules that encode the zinc finger peptides and polypeptides of the invention. Particularly, isolated polynucleotides are encompassed. In addition, the polynucleotides (or nucleic acid molecules) of the invention may be expression constructs for the expression of the peptide or polypeptide of the invention in vitro and/or in vivo. The nucleic acids of the invention may be adapted for expression in any desired system or organism, but preferred organisms are mouse—in which therapeutic effects for diseases targeted by the therapeutic polypeptides of the invention may be tested, and humans—which will likely be the ultimate recipients or any potential therapy.

For expression of polypeptides, nucleic acid molecules are conveniently inserted into a vector or plasmid. Vectors and plasmids may be adapted for replication (e.g. to produce large quantities of its own nucleic acid sequence in host cells), or may be adapted for protein expression (e.g. to produce large or suitable quantities of zinc finger-containing protein in host cells). Any vector may be used, but preferred are polypeptide expression vectors so that the encoded polypeptide is expressed in host cells (e.g. for purposes of therapeutic treatment).

Viral vectors are particularly useful for potential use in therapeutic applications due to their ability to target and/or infect specific cells types. Suitable viral vectors may include those derived from retroviruses (such as influenza, SIV, HIV, lentivirus, and Moloney murine leukaemia); adenoviruses; adeno-associated viruses (AAV); herpes simplex virus (HSV); and chimeric viruses.

Adeno-associated virus (AAV) vectors are considered particularly useful for targeting therapeutic peptides to the central and peripheral nervous systems and to the brain. A preferred viral vector delivery system is based on the AAV2/1 viral subtype.

Thus, the invention is particularly directed to an adeno-associated virus (AAV) vector comprising a nucleic acid expression construct capable of expressing a polypeptide comprising a zinc finger peptide, wherein the polypeptide and the zinc finger peptide are defined as disclosed herein.

The invention is also directed, in another aspect, to a gene therapy method comprising administering to a person, individual or patient in need thereof, nucleic acid expression construct according to the invention. A preferred nucleic acid expression construct is an deno-associated virus (AAV) vector comprising a nucleic acid sequence as disclosed herein.

The invention, in another aspect, also encompassed a method of treating a polyglutamine disease in a patient or individual in need thereof. The method suitably comprises administering to the patient or individual a nucleic acid expression construct according to the invention, such as an adeno-associated virus (AAV) vector. A preferred AAV vector is AAV2/1 as described herein.

Suitable polyglutamine diseases are selected from the group consisting of Huntington's disease (HD), Spinal and bulbar muscular atrophy (SBMA), Dentatorubropallidoluysian atrophy (DRPLA), Spinocerebellar ataxia Type 1 (SCA1), Spinocerebellar ataxia Type 2 (SCA2), Spinocerebellar ataxia Type 3 or Machado-Joseph disease (SCA3), Spinocerebellar ataxia Type 7 (SCA7), Spinocerebellar ataxia Type 6 (SCA6) and Spinocerebellar ataxia Type 17 (SCA17). A preferred disease is HD.

The invention also relates to polypeptides comprising zinc finger peptides as defined herein. Typically the polypeptides of the invention include a zinc finger portion comprising a plurality of zinc finger domains and one or more beneficial auxiliary sequences, such as effector domains. Effector domains include nuclear localisation sequences and transcriptional repressor domains as described elsewhere herein. It will be appreciated that the invention encompasses any polypeptides that may be encoded by the nucleic acid molecules defined herein; and any nucleic acid molecules capable of expressing a polypeptide as defined herein. The at least one effector domain may be selected from transcriptional repressor domains, transcriptional activator domains, transcriptional insulator domains, chromatin remodelling, condensation or decondensation domains, nucleic acid or protein cleavage domains, dimerisation domains, enzymatic domains, signalling/targeting sequences or domains.

Conveniently, the polypeptides according to the invention bind double-stranded trinucleotide repeat nucleic acid sequences comprising CAG-repeat, CTG-repeat, and/or CAGCTG-repeat sequences containing at least 22 triplet repeats. Such nucleic acid sequences are beneficially bound with a binding affinity is at least 1 nM; at least 100 pM or at least 10 pM.

Polypeptides of the invention may also be administered to an individual or patient in need thereof. Suitably, the polypeptides of the invention are to treat polyglutamine-based diseases.

A gene therapy method according to the invention may comprise administering to a person in need thereof or to cells of the person, a nucleic acid encoding a polypeptide of the invention, and causing the polypeptide to be expressed in cells of the person. In this way, the gene therapy method may be useful for treating a polyglutamine disease or condition selected from the group consisting of Huntington's disease (HD), Spinal and bulbar muscular atrophy (SBMA), Dentatorubropallidoluysian atrophy (DRPLA), Spinocerebellar ataxia Type 1 (SCA1), Spinocerebellar ataxia Type 2 (SCA2), Spinocerebellar ataxia Type 3 or Machado-Joseph disease (SCA3), Spinocerebellar ataxia Type 7 (SCA7), Spinocerebellar ataxia Type 6 (SCA6) and Spinocerebellar ataxia Type 17 (SCA17).

Pharmaceutical composition of the invention may comprise nucleic acid molecules (such as vectors) and/or polypeptides each of which are defined herein. It is envisaged that the pharmaceutical compositions of the invention may be used in a method of combination therapy with one or more additional therapeutic agent.

In another aspect, the invention relates to chimeric or fusion proteins comprising the zinc finger peptides of the invention conjugated to a non-zinc finger domain.

Some aspects and embodiments of the invention include formulations, medicaments and pharmaceutical compositions comprising the zinc finger peptides. In one embodiment, the invention relates to a zinc finger peptide for use in medicine. More specifically, the zinc finger peptides and therapeutics of the invention may be used for modulating the expression of a target gene in a cell: for example, Huntington's disease, and other diseases caused by or diagnosed by gene expansion of CAG trinucleotide repeat sequences. In some embodiments, the invention relates to the treatment of diseases or conditions associated with the mutated CAG-repeat gene and/or expression of gene products containing extended polyglutamine (polyQ) tracts. Treatment may also include preventative as well as therapeutic treatments and alleviation of a disease or condition.

The invention also provides promoter sequences for prolonged expression of exogeneous constructs, such as transgenes. Such promoter sequences may be particularly suitable for prolonged in vivo expression of constructs comprising sequences encoding zinc finger peptides according to aspects of the invention. In embodiments, the invention provides a new synthetic promoter-enhancer nucleic acid construct for neuron-specific sustained expression, comprising a portion of the sequence upstream and downstream of the transcription start site of the enolase gene. For example, an isolated nucleic acid transcription promoter construct may comprise the nucleic acid sequence extending from about 1.6 to about 1.7 kb upstream to about 100 bp to about 200 bp downstream of the transcription start site of the enolase gene. Suitably, the promoter construct may comprise a sequence selected from SEQ ID NO: 148 or SEQ ID NO: 151; or SEQ ID NO: 152 or SEQ ID NO: 153. The invention also provides a new synthetic promoter-enhancer construct for sustained expression in more than one cell type, comprising a portion of the sequence upstream and downstream of the transcription start site of the Hsp90ab1 gene. For example, an isolated nucleic acid transcription promoter construct may comprise the nucleic acid sequence extending from about 1.6 to about 1.7 kb upstream to about 100 bp to about 200 bp downstream of the transcription start site of the Hsp90ab1 gene. Suitably, the promoter construct may comprise a sequence selected from SEQ ID NO: 146, SEQ ID NO: 147, SEQ ID NO: 149 and SEQ ID NO: 150. Preferred promoter constructs of the invention have a length of approx. 1,750 to 1,820 bps, such as between 1,800 and 1,810 bps. However, the invention also encompasses nucleic acid constructs for use as promoter and/or enhancer sequences comprising fragments of the promoter/enhancer sequences of the invention. Suitable fragments may include up to 200, up to 400, up to 600, up to 800, up to 1,000, up to 1,200, up to 1,400 or up to 1,600 contiguous bases of the sequences disclosed herein. Such nucleic acid constructs may be isolated or may be comprised within a vector, especially an expression vector; e.g. a viral vector such as AAV, as disclosed herein.

Beneficially, promoter sequences according to the invention are suitable for sustained constitutive expression of operably linked/associated genes for a period of at least 3 weeks, at least 6 weeks, at least 12 weeks or at least 24 weeks. In the context of this invention, 'promoter' sequences may encompass both transcriptional promoter and enhancer elements within a nucleic acid sequence which have the effect of enabling, causing and/or enhancing transcription of an associated gene/nucleic acid construct. In other words, the use of the term 'promoter' does not exclude the possibility that the nucleic acid sequence concerned may also encompass other elements associated with transcription, such as enhancer elements.

Gene therapy methods are also disclosed, comprising administering to a subject in need thereof or to cells of the subject, a nucleic acid encoding a polypeptide under the control of the synthetic promoter-enhancers of the invention, and causing the polypeptide to be expressed in cells of the subject.

Thus, in embodiments there is provided a gene therapy method comprising administering to a subject in need thereof, or to cells of the subject, a vector comprising a pNSE or pHsp90 promoter-enhancer construct of the invention. In embodiments, the methods comprises administering to the subject to be treated a vector according to the invention with neuronal targeting specificity in combination with a promiscuous vector according to the invention. The method may comprise administering to the subject to be treated an AAV2/1 subtype adeno-associated virus (AAV) vector according to the invention in combination with an AAV2/9 subtype adeno-associated virus (AAV) vector according to the invention. The administering 'in combination' may be simultaneous, separate or sequential, as appropriate. Therapeutic uses of the constructs and viral vectors of the invention are also encompassed. The methods and constructs of the invention may be for treating a polyglutamine disease or condition selected from the group consisting of Huntington's disease (HD), Spinal and bulbar muscular atrophy (SBMA), Dentatorubropallidoluysian atrophy (DR-PLA), Spinocerebellar ataxia Type 1 (SCA1), Spinocerebellar ataxia Type 2 (SCA2), Spinocerebellar ataxia Type 3 or Machado-Joseph disease (SCA3), Spinocerebellar ataxia Type 7 (SCA7), Spinocerebellar ataxia Type 6 (SCA6) and Spinocerebellar ataxia Type 17 (SCA17).

It will be appreciated that any features of one aspect or embodiment of the invention may be combined with any combination of features in any other aspect or embodiment of the invention, unless otherwise stated, and such combinations fall within the scope of the claimed invention.

BRIEF DESCRIPTION OF THE DRAWINGS

The invention is further illustrated by the accompanying drawings in which:

FIG. 1(A) discloses SEQ ID NO: 170 (top strand) and SEQ ID NO: 180 (bottom strand). (B) Gel shift assays show 4-, 6- or 12-finger arrays binding poly-CAG dsDNA and forming distinct complexes; negative control, transcription-translation mix (TNT). FIG. 1(B) discloses SEQ ID NOs: 171, 172 and 173, respectively, in order of appearance from left to right. (C) Left hand column—a schematic illustration of a hybrid zinc finger design that recognises the nucleic acid sequence 5'-GC(A/T)-3', which allows binding to either the $(GCA)_n$ or the $(GCT)_n$ complementary strands of the CAG-repeat dsDNA sequence. Right hand column—a gel shift assay demonstrating that the hybrid zinc finger binds equally to GCA or GCT triplets in mixed sequences. FIG. 1(C) discloses SEQ ID NOs: 69, 174 and 175, respectively, in order of appearance from left to right. (D) Specificity gel shift assay illustrating that a zinc finger peptide according to one embodiment of the invention (ZF6xHunt), binds preferentially to CAG-repeats when compared to mutant sequences (D=A,G,T; S=C,G; H=A,C,T). FIG. 1(D) discloses SEQ ID NOs: 172 and 176 to 178, respectively, in order of appearance from left to right.

FIG. 10 discloses: top row—the target sequence of SEQ ID NO: 179 (11xAGC)—top strand; and SEQ ID NO: 181 (11xGCT)—bottom strand, the SV40 NLS of SEQ ID NO: 37 as part of the ZF-Kox-1 protein, and representative finger 2 and 3 zinc finger recognition helices according to SEQ ID NO: 69; middle row—the human KIAA2022 NLS of SEQ ID NO: 46 as part of the humanised hZF-Kox-1 protein, and representative finger 2 and 3 zinc finger recognition helices according to SEQ ID NOs: 3 and 4, respectively; and bottom row—the mouse primase p58 NLS of SEQ ID NO: 38 as part of the 'mousified' mZF-Kox-1 protein, and representative finger 2 and 3 zinc finger recognition helices according to SEQ ID NOs: 3 and 4, respectively.

DETAILED DESCRIPTION OF THE INVENTION

Figure 1:
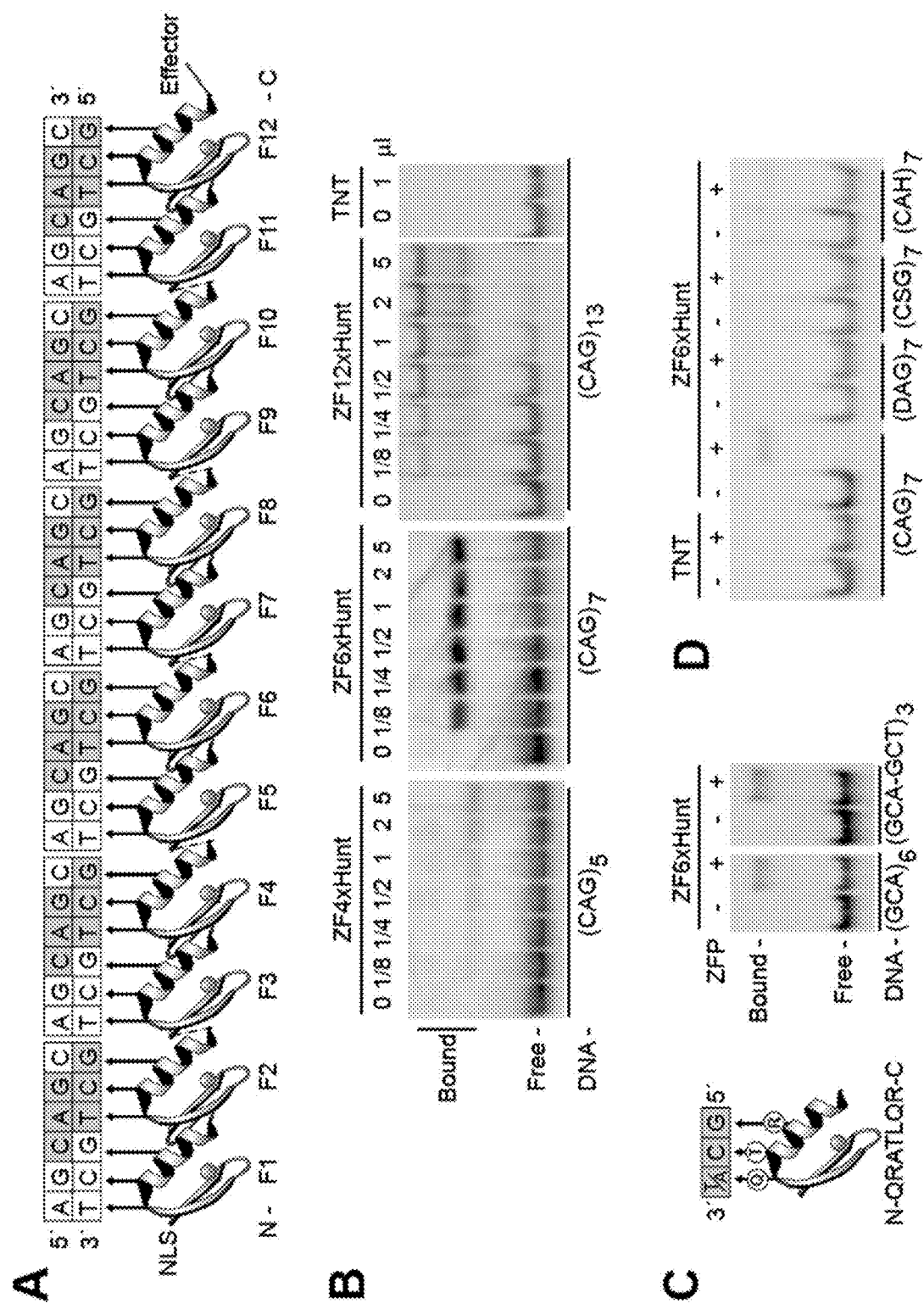
FIG. 1 Zinc finger arrays according to the invention bind to CAG-repeats. (A) A schematic illustration of a 12-finger array, showing recognition helices contacting 5'-GCT-3' bases on the lower DNA strand. Similar arrays of 4, 6, 8, 11, 12 and 18 zinc fingers were built (ZF4xHunt, ZF6xHunt, ZF8xHunt, ZF11xHunt, ZF12xHunt and ZF18xHunt; see WO 2012/049332). Nuclear localisation signals (NLS) and effectors (e.g. Kox-1 transcription repression domain) were added to N- and C-termini, respectively.

All references cited herein are incorporated by reference in their entirety. Unless otherwise defined, all technical and scientific terms used herein have the same meaning as commonly understood by one of ordinary skill in the art to which this invention belongs.

Unless defined otherwise, all technical and scientific terms used herein have the same meaning as commonly understood by one of ordinary skill in the art (e.g. in cell culture, molecular genetics, nucleic acid chemistry and biochemistry).

Unless otherwise indicated, the practice of the present invention employs conventional techniques of chemistry, molecular biology, microbiology, recombinant DNA technology, chemical methods, pharmaceutical formulations and delivery and treatment of animals, which are within the capabilities of a person of ordinary skill in the art. Such techniques are also explained in the literature, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N. Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

In order to assist with the understanding of the invention several terms are defined herein.

The term "amino acid" in the context of the present invention is used in its broadest sense and is meant to include naturally occurring L α-amino acids or residues. The commonly used one and three letter abbreviations for naturally occurring amino acids are used herein: A=Ala; C=Cys; D=Asp; E=Glu; F=Phe; G=Gly; H=His; I=11e; K=Lys; L=Leu; M=Met; N=Asn; P=Pro; Q=Gln; R=Arg; S=Ser; T=Thr; V=Val; W=Trp; and Y=Tyr (Lehninger, A. L., (1975) *Biochemistry*, 2d ed., pp. 71-92, Worth Publishers, New York). The general term "amino acid" further includes D-amino acids, retro-inverso amino acids as well as chemically modified amino acids such as amino acid analogues, naturally occurring amino acids that are not usually incorporated into proteins such as norleucine, and chemically synthesised compounds having properties known in the art to be characteristic of an amino acid, such as s-amino acids. For example, analogues or mimetics of phenylalanine or proline, which allow the same conformational restriction of the peptide compounds as do natural Phe or Pro, are included within the definition of amino acid. Such analogues and mimetics are referred to herein as "functional equivalents" of the respective amino acid. Other examples of amino acids are listed by Roberts and Vellaccio, *The Peptides: Analysis, Synthesis, Biology*, Gross and Meiehofer, eds., Vol. 5 p. 341, Academic Press, Inc., N.Y. 1983, which is incorporated herein by reference.

The term "peptide" as used herein (e.g. in the context of a zinc finger peptide (ZFP) or framework) refers to a plurality of amino acids joined together in a linear or circular chain. The term oligopeptide is typically used to describe peptides having between 2 and about 50 or more amino acids. Peptides larger than about 50 amino acids are often referred to as polypeptides or proteins. For purposes of the present invention, however, the term "peptide" is not limited to any particular number of amino acids, and is used interchangeably with the terms "polypeptide" and "protein".

As used herein, the term "zinc finger domain" refers to an individual "finger", which comprises a ββα-fold stabilised by a zinc ion (as described elsewhere herein). Each zinc finger domain typically includes approximately 30 amino acids. The term "domain" (or "module"), according to its ordinary usage in the art, refers to a discrete continuous part of the amino acid sequence of a polypeptide that can be equated with a particular function. Zinc finger domains are largely structurally independent and may retain their structure and function in different environments. Typically, a zinc finger domain binds a triplet or (overlapping) quadruplet nucleotide sequence. Adjacent zinc finger domains arranged in tandem are joined together by linker sequences. A zinc finger peptide of the invention is composed of a plurality of "zinc finger domains", which in combination do not exist in nature. Therefore, they may be considered to be artificial or synthetic zinc finger peptides.

The terms "nucleic acid", "polynucleotide", and "oligonucleotide" are used interchangeably and refer to a deoxyribonucleotide (DNA) or ribonucleotide (RNA) polymer, in linear or circular conformation, and in either single- or double-stranded form. For the purposes of the present invention such DNA or RNA polymers may include natural nucleotides, non-natural or synthetic nucleotides, and mixtures thereof. Non-natural nucleotides may include analogues of natural nucleotides, as well as nucleotides that are modified in the base, sugar and/or phosphate moieties (e.g. phosphorothioate backbones). Examples of modified nucleic acids are PNAs and morpholino nucleic acids. Generally an analogue of a particular nucleotide has the same base-pairing specificity, i.e. an analogue of G will base-pair with C. For the purposes of the invention, these terms are not to be considered limiting with respect to the length of a polymer.

A "gene", as used herein, is the segment of nucleic acid (typically DNA) that is involved in producing a polypeptide or ribonucleic acid gene product. It includes regions preceding and following the coding region (leader and trailer) as well as intervening sequences (introns) between individual coding segments (exons). Conveniently, this term also includes the necessary control sequences for gene expression (e.g. enhancers, silencers, promoters, terminators etc.), which may be adjacent to or distant to the relevant coding sequence, as well as the coding and/or transcribed regions encoding the gene product. Preferred genes in accordance with the present invention are those associated with polyglutamate repeat coding sequences.

As used herein the term "modulation", in relation to the expression of a gene refers to a change in the gene's activity. Modulation includes both activation (i.e. increase in activity or expression level) and repression or inhibition of gene activity. In preferred embodiments of the invention, the therapeutic molecules (e.g. peptides) of the invention are repressors of gene expression or activity.

A nucleic acid "target", "target site" or "target sequence", as used herein, is a nucleic acid sequence to which a zinc finger peptide of the invention will bind, provided that conditions of the binding reaction are not prohibitive. A target site may be a nucleic acid molecule or a portion of a larger polynucleotide. Particularly suitable target sites comprise repetitive nucleic acid sequences; especially trinucleotide repeat sequences. Preferred target sequences in accordance with the invention include those defined by CAG-repeat sequences (e.g. CAGCAG . . . ; AGCAGC . . . ; and GCAGCA . . . ), and their complementary sequences, CTG-repeats (e.g. CTGCTG . . . ; TGCTGC . . . ; and GCTGCT . . . ). In accordance with the invention, a target sequence for a poly-zinc finger peptide of the invention may comprise a single contiguous nucleic acid sequence, or more than one non-contiguous nucleic acid sequence (e.g. two separate contiguous sequences, each representing a partial target site), which are interspersed by one or more intervening nucleotide or sequence of nucleotides. These terms may also be substituted or supplemented with the terms "binding site", "binding sequence", "recognition site" or recognition sequence", which are used interchangeably.

As used herein, "binding" refers to a non-covalent interaction between macromolecules (e.g. between a zinc finger peptide and a nucleic acid molecule containing an appropriate target site). In some cases binding will be sequence-specific, such as between one or more specific nucleotides (or base pairs) and one or more specific amino acids. It will be appreciated, however, that not all components of a binding interaction need be sequence-specific (e.g. non-covalent interactions with phosphate residues in a DNA backbone). Binding interactions between a nucleic acid sequence and a zinc finger peptide of the invention may be characterised by binding affinity and/or dissociation constant (Kd). A suitable dissociation constant for a zinc finger peptide of the invention binding to its target site may be in the order of 1 µM or lower, 1 nM or lower, or 1 pM or lower. "Affinity" refers to the strength of binding, such that increased binding affinity correlates with a lower Kd value. Zinc finger peptides may have DNA-binding activity, RNA-binding activity, and/or even protein-binding activity. Preferably zinc finger peptides of the invention are designed or selected to have sequence specific nucleic acid-binding activity, especially to dsDNA. Preferably, the target site for a particular zinc finger peptide is a sequence to which the zinc finger peptide concerned is capable of nucleotide-specific binding. It will be appreciated, however, that depending on the amino acid sequence of a zinc finger peptide it may bind to or recognise more than one target sequence, although typically one sequence will be bound in preference to any other recognised sequences, depending on the relative specificity of the individual non-covalent interactions. Generally, specific binding is preferably achieved with a dissociation constant (Kd) of 1 nM or lower, 100 pM or lower; or 10 pM or lower. Preferably, a zinc finger peptide of the invention (or protein comprising a zinc finger peptide of the invention) binds to a specific target sequence with a dissociation constant of 1 µM or lower; such as 0.1 pM or lower, or even 10 fM or lower.

By "non-target" it is meant that the nucleic acid sequence concerned is not appreciably bound by the relevant zinc finger peptide. In some embodiments it may be considered that, where a zinc finger peptide of the invention has a known sequence-specific target sequence, essentially all other nucleic acid sequences may be considered to be non-target. From a practical perspective it can be convenient to define an interaction between a non-target sequence and a particular zinc finger peptide as being sub-physiological (i.e. not capable of creating a physiological response under physiological target sequence/zinc finger peptide concentrations). For example, if any binding can be measured between the zinc finger peptide and the non-target sequence, the dissociation constant (Kd) is typically weaker than 1 µM, such as 10 µM or weaker, 100 µM or weaker, or at least 1 mM.

Zinc Finger Peptides

The present invention relates to non-naturally occurring poly-zinc finger peptides for binding to repetitive nucleic acid sequences, such as trinucleotide repeat sequences, and particularly to expanded CAG-(polyglutamine-encoding) repeats, as may be found in naturally-occurring genomic DNA sequences. The invention also relates to the use of such poly-zinc finger peptides as therapeutic molecules and to related methods of treatment: for example, for treating polyglutamine-based diseases such as HD. Preferably, the poly-zinc finger peptides of the invention bind to expanded CAG-repeats associated with mutated gene sequences in preference to and/or selectively over the shorter CAG-repeat sequences of normal, non-pathogenic genes.

A "zinc finger" is a relatively small polypeptide domain comprising approximately 30 amino acids, which folds to form a secondary structure including an α-helix adjacent an antiparallel s-sheet (known as a ββα-fold). The fold is stabilised by the coordination of a zinc ion between four largely invariant (depending on zinc finger framework type) Cys and/or His residues, as described further below. Natural zinc finger domains have been well studied and described in the literature, see for example, Miller et al., (1985) *EMBO J.* 4: 1609-1614; Berg (1988) *Proc. Natl. Acad. Sci. USA* 85: 99-102; and Lee et al., (1989) *Science* 245: 635-637. A zinc finger domain recognises and binds to a nucleic acid triplet, or an overlapping quadruplet (as explained below), in a double-stranded DNA target sequence. However, zinc fingers are also known to bind RNA and proteins (Clemens, K. R. et al. (1993) *Science* 260: 530-533; Bogenhagen, D. F. (1993) *Mol. Cell. Biol.* 13: 5149-5158; Searles, M. A. et al. (2000) *J. Mol. Biol.* 301: 47-60; Mackay, J. P. & Crossley, M. (1998) *Trends Biochem. Sci.* 23: 1-4).

Zinc finger proteins generally contain strings or chains of zinc finger domains (or modules). Thus, a natural zinc finger protein may include two or more zinc finger domains, which may be directly adjacent one another, e.g. separated by a short (canonical) or canonical-like linker sequence, or a longer, flexible or structured polypeptide sequences. Adjacent zinc finger domains linked by short canonical or canonical-like linker sequences of 5, 6 to 7 amino acids are expected to bind to contiguous nucleic acid sequences, i.e. they typically bind to adjacent trinucleotides/triplets; or protein structures. In some cases, cross-binding may also occur between adjacent zinc fingers and their respective target triplets, which helps to strengthen or enhance the recognition of the target sequence, and leads to the binding of overlapping quadruplet sequences (Isalan et al., (1997) *Proc. Natl. Acad. Sci. USA*, 94: 5617-5621). By comparison, distant zinc finger domains within the same protein may recognise (or bind to) non-contiguous nucleic acid sequences or even to different molecules (e.g. protein rather than nucleic acid). Indeed, naturally occurring zinc finger-containing proteins may include both zinc finger domains for binding to protein structures as well as zinc finger domains for binding to nucleic acid sequences. In accordance with the invention, some pairs of adjacent zinc finger domains may be separated by relatively long, flexible linker sequences. Such adjacent zinc fingers may likely bind to non-contiguous nucleic acid sequences, although it is also possible for them to bind to contiguous sequences. In such embodiments, the relative binding location of the pairs of zinc finger domains separated by long linker sequences may be determined by the sequence context, i.e. by dominant binding interactions from other zinc finger domains within the peptide.

The majority of the amino acid side chains in a zinc finger domain that are important for dsDNA base recognition are located on the α-helix of the finger. Conveniently, therefore, the amino acid positions in a zinc finger domain are numbered from the first residue in the α-helix, which is given the number (+)1; and the helix is generally considered to end at the final zinc-coordinating Cys or His residue, which is typically position +11. Thus, "−1" refers to the residue in the framework structure immediately preceding the first residue of the α-helix. As used herein, residues referred to as "++" are located in the immediately adjacent (C-terminal) zinc finger domain. Generally, nucleic acid recognition by a zinc finger module is achieved primarily by the amino acid side chains at positions −1, +3, +6 and ++2; although other amino acid positions (especially of the α-helix) may sometimes contribute to binding between the zinc finger and the target molecule. Since the vast majority of base-specific interactions between dsDNA and a zinc finger domain come from this relatively short stretch of amino acids, it is convenient to define the sequence of the zinc finger domain from −1 to +6 (i.e. residues −1, 1, 2, 3, 4, 5 and 6) as a zinc finger "recognition sequence". For ease of understanding, it is worth noting that the first invariant histidine residue that coordinates the zinc ion is position (+)7 of the zinc finger domain.

When binding to a nucleic acid sequence, the zinc finger recognition sequence primarily interacts with one strand of a double-stranded nucleic acid molecule (the primary strand or sequence). However, there can be subsidiary interactions between amino acids of a zinc finger domain and the complementary (or secondary) strand of the double-stranded nucleic acid molecule. For example, the amino acid residue at the ++2 position typically may interact with a nucleic acid residue in the secondary strand.

During binding, the α-helix of the zinc finger domain almost invariably lies within the major groove of dsDNA and aligns antiparallel to the target nucleic acid strand. Accordingly, the primary nucleic acid sequence is arranged 3' to 5' in order to correspond with the N-terminal to C-terminal sequence of the zinc finger peptide. Since nucleic acid sequences are conventionally written 5' to 3', and amino acid sequences N-terminus to C-terminus, when a target nucleic acid sequence and a zinc finger peptide are aligned according to convention, the primary interaction of the zinc finger peptide is with the complementary (or minus) strand of the nucleic acid sequence, since it is this strand which is aligned 3' to 5'. These conventions are followed in the nomenclature used herein.

Zinc finger peptides according to the invention are non-natural and suitably contain 3 or more, for example, 4, 6, 8, 9, 10, 11, 12, 13, 14, 15, 16, 17, 18, 24 or more (e.g. up to approximately 30 or 32) zinc finger domains arranged adjacent one another in tandem. Such peptides may be referred to as "poly-zinc finger peptides". Particularly beneficial zinc finger peptides of the invention include at least 6 zinc finger domains, still more preferably at least 8, at least 11 or at least 12 or at least 18 zinc finger domains; and in some cases at least 24 zinc finger domains. Preferably, the zinc finger peptides of the invention have from 8 to 18, from 10 to 18 or from 11 to 18 zinc finger domains arranged in tandem (e.g. 8, 9, 10, 11, 12, 13, 14, 15, 16, 17 or 18).

As already noted, the zinc finger peptides of the invention may bind to non-contiguous or contiguous nucleic acid binding sites. When targeted to non-contiguous binding sites, each sub-site (or half-site where there are two non-contiguous sequences) is suitably at least approximately 18 bases long, but may alternatively be approximately 12, 15 or 24 bases long. Preferred 11 zinc finger peptides of the invention bind to full-length nucleic acid sequences which are approximately 33 nucleotides long, but which may contain two sub-sites of 18 and 15 nucleotides arranged directly adjacent to one another to form a contiguous sequence, or which are separated by intervening nucleotides to create a non-contiguous target site. Preferred 12 zinc finger peptides of the invention bind to full-length nucleic acid sequences which are approximately 36 nucleotides long, but which may contain two subsites of (suitably) 18 nucleotides arranged directly adjacent to one another to form a contiguous sequence, or separated by intervening nucleotides as in the case of a non-contiguous target site.

In (poly-)zinc finger peptides of the present invention, adjacent zinc finger domains are joined to one another by "linker sequences" that may be canonical, canonical-like, flexible or structured, as described, for example, in WO 01/53480 (Moore et al., (2001) *Proc. Natl. Acad. Sci. USA* 98: 1437-1441). Generally, a natural zinc finger linker sequence lacks secondary structure in the free form of the peptide. However, when the protein is bound to its target site a canonical linker is typically in an extended, linear conformation, and amino acid side chains within the linker may form local interactions with the adjacent nucleic acid. In a tandem array of zinc finger domains, the linker sequence is the amino acid sequence that lies between the last residue of the α-helix in an N-terminal zinc finger and the first residue of the β-sheet in the next (i.e. C-terminal adjacent) zinc finger. For the purposes of the present invention, the last amino acid of the α-helix in a zinc finger is considered to be the final zinc coordinating histidine (or cysteine) residue, while the first amino acid of the following finger is generally a tyrosine, phenylalanine or other hydrophobic residue.

It is desirable that the zinc finger peptides of the invention bind relatively specifically to their target sequence. It will be appreciated, however, that 'specificity' to a highly repetitive sequence is not a straightforward concept in the sense that relatively shorter and relatively longer repetitive sequences may both be targeted and bound with good affinity. In accordance with some embodiments of the invention (and as described elsewhere herein), the zinc finger peptides of the invention may beneficially exhibit preferential binding to relatively longer repeat sequences over relatively shorter repeat sequences.

Binding affinity (e.g. dissociation constant, Kd) is one way to assess the binding interaction between a zinc finger peptide of the invention and a potential target nucleic acid sequence. It is convenient to measure binding affinity of the host-optimised zinc finger peptides of the invention to ensure that modifications to the zinc finger peptide sequences-especially those in the recognition sequence region—have not adversely affected nucleic acid binding affinity. The binding affinity of a zinc finger peptide for its selected/potential target sequence can be measured using techniques known to the person of skill in the art, such as surface plasmon resonance, or biolayer interferometry. Bio-sensor approaches are reviewed by Rich et al. (2009), "A global benchmark study using affinity-based biosensors", *Anal. Biochem.,* 386:194-216. Alternatively, real-time binding assays between a zinc finger peptide and target site may be performed using biolayer interferometry with an Octet Red system (Fortebio, Menlo Park, CA).

Zinc finger peptides of the invention have pM or higher binding affinity for a target nucleic acid sequence. Suitably, a zinc finger peptide of the invention has nM or sub-nM binding affinity for its specific target sequence; for example, $10^{-9}$ M, $10^{-10}$ M, $10^{-11}$ M, or $10^{-12}$ M or less. In some particularly preferred embodiments the affinity of a zinc finger peptide of the invention for its target sequence is in the pM range or below, for example, in the range of $10^{-13}$ M, $10^{-14}$ M, or $10^{-15}$ M or less.

Binding affinity between a zinc finger peptide of the invention and a target nucleic acid sequence can conveniently be assessed using an ELISA assay, as is know to the person of skill in the art.

In some embodiments of the invention, zinc finger peptides for targeting to expanded CAG repeats may have a dissociation constant for sequences of 35 or more CAG repeats that is at least 2-fold higher, at least 5-fold, or at least 10-fold higher than for sequences of less that 22 CAG repeats. Suitably, the affinity of such zinc finger peptides of the invention for DNA sequences having at least 63 CAG repeats is at least 2-fold, at least 5-fold or at least 20-fold higher than for sequences having less that 22 CAG repeats. In some particularly advantageous embodiments, the affinity of such zinc finger peptides for DNA sequences having at least 104 CAG repeats is at least 2-fold, at least 10-fold or at least 50-fold higher than for sequences having less that 22 CAG repeats.

Zinc Finger Peptide Frameworks and Derivatives

Zinc finger peptides have proven to be extremely versatile scaffolds for engineering novel DNA-binding domains (e.g. Rebar & Pabo (1994) *Science* 263: 671-673; Jamieson et al., (1994) *Biochemistry* 33: 5689-5695; Choo & Klug (1994) *Proc. Natl. Acad. Sci. USA*. 91: 11163-11167; Choo et al., (1994) *Nature* 372: 642-645; Isalan & Choo (2000) *J. Mol. Biol.* 295: 471-477; and many others).

For specific biological functionality and therapeutic use, particularly in vivo (e.g. in gene therapy and transgenic animals), it is generally desirable that a poly-zinc finger peptide of the invention is able to target unique or virtually unique sites within any genome. For complex genomes, such as in humans, it is generally considered that an address of at least 16 bps is required to specify a potentially unique DNA sequence. Shorter DNA sequences have a significant probability of appearing several times in a genome, which increases the possibility of obtaining undesirable non-specific gene targeting and biological effects. Since individual zinc fingers generally bind to three consecutive nucleotides, 6 zinc finger domains with an 18 bp binding site could, in theory, be used for the specific recognition of a unique target sequence within any genome. Accordingly, a great deal of research has been carried out into so-called "designer transcription factors" for targeted gene regulation, which typically involve 4 or 6 zinc finger domains that may be arranged in tandem or in dimerisable groups (e.g. of three-finger units). Our earlier work (e.g. WO 2012/049332) was the first to demonstrate that tandem arrays of more than 6 zinc finger domains, such as 8, 9, 10, 11, 12 or more (e.g. 15, 16 or 18) zinc fingers can be synthesised and expressed; and, more importantly, that such long arrays of non-natural zinc finger domains can have in vitro or in vivo (specific) nucleic acid binding activity. In this earlier work we also reported that such extended arrays of zinc finger peptides were capable of targeting genomic DNA sequences and have gene modulation activity in vitro and/or in vivo.

Following on from this earlier work, in the present invention, we provide improved novel extended zinc finger peptide frameworks comprising at least 4, at least 6, at least 8, at least 10, at least 11, at least 12, or at least 18 zinc finger domains. Suitable zinc finger peptide frameworks of the invention comprise from 8 to 32 zinc finger domains, from 8 to 28 zinc finger peptides, from 8 to 24 zinc finger peptides, or from 8 to 18 zinc finger peptides. Preferred zinc finger peptides of the invention comprise 8, 10, 11, 12 or 18 zinc finger domains; and particularly preferred zinc finger peptides of the invention comprise 10, 11 or 12 zinc finger domains.

The zinc finger peptide frameworks of the invention may comprise directly adjacent zinc finger domains having canonical (or canonical-like) linker sequences between adjacent zinc finger domains, such that they preferentially bind to contiguous nucleic acid sequences. Accordingly, a 6-zinc finger peptide (framework) of the invention is particularly suitable for binding to contiguous stretches of approximately 18 nucleic acid bases or more, particularly of the minus nucleic acid strand. Particularly preferred zinc finger peptides of the invention comprise more than 6 zinc finger domains, such as 8, 10, 11, 12, 18, 24 or 32 zinc finger domains. Typically such extended poly-zinc finger peptides, according to the invention are designed to bind nucleic acid sequences which may be arranged as a contiguous stretch or as a non-contiguous stretch comprising two or three sub-sites. For example, an 8-zinc finger peptide is particularly suitable for binding a target sequence of approximately 24 nucleotides; a 10-zinc finger peptide is suitable for binding approximately 30 nucleotides; an 11-zinc finger peptide is suitable for binding approximately 33 nucleotides; a 12-zinc finger peptide is capable of binding approximately 36 nucleotides; and an 18-zinc finger peptide of the invention is particularly suitable for binding to approximately 54 nucleic acid bases or more. As already described, such target sequences may be arranged contiguously or in non-contiguous sub-sites especially arranged in e.g. 12, 15 or 18 nucleotide lengths.

The extended arrays of zinc finger domains in the peptides and polypeptides of the invention typically comprise canonical linker sequences, short flexible (canonical-like) linker sequences and long flexible linker sequences. Thus, in some embodiments, one or more pairs of adjacent zinc finger domains of a zinc finger peptide according to the invention may be separated by short canonical linker sequences (e.g. TGERP, SEQ ID NO: 66; TGEKP, SEQ ID NO: 6; etc.). In some embodiments, one or more pairs of adjacent zinc finger domains of a zinc finger peptide according to the invention may be separated by short flexible linker sequences (e.g. of 6 or 7 amino acids), "canonical-like" linker sequences, which preferably comprises the amino acid residues of a canonical linker with an additional one or two amino acid residues within, before or after the canonical sequence (preferably within). Adjacent zinc finger domains separated by canonical and short flexible linker sequences (i.e. which are between 5 and 7 amino acids long) typically bind to contiguous DNA target sites. In accordance with the invention, however, one or more pairs of adjacent zinc finger domains of a zinc finger peptide according to the invention may be separated by long flexible linker sequences, for example, comprising 8 or more amino acids, such as between 8 and 50 amino acids. Particularly suitable long flexible linkers have between approximately 10 and 40 amino acids, between 15 and 35 amino acids, or between 20 and 30 amino acids. Preferred long flexible linkers may have 18, 23 or 29 amino acids. Adjacent zinc finger domains separated by long flexible linkers have the capacity to bind to non-contiguous binding sites in addition to the capacity to bind to contiguous binding sites. The length of the flexible linker may influence the length of DNA that may lie between such non-contiguous binding sub-sites. This can be a particular advantage in accordance with the invention, since poly-zinc finger peptides that target extended triplet repeat sequences may have a number of options for binding to contiguous as well as discontiguous target sequences.

Suitably, the zinc finger peptides/frameworks of the invention may comprise two or more (e.g. 2, 3 or 4) arrays of 4, 5, 6 or 8 directly adjacent zinc finger domains (or any combination thereof) separated by long flexible (or structured) linkers. Preferably, such extended (poly-)zinc finger peptides are arranged in multiple arrays of 5 and/or 6-finger units separated by long flexible linkers.

The inventors have shown that such extended zinc finger peptides of more than 6 zinc fingers in total can exhibit specific and high affinity binding to desired target sequences, both in vitro and in vivo. Furthermore, it has been demonstrated that the extended zinc finger peptides of the invention can be stably expressed within a target cell, can be non-toxic to the target cell, and can have a specific and desired gene modulation activity. In particular, it has been shown that the zinc finger repressor proteins of the invention can have prolonged expression in target cells in vivo, without causing toxic side-effects that are often associated with the expression of heterologous/foreign protein sequences in vivo.

As noted above, the extended zinc finger peptides of the invention are adapted for binding to repeat sequences (i.e. trinucleotide repeats) in target genes. Suitable target repeat sequences comprise at least 10 trinucleotide repeats, at least 12 trinucleotide repeats, or at least 20 trinucleotide repeats. Beneficially, there are at least 22 trinucleotide repeats, at least 29 trinucleotide repeats, at least 35 trinucleotide repeats or more. In some embodiments there may be 36, 40, 42 or more trinucleotide repeats, as indicated in the repeat numbers for potential pathogenic gene targets in Table 1.

The extended zinc finger peptides of the invention preferably bind to sequences within expanded CAG and/or CTG-repeat sequences in double-stranded DNA e.g. DNA molecules, fragments, gene sequences or chromatin. Suitably, the binding site comprises repeats of 5'-GCA-3' and/or 5'-GCT-3'. Thus, the binding site preferably comprises repeats of the sequence 5'-GCT/A-3'. Desirably, target sequences for the preferred extended zinc finger peptides of the invention comprise 22 or more contiguous CAG (or CTG) repeats, such as at least 35 contiguous CAG (or CTG) repeats, at least 63 contiguous CAG (or CTG) repeats, at least 104 contiguous CAG (or CTG) repeats, or at least 111 contiguous CAG (or CTG) repeats.

A particular advantage of the zinc finger peptides of one embodiment of the invention is that they bind to longer arrays of CAG or CTG-repeat sequences in preference to shorter arrays. Accordingly, the CAG (or CTG) targeting zinc finger peptides of the invention bind more effectively (e.g. with higher affinity or greater gene modulation ability) to expanded CAG or CTG-repeat sequences containing at least 22 repeats, compared to sequences containing e.g. 10 or less repeats. Similarly, sequences containing at least 35 CAG or CTG-repeats may be bound preferentially over sequences containing 22 or less repeats (including 10 or less); sequences containing at least 63 CAG or CTG-repeats may be bound preferentially over sequences containing 35 or less repeats (including 22 or less, or 10 or less); and sequences containing at least 104 CAG or CTG-repeats may be bound preferentially over sequences containing 63 or less repeats (including 35 or less, 22 or less, or 10 or less).

There are a number of natural zinc finger frameworks known in the art, and any of these frameworks may be suitable for use in the extended zinc finger peptide frameworks of the invention. In general, a natural zinc finger framework has the sequence, Formula 1: $X_{0-2}$ C $X_{1-5}$ C $X_{9-14}$ H $X_{3-6}$ H/C; or Formula 2: $X_{0-2}$ C $X_{1-5}$ C $X_{2,7}$ $X^{-1}$ $X^{+1}$ $X^{+2}$ $X^{+3}$ $X^{+4}$ $X^{+5}$ $X^{+6}$ H $X_{3-6}$ H/C where X is any amino acid, the numbers in subscript indicate the possible numbers of residues represented by X, and the numbers in superscript indicate the position of the amino acid in the α-helix. In one embodiment of the invention, the extended zinc finger peptide framework is based on an array of zinc finger domains of Formula 1 or 2. Alternatively, the zinc finger motif may be represented by the general sequence, Formula 3: $X_2$ C $X_{2,4}$ C $X_{12}$ H $X_{3,4,5}$ H/C; or Formula 4: $X_2$ C $X_{2,4}$ C $X_5$ $X^{-1}$ $X^{+1}$ $X^{+2}$ $X^{+3}$ $X^{+4}$ $X^{+5}$ $X^{+6}$ H $X_{3,4,5}$ H/C. Still more preferably the zinc finger motif may be represented by the general sequence, Formula 5: $X_2$ C $X_2$ C $X_{12}$ H $X_3$ H; or Formula 6: $X_2$ C $X_2$ C $X_5$ $X^{-1}$ $X^{+1}$ $X^{+2}$ $X^{+3}$ $X^{+4}$ $X^{+5}$ $X^{+6}$ H $X_3$ H. Accordingly, an extended zinc finger peptide framework of the invention may be based on zinc finger domains of Formulas 1 to 6, or combinations of Formulas 1 to 6, joined together in an array using the linker sequences described herein.

In these formulas, the fixed C and H residues coordinate the zinc ion to stabilise the zinc finger structure: the first H residue is position +7 of the α-helix. Particularly preferred positions for diverisification within the zinc finger domain frameworks of the invention, in order to direct binding to a desired target, are those within or adjacent the α-helix, for example, positions −1, 2, 3 and 6.

In one embodiment of the invention, the extended zinc finger peptide framework comprises at least 11 zinc finger domains of one of Formulas 1 to 6, joined together by linker sequences, i.e. Formula 7: [(Formula 1-6)-linker]$_n$-(Formula 1-6)], where n is ≥10, such as between 10 and 31. As indicated, in Formula 7 any combination of Formulas 1 to 6 may be used. In another embodiment the extended zinc finger peptide framework comprises between 10 and 18 (e.g. 11 to 18) zinc finger domains of the above Formulas. Suitably, therefore, n is 9 to 17 (e.g. 10 to 17); more suitably n is 9, 10, 11, 13, 14, 15 or 17; and preferably n is 10, 11 or 17.

In a preferred embodiment of the invention, the recognition sequence of one or more of the zinc finger domains (i.e. positions $X^{-1}$, $X^{+1}$, $X^{+2}$, $X^{+3}$, $X^{+4}$, $X^{+5}$ and $X^{+6}$ in Formulas 2, 4 and 6 above is represented by the amino acid sequence of SEQ ID NO: 1, i.e. QSA/GDL/RT/KR. In some embodiments, the recognition sequence of one or more zinc finger domain is selected from SEQ ID NO: 2 (QSADLTR), SEQ ID NO: 3 (QSGDLTR), SEQ ID NO: 4 (QSGDRKR), and SEQ ID NO: 5 (QSADRKR) or any combination or two or more thereof. Preferably the recognition sequences of each zinc finger domain in a poly-zinc finger peptide of the invention for targeting poly-CAG target sequences are selected from a combination of SEQ ID NOs: 2 and 5; or from a combination of SEQ ID NOs: 3 and 4. Thus, in one embodiment, there is provided an engineered zinc finger (DNA-binding) peptide comprising at least 10, 11, 12 or 18 zinc finger domains having the zinc finger recognition sequences of SEQ ID NO: 2 and/or SEQ ID NO: 5. In another embodiment, there is provided an engineered zinc finger (DNA-binding) peptide comprising at least 10, 11, 12 or 18 zinc finger domains having the recognition sequences of SEQ ID NO: 3 and/or SEQ ID NO: 4. Beneficially, therefore, the engineered zinc finger peptides of the invention comprise at least 10, 11, 12 or 18 zinc finger modules. In some embodiments, the zinc finger peptides of the invention comprise more than 10, 11, 12 or 18 zinc finger domains-such as any number between 11 and 32 zinc finger domains, provided that at least 10, 11, 12 or 18 adjacent domains have the specified recognition sequence. In embodiments of the invention wherein each zinc finger domain of the poly-zinc finger peptide has the above recognition sequences, it will be understood that one or more recognition sequence of SEQ ID NO: 2 may be replaced with the sequence of SEQ ID NO: 5 and vice versa, and one or more recognition sequence of SEQ ID NO: 3 may be replaced with the sequence of SEQ ID NO: 4 and vice versa without substantially changing the nucleic acid recognition and binding characteristics of the zinc finger peptide, and such alternative zinc finger peptides are encompassed within the scope of the invention.

As already described, adjacent zinc finger domains are joined together by linker sequences. In a natural zinc finger protein, threonine is often the first residue in the linker, and proline is often the last residue of the linker. On the basis of sequence homology, the canonical natural linker sequence is considered to be -TGEKP-(Linker 1 or $L_1$; SEQ ID NO: 6). However, natural linkers can vary greatly in terms of amino acid sequence and length. Therefore, a common consensus sequence based on natural linker sequences may be represented by -TGE/QK/RP-(Linker 2 or $L_2$; SEQ ID NO: 7), and this sequence is preferred for use as a "canonical" (or "canonical-like") linker in accordance with the invention. Thus, another useful canonical linker sequence is -TGQKP-(SEQ ID NO: 65).

However, in extended zinc finger arrays of e.g. 4 or more zinc finger domains, it has been shown that it can be beneficial to periodically disrupt the canonical linker sequence, when used between adjacent zinc fingers in an array, by adding one or more amino acid residue (e.g. Gly and/or Ser), so as to create sub-arrays of zinc finger domains (e.g. groups of 2 or 3 zinc finger domains) within the array (Moore et al., (2001) *Proc. Natl. Acad. Sci. USA* 98: 1437-1441; and WO 01/53480).

Therefore, suitable linker sequences for use in accordance with the invention include canonical linker sequences of 5 amino acids (e.g. Linker 1 or Linker 2, above), and related canonical-like linker sequences of 6 or 7 amino acids.

Canonical-like linkers for use in accordance with the invention may suitably be based on the sequence, -TGG/SE/QK/RP-(Linker 3 or $L_3$; SEQ ID NO: 8). Preferred canonical-like linkers thus include the specific sequences: TGGERP (SEQ ID NO: 9), TGSERP (SEQ ID NO: 10), TGGQRP (SEQ ID NO: 11), TGSQRP (SEQ ID NO: 12), TGGEKP (SEQ ID NO: 13), TGSEKP (SEQ ID NO: 14), TGGQKP (SEQ ID NO: 15), or TGSQKP (SEQ ID NO: 16). A particularly preferred canonical-like linker is TGSERP (Linker 4 or L4; SEQ ID NO: 10). Another particularly preferred canonical-like linker is TGSQKP (Linker 5 or L5; SEQ ID NO: 16). However, other linker sequences may also be used between one or more pairs of zinc finger domains, for example, linkers of the sequence -TG(G/S)$_{0-2}$E/QK/RP-(SEQ ID NO: 17) or -T(G/S)$_{0-2}$GE/QK/RP-(Linker 6 or L6; SEQ ID NO: 18).

In some embodiments still longer flexible linkers of 8 or more amino acids may be used, as previously described. Linkers of 8 amino acids include the sequences -TG(G/S)$_3$E/QK/RP-(SEQ ID NO: 19) and -T(G/S)$_3$GE/QK/RP-($L_{12}$;

SEQ ID NO: 20). Alternative long flexible linkers are: LRQKD(GGGGS)$_{1-4}$QLVGTAERP (Linker 7 or L7; SEQ ID NO: 21) and LRQKD(GGGGS)$_{1-4}$QKP (Linker 8 or L8; SEQ ID NO: 22). Preferred long flexible linkers for use in the zinc finger peptides of the invention are, LRQKDGGGGSGGGGSGGGGSQLVGTAERP (Linker 9 or L9; SEQ ID NO: 23), and LRQKDGGGGSGGGGSGGGGSQKP (Linker 10 or L$_{10}$; SEQ ID NO: 24).

The present inventors have shown that by selecting appropriate linker sequences and suitable combinations of linker sequences within an array of zinc fingers, extended arrays of zinc finger peptides of at least 8 or 10 zinc fingers (such as 10, 11, 12 or 18) can be synthesised, expressed and can have selective gene targeting activity. The extended arrays of zinc finger peptides of the invention are conveniently arranged in tandem. Such 11, or 12-zinc finger peptides can recognise and specifically bind 33 or 36 nucleic acid residues, respectively, and longer arrays (such as 18-zinc finger peptides) recognise still longer nucleic acid sequences. In this way, the extended zinc finger peptides of the invention can be targeted to preferred genomic sequences, i.e. expanded CAG repeat sequences, especially those associated with polyglutamine disease genes.

In addition, a significant increase in binding affinity might also be expected, compared to zinc finger peptides with fewer fingers. For example, whereas a 3-finger peptide (with a 9 bp recognition sequence) may bind DNA with nanomolar affinity, a 6-finger peptide might be expected to bind an 18 bp sequence with an affinity of between $10^{-9}$ and $10^{-18}$ M, depending on the arrangement and sequence of zinc finger peptides. To optimise both the affinity and specificity of 6-finger peptides, a fusion of three 2-finger domains has been shown to be advantageous (Moore et al., (2001) *Proc. Natl. Acad. Sci. USA* 98: 1437-1441; and WO 01/53480). Therefore, in some embodiments of the invention, the zinc finger peptides of the invention comprise sub-arrays of 2-finger units arranged in tandem. Zinc finger peptides of the invention may alternatively include or comprise sub-arrays of 3-finger units.

Accordingly, the extended zinc finger framework of the invention may comprise a sequence selected from:

SEQ ID NO: 25 N'-[(Formula 2)-X$_6$]$_{n0}$-{[(Formula 2)-X$_5$-(Formula 2)-X$_6$]$_{n1}$-[(Formula 2)-X$_5$-(Formula 2)-X$_L$]}$_{n2}$-[(Formula 2)-X$_5$-(Formula 2)-X$_6$]$_{n3}$-[(Formula 2)-X$_5$-(Formula 2)]-[X$_6$-(Formula 2)]$_{n4}$-C', wherein n0 is 0 or 1, n1 is from 1 to 4, n2 is 1 or 2, n3 is from 1 to 4, n4 is 0 or 1, X$_5$ is a linker sequence of 5 amino acids, X$_6$ is a linker sequence of 6 or 7 amino acids, and X$_L$ is a linker of at least 8 amino acids, and wherein the sequence of Formula 2 comprises the recognition sequence of SEQ ID NO: 1.

SEQ ID NO: 26 N'-[(Formula 1-6)-L$_3$]$_{n0}$-{[(Formula 1-6)-L$_2$-(Formula 1-6)-L$_3$]$_{n1}$-[(Formula 1-6)-L$_2$-(Formula 1-6)-X$_L$]}$_{n2}$-[(Formula 1-6)-L$_2$-(Formula 1-6)-L$_3$]$_{n3}$-[(Formula 1-6)-L$_2$-(Formula 1-6)]-[L$_3$-(Formula 1-6)]$_{n4}$-C' where n0, n1, n2, n3, n4 and X$_L$ are as defined above, and wherein the sequences of each of Formulas 1-6 comprises the recognition sequence of SEQ ID NO: 1.

SEQ ID NO: 27 N'-[(Formula 1-6)-L$_4$]$_{n0}$-{[(Formula 1-6)-L$_1$-(Formula 1-6)-L$_4$]$_{n1}$-[(Formula 1-6)-L$_1$-(Formula 1-6-X$_L$]}$_{n2}$-[(Formula 1-6)-L$_1$-(Formula 1-6)-L$_4$]$_{n3}$-[(Formula 1-6)-L$_1$-(Formula 1-6)]-[L$_4$-(Formula 1-6)]$_{n4}$-C', where n0, n1, n2, n3, n4 and X$_L$ are as defined above, and wherein the sequences of each of Formulas 1-6 comprises the recognition sequence of SEQ ID NO: 1. Preferably, X$_L$ is selected from L7, L8, L9 or L$_{10}$; and most preferably X$_L$ is L9 (SEQ ID NO: 23). In a particularly useful 11-zinc finger peptide of the invention, n0 is 1, n1 is 1, n2 is 1, n3 is 2, n4 is 0 and X$_L$ is L9. In a particularly useful 12-zinc finger peptide of the invention, n0 is 0, n1 is 2, n2 is 1, n3 is 2, n4 is 0 and X$_L$ is L9. In a particularly useful 10-zinc finger peptide of the invention, n0 is 0, n1 is 1, n2 is 1, n3 is 2, n4 is 0 and X$_L$ is L9. Most preferably, the zinc finger framework in each of the domains of SEQ ID NO: 27 corresponds to Formula 6.

SEQ ID NO: 28 N'-[(Formula 1-6)-L5]$_{n0}$-{[(Formula 1-6)-L$_1$-(Formula 1-6)-L5]$_{n1}$-[(Formula 1-6)-L$_1$-(Formula 1-6)-X$_L$]}$_{n2}$-[(Formula 1-6)-L$_1$-(Formula 1-6)-L5]$_{n3}$-[(Formula 1-6)-L$_1$-(Formula 1-6)]-[L5-(Formula 1-6)]$_{n4}$-C', where n0, n1, n2, n3, n4 and X$_L$ are as defined above, and wherein the sequences of each of Formulas 1-6 comprises the recognition sequence of SEQ ID NO: 1. Preferably, X$_L$ is selected from L7, L8, L9 or L$_{10}$; and most preferably X$_L$ is L$_{10}$ (SEQ ID NO: 24). In a particularly useful 11-zinc finger peptide of the invention, n0 is 1, n1 is 1, n2 is 1, n3 is 2, n4 is 0 and X$_L$ is L$_{10}$. In a particularly useful 12-zinc finger peptide of the invention, n0 is 0, n1 is 2, n2 is 1, n3 is 2, n4 is 0 and X$_L$ is L$_{10}$. In a particularly useful 10-zinc finger peptide of the invention, n0 is 0, n1 is 1, n2 is 1, n3 is 2, n4 is 0 and X$_L$ is L$_{10}$. Most preferably, the zinc finger framework in each of the domains of SEQ ID NO: 28 corresponds to Formula 6.

For the avoidance of doubt, hyphens ("-") in the Formulas and SEQ ID NOs of the invention represent linkages only, and so these Formulas and SEQ IDs may also be represented without hyphens.

In some embodiments of the invention, in SEQ ID NOs: 25 to 28, n0 is 0 or 1, n1 is from 1 to 3, n2 is 1 or 2, n3 is 2 or 3, n4 is 0 and X$_L$ is about 8 to 50. Alternatively, n0 is 0, n1 is 2 or 3, n2 is 1 or 2, n3 is 2 and n4 is 0, and/or X$_L$ is about 11 to 40 amino acids. In still further embodiments, n0 is 0, n1 is 2, n2 is 1 or 2, n3 is 2 and n4 is 0; and/or X$_L$ is about 15 to 35 amino acids. In alternative embodiments X$_L$ is about 18 to 29 amino acids. Most preferably X$_L$ is selected from L7, L8, L9 and L$_{10}$. In embodiments of the invention "(Formula 1-6)" SEQ ID NOs: 25 to 28 represents any one of Formulas 1 to 6, and each "(Formula 1-6)" may be the same or different; but is conveniently the same.

In the zinc finger frameworks above, the total number of zinc finger domains is preferably from 10 to 18, especially 10, 11, 12 or 18, and the zinc finger recognition sequence is preferably selected from a sequence of SEQ ID NO: 1. Particularly preferred zinc finger peptides have 11 or 12 zinc finger domains, each of which has a recognition sequence selected from the group of SEQ ID NO: 2 or 5, or the group of SEQ ID NO: 3 or 4. These recognition sequences are selected such that the poly-zinc finger peptide binds effectively to CAG-repeat nucleic acid sequences and, also, so as to minimise non-host peptide sequences in the preferred expression host (e.g. mouse or human). Exemplary 11-zinc finger peptide sequences of the invention comprise the sequences of SEQ ID NO: 29, SEQ ID NO: 31, SEQ ID NO: 33 or SEQ ID NO: 35 (see Table 9).

The invention also encompasses nucleic acid molecules that encode the peptide sequences of the invention. In view of codon redundancy, it will be appreciated that many slightly different nucleic acid sequences may accurately code for each of the zinc finger peptides of the invention, and each of these variants is encompassed within the scope of the present invention. Exemplary zinc finger peptide encoding sequences comprise SEQ ID NOs: 30, 32, 34 and 36 which encode the zinc finger peptides of SEQ ID NOs: 29, 31, 33 and 35, respectively (see Table 9). Any other nucleic acid sequences that encode for the peptides of SEQ ID NOs: 29, 31, 33 and 35 are also encompassed within the invention.

It will be appreciated that the zinc finger peptide framework sequences of the invention may further include optional (N-terminal) leader sequences, such as: amino acids to aid expression (e.g. N-terminal Met-Ala or Met-Gly dipeptide); purification tags (e.g. FLAG®-tags); and localisation/targeting sequences (e.g. nuclear localisation sequences (NLS), such as PKKKRKV; (SV40 NLS, SEQ ID NO: 37), PKKRRKVT; (human protein KIAA2022, SEQ ID NO: 46) or RIRKKLR; (mouse primase p58 NLS9, SEQ ID NO: 38). Also, the peptides may optionally include additional C-terminal sequences, such as: linker sequences for fusing zinc finger domains to effector molecules; and effector molecules. Other sequences may be employed for cloning purposes. The sequences of any N- or C-terminal sequences may be varied, typically without altering the binding activity of the zinc finger peptide framework, and such variants are encompassed within the scope of the invention. Preferred host-compatible additional sequences are Met-Gly dipeptide for expression in humans and mice; human (PKKRRKVT, SEQ ID NO: 46) or mouse (RIRKKLR, SEQ ID NO: 38) nuclear localisation sequences for expression in human or mouse respectively; and host-derived effector domain sequences as discussed below. Suitably a zinc finger peptide of the invention for expression and use in mouse or human respectively, does not include purification tags where it is not intended to purify the zinc finger-containing peptide, e.g. where gene regulatory and/or therapeutic activities are intended. Thus, for reason of improved host-matching (reduced toxicity and reduced immunogenicity) the peptides and polypeptides of the invention are preferably devoid of peptide purification tags and the like, which are not found in endogenous, wild-type proteins of a host organism.

Particularly preferred polypeptides of the invention comprise an appropriate nuclear localisation sequence arrange N-terminal of a poly-zinc finger peptide, which is itself arranged N-terminal to an effector domain that may repress expression of a target gene. Effector domains are conveniently attached to the poly-zinc finger peptide covalently, such as by a peptide linker sequence as disclosed elsewhere herein.

The invention also encompasses derivatives of the zinc finger peptides of the invention. In this regard, it will be appreciated that modifications, such as amino acid substitutions may be made at one or more positions in the peptide without adversely affecting its physical properties (such as binding specificity or affinity). By "derivative" of a zinc finger peptide it is meant a peptide sequence that has the selected desired activity (e.g. binding affinity for a selected target sequence, especially poly CAG sequences), but that further includes one or more mutations or modifications to the primary amino acid sequence. Thus, a derivative of the invention may have one or more (e.g. 1, 2, 3, 4, 5 or more) chemically modified amino acid side chains, such as pegylation, sialylation and glycosylation modifications. In addition, or alternatively, a derivative may contain one or more (e.g. 1, 2, 3, 4, 5 or more) amino acid mutations, substitutions deletions or combinations thereof to the primary sequence of a selected zinc finger peptide. Accordingly, the invention encompasses the results of maturation experiments conducted on a selected zinc finger peptide or a zinc finger peptide framework to improve or change one or more characteristics of the initially identified peptide. By way of example, one or more amino acid residues of a selected zinc finger domain may be randomly or specifically mutated (or substituted) using procedures known in the art (e.g. by modifying the encoding DNA or RNA sequence). The resultant library or population of derivatised peptides may further be selected—by any known method in the art—according to predetermined requirements: such as improved specificity against particular target sites; or improved drug properties (e.g. solubility, bioavailability, immunogenicity etc.). A particular benefit of the invention is improved compatibility with the host/target organism as assessed by sequence similarity to known host peptide sequences and/or immunogenicity/adverse immune response to the heterologous peptide when expressed. Peptides selected to exhibit such additional or improved characteristics and that display the activity for which the peptide was initially selected are derivatives of the zinc finger peptides of the invention and also fall within the scope of the invention.

Zinc finger frameworks of the invention may be diversified at one or more positions in order to improve their compatibility with the host system in which it is intended to express the proteins. In particular, specific amino acid substitutions may be made within the zinc finger peptide sequences and in any additional peptide sequences (such as effector domains) to reduce or eliminate possible immunological responses to the expression of these heterologous peptides in vivo. Target amino acid residues for modification or diversification are particularly those that create non-host amino acid sequences or epitopes that might not be recognised by the host organism and, consequently, might elicit an undesirable immune response. In some embodiments the framework is diversified or modified at one or more of amino acids positions −1, 1, 2, 3, 4, 5 and 6 of the recognition sequence. The polypeptide sequence changes may conveniently be achieved by diversifying or mutating the nucleic acid sequence encoding the zinc finger peptide frameworks at the codons for at least one of those positions, so as to encode one or more polypeptide variant. All such nucleic acid and polypeptide variants are encompassed within the scope of the invention.

The amino acid residues at each of the selected positions may be non-selectively randomised, i.e. by allowing the amino acid at the position concerned to be any of the 20 common naturally occurring amino acids; or may be selectively randomised or modified, i.e. by allowing the specified amino acid to be any one or more amino acids from a defined sub-group of the 20 naturally occurring amino acids. It will be appreciated that one way of creating a library of mutant peptides with modified amino acids at each selected location, is to specifically mutate or randomise the nucleic acid codon of the corresponding nucleic acid sequence that encodes the selected amino acid. On the other hand, given the knowledge that has now accumulated in relation to the sequence specific binding of zinc finger domains to nucleic acids, in some embodiments it may be convenient to select a specific amino acid (or small sub-group of amino acids) at one or more chosen positions in the zinc finger domain, for example, where it is known that a specific amino acid provides optimal binding to a particular nucleotide residue in a specific target sequence. Such peptides or frameworks are the result of "intelligent" design. Conveniently the whole of the zinc finger recognition sequence may be selected by intelligent design and inserted/incorporated into an appropriate zinc finger framework both of which, ideally, are derived from the intended host organism, such as mouse or human. The person of skill in the art is well aware of the codon sequences that may be used in order to specify one or more than one particular amino acid residue within a library. Preferably all amino acid positions in each zinc finger domain and in any additional peptide sequences (such as effector domains and leader sequences) are chosen from known wild-type sequences from that host organism.

Zinc Finger Peptide Modulators and Effectors

While the zinc finger peptides of the invention may have useful biological properties in isolation, they can also be given useful biological functions by the addition of effector domains. Therefore, in some cases it is desirable to conjugate a zinc finger peptide of the invention to one or more non-zinc finger domain, thus creating chimeric or fusion zinc finger peptides. It may also be desirable, in some instances, to create a multimer (e.g. a dimer), of a zinc finger peptide of the invention—for example, to bind more than one target sequence simultaneously.

Thus, having identified a desirable zinc finger peptide, an appropriate effector or functional group may then be attached, conjugated or fused to the zinc finger peptide. The resultant protein of the invention, which comprises at least a zinc finger portion (of more than one zinc finger domain) and a non-zinc finger effector domain, portion or moiety may be termed a "fusion", "chimeric" or "composite" zinc finger peptide. Beneficially, the zinc finger peptide will be linked to the other moiety via sites that do not interfere with the activity of either moiety.

A "non-zinc finger domain" (or moiety) as used herein, refers to an entity that does not contain a zinc finger (ββα-) fold. Thus, non-zinc finger moieties include nucleic acids and other polymers, peptides, proteins, peptide nucleic acids (PNAs), antibodies, antibody fragments, and small molecules, amongst others.

Chimeric zinc finger peptides or fusion proteins of the invention are used to up- or down-regulate desired target genes, in vitro or in vivo. Thus, potential effector domains include transcriptional repressor domains, transcriptional activator domains, transcriptional insulator domains, chromatin remodelling, condensation or decondensation domains, nucleic acid or protein cleavage domains, dimerisation domains, enzymatic domains, signalling/targeting sequences or domains, or any other appropriate biologically functional domain. Other domains that may also be appended to zinc finger peptides of the invention (and which have biological functionality) include peptide sequences involved in protein transport, localisation sequences (e.g. subcellular localisation sequences, nuclear localisation, protein targeting) or signal sequences. Zinc finger peptides can also be fused to epitope tags (e.g. for use to signal the presence or location of a target nucleotide sequence recognised by the zinc finger peptide. Functional fragments of any such domain may also be used.

Beneficially, zinc finger peptides and fusion proteins/polypeptides of the invention have transcriptional modulatory activity and, therefore, preferred biological effector domains include transcriptional modulation domains such as transcriptional activators and transcriptional repressors, as well as their functional fragments. The effector domain can be directly derived from a basal or regulated transcription factor such as, for example, transactivators, repressors, and proteins that bind to insulator or silencer sequences (see Choo & Klug (1995) *Curr. Opin. Biotech.* 6: 431-436; Choo & Klug (1997) *Curr. Opin. Str. Biol.* 7:117-125; and Goodrich et al. (1996) *Cell* 84: 825-830); or from receptors such as nuclear hormone receptors (Kumar & Thompson (1999) *Steroids* 64: 310-319); or co-activators and co-repressors (Ugai et al. (1999) *J. Mol. Med.* 77: 481-494).

Other useful functional domains for control of gene expression include, for example, protein-modifying domains such as histone acetyltransferases, kinases, methylases and phosphatases, which can silence or activate genes by modifying DNA structure or the proteins that associate with nucleic acids (Wolffe (1996) *Science* 272: 371-372; and Hassig et al., (1998) *Proc. Natl. Acad. Sci. USA* 95: 3519-3524). Additional useful effector domains include those that modify or rearrange nucleic acid molecules such as methyltransferases, endonucleases, ligases, recombinases, and nucleic acid cleavage domains (see for example, Smith et al. (2000) *Nucleic Acids Res.*, 17: 3361-9; WO 2007/139982 and references cited therein), such as the FokI endonuclease domain, which in conjunction with zinc finger peptides of the invention may be used to truncate poly-CAG repeat genome sequences.

Potential transcriptional/gene activation domains for fusing to zinc finger peptides of the invention include the VP64 domain (see Seipel et al., (1996) *EMBO J.* 11: 4961-4968) and the herpes simplex virus (HSV) VP16 domain (Hagmann et al. (1997) *J. Virol.* 71: 5952-5962; Sadowski et al. (1988) *Nature* 335: 563-564); and transactivation domain 1 and/or 2 of the p65 subunit of nuclear factor-KB (NFκB; Schmitz et al. (1995) *J. Biol. Chem.* 270: 15576-15584).

Generally, for a useful therapeutic or diagnostic effect, it is desirable to down-regulate or repress the expression of the polyglutamine disease-associated genes that are the subject of the present invention. Therefore, effector domains that effect repression or silencing of target gene expression are preferred. In particular, the peptides of the invention suitably comprise effector domains that cause repression or silencing of target genes when the zinc finger nucleic acid binding domain of the protein directly binds with CAG repeat sequences associated with the target gene.

In one embodiment the transcriptional repression domain is the Kruppel-associated box (KRAB) domain, which is a powerful repressor of gene activity. In some preferred embodiments, therefore, zinc finger peptides or frameworks of the invention are fused to the KRAB repressor domain from the human Kox-1 protein in order to repress a target gene activity (e.g. see Thiesen et al. (1990) *New Biologist* 2: 363-374). Fragments of the Kox-1 protein comprising the KRAB domain, up to and including full-length Kox protein may be used as transcriptional repression domains, as described in Abrink et al. (2001) *Proc. Natl. Acad. Sci. USA,* 98: 1422-1426. A useful human Kox-1 domain sequence for inhibition of target genes in humans is shown in Table 6 (SEQ ID NO: 39). A useful mouse KRAB repressor domain sequence for inhibition of target genes in mice is the mouse analogue of human Kox-1, i.e. the KRAB domain from mouse ZF87 (SEQ ID NO: 40). Other transcriptional repressor domains known in the art may alternatively be used according to the desired result and the intended host, such as the engrailed domain, the snag domain, and the transcriptional repression domain of v-erbA.

All known methods of conjugating an effector domain to a peptide sequence are incorporated. The term "conjugate" is used in its broadest sense to encompass all methods of attachment or joining that are known in the art, and is used interchangeably with the terms such as "linked", "bound", "associated" or "attached". The effector domain(s) can be covalently or non-covalently attached to the binding domain: for example, where the effector domain is a polypeptide, it may be directly linked to a zinc finger peptide (e.g. at the C-terminus) by any suitable flexible or structured amino acid (linker) sequence (encoded by the corresponding nucleic acid molecule). Non-limiting suitable linker sequences for joining an effector domain to the C-terminus of a zinc finger peptide are illustrated in Table 6 (e.g. LRQKDGGGGSGGGGSGGGGSQLVSS, SEQ ID NO: 41; LRQKDGGGGSGGGGSS, SEQ ID NO: 42; and LRQKDGGGSGGGGS, SEQ ID NO: 43).

Alternatively, a synthetic non-amino acid or chemical linker may be used, such as polyethylene glycol, a maleimide-thiol linkage (useful for linking nucleic acids to amino acids), or a disulphide link. Synthetic linkers are commercially available, and methods of chemical conjugation are known in the art. A preferred linker for conjugating the human kox-1 domain to a zinc finger peptide of the invention is the peptide of SEQ ID NO: 42. A preferred linker for conjugating the mouse ZF87 domain to a zinc finger peptide of the invention is the peptide of SEQ ID NO: 43.

Non-covalent linkages between a zinc finger peptide and an effector domain can be formed using, for example, leucine zipper/coiled coil domains, or other naturally occurring or synthetic dimerisation domains (Luscher & Larsson (1999) *Oncogene* 18: 2955-2966; and Gouldson et al. (2000) *Neuropsychopharm.* 23: S60-S77. Other non-covalent means of conjugation may include a biotin-(strept)avidin link or the like. In some cases, antibody (or antibody fragment)-antigen interactions may also be suitably employed, such as the fluorescein-antifluorescein interaction.

To cause a desired biological effect via modulation of gene expression, zinc finger peptides or their corresponding fusion peptides are allowed to interact with, and bind to, one or more target nucleotide sequence associated with the target gene, either in vivo or in vitro depending to the application. Beneficially, therefore, a nuclear localisation domain is attached to the DNA binding domain to direct the protein to the nucleus. One useful nuclear localisation sequence is the SV40 NLS (PKKKRKV, SEQ ID NO: 37). Desirably, however, the nuclear localisation sequence is a host-derived sequence, such as the NLS from human protein KIAA2022 NLS (PKKRRKVT; NP_001008537.1, SEQ ID NO: 46) for use in humans; or the NLS from mouse primase p58 (RIRKKLR; GenBank®: BAA04203.1, SEQ ID NO: 38).

Thus, preferred zinc finger-containing polypeptides of the invention include nuclear localisation sequence, a poly-zinc finger peptide sequence and a transcriptional repressor KRAB domain. Particularly preferred polypeptide sequences of the invention include SEQ ID NOs: 49, 50, 51, 52, 53, 54, 55, 56, 59, 61 and 63 (Table 9).

As described herein, DNA regions from which to effect the up- or down-regulation of specific genes include promoters, enhancers or locus control regions (LCRs). In accordance with the invention, suitable target sequences are trinucleotide repeat sequences comprising at least 10 such repeats. In preferred embodiments, the genomic DNA target sequence comprises a CAG-repeat sequence as found in expanded CAG-repeats of mutant genes. In yet another embodiment the DNA target sequence comprises a CTG-repeat sequence, which is the complement of an expanded CAG-repeat sequence or any other sequence repeat based on the repetitive sequence -CAGCAGCAG-.

Nucleic Acids and Peptide Expression

The zinc finger peptides according to the invention and, where appropriate, the zinc finger peptide modulators (conjugate/effector molecules) of the invention may be produced by recombinant DNA technology and standard protein expression and purification procedures. Thus, the invention further provides nucleic acid molecules that encode the zinc finger peptides of the invention as well as their derivatives; and nucleic acid constructs, such as expression vectors that comprise nucleic acids encoding peptides and derivatives according to the invention.

For instance, the DNA encoding the relevant peptide can be inserted into a suitable expression vector (e.g. pGEM®, Promega Corp., USA), where it is operably linked to appropriate expression sequences, and transformed into a suitable host cell for protein expression according to conventional techniques (Sambrook J. et al., Molecular Cloning: a Laboratory Manual, Cold Spring Harbor Press, Cold Spring Harbor, NY). Suitable host cells are those that can be grown in culture and are amenable to transformation with exogenous DNA, including bacteria, fungal cells and cells of higher eukaryotic origin, preferably mammalian cells.

To aid in purification, the zinc finger peptides (and corresponding nucleic acids) of the invention may include a purification sequence, such as a His-tag. In addition, or alternatively, the zinc finger peptides may, for example, be grown in fusion with another protein and purified as insoluble inclusion bodies from bacterial cells. This is particularly convenient when the zinc finger peptide or effector moiety may be toxic to the host cell in which it is to be expressed. Alternatively, peptides of the invention may be synthesised in vitro using a suitable in vitro (transcription and) translation system (e.g. the *E. coli* S30 extract system, Promega corp., USA). The present invention is particularly directed to the expression of zinc finger-containing peptides of the invention in host cells in vivo or in host cell for ex vivo applications, to modulate the expression of endogenous genes. Preferred peptides of the invention may therefore be devoid of such sequences (e.g. His-tags) that are intended for purification or other in vitro based manipulations.

The term "operably linked", when applied to DNA sequences, for example in an expression vector or construct, indicates that the sequences are arranged so that they function cooperatively in order to achieve their intended purposes, i.e. a promoter sequence allows for initiation of transcription that proceeds through a linked coding sequence as far as the termination sequence.

It will be appreciated that, depending on the application, the zinc finger peptide or fusion protein of the invention may comprise an additional peptide sequence or sequences at the N- and/or C-terminus for ease of protein expression, cloning, and/or peptide or RNA stability, without changing the sequence of any zinc finger domain. For example, suitable N-terminal leader peptide sequences for incorporation into peptides of the invention are MA or MG and ERP. Nuclear localisation sequences may be suitably incorporated at the N-terminus of the peptides of the invention to create an N-terminal leader sequence. A useful N-terminal leader sequence for expression and nuclear targeting in human cells is MGPKKRRKVTGERP (SEQ ID NO: 44), and a useful N-terminal leader sequence for expression and nuclear targeting in mouse cells is MGRIRKKLRLAERP (SEQ ID NO: 45)

In some applications it may be desirable to control the expression of zinc finger (fusion) polypeptides of the invention by tissue specific promoter sequences or inducible promoters, which may provide the benefits of organ or tissue specific and/or inducible expression of polypeptides of the invention. These systems may be particularly advantageous for in vivo applications and gene therapy in vivo or ex vivo. Examples of tissue-specific promoters include the human CD2 promoter (for T-cells and thymocytes, Zhumabekov et al. (1995) *J. Immunological Methods* 185: 133-140); the alpha-calcium-calmodulin dependent kinase II promoter (for hippocampus and neocortex cells, Tsien et al. (1996) *Cell*

87: 1327-1338); the whey acidic protein promoter (mammary gland, Wagner et al. (1997) *Nucleic Acids Res.* 25: 4323-4330); the mouse myogenin promoter (skeletal muscle, Grieshammer et al. (1998) *Dev. Biol.* 197: 234-247); and many other tissue specific promoters that are known in the art.

It is particularly desirable to express the zinc finger peptides and other zinc finger constructs of the invention, such as zinc finger repressor proteins, from vectors suitable for use in vivo or ex vivo, e.g. for therapeutic applications (gene therapy). Where the therapy involves use of zinc finger nucleic acid constructs for expression of protein in vivo, the expression system selected should be capable of expressing protein in the appropriate tissue/cells where the therapy is to take effect. Desirably an expression system for use in accordance with the invention is also capable of targeting the nucleic acid constructs or peptides of the invention to the appropriate region, tissue or cells of the body in which the treatment is intended. A particularly suitable expression and targeting system is based on recombinant adeno-associated virus (AAV), e.g. the AAV2/1 subtype.

For Huntington's disease gene therapy, it is desirable to infect particular parts of the brain (the striatum). Therefore, AAV2/1 subtype vectors (see e.g. Molecular Therapy (2004) 10: 302-317) are ideal for this purpose and can be used with a strong AAV promoter included in the vectors.

Instead or in addition to AAV2/1 subtype vectors, other AAV subtype vectors may be used, such as AAV2/9 subtype vectors. The AAV2/1 tropism is more specific for infecting neurons, whereas AAV2/9 infects more widely (*Expert Opin Biol Ther.* 2012 June; 12(6): 757-766.) and certain variants can even be applied intravenously (*Nature Biotech* 34(2): 204-209). Therefore, using the AAV2/9 subtype (alone or in combination with AAV2/1) advantageously allows targeting of a wider variety of cell types. In the context of HD, this allows targeting of other (non-neuron) cell types in the brain that may also play a role in HD, such as glia. Additionally, this may advantageously allow targeting to peripheral tissues, such as the heart, which may be advantageous in some embodiments and therapeutic applications.

A promoter for use in AAV2/1 viral vectors and that is suitable for use in humans and mice is the pCAG promoter (CMV early enhancer element and the chicken β-actin promoter). Another useful sequence for inclusion in AAV vectors is the Woodchuck hepatitis virus posttranscriptional regulatory element (WPRE; Garg et al., (2004) *J. Immunol.*, 173: 550-558). Another promoter that may be advantageous for sustained expression in human and mice is the pNSE promoter (neuron-specific promoter of the enolase gene).

In this regard, the present inventors have designed synthetic mouse and human pNSE promoter-enhancers (see e.g. Example 17) comprising a portion of sequence upstream and downstream of the transcription start site of the enolase gene from human and rat (SEQ ID NO: 148, SEQ ID NO: 151, SEQ ID NO: 152 and SEQ ID NO: 153). Flanking restriction sites may be added to the sequence for cloning into an appropriate vector. Since the pNSE promoter is neuron-specific, it is particularly advantageously used in combination with AAV2/1 or other neuron-specific vectors.

A promoter that may be suitable for use with AAV2/9 viral vectors is the pHSP promoter (promoter of the ubiquitously expressed Hsp90ab1 gene). This promoter may also be suitable for use in humans and mice. As discussed in Example 17 below, the present inventors have found that a synthetic promoter-enhancer design comprising a portion of the sequence upstream and downstream of the transcription start site of the mouse or human Hsp90ab1 gene could be advantageously used to obtain sustained expression of a transgene, such as the zinc finger peptides of the invention. In particular, the inventors have defined a 1.7 kb region upstream of the transcription start site of the Hsp90ab1 gene that comprises multiple enhancers and can be advantageously used as a minimal hsp90ab1 constitutive promoter, in combination with a portion of exon 1 of the gene. The sequences of the mouse and human minimal promoters according to embodiments of the invention, with flanking restriction sites for cloning into a vector, are provided as SEQ ID NO: 146 and SEQ ID NO: 147. Mouse and human minimal promoters according to embodiments of the invention, without flanking restriction sites, are also provided as SEQ ID NO: 149 and SEQ ID NO: 150. The present invention encompasses such novel promoter sequences, expression constructs and vectors (e.g. AAV2/1 or AAV2/9 viral vectors) comprising these sequences, as well as the use of such promotor sequences for expression of peptides, such as zinc finger peptides. In particular, the invention encompasses expression constructs comprising the promoter sequences of SEQ ID NO: 149 and/or SEQ ID NO: 150; expression constructs comprising the promoter sequences of SEQ ID NO: 149 and/or SEQ ID NO: 150 that are operably associated with/linked to nucleic acid sequences encoding the zinc finger peptides and modulators of the invention; and the use/methods of using such constructs for sustained expression of (zinc finger) peptides in vivo. Particularly appropriate in vivo systems are human and mouse.

Suitable medical uses and methods of therapy may, in accordance with the invention, encompass the combined use—either separate, sequential or simultaneous—of the viral vectors AAV2/1 and AAV2/9, wherein at least the AAV2/9 vector comprises a hsp90ab1 constitutive promoter in accordance with the invention, e.g. of SEQ ID NO: 149 and/or SEQ ID NO: 150. Suitably, these medical uses and methods of therapy further comprise said vectors encoding one or more zinc finger peptide/modulator of the invention. Most suitably the medical uses and methods of therapy are directed to the treatment of HD in a subject, such as a human, or the study of HD in a subject, such as a mouse.

As the person skilled in the art would understand, strict compliance to the sequences provided is not necessary for the function of the promoter, provided that functional elements, e.g. enhancers, and their spatial relationships are essentially maintained. In particular, the promoter sequences provided comprise flanking restriction sites for cloning into a vector. The person skilled in the art would know to adapt these restriction sites to the particular cloning system used, as well as to make any point mutations that may be required in the sequence of the promoter to remove e.g. a cryptic restriction site (see e.g. SEQ ID NO: 147).

Suitable inducible systems may use small molecule induction, such as the tetracycline-controlled systems (tet-on® and tet-off®), the radiation-inducible early growth response gene-1 (EGR1) promoter, and any other appropriate inducible system known in the art.

Therapeutic Compositions

A zinc finger peptide or chimeric modulator of the invention may be incorporated into a pharmaceutical composition for use in treating an animal; preferably a human. A therapeutic peptide of the invention (or derivative thereof) may be used to treat one or more diseases or infections, depending on which binding site the zinc finger peptide was selected or designed to recognise. Alternatively, a nucleic acid encoding the therapeutic peptide may be inserted into an expression construct/vector and incorporated into pharmaceutical formulations/medicaments for the same purpose.

As will be understood by the person of skill in the art, potential therapeutic molecules, such as zinc finger peptides and modulators of the invention may be tested in an animal model, such as a mouse, before they can be approved for use in human subjects. Accordingly, zinc finger peptide or chimeric modulator proteins of the invention may be expressed in vivo in mice or ex vivo in mouse cells as well as in humans and, in accordance with the invention, appropriate expression cassettes and expression constructs/vectors may be designed for each animal system specifically.

Zinc finger peptides and chimeric modulators of the invention typically contain naturally occurring amino acid residues, but in some cases non-naturally occurring amino acid residues may also be present. Therefore, so-called "peptide mimetics" and "peptide analogues", which may include non-amino acid chemical structures that mimic the structure of a particular amino acid or peptide, may also be used within the context of the invention. Such mimetics or analogues are characterised generally as exhibiting similar physical characteristics such as size, charge or hydrophobicity, and the appropriate spatial orientation that is found in their natural peptide counterparts. A specific example of a peptide mimetic compound is a compound in which the amide bond between one or more of the amino acids is replaced by, for example, a carbon-carbon bond or other non-amide bond, as is well known in the art (see, for example Sawyer, in Peptide Based Drug Design, pp. 378-422, ACS, Washington D.C. 1995). Such modifications may be particularly advantageous for increasing the stability of zinc finger peptide therapeutics and/or for improving or modifying solubility, bioavailability and delivery characteristics (e.g. for in vivo applications) when a peptide is to be administered as the therapeutic molecule.

The therapeutic peptides and nucleic acids of the invention may be particularly suitable for the treatment of diseases, conditions and/or infections that can be targeted (and treated) intracellularly, for example, by targeting genetic sequences within an animal cell; and also for in vitro and ex vivo applications. As used herein, the terms "therapeutic agent" and "active agent" encompass both peptides and the nucleic acids that encode a therapeutic zinc finger peptide of the invention.

Therapeutic nucleic acids include vectors, viral genomes and modified viruses, such as AAV, which comprise nucleic acid sequences encoding zinc finger peptides and fusion proteins of the invention.

Therapeutic uses and applications for the zinc finger peptides and nucleic acids include any disease, disorder or other medical condition that may be treatable by modulating the expression of a target gene or nucleic acid.

Diseases of trinucleotide repeat expansion are particularly useful and amenable to therapies based on poly-zinc finger therapeutic molecules, for example: Huntington's disease (poly-CAG), spinocerebellar ataxias (poly-CAG), dentatorubropallidoluysian atrophy (poly-CAG), juvenile myoclonic epilepsy (dodecamer repeats; poly-CCCCGCCCCGCG, SEQ ID NO: 67), Friedreich's ataxia (poly-GAA), fragile-X syndrome (poly-CGG), fragile X-E syndrome (poly-CCG) and myotonic dystrophy (poly-CTG).

The zinc finger peptides of the invention are particularly adapted to target and bind to CAG-repeat sequences and/or CTG-repeat sequences within human or animal genomes. Preferred genes are those associated with polyglutamine diseases, and especially the nine genes that have already been identified as being associated with polyglutamine diseases in humans, as listed in Table 1 below.

TABLE 1

Polyglutamine-based disease genes.

| Gene | Disease | Normal CAG repeat number | Pathogenic CAG repeat number |
|---|---|---|---|
| HTT | Huntington's disease (HD) | 6-35 | 36-250 |
| AR | Spinal and bulbar muscular atrophy (SBMA) | 6-36 | 38-62 |
| ATN1 or DRPLA | Dentatorubropallidoluysian atrophy (DRPLA) | 6-35 | 49-88 |
| ATXN1 | Spinocerebellar ataxia Type 1 (SCA1) | 6-35 | 49-88 |
| ATXN2 | Spinocerebellar ataxia Type 2 (SCA2) | 14-32 | 33-77 |
| ATXN3 | Spinocerebellar ataxia Type 3 or Machado-Joseph disease (SCA3) | 12-40 | 55-86 |
| ATXN7 | Spinocerebellar ataxia Type 7 (SCA7) | 7-17 | 38-120 |
| CACNA1A | Spinocerebellar ataxia Type 6 (SCA6) | 4-18 | 21-30 |
| TBP | Spinocerebellar ataxia Type 17 (SCA17) | 25-42 | 47-63 |

A most preferred gene to be targeted by the zinc finger peptides and therapeutic molecules of the invention is the human expanded HTT gene. Abnormal HTT disease genes comprise 36 or more CAG repeat sequences.

One or more additional pharmaceutical acceptable carrier (such as diluents, adjuvants, excipients or vehicles) may be combined with the therapeutic peptide(s) of the invention in a pharmaceutical composition. Suitable pharmaceutical carriers are described in "Remington's Pharmaceutical Sciences" by E. W. Martin. Pharmaceutical formulations and compositions of the invention are formulated to conform to regulatory standards and can be administered orally, intravenously, topically, or via other standard routes.

In accordance with the invention, the therapeutic peptide or nucleic acid may be manufactured into medicaments or may be formulated into pharmaceutical compositions. When administered to a subject, a therapeutic agent is suitably administered as a component of a composition that comprises a pharmaceutically acceptable vehicle. The molecules, compounds and compositions of the invention may be administered by any convenient route, for example, intradermal, intramuscular, intraperitoneal, intravenous, subcutaneous, intranasal, epidural, oral, sublingual, intranasal, intravaginal, transdermal, rectally, by inhalation, or topically to the skin. Administration can be systemic or local. Delivery systems that are known also include, for example, encapsulation in microgels, liposomes, microparticles, microcapsules, capsules, etc., and any of these may be used in some embodiments to administer the compounds of the invention. Any other suitable delivery systems known in the art are also envisaged in use of the present invention.

Acceptable pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilising, thickening, lubricating and colouring agents may be used. When administered to a subject, the pharmaceutically acceptable vehicles are preferably sterile. Water is a suitable vehicle particularly when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or buffering agents.

The medicaments and pharmaceutical compositions of the invention can take the form of liquids, solutions, suspensions, lotions, gels, tablets, pills, pellets, powders, modified-release formulations (such as slow or sustained-release), suppositories, emulsions, aerosols, sprays, capsules (for example, capsules containing liquids or powders), liposomes, microparticles or any other suitable formulations known in the art. Other examples of suitable pharmaceutical vehicles are described in Remington's Pharmaceutical Sciences, Alfonso R. Gennaro ed., Mack Publishing Co. Easton, Pa., 19th ed., 1995, see for example pages 1447-1676.

In some embodiments the therapeutic compositions or medicaments of the invention are formulated in accordance with routine procedures as a pharmaceutical composition adapted for oral administration (more suitably for human beings). Compositions for oral delivery may be in the form of tablets, lozenges, aqueous or oily suspensions, granules, powders, emulsions, capsules, syrups, or elixirs, for example. Thus, in one embodiment, the pharmaceutically acceptable vehicle is a capsule, tablet or pill.

Orally administered compositions may contain one or more agents, for example, sweetening agents such as fructose, aspartame or saccharin; flavouring agents such as peppermint, oil of wintergreen, or cherry; colouring agents; and preserving agents, to provide a pharmaceutically palatable preparation. When the composition is in the form of a tablet or pill, the compositions may be coated to delay disintegration and absorption in the gastrointestinal tract, so as to provide a sustained release of active agent over an extended period of time. Selectively permeable membranes surrounding an osmotically active driving compound are also suitable for orally administered compositions. In these dosage forms, fluid from the environment surrounding the capsule is imbibed by the driving compound, which swells to displace the agent or agent composition through an aperture. These dosage forms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade. For oral formulations, the location of release may be the stomach, the small intestine (the duodenum, the jejunem, or the ileum), or the large intestine. One skilled in the art is able to prepare formulations that will not dissolve in the stomach, yet will release the material in the duodenum or elsewhere in the intestine. Suitably, the release will avoid the deleterious effects of the stomach environment, either by protection of the peptide (or derivative) or by release of the peptide (or derivative) beyond the stomach environment, such as in the intestine. To ensure full gastric resistance a coating impermeable to at least pH 5.0 would be essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit® $L_{30}D$, Aquateric®, cellulose acetate phthalate (CAP), Eudragit® L, Eudragit® S, and Shellac, which may be used as mixed films.

To aid dissolution of the therapeutic agent or nucleic acid (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. Potential nonionic detergents that could be included in the formulation as surfactants include: lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants, when used, could be present in the formulation of the peptide or nucleic acid or derivative either alone or as a mixture in different ratios.

Typically, compositions for intravenous administration comprise sterile isotonic aqueous buffer. Where necessary, the compositions may also include a solubilising agent.

Another suitable route of administration for the therapeutic compositions of the invention is via pulmonary or nasal delivery.

Additives may be included to enhance cellular uptake of the therapeutic peptide (or derivative) or nucleic acid of the invention, such as the fatty acids, oleic acid, linoleic acid and linolenic acid.

In one pharmaceutical composition, a zinc finger peptide or nucleic acid of the invention (and optionally any associated non-zinc finger moiety, e.g. a modulator of gene expression and/or targeting moiety) may be mixed with a population of liposomes (i.e. a lipid vesicle or other artificial membrane-encapsulated compartment), to create a therapeutic population of liposomes that contain the therapeutic agent and optionally the modulator or effector moiety. The therapeutic population of liposomes can then be administered to a patient by any suitable means, such as by intravenous injection. Where it is necessary for the therapeutic liposome composition to target specifically a particular cell-type, such as a particular microbial species or an infected or abnormal cell, the liposome composition may additionally be formulated with an appropriate antibody domain or the like (e.g. Fab, $F(ab)_2$, scFv etc.) or alternative targeting moiety, which naturally or has been adapted to recognise the target cell-type. Such methods are known to the person of skill in the art.

The therapeutic peptides or nucleic acids of the invention may also be formulated into compositions for topical application to the skin of a subject.

Zinc finger peptides and nucleic acids of the invention may also be useful in non-pharmaceutical applications, such as in diagnostic tests, imaging, as affinity reagents for purification and as delivery vehicles.

Gene Therapy

One aspect of the invention relates to gene therapy treatments utilising zinc finger peptides of the invention for treating diseases.

Gene therapy relates to the use of heterologous genes in a subject, such as the insertion of genes into an individual's cell (e.g. animal or human) and biological tissues to treat disease, for example: by replacing deleterious mutant alleles with functional/corrected versions, by inactivated mutant alleles by removing all or part of the mutant allele, or by inserting an expression cassette for sustained expression of a therapeutic zinc finger construct according to the invention. The most promising target diseases to date are those that are caused by single-gene defects, such as cystic fibrosis, haemophilia, muscular dystrophy, sickle cell anaemia, and HD. Other common gene therapy targets are aimed at cancer and hereditary diseases linked to a genetic defect, such as expanded nucleotide repeats. The present invention is particularly concerned with the treatment of polyglutamine-based diseases, such as HD (see Table 1).

Gene therapy is classified into two types: germ line gene therapy, in which germ cells, (i.e. sperm or eggs), are modified by the introduction of therapeutic genes, which are typically integrated into the genome and have the capacity to be heritable (i.e. passed on to later generations); and somatic gene therapy, in which the therapeutic genes are transferred into somatic cells of a patient, meaning that they may be localised and are not inherited by future generations.

Gene therapy treatments require delivery of the therapeutic gene (or DNA or RNA molecule) into target cells. There are two categories of delivery systems, either viral-based delivery mechanisms or non-viral mechanisms, and both mechanisms are envisaged for use with the present invention.

Viral systems may be based on any suitable virus, such as: retroviruses, which carry RNA (e.g. influenza, SIV, HIV, lentivirus, and Moloney murine leukaemia); adenoviruses, which carry dsDNA; adeno-associated viruses (AAV), which carry ssDNA; herpes simplex virus (HSV), which carries dsDNA; and chimeric viruses (e.g. where the envelop of the virus has been modified using envelop proteins from another virus).

A particularly preferred viral delivery system is AAV. AAV is a small virus of the parvovirus family with a genome of single stranded DNA. A key characteristic of wild-type AAV is that it almost invariably inserts its genetic material at a specific site on human chromosome 19. However, recombinant AAV, which contains a therapeutic gene in place of its normal viral genes, may not integrate into the animal genome, and instead may form circular episomal DNA, which is likely to be the primary cause of long-term gene expression. Advantages of AAV-based gene therapy vectors include: that the virus is non-pathogenic to humans (and is already carried by most people); most people treated with AAV will not build an immune response to remove either the virus or the cells that have been successfully infected with it (in the absence or heterologous gene expression); it will infect dividing as well as non-dividing (quiescent) cells; and it shows particular promise for gene therapy treatments of muscle, eye, and brain. AAV vectors have been used for first- and second-phase clinical trials for the treatment of cystic fibrosis; and first-phase clinical trials have been carried out for the treatment of haemophilia. There have also been encouraging results from phase I clinical trials for Parkinson's disease, which provides hope for treatments requiring delivery to the central nervous system. Gene therapy trials using AAV have also been reported for treatment of Canavan disease, muscular dystrophy and late infantile neuronal ceroid lipofuscinosis. HSV, which naturally infects nerve cells in humans, may also offer advantages for gene therapy of diseases involving the nervous system.

Suitably, in accordance with the invention, zinc finger encoding nucleic acid constructs (as described herein) are inserted into an adeno-associated virus (AAV) vector, particularly the AAV2/1 subtype (see e.g. Molecular Therapy (2004) 10: 302-317). This vector is particularly suitable for injection and infection of the striatum, in the brain, where the deleterious effects of mutant Htt aggregation are most prevalent in HD. In this way, the zinc finger encoding nucleic acid constructs of the invention can be delivered to desired target cells, and the zinc finger peptides expressed in order to repress the expression of pathogenic genes associated with CAG repeat sequences, such as mutant htt genes.

In embodiments, viral vectors with a wider tropism are used instead, or in addition to, vectors with a more specific tropism. For example, the neuron specific AAV2/1 subtype may be used in combination with the AAV2/9 subtype. This may advantageously allow targeting of both neurons and other types of cells present in the brain, such as glial cells. Ubiquitous/promiscuous viral vectors, such as AAV2/9, may also be used alone, for example, where the therapy is targeted at peripheral tissues.

Although HD is widely considered to be primarily a neurological disease, it is in fact a complex disease that may have a peripheral component to its pathophysiology, including possible effects on/in the heart, skeletal muscle, kidney and liver. For example, heart failure is the second most common cause of death in HD patients. Therefore, targeting of tissues such as the heart with the zinc finger peptides/modulators of the invention may prove beneficial. In such applications use of a promiscuous vector or an organ/tissue specific vector may be particularly useful.

In embodiments, the tropism of the viral vector and the specificity of the promoter used for expression of the therapeutic construct can be tailored for targeting of specific populations of cells. For example, neuron-specific viral vectors may be used in combination with neuron-specific promoters. Conversely, promiscuous vectors may be used in combinations with ubiquitous promoters (or tissue specific promoters as desired).

In specific embodiments, AAV2/1 viruses may be used in combination with a synthetic pNSE promoter, as described above and in Example 17 which should be considered a non-limiting example of this application. In other embodiments, AAV2/9 viruses may be used in combination with a synthetic pHSP vector, as described above and in Example 17 which should be considered a non-limiting example of this application. In embodiments, combinations of these two types of constructs may be used in order to simultaneously target multiple cell types, e.g. for the treatment of HD.

For some applications non-viral based approaches for gene therapy can provide advantages over viral methods, for example, in view of the simple large-scale production and low host immunogenicity. Types of non-viral mechanism include: naked DNA (e.g. plasmids); oligonucleotides (e.g. antisense, siRNA, decoy ds oligodeoxynucleotides, and ssDNA oligonucleotides); lipoplexes (complexes of nucleic acids and liposomes); polyplexes (complexes of nucleic acids and polymers); and dendrimers (highly branched, roughly spherical macromolecules).

Accordingly, the zinc finger-encoding nucleic acids of the invention may be used in methods of treating diseases by gene therapy. As already explained, particularly suitable diseases are those of the nervous system (peripheral and/or central); and preferably those associated with CAG repeat sequences, such as HD.

Accordingly, the gene therapy therapeutics and regimes of the invention may provide for the expression of therapeutic zinc fingers in target cells in vivo or in ex vivo applications for repressing the expression of target genes, such as those having non-wild-type expanded CAG-repeat sequences, and especially the mutant htt gene.

Zinc finger nucleases of the invention (e.g. as fusion proteins with Fok-1 nuclease domain) may also be useful in gene therapy treatments for gene cutting or directing the site of integration of therapeutic genes to specific chromosomal sites, as previously reported by Durai et al. (2005) *Nucleic Acids Res.* 33, 18: 5978-5990.

Huntington's Disease (HD) and Therapies

Unlike other neurological disorders, such as Alzheimer's and Parkinson's diseases, HD is monogenic (The Huntington's Disease Collaborative Research Group (1993) Cell, 72(6): 971-983). Therefore, a useful therapeutic strategy against HD may only need to target the expression of the single causal gene in order to reverse and treat the effects of the mutant protein. However, since wt Htt protein is widely expressed (Sharp et al. (1995) *Neuron* 14(5): 1065-1074); is essential for early embryonic development (Duyao et al. (1995) *Science* 269(5222): 407-410); and is required for neuronal function and survival in the brain (Dragatsis et al. (2000) *Nat. Genet.* 26(3): 300-306); it is important to reduce the expression of the mutant protein specifically, and to leave the expression of the wt protein unaffected.

RNA interference (RNAi) has been shown to reduce expression of mutant htt (van Bilsen et al. (2008) *Hum. Gene Ther.* 19(7): 710-719; Zhang et al. (2009) *J. Neurochem.* 108(1): 82-90; Pfister et al. (2009) *Curr. Biol.* 19(9): 774-778). Although this technique may have the potential to be quite powerful, the success of RNAi depends on targeting single nucleotide or deletion polymorphisms that differentiate between mutant and wild-type alleles, and these often differ from patient to patient. The requirement for personalised siRNA designs currently raises challenges for clinical trials and approved use in humans.

In a more general approach, Hu et al. used peptide nucleic acid (PNA), and locked nucleic acid (LNA) antisense oligomers, to target expanded CAG-repeats of the ataxin-3 and htt genes (Hu et al. (2009) *Nat. Biotechnol.* 27(5): 478-484; Hu et al. (2009) *Ann. NY Acad. Sci.* 1175: 24-31). They observed selective inhibition of the mutant allele with peptide nucleic acids (PNAs) for up to 22 days (3 weeks). Although these results also appear promising, PNAs cannot be delivered to the central nervous system. Therefore, the authors also tried to use locked nucleic acids (LNAs), which are more suitable for in vivo applications. In this experiment inhibition of the mutant allele was observed, but up to 30% inhibition of wt htt was also seen at the most effective concentration of LNA used, which is of course undesirable.

Therefore, there is still a clear need in the art for effective therapies for inhibiting the expression of mutant Htt protein, while leaving the expression of the wild-type allele largely unaffected.

In this regard, we have previously described (WO 2012/049332), the rational design of zinc finger peptides to recognise and bind poly-5'-GC(A/T)-3' sequences, such that they recognise both poly-CAG and its complementary DNA strand, poly-CTG. The zinc finger peptides described therein were able to repress a target gene with expanded CAG-repeat sequences preferentially over shorter repeat sequences in transient transfection reporter assays. Using a model cell line for HD, the inventors achieved stable expression of zinc finger peptides, which also reduced expression of the chromosomal mutant htt gene (having 111 CAG-repeats). Repression of gene expression was demonstrated both at the protein and the RNA levels. Repression of the mutant genes that were targeted was shown to persist for extended periods (e.g. at least 20 days), and the expression of genes having shorter genomic CAG-repeat sequences was found to remain broadly unaffected. Thus, the zinc finger peptides were able to target the expanded CAG repeats associated with the mutant Htt gene in preference to the normal CAG repeats associated with the wild-type Htt gene. Therefore, the zinc finger peptides were efficient and selective repressors of genes with long CAG-tracts.

However, mid to long-term expression (e.g. for 4 or more weeks) of the zinc finger peptide repressors described in WO 2012/049332 in target cells was unsustainable, resulting in loss of specific target gene repression and cell death in vivo.

Toxicity effects of therapeutic molecules, especially for use in gene therapy and other similar strategies that require mid or long-term expression of a heterologous protein, is a particular issue. Indeed, studies have previously shown that non-self proteins can elicit immune responses in vivo that are severe enough to cause widespread cell death.

In order to improve the mid to long-term effects of zinc finger peptide expression in target organisms, especially in the brain, the present invention seeks to reduce the toxicity and immunogenicity of the potentially therapeutic zinc finger peptides and repressor proteins of the invention.

As demonstrated herein, the present invention thus provides zinc finger peptide and nucleic acid sequences that are suitable for repression of mutant Htt protein in vivo and ex vivo in both mouse and human cells. Likewise, the zinc finger peptides of the invention are suitable for the targeting and modulation of other genes—especially those containing long CAG trinucleotide repeat sequences (i.e. associated with diseases other than HD), as previously indicated.

Host Organism Toxicity and Immunogenicity

It was proposed that toxicity and immunogenicity (immunotoxicity) of heterologous peptides when expressed in host organisms might be reduced by optimising the primary peptide sequence to match the primary peptide sequence of natural host peptides.

As previously described (Garriga et al., 2012 and herein), the zinc finger peptides of the present invention are based on a generic/universal zinc finger peptide framework, and particularly on the peptide framework of Zif268, which is a natural zinc finger protein having homologues in both mice and humans. However, as described in WO 2012/049332, the recognition sequences of the zinc finger domains were based on the perceived best match for the target nucleic acid sequences (i.e. the recognition code for zinc finger-dsDNA interactions) and on binding optimisation studies. Such design had no regard to the target host organism in which the zinc finger peptides would be ultimately expressed (e.g. mouse or human).

Furthermore, the zinc finger repressor proteins described in WO 2012/049332 incorporated a KRAB transcription repressor domain from human Kox-1: even in studies on mice or involving mouse cells; and similarly, other effector functions, such as nuclear localisation and purification tags were selected without regard to the host organism.

As a consequence of the above, and by way of example, one of the preferred zinc finger peptide repressors described in WO 2012/049332, ZF11xHunt-Kox-1 (SEQ ID NO: 68; see also Garriga et al., 2012); hereafter named ZF11-Kox-1), contained 260 out of 509 (51%) non-mouse amino acid residues when compared to wild-type mouse protein sequences. The present invention is directed to reducing the number of non-host amino acid residues for expression in mouse and in human cells.

Preferred zinc finger peptides and modulator peptides of the invention have greater than 50%, greater than 60%, greater than 70% or even greater than 75% identity to endogenous/natural proteins in the target, host organism in which they are intended to be expressed for therapeutic use. In still more preferred embodiments, the peptides of the invention have approximately 80%, 81%, 82%, 83%, 84% or approximately 85% identity to endogenous/natural proteins in the target organism. In some cases it is desirable to have still greater identity to peptide sequences of the target/host organism, such as between approximately 75% and 95% identity, or between 78% and 92% identity, or between 80% and 90% identity. At the same time, it will be appreciated that the peptides of the invention are different to known peptide sequences. Thus, the peptides may be up to 50%, up to 40%, up to 30% or up to 25% non-identical to endogenous/natural peptide sequences found in the host organism. It will be appreciated that by "up to x%", in this context, means greater than 0% and less than x%. Preferably, the peptides of the invention are approximately 20%, 19%, 18%, 17%, 16%, 15%, 14%, 13%, 12%, 11% or 10% non-identical to endogenous/natural peptide sequences found in the host organism.

Sequence identity can be assessed in any way known to the person of skill in the art, such as using the algorithm described by Lipman & Pearson (1985), *Science* 227, pp1435; or by sequence alignment.

As used herein, "percent identity" means that, when aligned, that percentage of amino acid residues (or bases in the context of nucleic acid sequences) are the same when comparing the two sequences. Amino acid sequences are not identical, where an amino acid is substituted, deleted, or added compared to the reference sequence. In the context of the present invention, since the subject proteins may be considered to be modular, i.e. comprising several different domains or effector and auxiliary sequences (such as NLS sequences, expression peptides, zinc finger modules/domains, and effector domains (e.g. repressor peptides)), sequence identity is assessed separately for each domain/module of the peptide relative to any homologous endogenous or natural peptide domain/module known in the host organism. This is considered to be an acceptable approach since relatively short peptide fragments (epitopes) of any host-expressed peptides may be responsible for determining immunogenicity through recognition or otherwise of self/non-self peptides when expressed in a host organism in vivo. By way of example, a peptide sequence of 100 amino acids comprising a host zinc finger domain directly fused to a host repressor domain wherein neither sequence has been modified by mutation would be considered to be 100% identical to host peptide sequences. It does not matter for this assessment whether such zinc finger domain(s) or non-zinc finger domain, e.g. repressor domain is only a fragment from a natural, larger protein expressed in the host. If one of 100 amino acids has been modified from the natural sequence, however, the modified sequence would be considered 99% identical to natural protein sequences of the host; whilst if the same zinc finger domain were linked to the same repressor domain by a linker sequence of 10 amino acids and that linker sequence is not naturally found in that context in the host organism, then the resultant sequence would be (10/110) ×100% non-identical to host sequences.

Thus, the degree of sequence identity between a query sequence and a reference sequence may, in some embodiments be determined by: (1) aligning the two sequences by any suitable alignment program using the default scoring matrix and default gap penalty; (2) identifying the number of exact matches, where an exact match is where the alignment program has identified an identical amino acid or nucleotide in the two aligned sequences on a given position in the alignment; and (3) dividing the number of exact matches with the length of the reference sequence. In other embodiments, step (3) may involve dividing the number of exact matches with the length of the longest of the two sequences; and in other embodiments, step (3) may involve dividing the number of exact matches with the "alignment length", where the alignment length is the length of the entire alignment including gaps and overhanging parts of the sequences. As explained above, in this context, the alignment length is the accumulative amino acid length of all peptide domains, modules or fragments that have been used as reference sequences for each respective domain or module of the query peptide.

Sequence identity comparisons can be conducted by eye, or more usually, with the aid of readily available sequence comparison programs. Commercially available computer programs may use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms may include one or more and typically all of (i) assignment of a penalty score each time a gap is inserted (gap penalty score); (ii) assignment of a penalty score each time an existing gap is extended with an extra position (extension penalty score); (iii) assignment of high scores upon alignment of identical amino acids; and (iv) assignment of variable scores upon alignment of non-identical amino acids. Most alignment programs allow the gap penalties to be modified. However, it is preferred to use the default values when using such software for sequence comparisons.

In some algorithms, the scores given for alignment of non-identical amino acids are assigned according to a scoring matrix, which may also be called a substitution matrix. The scores provided in such substitution matrices may reflect the fact that the likelihood of one amino acid being substituted with another during evolution varies and depends on the physical/chemical nature of the amino acid to be substituted. For example, the likelihood of a polar amino acid being substituted with another polar amino acid is higher compared to the likelihood that the same amino acid would be substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are perhaps the PAM matrices (Dayhoff et al. (1978), Jones et al. (1992)), the BLOSUM matrices (Henikoff & Henikoff (1992)) and the Gonnet matrix (Gonnet et al. (1992)).

Suitable computer programs for carrying out such an alignment include, but are not limited to, Vector NTI® (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools is available from the ExPASy Proteomics server on the world wide web at expasy.org. Another example of software that can perform sequence alignment is BLAST (Basic Local Alignment Search Tool), which is available from the webpage of National Center for Biotechnology Information which can currently be found on the world wide wed at ncbi.nlm.nih.gov/and which was firstly described in Altschul et al. (1990), *J. Mol. Biol.* 215; pp 403-410. Examples of programs that perform global alignments are those based on the Needleman-Wunsch algorithm, e.g. the EMBOSS Needle and EMBOSS Stretcher programs. In one embodiment, it is preferred to use the ClustalW software for performing sequence alignments. ClustalW2 is for example made available on the internet by the European Bioinformatics Institute at the EMBL-EBI webpage on the world wide web at ebi.ac.uk under tools—sequence analysis—ClustalW2.

Once an appropriate software program has produced an alignment or a group of alignments, it is possible to calculate % similarity and % sequence identity. The software typically does this as part of the sequence comparison and generates a numerical result. In a preferred embodiment of the present invention, the alignment is run over domain stretches rather than by performing a global alignment to attempt to optimise the alignment over the full-length of a sequence. Therefore, in preferred embodiments, whilst an alignment program may be used for ease of reference and consistency, since sequence lengths are relatively short and peptides of the invention may contain domains derived from several different proteins, sequence identity is most simply carried out by visual inspection of aligned full or partial sequences and manual calculation of identity.

The present inventors have designed a series of mutated zinc finger derivative peptides, based on the zinc finger peptides/repressors described in WO 2012/049332, which have been adapted to increase their compatibility with the host organism in which they are to be expressed, e.g. mouse or human. These so-called 'mousified' and 'humanised' zinc finger peptides have been found to substantially reduce potential immunogenicity and toxicity effects in vivo.

The main design constraints in modifying the prior art peptides to improve in vivo therapeutic activity were that the new peptides had to match host protein sequences as closely as possible whilst maintaining specific binding activity against target nucleic acid sequences; in particular, poly(CAG) binding activity. Preferably, the resultant zinc finger peptides are adapted so as to be tolerated in both mice and humans, so that essentially the same zinc finger peptide can be used for animal models of effect as well as in downstream therapeutic studies and treatments. Such an approach may simplify the development of useful therapeutics, especially in the case that a designed protein can match both endogenous host mouse and human peptide sequences with a sufficiently high sequence identity.

The aim of 'humanisation' or 'mousification' according to the invention is to minimise the amino acid sequence differences between an artificial zinc finger design, chosen to bind poly(CAG) DNA, and a naturally-occurring zinc finger repeat, Zif268 (which has human and mouse homologues, and which naturally binds GCG-TGG-GCG; Pavletich, 1991). In practice, humanisation or 'mousification', according to the invention, had the intention of reducing the potential for foreign epitopes in the zinc finger peptide sequences of the invention. These changes were carried out within the constraint of retaining CAG-binding activity, as determined by zinc finger ELISA experiments (Isalan, 2001).

Importantly, since Zif268 has homologues in mouse and human cells, and the zinc finger scaffold framework of Zif268 is almost identical in mice and humans (see SEQ ID NO: 47; SEQ ID NO: 48), it was considered possible that a single appropriately modified host-optimised zinc finger peptide sequence of the invention may be suitable for use in both mouse and human cells without resulting in adverse immunogenic effects: thus, one host optimised zinc finger design for binding poly(CAG) can be useful in both species. Desirably, the sequence identity of a peptide of the invention to each of native mouse and human sequences is at least about 75%, at least about 80% or at least about 85%; such as between about 75% and 95%, or between about 80% and 90%.

In order to improve sequence identity, for mouse studies, the KRAB repressor domain, Kox-1, which was suitable for and 'host-matched' for use in humans, was replaced by the mouse analogue KRAB domain from ZF87, also called MZF22 (Abrink et al., 2001).

Furthermore, design modifications for host-matching/improving host optimisation included the removal of FLAG® epitope tags (not required for mid to long-term expression in vivo). To further improve host optimisation, nuclear localisation signals were selected from human (KIAA2022) and mouse (p58 protein) sequences for expression in humans or mice, respectively.

In addition, bearing in mind the over-riding intention of the invention to provide zinc finger peptides for high affinity and specific binding to polyCAG nucleic acid sequences, the inventors also altered the originally designed zinc finger sequences to better match with host sequences. Since Zif268 is found in both humans and mice, the peptide 'framework' was essentially invariant. However, improved host-optimisation was achieved by modifying the originally designed recognition helices and zinc finger linkers in order to match them as closely as possible to the human Zif268 transcription factor sequence (SEQ ID NO: 48; Pavletich, 1991).

A 'humanised' zinc finger peptide of the invention (having 11 zinc fingers) is termed herein, hZF-Kox-1, whereas a mousified version of the zinc finger peptide is termed mZF-ZF87.

A series of host-optimised designs were developed based on ZF11xHunt-Kox-1 in order to balance the result in terms of reduction in immunogenicity and toxicity in vivo and ability to bind the target poly-CAG sequences.

SEQ ID NO: 49 illustrates an advantageous zinc finger modulator which binds the target nucleic acid sequence with high affinity (as assessed by ELISA), whilst substantially reducing in vivo toxicity during mid to long-term expression in mouse cells. This modified sequence (which comprises the zinc finger peptide sequence of SEQ ID NO: 31) contains 33 differences from the starting sequence of ZF11xHunt-Kox-1. These differences were chosen to make the sequence closer to human Zif268, while retaining poly(CAG) DNA binding (see Table 9).

The sequence of SEQ ID NO: 49 was then further modified to increase host-matching (SEQ ID NO: 50; mousified 11-zinc finger modulator 1 mZF-ZF87), which comprises the zinc finger peptide sequence of SEQ ID NO: 29. In this embodiment, the alpha helices and linkers of the zinc finger peptide were redesigned to be as close to human Zif268 as possible, while still binding poly(CAG) through the alpha helices (e.g. QSGDLTR (SEQ ID NO: 3) and QSGDRKR (SEQ ID NO: 4)). These host-optimised peptide sequences were developed for expression in mice for initial in vivo studies of potential therapeutic value and toxicity, and are denoted mZF-ZF87 herein; and the equivalent human variants (see SEQ ID NO: 53, humanised 11-zinc finger modulator 2 hZF-ZF-kox1; and SEQ ID NO: 54, humanised 11-zinc finger modulator 2 hZF-ZF-kox1) are denoted as hZF-ZF-kox1. Differences between the mouse and human variants lie in the repressor domain, which is the ZF87 KRAB domain for mouse and the Kox-1 KRAB domain for humans; and the nuclear localization signal (NLS), which is derived from a human variant peptide for use in humans (Human protein KIAA2022 NLS), and a mouse peptide for use in mouse, as described elsewhere herein.

Further host-matched zinc finger peptide modulators of the invention particularly suited for use in mouse include SEQ ID NOs: 51 and 52, which incorporate zinc finger peptide sequences 33 and 35, respectively. Humanised equivalent zinc finger peptide modulators are SEQ ID NOs: 55 and 56, which incorporate zinc finger peptide sequences 33 and 35, respectively. These sequences are considered to be sufficiently identical to human zinc finger peptide sequences while still binding poly(CAG) target sequences.

It has thus been found that several design variants of zinc finger peptide sequences can be synthesised to retain desired poly(CAG) binding characteristics, while improving/maximising host matching properties and minimising toxicity in vivo. Surprisingly, such design variants can include a relatively high number of modifications within zinc finger alpha-helical recognition sequences and within zinc finger linker sequences, both of which might be expected to affect (e.g. reduce) target nucleic acid binding affinity and specificity, without adversely affecting the efficacy of the potential therapeutic for use in vivo. Moreover, by beneficially reducing immunogenicity and toxicity effects in vivo, mid to long-term activity of the therapeutic peptides of the invention are significantly increased.

Based on these studies to develop beneficial derivatives of ZF11xHunt-kox-1, similar modifications to improve host optimisation-especially in the zinc finger peptide portion—can be made to other zinc finger peptide therapeutics molecules based on 10-zinc finger domains (ZF10xHunt-kox-1), 12-zinc finger domains (ZF12xHunt-kox-1) and 18 zinc finger domains (ZF18xHunt-kox-1), see SEQ ID Nos: 59 to 64 (Table 9).

The invention will now be further illustrated by way of the following non-limiting examples.

EXAMPLES

Unless otherwise indicated, commercially available reagents and standard techniques in molecular biological and biochemistry were used.

Materials and Methods

The following procedures used by the Applicant are described in Sambrook, J. et al., 1989 supra.: analysis of restriction enzyme digestion products on agarose gels and preparation of phosphate buffered saline. General purpose reagents, oligonucleotides, chemicals and solvents were purchased from Sigma-Aldrich Quimica SA (Madrid, Spain). Enzymes and polymerases were obtained from New England Biolabs (NEB Inc.; c/o IZASA, S.A. Barcelona, Spain).

Vector and Zinc Finger Peptide (ZFP) Construction

To build a zinc finger peptide (ZFP) framework that recognises both GCA and GCT DNA sequences (which are found within expanded CAG-repeats), a zinc finger scaffold based on the wild-type backbone sequence of the zinc finger region of wild-type human Zif268 was selected.

Amino acid residues responsible for DNA target recognition (i.e. the "recognition sequence", which essentially corresponds to the α-helical region of the framework) were first designed having regard to two previously reported studies: (1) Choo et al. (1994) *Nature* 372(6507): 642-645, for binding to the GCT triplet; and (2) Isalan et al. (1998) *Biochemistry* 37(35): 12026-12033, for binding to GN(T/A) triplets, as previously described (WO 2012/049332). These α-helical amino acid sequences were initially combined to generate a novel hybrid α-helix sequence, QRATLQR (SEQ ID NO: 69), comprising positions −1, 1 and 2 from Isalan et al. NO: and residues 3, 4, 5 and 6 from Choo et al. The resultant zinc finger domain was expected to and shown to bind the sequence GC(T/A), and was termed ZFxHunt (see FIG. 1). A pUC57 vector containing 6 such zinc finger domains, termed ZF6xHunt, was synthesised (Genscript Corporation (Piscataway, NJ). This vector also included a T7 promoter, an N-terminal NLS (PKKKRKV; (SEQ ID NO: 37), and restriction sites for deriving 4 (ZF4), 11 (ZF11), 12 (ZF12) and 18 (ZF18) zinc finger peptides in tandem arrays by subcloning as described in WO 2012/049332.

The zinc finger peptides were then subcloned into the mammalian expression vector pTarget™ (Promega). A 3xFLAG® tag sequence was introduced by PCR at the N-terminus, and either the FokI endonuclease domain or the Kox-1 (KRAB repression domain) coding sequences were introduced at the C-terminus, with a peptide linker sequence based on G and S amino acids was placed between the zinc finger peptide and the effector domain, again, as described in WO 2012/049332.

The pEH vector series was cloned in two steps. First, the EGFP coding region was excised from pEGFP-N1 (Clontech), using HindIII/XbaI, and cloned into pGL4.13 (Promega) to give pSV40-EGFP. Then, a PCR product containing CMV-HcRed-polyA and ClaI linkers was cloned into pSV40-EGFP (partially digested with ClaI). The EGFP start codon was mutated to alanine by site directed mutagenesis, and PCR fragments containing human Htt exon I from different human genomic templates (to obtain different numbers of CAG repeats), were cloned into the pEH EcoRI site, upstream and in frame with EGFP (pEH-Q series). The pSV40-mCherry vector series were generated by replacing EGFP from the pSV40-EGFP vector series with mCherry using XmaI/XbaI sites.

Design of 'Mousified' Zinc Finger Peptides

ZF11-kox-1 described in WO 2012/049332 (ZF-kox-1 herein) was converted into a series of more mouse-compatible peptides, mZF-ZF87 (SEQ ID NOs 49 to 52), as follows:

(1) The triple FLAG&-tag reporter from ZF-Kox-1 was removed.

(2) The viral SV40 nuclear localisation signal (NLS) was replaced with a mouse primase p58 NLS (RIRKKLR; GenBank®-BAA04203.1; SEQ ID NO: 38) using native adjacent residues as linkers.

(3) A zinc finger framework that was as close as possible to the mouse Zif268 sequence (Pavletich & Pabo (1991), *Science* 252: 809-817) was used while retaining functional CAG-binding residues on the DNA recognition helices. Thus, the QRATLQR (SEQ ID NO: 69) sequence used in ZF11-kox-1 of WO 2012/049332 was changed to a sequences corresponding to SEQ ID NO: 1, such as one or SEQ ID NOs: 2 to 5, or a combination of SEQ ID NOs: 2 and 5 or 3 and 4, as described herein, based on the natural variation in recognition sequence between adjacent zinc finger domains within the Zif268 scaffold; see FIG. 10).

Phage ELISA experiments as previously described (Isalan et al. (2001), *Nat. Biotechnol.* 19: 656-660), were performed to guide the alpha-helix recognition sequence design to ensure that the modified sequences retained appropriate binding to CAG triplets.

(4) Zinc finger linker peptides were modified to make them as close as possible to canonical zinc finger linkers (e.g. TGEKP, TGQKP, SEQ ID NOs: 6 and 65), while retaining non-wild-type canonical-like linkers (e.g. TGSQKP, SEQ ID NO: 16) after every 2 fingers, which are considered important for function of long zinc finger arrays (Moore et al. (2001), Proc. Natl.

Acad. Sci. USA, 98: 1437-1441); and retaining long linkers at appropriate spacings, i.e. after finger 5 (for the 11-finger construct) and after the last finger (finger 11 of the 11-finger construct) between the zinc finger domain and the repressor domain. However, these linkers were reduced in length from those of ZF-kox-1 in order to further reduce the amount of non-host sequence.

(5) For mouse constructs, human Kox-1 was replaced with the mouse KRAB repression domain from ZF87 (SEQ ID NO: 40; a.k.a. MZF22 (Abrink et al. (2001), Proc. Natl. Acad. Sci. USA, 98: 1422-1426.); refSeq_NM_133228.3). The 1-76 amino acid KRAB-domain fragment of ZF87, when fused to Gal4 DNA-binding domain, has been previously reported to have similar levels of repression compared to Gal4-Kox-1 (Abrink et al. (2001), *Proc. Natl. Acad. Sci. USA*, 98: 1422-1426.) in mice.

In Vitro Gel Shift Assays

Based on the pUC57 vector zinc finger constructs, appropriate forward and reverse primers were used to generate PCR products for in vitro expression of the ZFP, using the TNT® T7 Quick PCR DNA kit (Promega). Double stranded DNA probes with different numbers of CAG repeats were produced by Kenow fill-in as described in WO 2012/049332. 100 ng of double stranded DNA was used in a DIG-labeling reaction using Gel Shift kit, $2^{nd}$ generation (Roche), following the manufacturer's instructions. For gel shift assays, 0.005 pmol of DIG-labelled probe were incubated with increasing amounts of TNT-expressed protein in a 20 µl reaction containing 0.1 mg/ml BSA, 0.1 pg/ml polydI:dC, 5% glycerol, 20 mM Bis-Tris Propane, 100 mM NaCl, 5 mM $MgCl_2$, 50 mg/ml $ZnCl_2$, 0.1% NonidetP40™ and 5 mM DTT for 1 hour at 25° C. Binding reactions were separated in a 7% non-denaturing acrylamide gel for 1 hour at 100 V, transferred to a nylon membrane for 30 min at 400 mA, and visualisation was performed following manufacturer's instructions.

Cell Culture and Gene Delivery

The cell line HEK-293T (ATCC) was cultured in 5% $CO_2$ at 37° C. in DMEM (Gibco) supplemented with 10% FBS (Gibco). Qiagen purified DNA was transfected into cells using Lipofectamine2000 ™ (Invitrogen) according to the manufacturer's instructions. Briefly, cells were plated onto 10 mm wells to a density of 50% and 70 ng of reporter plasmid, 330 ng of ZFP expression plasmid and 2 µl of Lipofectamine2000™ were mixed and added to the cells. Cells were harvested for analysis 48 hours later.

STHdh+/Hdh+ and STHdhQ111/Hdh111 cells (gift from M. E. MacDonald) were cultured in 5% $CO_2$ at 33° C. in DMEM supplemented with 10% FBS (Gibco) and 400 µg/ml G418 (PAA). Cells were infected with retroviral particles using the pRetroX system (Clontech) according to the manufacturer's instructions.

Flow Cytometry Analysis

Cells were harvested 48 hours post-transfection and analysed in a BD FACS Canto™ Flow cytometer using BD FACSDiva™ software.

Western Blot 293T cells were harvested 48 hours post-transfection in 100 µl of 2xSDS loading dye with Complete™ protease inhibitor (Roche). 20 µl of sample was separated in 4-15% Criterion™ Tris-HCl ready gels (BioRad) for 2 hours at 100V, transferred to Hybond®-C membrane (GE Healthcare) for 1 hour at 100V. Proteins were detected with either the primary antibody anti β-actin (Sigma A1978) at 1:3000 dilution or anti-EGFP (Roche) at 1:1500 dilution and with a peroxidase-conjugated donkey anti-mouse secondary antibody (Jackson ImmunoResearch) at 1:10000 dilution. Visualisation was performed with ECL™ system (GE Healthcare) using a LAS-3000 imaging system (Fujifilm). STHdh cells were trypsinised and harvested in PBS containing Complete™ protease inhibitor (Roche). Cells were resuspended in RIPA buffer (1% Triton™ X-100, 1% sodium deoxycholate, 40 mM Tris-HCl, 150 mM NaCl, 0.2% SDS, Complete™), incubated in ice for 15 min, and were centrifuged at 13000 rpm for 15 min. The supernatant was collected and protein concentration was determined using BioRad's Dc protein assay. 60 µg of protein was separated in a 5% Criterion™ Tris-HCl ready gel (BioRad) for 2 hours at 100V, transferred using iBlot™ Dry Blotting System (Invitrogen) for 8 min and endogenous Htt protein was detected with anti-Huntingtin primary antibody (Millipore MAB2166) at a 1:1000 dilution.

Production of Adeno-Associated Viral Vector rAAV2/1-GFP, rAAV2/1-ZF11-Kox1 and rAAV2/1-mZF-ZF87 containing a pCAG promoter (CMV early enhancer element and the chicken beta-actin promoter) and WPRE (Woodchuck post-translational regulatory element), were produced at the Centre for Animal Biotechnology and Gene Therapy of the Universitat Autonoma of Barcelona (CBATEG-UAB) as previously described (Salvetti et al. (1998) *Hum. Gene Ther.* 9: 695-706). Recombinant virus was purified by precipitation with PEG8000 followed by iodixanol gradient ultracentrifugation with a final titre of approx $10^{12}$ genome copies/ml.

Animals—R6/2 Transgenic Mice

For this study we used R6/1, R6/2 and wild-type (WT) mice.

R6/2 transgenic mice were purchased form Jackson Laboratories (B6CBA-Tg(HDexon1)62Gpb/3J). Ovarian transplanted hemizygous females and wt B6CBAF1/J males were bred in house, and progeny was genotyped as previously described (Benn, et al. (2009), *PLoS One* 4, e5747).

R6/1 transgenic mice (B6.Cg-Tg(HDexon1)61Gpb/J) and wt controls (C57BL/6J) were also purchased form Jackson Laboratories. For the testing of mZF-ZF87, R6/1 mice were preferred over R6/2 mice to avoid early onset of symptoms and to comply with animal welfare conditions in the UK, since the aim of this study was not to check for a phenotype reversal.

Stereotaxic injections were performed on 4-week-old R6/2 mice, 8-week old R6/1 mice and 4 to 8-week-old wt mice. All animal experiments were conducted in accordance with Directive 86/609/EU of the European Commission, the Animals (Scientific Procedures) 1986 Act of the United Kingdom, and following protocols approved by the Ethical Committee of the Barcelona Biomedical Research Park and the Animal Welfare and Ethical Review Body of Imperial College London. The number of mice for each experiment is given in Table 2.

TABLE 2

Summary of number of mice injected with ZF-Kox-1, mZF-ZF87, GFP or PBS.

| Experiment | Treatment | Genotype | Weeks post-injection | n |
|---|---|---|---|---|
| Histology analysis: inflammatory responses and neuronal loss | ZF-Kox-1 | WT | 4 | 4 |
| | | | 6 | 4 |
| | mZF-ZF87 | | 4 | 4 |
| | | | 6 | 4 |
| | GFP | | 4 | 4 |
| | | | 6 | 4 |

TABLE 2-continued

Summary of number of mice injected with
ZF-Kox-1, mZF-ZF87, GFP or PBS.

| Experiment | Treatment | Genotype | Weeks post-injection | n |
|---|---|---|---|---|
| | PBS | | 4 | 3 |
| | | | 6 | 3 |
| Gene expression analysis | ZF-Kox-1 | R6/2 | 2 | 3 |
| | | | 4 | 3 |
| | | | 6 | 3 |
| | mZF-ZF-87 | R6/1 | 2 | 6 |
| | | | 4 | 7 |
| | | | 6 | 7 |

Stereotaxic Surgery

Briefly, mice were anesthetised with a mix of ketamine (75 mg/kg) and medetomidine (1 mg/kg, i.p.) or isofluorane (preferred) and fixed on a stereotaxic frame. Buprenorphine was injected at 8 μg/kg to provide analgesia.

AAVs were injected bilaterally or unilaterally (depending on the study) into the striatum (A/P+0.7 mm, M/L±1.8 mm, D/V −3.0 and/or −2.5 mm relative to bregma) using a 10 μl Hamilton syringe at a rate of 0.25 μl/min controlled by an Ultramicropump (World Precision Instruments). For each hemisphere, a total volume of 1.5 to 3 μl (approx. $2 \times 10^9$ genomic particles) or 1.5 μl PBS were injected. For example, a two step administration may be performed as follows: 1.5 μl were injected at −3.0 mm DV, the needle was let to stand for 3 minutes in position, and then the other half was injected at −2.5 mm DV.

In some studies, females were randomly injected with AAV expressing zinc finger repressor peptides (i.e. ZF-kox-1 or mZF-ZF87) in one hemisphere and with control AAV expressing GFP (AAV2/1-GFP) into the other hemisphere.

In some studies, females were injected only in one hemisphere with AAV expressing the test protein (either zinc finger or GFP control protein), rAAV2/1-ZF-kox-1, rAAV2/1-hZF-kox-1, AAV2/1-mZF-ZF87 or AAV2/1-GFP; or with PBS as a negative control.

Mice were sacrificed at different ages for posterior analysis by RT-PCR, immunohistochemistry or western blot; typically at 2, 4 or 6 weeks after administration of agent Males were bilaterally injected with 3 μl of the same virus in both hemispheres for behavioral assays.

Animal Behavioral Tests

Behavioural monitoring commenced at 3 weeks of age and tests took place bimonthly until 11 weeks of age. All the experiments were performed double-blind with respect to the genotype and treatment of the mice.

Clasping behaviour was checked by suspending the animal by the tail for 20 seconds. Mice clasping their hindlimbs were given a score of 1, and mice that did not clasp were given a score of 0.

Grip strength was measured by allowing the mice to secure to a grip strength meter and pulling gently by the tail. The test was repeated three times and the mean and maximum strength recorded.

For the accelerating rotarod test, mice were trained at 3 weeks of age to stay in the rod at a constant speed of 4 rpm until they reached a criterion of 3 consecutive minutes in the rod. In the testing phase, mice were put in the rotarod at 4 rpm and the speed was constantly increased for 2 minutes until 40 rpm. The assay was repeated twice and the maximum and average latency to fall from the rod was recorded.

For the open field test, mice were put in the centre of a white methacrylate squared open field (70×70 cm) illuminated by a dim light (70 lux) to avoid aversion, and their distance travelled, speed and position was automatically measured with a video tracking software (SMART system, Panlab, Spain). Other activities, such as rearing, leaning, grooming and number of faeces were monitored de visu.

For the paw print test, mice hindpaws were painted with a non-toxic dye and mice were allowed to walk through a small tunnel (10×10×70 cm) with a clean sheet of white paper in the floor. Footsteps were analysed for three step cycles and three parameters measured: (1) stride length—the average distance between one step to the next; (2) hind-base width—the average distance between left and right hind footprints; and (3) splay length—the diagonal distance between contralateral hindpaws as the animal walks.

qRT-PCR

Mice were humanely killed by cervical dislocation. As rapidly as possible, they were decapitated and the striata were dissected on ice and immediately frozen in liquid nitrogen, for later RNA extraction.

RNA was prepared with RNeasy® kit (Qiagen) and reversed transcribed with Superscript II (Invitrogen). Real Time PCR was performed in a LightCycler® 480 Instrument (Roche) using LightCycler® 480 SYBR™ Green I Master (Roche). SYBR™ Advantage™ GC qPCR Premix (Clontech) was used to amplify the human HTT transgene in R6/2 and R6/1 templates. For technical replicates, each PCR was done at least in triplicate, and results normalised to three housekeeping genes (mHPRT, mActb and mAtp5m as in our previous study (Garriga-Canut et al. (2012), *Proc. Natl. Acad. Sci.;* 109, E3136-3145)). At least three independent biological replicates were done for each experiment. Primer sets are given in full in Table 3.

TABLE 3

Primers used in qRT-PCR analyses.
CAG-repeat number per gene and corresponding primer sets for qRT-PCR.
Name prefixes: mut = mutant; m = mouse. Approximate CAG repeat number for
wild-type genes was obtained from Genbank mRNA data. CAG-repeat length:
the first number corresponds to pure CAG repeats, the second number to
broken CAG repeats (containing CAA or CAT).

| Gene | CAG repeat length | Forward primer (SEQ ID NO:) | Reverse primer (SEQ ID NO:) |
|---|---|---|---|
| ZF-Kox-1 | N/A | GTGGAAGCTGCTGGACACT (70) | AACGTAAAGTGACCGGGGCCG (71) |
| mZF-ZF87 | N/A | GGTCCGAAGAGATGCTCAGT (72) | CAGGAAGACCAGGTGGCTAT (73) |
| mut HTT | ~150 | GCTGCACCGACCGTGAGT (74) | CGCAGGCTGCAGGGTTAC (75) |

TABLE 3-continued

Primers used in qRT-PCR analyses.
CAG-repeat number per gene and corresponding primer sets for qRT-PCR.
Name prefixes: mut = mutant; m = mouse. Approximate CAG repeat number for
wild-type genes was obtained from Genbank mRNA data. CAG-repeat length:
the first number corresponds to pure CAG repeats, the second number to
broken CAG repeats (containing CAA or CAT).

| Gene | CAG repeat length | Forward primer (SEQ ID NO:) | Reverse primer (SEQ ID NO:) |
|---|---|---|---|
| mHtt | 4,7 | CAGATGTCAGAATGGTGGCT (76) | GCCTTGGAAGATTAGAATCCA (77) |
| mATN1 | 3,10 | CACCTGCCTCCACCTCATGGC (78) | ATGCTCCTTGGGGGCCCTGG (79) |
| mATXN2 | 6,10 | ATCCCAATGCAAAGGAGTTC (80) | CTGCTGATGACCCACCATAG (81) |
| mTBP | 3,13 | ACTTCGTGCAAGAAATGCTG (82) | GCTCATAGCTCTTGGCTCCT (83) |
| mHPRT | N/A | GGTTAAGCAGTACAGCCCCA (84) | AGAGGTCCTTTTCACCAGCA (85) |
| mActb | N/A | GCTTCTTTGCAGCTCCTTCGT (86) | CCAGCGCAGCGATATCG (87) |
| mAtp5b | N/A | CCACCGACATGGGCACAATGCA (88) | ATGGGCAAAGGTGGTTGCAGGG (89) |

Immunohistochemistry

Mice were transcardially perfused with PBS followed by formalin 4% (v/v). Brains were removed and post-fixed overnight at 4° C. in formalin 4% (v/v). Brains were then cryoprotected in a solution of sucrose 30% (w/v), at 4° C., until they sank. Brains were frozen and sliced with a freezing microtome in six parallel coronal series of 40 µm (distance between slices in each parallel series: 240 µm). The indirect ABC procedure was employed for the detection of the neuronal marker Neu-N (1:100, MAB377 Millipore) in the first series; the reactive astroglial marker GFAP (1:500, Dako) in the second series; and the microglial marker Iba1 (1:1000, Wako) in the third series. Briefly, sections were blocked with 2% (v/v) Normal Goat Serum (NGS, Vector Laboratories) in PBS-Triton™100 0.3% (v/v) and endogenous peroxidase activity blocked with 1% (v/v) hydrogen peroxide ($H_2O_2$) in PBS for 30 minutes at room temperature.

Subsequently, sections were incubated for 30 minutes at room temperature in: (i) primary antibody (at the concentration indicated above) in PBS with 0.3% (v/v) Triton™ X100 and 2% (v/v) NGS; (ii) biotinylated secondary antibody in the same buffer; and (iii) avidin-biotin-peroxidase complex (ABC Elite kit Vector Laboratories) in PBS-Triton™ X-100 0.3% (v/v). Sections were washed 3×10 min in PBS and peroxidase activity was revealed with SIGMA-FAST™-DAB (3,3'-Diaminobenzidine tetrahydrochloride, Sigma-Aldrich) in PBS for 5 min. Sections were rinsed and mounted onto slides, cleared with Histoclear® (Fisher Scientific) and cover-slipped with Eukitt® (Fluka).

The fourth GFP-injected series was mounted onto slides and covered with Mowiol® (Sigma-Aldrich) for fluorescence analysis.

Image Analysis

Determination of the volume of injection:
Five coronal slices per GFP-injected hemisphere from bregma 1.5 mm levels, separated by 240 µm, were photographed with a digital camera attached to a macrozoom microscope (Leica). The contours around the GFP-expressing area and dorsal striatum were manually defined and the area was measured with ImageJ software (National Institute of Health, USA). Volume was calculated as area per distance between slices, according to the Cavalieri principle (Oorschot (1996), J. Comp. Neurol.; 366: 580-599).

Determination of O.D. for GFAP and Iba1 stainings:
Four coronal slices per mouse and hemisphere covering the striatum from bregma 1.5 mm levels were selected, and a region of interest of 670×897 µm$^2$ in the middle of the dorsal striatum was captured with a 10× objective using a digital camera attached to a microscope (Leica DMIRBE). The O.D. of the areas was measured with ImageJ, the mean density per hemisphere calculated and O.D. for GFAP and Iba1 of control hemispheres were subtracted from the injected hemisphere.

Determination of the neuronal density of the striatum:
Cell density was calculated using an adaptation of the unbiased fractionator method (Oorschot (1996), J. Comp. Neurol.; 366: 580-599). Four coronal slices per mouse and hemisphere covering the striatum from bregma 1.5 mm levels were selected, and a region of interest of 447×598 µm$^2$ in the middle of the dorsal striatum was captured with a 15× objective using a digital camera attached to a microscope (Leica DMIRBE). A grid image leaving 16 squares of 35×35 µm$^2$ was superimposed to the pictures and a person blinded to sample treatment counted the number of stained nuclei.

Statistical Analysis

Data were analysed using the StatPlus package for Excel (Microsoft) and IBM SPSS Statistics 22.

To test the inflammatory response the difference of O.D. of the injected hemisphere versus the control hemisphere was calculated and a Student's t test was performed against no difference value (0).

For neuronal density, a paired Student's t test of neuronal density in the injected hemisphere versus the control hemisphere was performed. Neuronal density was analysed across contralateral hemispheres with an ANOVA, followed by post-hoc comparisons with the contralateral hemispheres of the PBS samples. To test repression, the percentage of mutant HTT (mut HTT) or the gene of interest (HTT, ATN1, ATXN2, TBP) in the injected brain was calculated with respect to the control hemisphere, and a one sample Student's t test against the no repression value (100%) was performed. To ensure a fair comparison between injected and contralateral hemispheres, only mice with <1% ZF expression in the contralateral hemisphere, relative to the injected hemisphere, were used for statistical analyses (Table 4). To test the correlation between RNA levels of the different genes and ZF expression a linear regression test was applied. To test expression levels across different times post-injection a one-way ANOVA was performed. All significance values are set at p=0.05.

TABLE 4

Raw data for the expression of ZF-Kox-1 and mZF-ZF87. Complete data set showing the values of ZF expression in each of the hemispheres (injected vs. control) and the percentage of mut HTT RNA expression with respect to the control. Mice showing leaky expression of ZF in the contralateral control hemisphere (>1% of the injected hemisphere, bold italics) are not taken into account in the statistical analysis of repression of mut HTT shown in FIG. 16.

| ZF | Time point | ZF RNA levels control (a.u) | ZF RNA levels injected (a.u.) | % ZF in control vs injected | % mut HTT injected vs control |
|---|---|---|---|---|---|
| ZF-Kox-1 | 2 | $1.33 \times 10^{-5}$ | $1.37 \times 10^{-2}$ | 0.09 | 45.5 |
|  |  | 0 | $4.4 \times 10^{-3}$ | 0 | 59.1 |
|  |  | 0 | $2.7 \times 10^{-3}$ | 0 | 62.8 |
|  | 4 | $1.06 \times 10^{-5}$ | $7.1 \times 10^{-3}$ | 0.14 | 39.49 |
|  |  | 0 | $1.0 \times 10^{-3}$ | 0 | 88.1 |
|  |  | $6.35 \times 10^{-6}$ | $2.9 \times 10^{-3}$ | 0.22 | 68.4 |
|  | 6 | $6.2 \times 10^{-4}$ | $1.2 \times 10^{-3}$ | 50.2 | 74.5 |
|  |  | $5.0 \times 10^{-4}$ | $8.3 \times 10^{-3}$ | 60.7 | 88.9 |
|  |  | $4.4 \times 10^{-5}$ | $1.0 \times 10^{-3}$ | 4.4 | 81.2 |
| mZF-ZF87 | 2 | $6.68 \times 10^{-8}$ | $2.80 \times 10^{-6}$ | 2.4 | 40.7 |
|  |  | $5.59 \times 10^{-9}$ | $3.85 \times 10^{-6}$ | 0.14 | 35.4 |
|  |  | 0 | $9.85 \times 10^{-11}$ | 0 | 98.9 |
|  |  | $8.38 \times 10^{-10}$ | $2.62 \times 10^{-7}$ | 0.31 | 84.6 |
|  |  | 0 | $2.35 \times 10^{-7}$ | 0 | 59.6 |
|  |  | $1.42 \times 10^{-9}$ | $5.41 \times 10^{-7}$ | 0.26 | 68.9 |
|  | 4 | $2.97 \times 10^{-9}$ | $6.46 \times 10^{-7}$ | 0.45 | 82.8 |
|  |  | $2.77 \times 10^{-11}$ | $2.70 \times 10^{-7}$ | 0.01 | 100.6 |
|  |  | $3.26 \times 10^{-10}$ | $3.81 \times 10^{-7}$ | 0.08 | 94.2 |
|  |  | $3.00 \times 10^{-9}$ | $9.66 \times 10^{-7}$ | 0.31 | 55.6 |
|  |  | $2.58 \times 10^{-10}$ | $1.02 \times 10^{-7}$ | 0.25 | 87.9 |
|  |  | $2.27 \times 10^{-9}$ | $4.92 \times 10^{-7}$ | 0.46 | 64.8 |
|  |  | $5.59 \times 10^{-10}$ | $1.53 \times 10^{-8}$ | 3.63 | 108.0 |
|  | 6 | 0 | $2.81 \times 10^{-7}$ | 0 | 80.4 |
|  |  | $3.19 \times 10^{-9}$ | $4.89 \times 10^{-7}$ | 0.65 | 83.6 |
|  |  | $3.00 \times 10^{-11}$ | $2.15 \times 10^{-7}$ | 0.01 | 105.8 |
|  |  | $2.35 \times 10^{-9}$ | $2.71 \times 10^{-7}$ | 0.86 | 76.4 |
|  |  | $5.22 \times 10^{-10}$ | $1.16 \times 10^{-7}$ | 0.44 | 87.3 |
|  |  | $5.75 \times 10^{-9}$ | $1.28 \times 10^{-7}$ | 4.49 | 121.1 |
|  |  | $7.95 \times 10^{-11}$ | $6.64 \times 10^{-8}$ | 0.11 | 42.6 |

Example 1

Design of Zinc Finger Peptide (ZFP) Arrays to Bind CAG Repents

It is known that zinc finger domains can be concatenated to form multi-finger (e.g. 6-finger) chains (Moore et al. (2001) *Proc. Natl. Acad. Sci. USA* 98(4): 1437-1441; and Kim & Pabo (1998) *Proc. Natl. Acad. Sci. USA* 95(6): 2812-2817). Our previous study, see WOK 2012/049332 was the first to report on the systematic exploration of the binding modes of different-length ZFP to long repetitive DNA tracts.

In this earlier study, rational design was used to construct a zinc finger domain (ZFxHunt) that would bind the 5'-GC (A/T) -3' sequence in double stranded DNA. Poly-zinc finger proteins comprising arrays of ZfxHunt were, therefore, expected to bind to poly-GCA and poly-GCT sequences (see Materials and Methods above and FIG. 1). Both DNA strands of the CAG double-stranded repeat were targeted because: (i) it was thought that this would increase the avidity of the zinc finger peptides for low-copy chromosomal targets; and (ii) it enabled FokI nuclease fusion designs to be tested (as described below). To try to avoid the zinc finger peptides of the invention losing their register with cognate DNA (after 3 or more adjacent fingers and 9 contiguous base pairs of double helical DNA), the linker sequences were carefully designed. In particular, the length of the linkers between adjacent zinc fingers in the arrays was modulated. In this way, the register between the longer arrays of zinc finger peptides, especially on binding to dsDNA, could be optimised. Using structural considerations, it was decided to periodically modify the standard canonical linker sequences in the arrays. Therefore, canonical-like linker sequences containing an extra Gly (or Ser) residue or flexible (up to 29-residue) linker sequences were included in the long zinc finger array after every 2- and 6-fingers, respectively (see Table 5 and SEQ ID NOs: 90 to 94). In this way, different numbers of zinc fingers could be tested for optimal length-dependent discrimination.

TABLE 5

Zinc finger peptide framework amino acid sequences of non-humanised or mousified CAG-repeat binding peptides. In amino acid sequences recognition sequences are underlined and linker sequences are shown in bold.

ZF4xHunt amino acid sequence (SEQ ID NO: 90):
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH ZF6xHunt amino acid sequence (SEQ ID NO: 91):
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH ZF11xHunt amino acid sequence (SEQ ID NO: 92):
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH LRQKDGGGGSGGGGSGGGGSQLVGTAERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH ZF12xHunt amino acid sequence (SEQ ID NO: 93):
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH LRQKDGGGGSGGGGSGGGGSQLVGTAERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH TABLE 5-continued Zinc finger peptide framework amino acid sequences of non-humanised or mousified CAG-repeat binding peptides. In amino acid sequences recognition sequences are underlined and linker sequences are shown in bold.

ZF18xHunt amino acid sequence (SEQ ID NO: 94):
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH LRQKDGGGSQLVGTAERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH LRQKDGGGSGTAERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH TGSERP
FQCRICMRNFSQRATLQRHIRTH TGEKP
FACDICGRKFAQRATLQRHTKIH Example 2

Binding of Zinc Finger Peptides to DNA Target Sequences In Vitro

To show that the zinc finger peptides of Example 1 are capable of binding to CAG repeat sequences, in vitro gel shift assays were carried out as follows.

Zinc finger peptide arrays containing either 4, 6 or 12 ZFxHunt domains were constructed and tested in gel shift assays, for binding to double-stranded CAG probes (SEQ ID NOs: 171 to 173; FIG. 1B). The results showed that the longer ZFPs gave more complete binding of the probe. Interestingly, distinct bound complexes were observed in the gel shift, indicating that the ZFPs found single thermodynamic equilibria and were not trapped by kinetic intermediates. Highly-repetitive zinc finger and DNA sequences might have been expected to form contiguous partial binding events, which would have been expected to result in broad smears in gel shifts; but this was not the case. Notably, the 12-finger ZFP did give a lower, secondary shift, which is presumably caused by a 6-finger degradation by-product (zinc fingers can be unstable in linker regions; Miller et al. (1985) *EMBO J.* 4(6): 1609-1614).

To test whether ZFxHunt zinc finger domains were able to bind both strands of a CAG-repeat DNA probe, ZF6xHunt (i.e. the 6-finger peptide) was assayed by gel shift, and was shown to bind equally to both a CAG repetitive probe containing six contiguous GCA repeats (SEQ ID NO: 174), and to an alternate CAG-CTG probe with three contiguous repeats (SEQ ID NO: 175), as shown in FIG. 1C. Furthermore, when compared to mutated sequences (SEQ ID NOs: 176 to 178). ZF6xHunt showed specificity for a target sequence having seven contiguous CAG trinucleotide repeats (SEQ ID NO: 172: see FIG. 1D).

In summary, 4-, 6- and 12-finger ZFPs were synthesised and demonstrated to be able to bind poly 5'-GC(A/T) -3' DNA probes in vitro. Furthermore, it was shown that the longer ZFPs bound most specifically and efficiently to their target sequences.

Example 3

Repression of polyQ Reporter Genes In Vivo

The intracellular activity of the ZFxHunt zinc finger domain was tested in vivo using reporter vectors with different numbers of 5' CAG-repeats in frame with EGFP (Q0, Q10, Q35 and Q104; where Q=CAG and the number indicates the number of repeats). To assess whether there were any non-specific effects caused by the zinc finger proteins, an HcRed reporter was cloned in a different region of the same vector, under an independent promoter (FIG. 2A).

HEK293T cells were transiently cotransfected with the indicated reporter and ZFxHunt vectors, in which zinc finger expression was driven by CMV promoters. Three sets of assays were carried out: quantifying EGFP and HcRed fluorescent cells using Fluorescence-Activated Cell Sorting (FACS); EGFP protein levels in Western blots; and EGFP and HcRed mRNA levels in qRT-PCR (FIGS. 2B to 2D). Whereas shorter CAG-repeats (Q0, Q10) were essentially unaffected by any of ZF4, ZF6, ZF11 or ZF18xHunt peptides, the longer CAG-repeat targets (Q35, Q104) were strongly repressed in all three assays, e.g. up to 10-fold EGFP repression by FACS, which equates to a 90% reduction (FIG. 2B).

Figure 2:
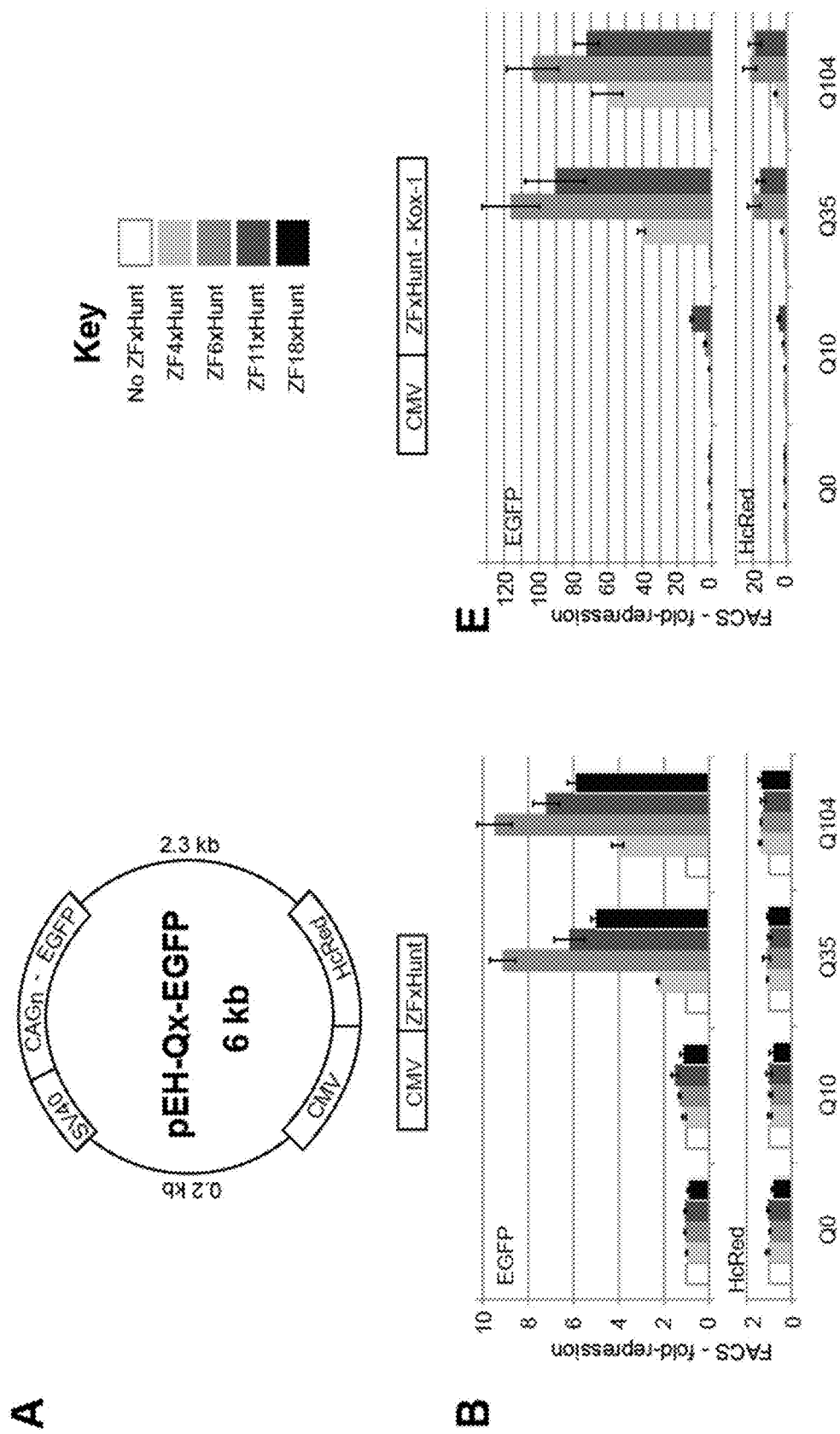
FIG. 2 Episomal poly-CAG-reporter repression by zinc finger peptides. Results are illustrated for ZFPs without effector domains (panels B to D), or fused to the Kox-1 repressor domain (panels E to G). (A) The pEH reporter plasmid contains EGFP, fused to different-length poly-Q coding sequences, under an SV40 promoter. A control HcRed gene, under a CMV promoter, measures off-target or long-range repression; key: ZFP expression constructs containing 0, 4, 6, 11 or 18 fingers. (B) FACS assay measuring the fold-reduction in EGFP and HcRED fluorescent cells, in response to exposure to different zinc fingers. A 10-fold repression is equivalent to a 90% reduction in protein fluorescence. (C) Illustrates an EGFP Western blot for ZFP repression of pEH-Qx targets. (D) Shows the results of a qRT-PCR assay to measure fold-repression of EGFP or HcRED mRNA by ZFP. (E to G) The same three assays (FACS, Western, qRT-PCR) repeated for ZFPs fused to Kox-1. In panels E to G the vertical scales are larger, which reflects the stronger repression caused by the Kox-1 domain (>100-fold repression; >99% reduction in protein fluorescence), and long-range repression of the HcRed gene by Kox-1.
Figure 2:
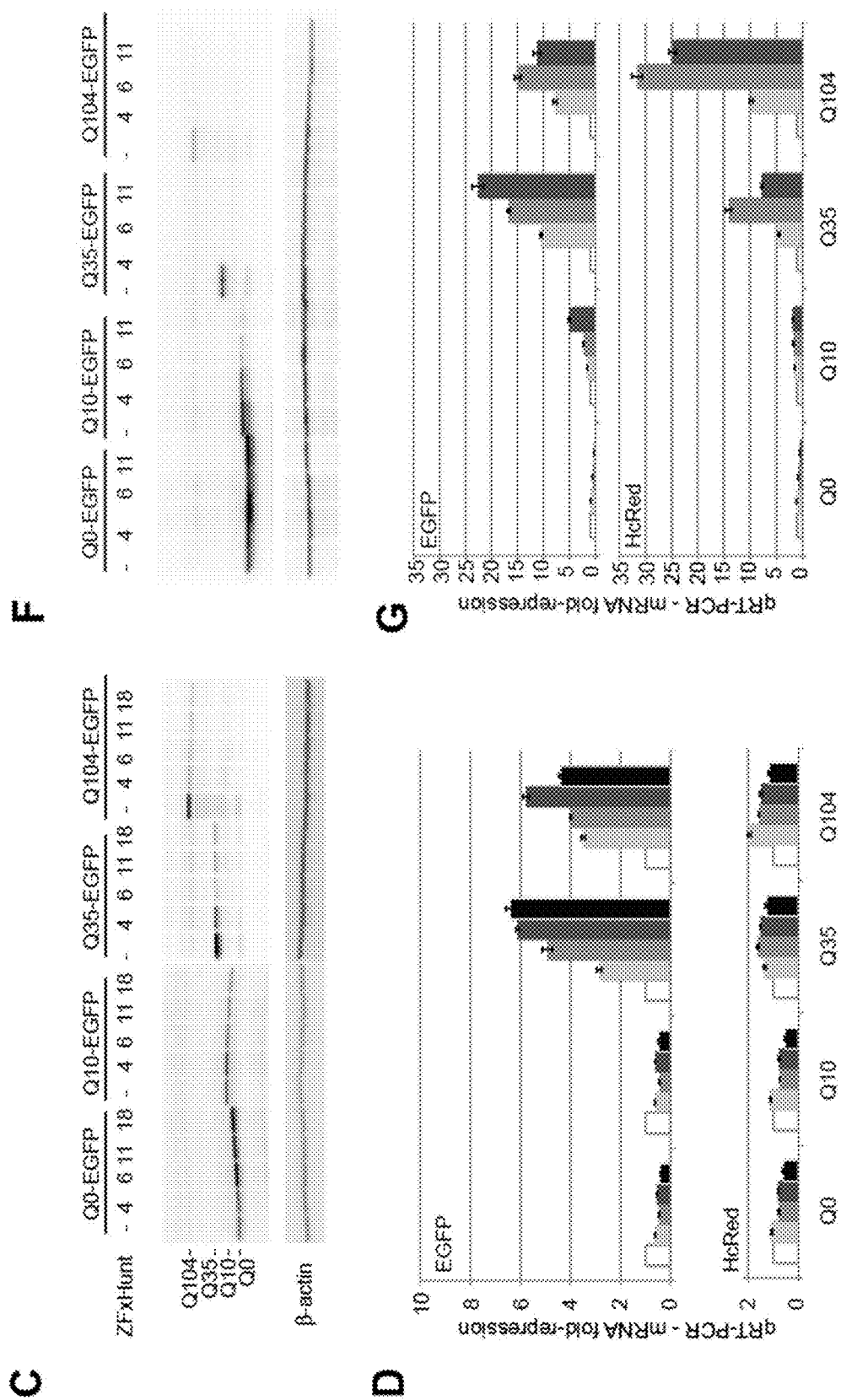

It was also found that longer zinc finger chains gave greater repression of target gene expression as determined in qRT-PCR (FIG. 2D). The 6-finger protein, ZF6xHunt, was found to be effective in FACS (FIG. 2B) and Western blots (FIG. 2C).

To test the potential for even stronger repression, the KRAB repression domain Kox-1 (Groner et al. *PLoS Genet* 6(3): e1000869) was fused to the C-terminus of ZFxHunt proteins (FIGS. 2E to 2G; Table 6). As expected, Kox-1 repression was indeed much stronger. For example, there was up to 98% reduction of green cells by FACS for Q35- and Q104-EGFP, with undetectable levels of EGFP protein by western blot analysis (FIG. 2F). Although repression was generally stronger, it was still proportional to ZFP and CAG-length: for example, the EGFP construct lacking CAG repeats was not repressed, and the constructs having longer CAG-repeats (e.g. Q35) were repressed more strongly than shorter repeat constructs (e.g. Q10-EGFP). In this assay, the ZF11xHunt-Kox-1 protein was found to provide the strongest level of repression, as shown in FIGS. 2E and 2G. This demonstrates that, with suitable linker designs, long chains containing odd-numbers of zinc fingers can also function effectively. Moreover, the mechanism of Kox-1-mediated HcRed repression is demonstrated to be dependent on the presence of long CAG-repeats in the plasmid. The unintended level of repression of the neighbouring gene (HcRed) with Kox-1 proteins may be due to the long-range effects of Kox-1 on chromatin structure.

Figure 3A:
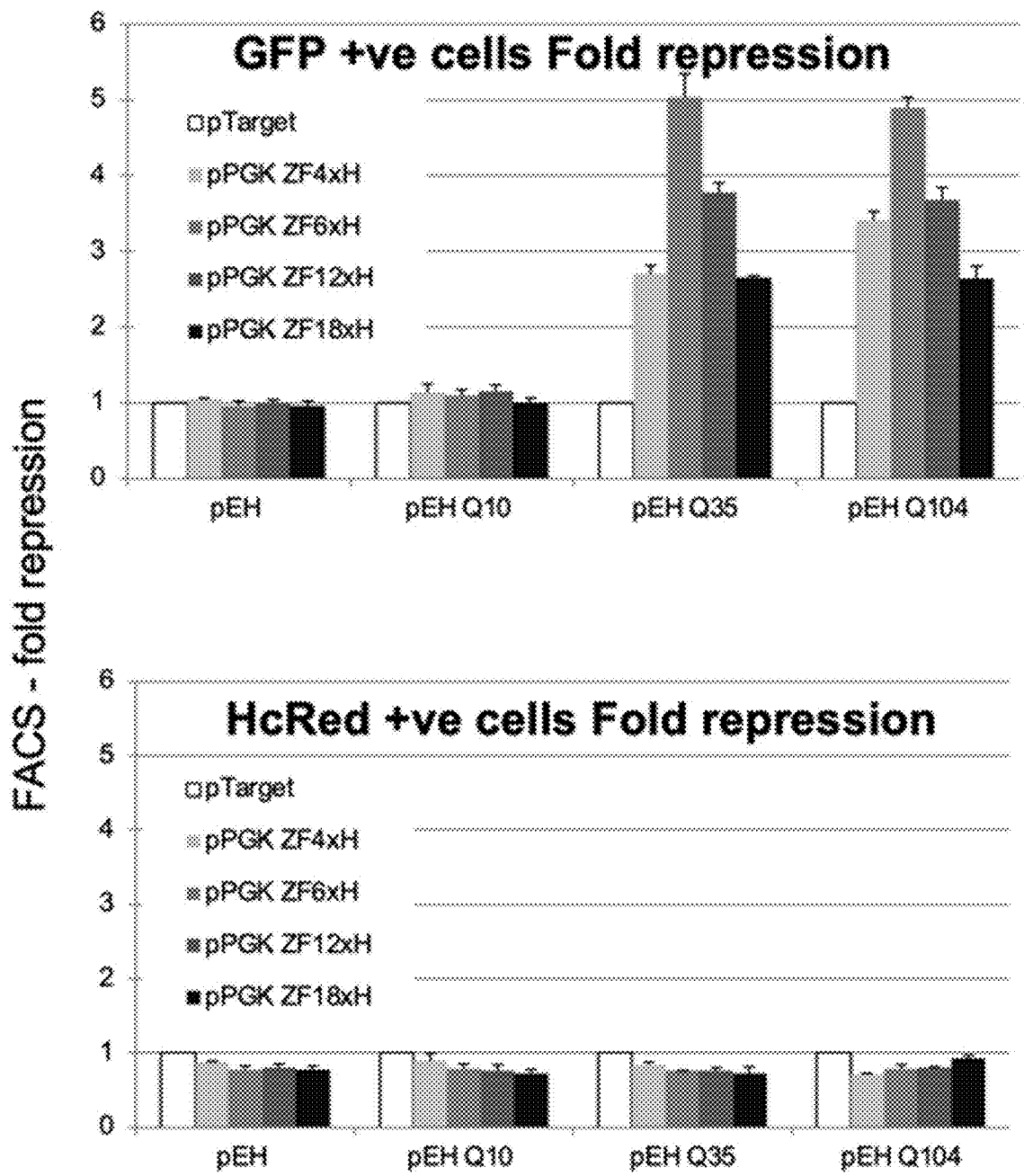
FIG. 3 Episomal reporter repression by ZFPs for targeting CAG-repeat sequences. Cells were cotransfected with reporter and zinc finger plasmids: the pEH reporter plasmid contains EGFP, fused to different-length poly-Q coding sequences, under an SV40 promoter. A control HcRed gene, under a CMV promoter, measures off-target or long-range repression. pPGK-ZF (PGK-promoter) expression constructs contain chains of ZFxHunt (0, 4, 6, 12 or 18 fingers, as indicated). ZFPs are not fused to any effector domains. The pTarget™ vector does not contain a ZFP and is used as a control. (A) FACS assay measuring the fold-reduction in EGFP or HcRED fluorescent cells, in response to different zinc fingers. A 5-fold repression is equivalent to 80% reduction. (B) qRTPCR assay to measure fold-repression of EGFP or HcRED mRNA by ZFP. (C) EGFP Western blot for ZFP repression of pEH-Qx targets. β-actin staining is used as a loading control.
Figure 3B:
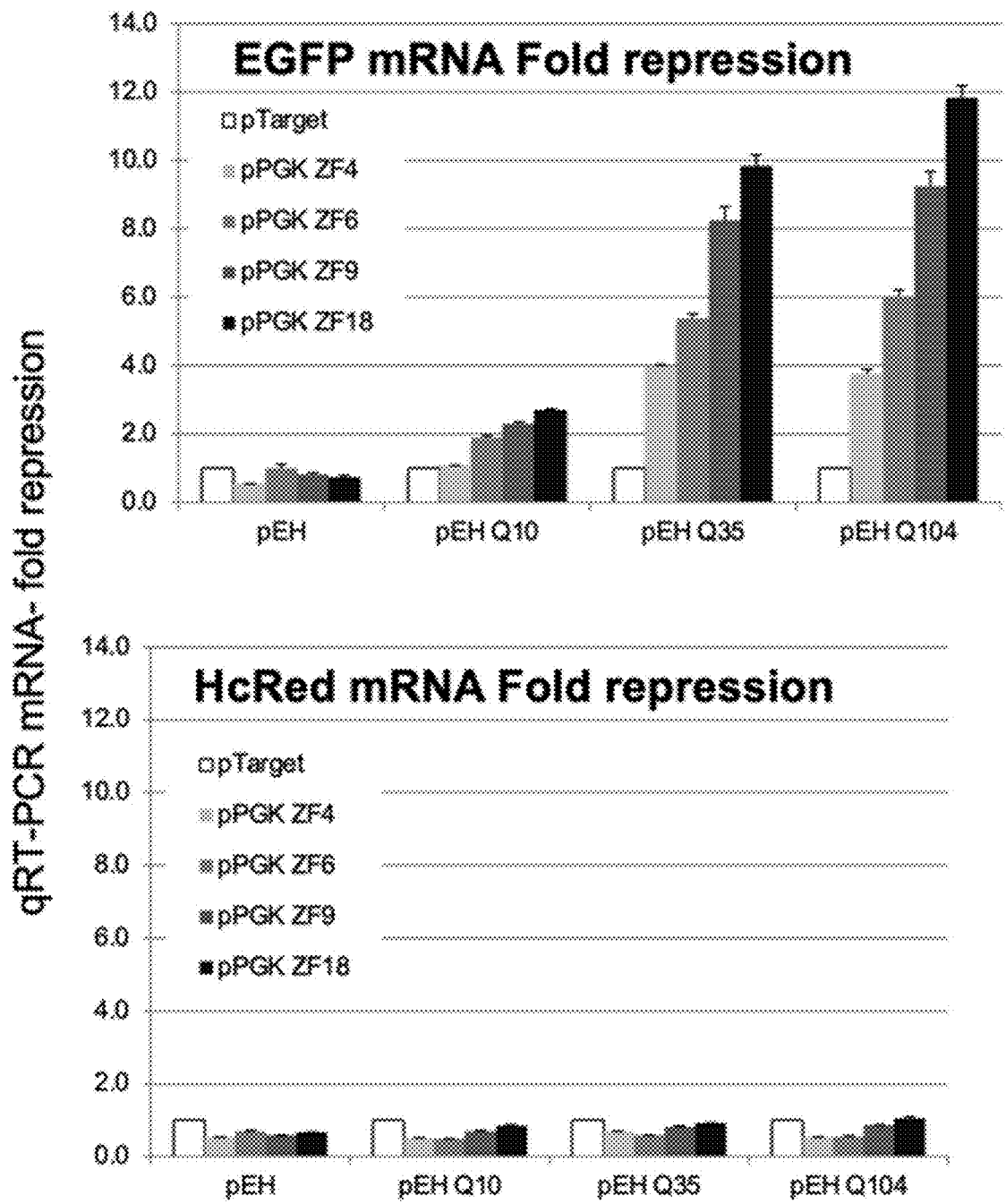
Figure 3C:
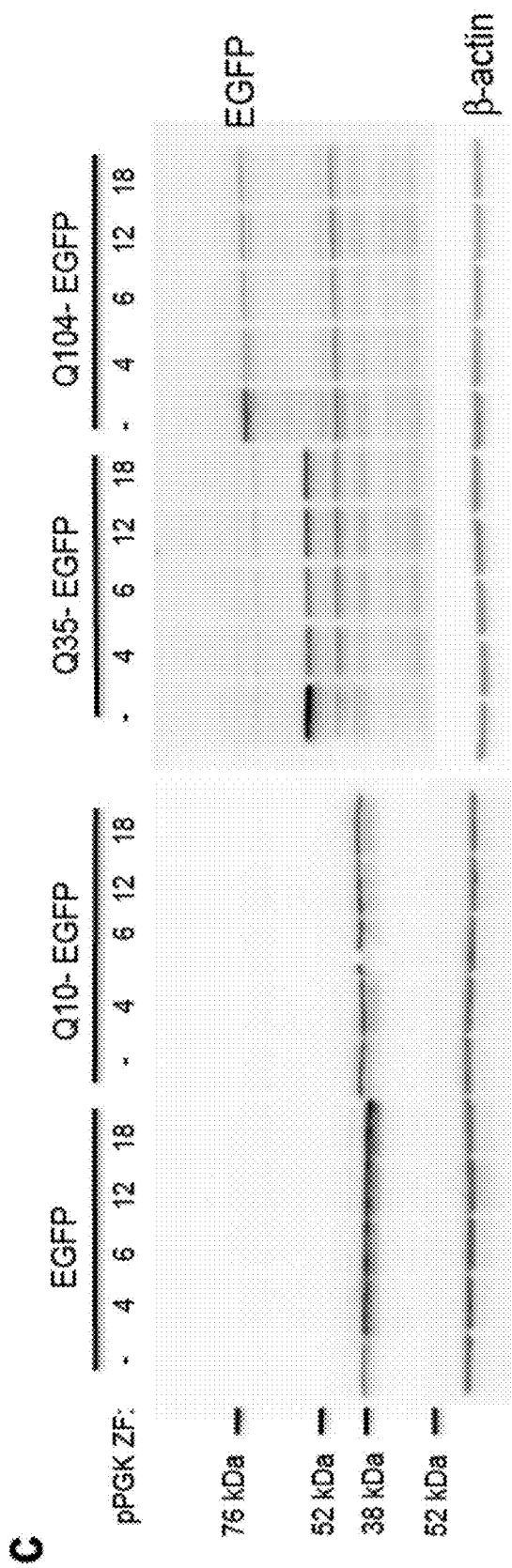

In order to check that these results were not purely specific to ZFPs under the control of the CMV promoter, equivalent tests were also carried out with the ZFPs being expressed under the control of the phosphoglycerate kinase (PGK) promoter. As illustrated in FIG. 3, essentially the same results were obtained for the naked zinc finger peptide constructs.

Importantly, no non-specific repression of HcRed was observed with naked ZFP, suggesting that specific binding of the ZFxHunt proteins to long CAG repeats is required for repression.

Thus, in transient transfection assays, naked ZFxHunt proteins specifically repressed the expression of a reporter gene containing 35 or more CAG repeats. ZFxHunt proteins fused to the Kox-1 domain had a stronger repressive effect, and reduced expression of all CAG-containing reporter genes, with the longer constructs also having a slight affect on a neighbouring control reporter gene.

TABLE 6

Kox-1 domain peptide and encoding nucleic acid sequences, and zinc finger-effector domain linker peptide and encoding nucleic acid sequences.

Kox-1 domain amino acid sequence (SEQ ID NO: 39):
LSPQHSAVTQGSIIKNKEGMDAKSLTAWSRTLVTFKDVFVDFTREEWKLL
DTAQQIVYRNVMLENYKNLVSLGYQLTKPDVILRLEKGEEPWLVEREIHQ
ETHPDSETAFEIKSSV KRAB domain from mouse ZF87 (SEQ ID NO: 40):
EEMLSFRDVAIDFSAEEWECLEPAQWNLYRDVMLENYSHLVFLGLASCKP
YLVTFLEQRQEPSVVKRPAAATVHP Zinc finger-effector domain peptide linker sequence (SEQ ID NO: 41):
LRQKDGGGSGGGGSGGGGSQLVSS Zinc finger-effector domain peptide linker sequence (SEQ ID NO: 42):
LRQKDGGGSGGGGSS Zinc finger-effector domain peptide linker sequence (SEQ ID NO: 43):
LRQKDGGGSGGGGS Example 4

Competition Binding Assays for Repression of Long CAG-Repeats

For human therapeutic use, ZFPs should preferentially repress long mutant CAG-alleles and have less effect on short wt alleles (e.g. 10 to 29-repeats; the length of wt htt varies in the human population, but is usually in this range; median=18). Therefore, a competition assay was developed to measure length-preference directly. HEK293T cells were cotransfected with three plasmids: the indicated polyQ-EGFP and polyQ-mCherry reporter vectors, together with various ZFxHunt vectors.

Figure 4:
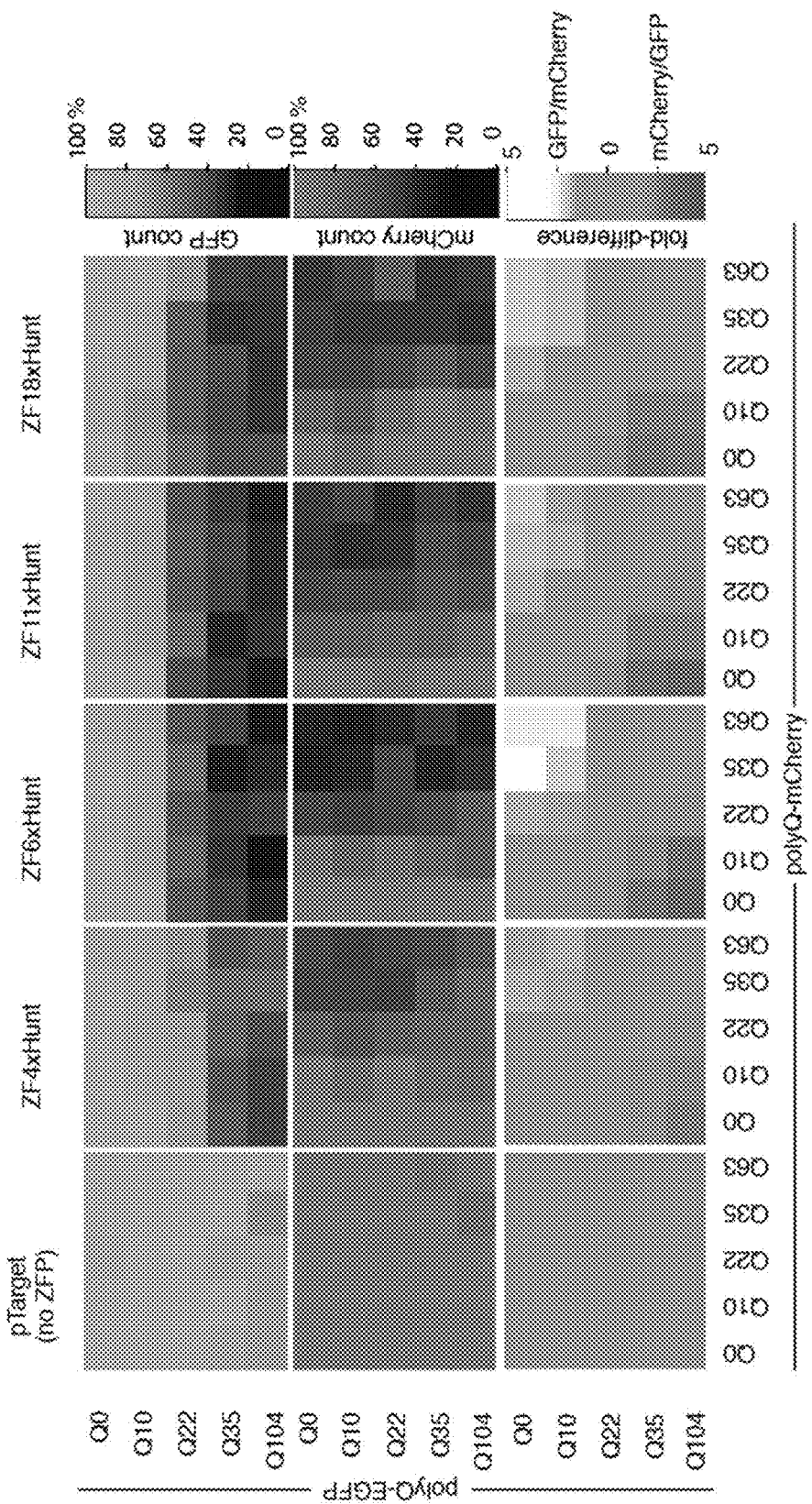
FIG. 4 ZFP competition assay against pairs of different-length CAG-repeat sequences. Each small square represents one transfection experiment, where cells simultaneously receive two reporter plasmids: poly-Q-EGFP and poly-Q-mCherry of different length CAG-repeats (Q0=no repeats; Q10=10 repeats; Q22=22 repeats; Q35=35 repeats; Q63=63 repeats; and Q104=104 repeats). Zinc finger peptides of the invention with 4-, 6-, 11- or 18-fingers were tested for their ability to reduce the number of detectable green and red cells in FACS assays (%). Top row: light grey boxes represent high levels of GFP protein expression, dark grey boxes represent low levels of GFP protein expression; middle row: light grey boxes represent high levels of mCherry protein expression, dark grey boxes represent low levels of mCherry protein expression; bottom row: light (grey) boxes represent higher levels of GFP protein expression compared to mCherry, dark grey boxes represent higher levels of mCherry protein expression compared to GFP. Similar results were obtained using ZFPs fused to the FokI nuclease domain (not shown).

The relative expression of the two reporters was measured by FACS (EGFP or mCherry positive cells), and the results are displayed in FIG. 4. In the top row, light grey boxes represent high levels of GFP protein expression, while dark grey boxes represent low levels of GFP protein expression; in the middle row, light grey boxes represent high levels of mCherry protein expression, while dark grey boxes represent low levels of mCherry protein expression; and in the bottom row, light (grey) boxes represent higher levels of GFP protein expression compared to mCherry, dark grey boxes represent higher levels of mCherry protein expression compared to GFP. The results demonstrate that longer CAG-repeats are preferentially targeted and repressed by all ZFxHunt peptides, so that cells are dominated by the expression of the shorter green or red constructs when the number of CAG-repeat sequences of their opposite counterpart is longer. This is seen directly by looking at the ratio of green-to-red expression in the bottom row, in which the top right hand corner of each grid is a lighter shade, indicating higher expression levels of GFP; and the bottom left corner of each grid is a darker shade, indicating higher expression levels of mCherry. All constructs, up to 18-finger chains demonstrate active repression of the longer CAG-repeat reporters.

It is possible that the selective inhibition of longer target sequences is at least partly due to a mass action effect (i.e. longer CAG-repeats contain more potential binding sites for the zinc finger peptides). However, it is also possible that in the case of longer arrays of zinc fingers and shorter CAG-repeat sequences, the peptides may compete with each other for the binding site, and as a consequence, the longer arrays of zinc fingers may bind more transiently or more weakly (e.g. to partial or sub-optimal recognition sequences).

Example 5

Chromosomal Repression of Mutant htt

Figure 5:
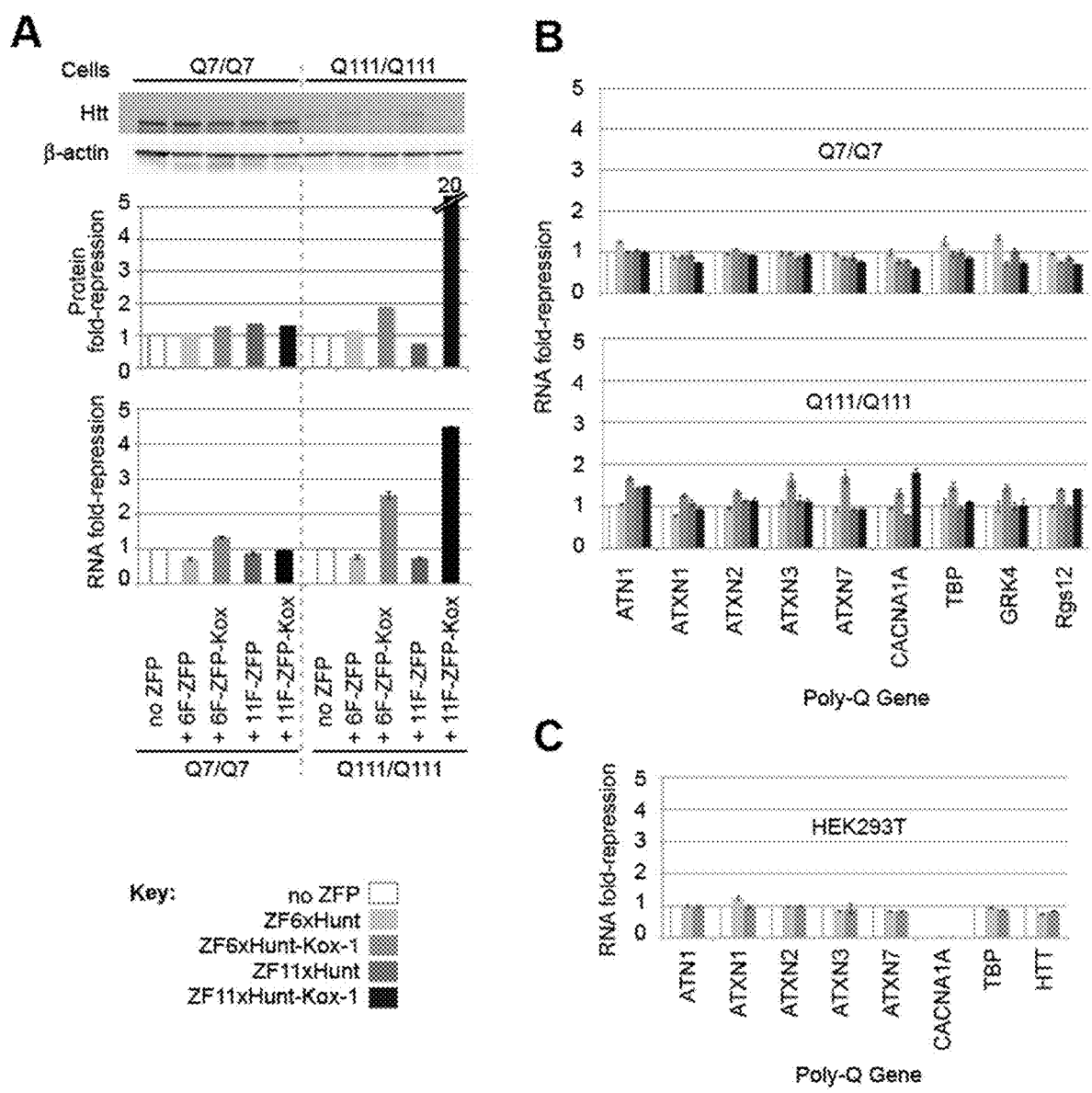
FIG. 5 Expression of chromosomal CAG-repeat genes, 20 days after retroviral ZFP delivery. Assays were carried out in wild-type (wt) mouse STHdh cells with 7 CAG-repeats associated with each copy of the Hdh gene (Q7/Q7); in poly-Q STHdh mutant mice with 111 CAG-repeats associated with each copy of the Hdh gene (Q111/Q111); and in human HEK293T, as indicated. (A) Illustrating the repression of endogenous htt by 6- and 11-finger peptides of the invention (ZF6xHunt and ZF11xHunt, respectively), with or without the Kox-1 repressor domain. Western blots for Htt (top row) were controlled with β-actin staining and quantified using ImageJ (Protein fold-repression; middle row). qRT-PCR was used to compare htt mRNA levels (RNA fold repression; bottom row). (B) Shows that the mRNA levels of other wt CAG-repeat genes are broadly unaffected. The expression levels of seven wt genes associated with CAG-repeats were tested by qRT-PCR (atrophin1: ATN1; ataxin-1, -2, -3 and -7: ATXN1, ATXN2, ATXN3 and ATXN7; calcium channel alpha 1A subunit: CACNA1A; and TATA binding protein: TBP). CAG-repeat numbers are illustrated in Table 1. Two genomic neighbours of htt (G protein-coupled receptor kinase 4: GRK4; and G-protein signaling 12: Rgs12) were also unaffected in STHdh cells. (C) The mRNA levels of the seven wt CAG genes and wt HTT (huntingtin; 21 CAG-repeats) were also broadly unaffected in HEK293T cells (N.B. CACNA1A is not expressed in HEK293T cells).

The effects of the zinc finger repressor peptides, ZF6xHunt and ZF11xHunt, on chromosomal htt genes were tested. STHdh cells (Trettel et al. (2000) *Hum. Mol. Genet.* 9(19): 2799-2809) are an established neuronal progenitor cell line from E14 striatal primordia, derived from wt mice (STHdh$^{Q7}$/Hdh$^{Q7}$), or knock-ins, where the first exon of the mouse htt gene with 7 CAG-repeats has been replaced by a human exon with 111 CAG repeats (STHdh$^{Q111}$/Hdh$^{Q111}$). STHdh cells stably expressing naked or Kox-1-fused ZF6xHunt and ZF11xHunt peptides were harvested 20 days after retroviral infection, and htt levels were analysed by western blot and qRT-PCR. The experiment was repeated independently twice, and similar results were obtained both times. The results of one experiment are displayed in FIG. 5.

As illustrated in FIG. 5A, neither protein nor RNA levels of wt htt (Q7) were reduced by naked or Kox-1 fused ZF6xHunt and ZF11xHunt. By contrast, Q111-mutant htt RNA and protein levels were repressed with ZF6xHunt-Kox-1 by up to 2.5-fold (60% reduction) and 2-fold (50% reduction), respectively. ZF11xHunt-Kox-1 showed even stronger repression, with almost 80% reduction in mRNA expression and 95% reduction in the protein levels. Naked ZF6xHunt and ZF11xHunt had less effect repressing the chromosomal mutant htt gene, suggesting that the stronger Kox-1 repression effect may be beneficial for chromosomal repression of htt.

Example 6

Specificity of Repression in Wild-Type Genomes

Normal genomes contain several endogenous genes that are known to have CAG-repeat sequences. Therefore, the potential side-effects of stably expressed ZFxHunt proteins in cells were assayed by qRT-PCR for the wt genes atrophin1, ataxin-1, ataxin-2, ataxin-3, ataxin-7, calcium channel alpha 1A subunit, and TATA binding protein, which all contain CAG-repeat sequences. The number of CAG-repeat sequences in each wild-type gene is shown in Table 7 below.

The results of these assays are displayed in FIGS. 5B and 5C. As illustrated, no adverse effects were measured in either STHdh mouse cells (FIG. 5B), or in HEK293T human cells (FIG. 5C In the latter, even human htt, which has the most wt CAG repeats in this particular cell line (21-repeats), was also not repressed.

Since Kox-1 repression spreads by establishing heterochromatin (Groner et al. *PLoS Genet* 6(3): e1000869), the effects of ZF6xHunt-Kox-1 and ZF11xHunt-Kox-1 on genes neighbouring hit, in stably-transduced STHdh cells, were also tested by qRT-PCR (FIG. 5B). The two adjacent genes, G protein-coupled receptor kinase 4, which is approximately 7 kb upstream; and G-protein signaling 12, which is approximately 188 kb downstream, were assayed and found to be unaffected by the presence of the zinc finger repressor proteins. This suggests that both of these neighbouring genes are out of the range of Kox-1 effects.

The results indicate that both ZF6xHunt-Kox-1 and ZF11xHunt-Kox-1 repression is specific for mutant htt in chromosomal loci.

TABLE 7

CAG-repeat number per gene and corresponding primer sets for qRT-PCR. Name prefixes: h = human; m = mouse. Approximate CAG repeat number for wild-type genes was obtained from Genbank® mRNA data.

| Gene | CAG repeat length | Forward primer (SEQ ID NO:) | Reverse primer (SEQ ID NO:) |
|---|---|---|---|
| EGFP | 0-104 | CCTGAAGTTCATCTGCACCA (95) | AAGTCGTGCTGCTTCATGTG (96) |
| HcRed | 0 | AGATGCTGCGGAAGAAGAAG (97) | GGTACCGTCGACTGCAGAA (98) |
| hHPRT | N/A | CTTTGCTTTCCTTGGTCAGG (99) | TATCCAACACTTCGTGGGGT (100) |
| hATN1 | 15 | GTCTCCCTCCGATCTGGATA (101) | CACACTTCCAGGGCTGTAGA (102) |
| hATXN1 | 12 | CCAGCACCGTAGAGAGGATT (103) | AGCCCTGTCCAAACACAAA (104) |
| hATXN2 | 13 | GACGCAGCTGAGCAAGTTAG (105) | GAAGGAACGTGGGTTGAACT (106) |
| hATXN3 | 7 | AGAGCTTCGGAAGAGACGAG (107) | ACTCCCAAGTGCTCCTGAAC (108) |
| hATXN7 | 10 | AACTGTGTGGCTCACTCTGG (109) | TGGGAAGATGTTACCGTTGA (110) |
| hCACNA1A | 13 | GGGAACTACACCCTCCTGAA (111) | CGCTGCTTCTTCTTCCTCTT (112) |
| hTBP | 19 | ACGCCGAATATAATCCCAAG (113) | CTTCACTCTTGGCTCCTGTG (114) |
| hHtt | 21 | CAGATGTCAGAATGGTGGCT (115) | GCCTTGGAAGATTAGAATCCA (116) |
| mATN1 | 3 | CACCTGCCTCCACCTCATGGC (117) | ATGCTCCTTGGGGGCCCTGG (118) |
| mATXN1 | 2 | TGTGGAGAGAATCGAGGAGA (119) | CAGCCCTGTCCAAATACAAA (120) |
| mATXN2 | 6 | ATCCCAATGCAAAGGAGTTC (121) | CTGCTGATGACCCACCATAG (122) |
| mATXN3 | 5 | ACCTCGCACTATTCTTGGCT (123) | TGCATCTGTTGGACCTTGAT (124) |
| mATXN7 | 5 | TGCCCGTGTTCCTCACCGGA (125) | GCGCGGAGACAGTGGTTGCT (126) |
| mCACNA1A | 2 | CACTGGCAATAGCAAAGGAA (127) | TTCTTGAGCGAGTTCACCAC (128) |
| mTBP | 3 | ACTTCGTGCAAGAAATGCTG (129) | GCTCATAGCTCTTGGCTCCT (130) |
| mGRK4 | N/A | TCCTGGCTTTGAGGAGCCGA (131) | CCACAGCACAGCTCTGCAGCAT (132) |
| mRgs12 | N/A | GGGGGCTCAAGCAGGCATGG (133) | GGGAGCCAGCCTCCGAGTCA (134) |
| mHtt | 7 or 111 | CAGATGTCAGAATGGTGGCT (135) | GCCTTGGAAGATTAGAATCCA (136) |
| mHPRT | N/A | GGTTAAGCAGTACAGCCCCA (137) | AGAGGTCCTTTTCACCAGCA (138) |

TABLE 7-continued

CAG-repeat number per gene and corresponding primer sets for qRT-PCR.
Name prefixes: h = human; m = mouse. Approximate CAG repeat number
for wild-type genes was obtained from Genbank® mRNA data.

| Gene | CAG repeat length | Forward primer (SEQ ID NO:) | Reverse primer (SEQ ID NO:) |
|---|---|---|---|
| M13 | N/A | GTAAAACGACGGCCAG (139) | CAGGAAACAGCTATGAC (140) |

Example 7

Cell Toxicity Assay

Since it would be advantageous for a ZFP-repressor therapy to have low toxicity, dye-labelling cell viability assays were performed to test the (non-specific) toxicity of the ZFPs.

Figure 6:
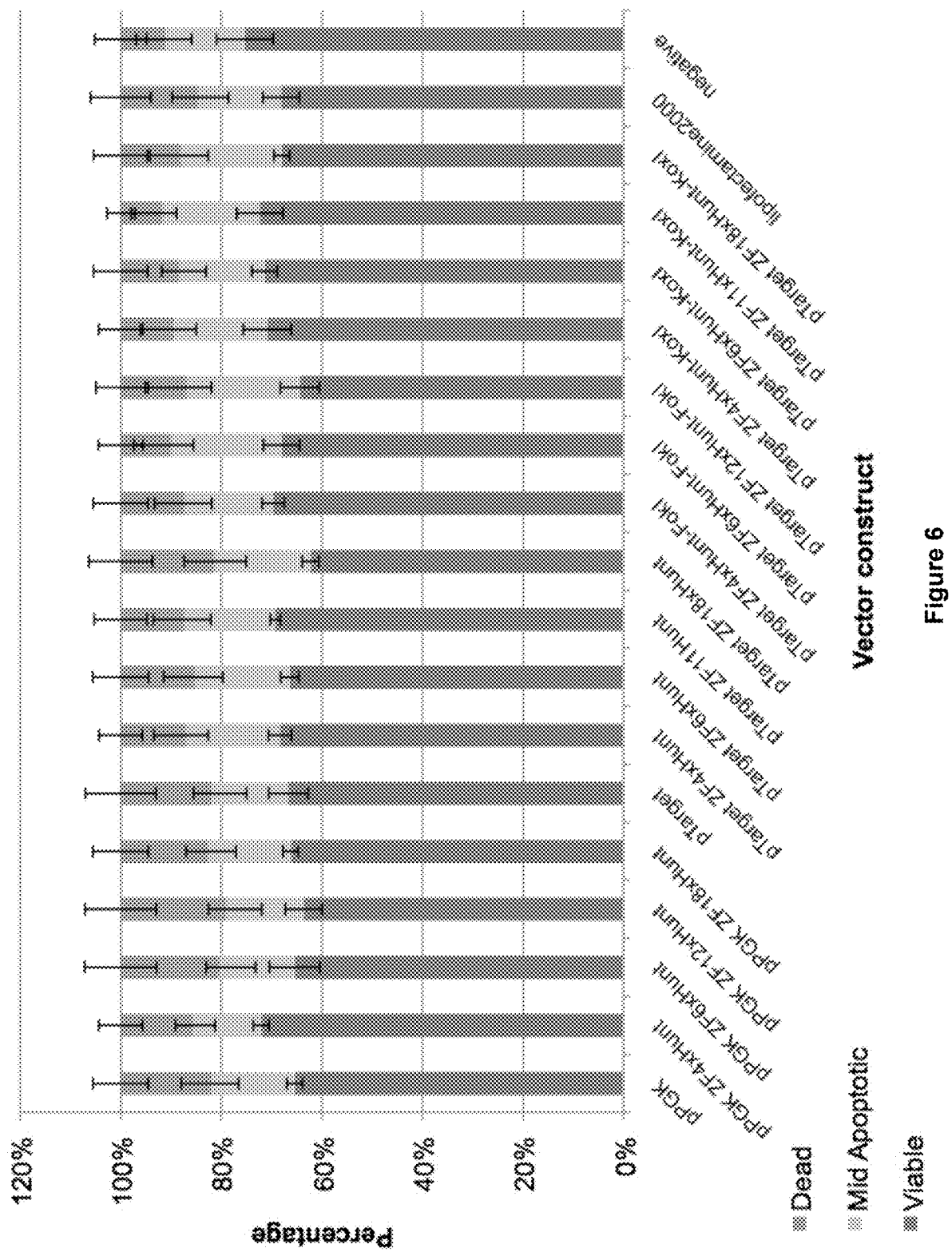
FIG. 6 ZFP toxicity assay. HEK-293T cells were transfected with the indicated vector constructs. As a control Lipofectamine2000™ only or untransfected cells (negative) were used. Cytotoxicity was analysed using Guava® Cell Toxicity (PCA) Assay and the bars show the percentage of dead mid-apoptotic and viable cells. The results are an average of at least 3 independent experiments.

HEK-293T cells were transfected with 400 ng of the indicated vector constructs using Lipofectamine2000™ and harvested 48 hours after transfection. As a control Lipofectamine2000™-only or untransfected cells (negative) were used. Cytotoxicity was analysed using the Guava® Cell Toxicity (PCA) Assay according to the manufacturer's instructions. The results are presented as the percentage of dead, mid-apoptotic and viable cells (see FIG. 6), in which the bars express results of at least 3 independent experiments.

These data show that no statistically significant toxicity effects were produced in cells expressing zinc finger peptides of the invention, as compared to control experiments. Moreover, ZF6xHunt-Kox-1 and ZF11xHunt-Kox-1 were tolerated for over 20 days (approximately 3 weeks) following stable retroviral transfection, without any apparent adverse cellular effects. Overall, the repressor properties of these zinc finger peptides and their potential for stable expression, particularly of ZF6xHunt-Kox-1 and ZF11xHunt-Kox-1 proteins, suggest that the peptides of the invention have significant potential for gene therapeutic applications.

Example 8

Repression of Mutant Ha Gene in a Mouse Model for Huntington's Disease

As described above, long zinc finger peptide chains having 6 or more adjacent zinc finger domains were designed with the aim of specifically targeting CAG trinucleotide repeat sequences. Beneficially, it was also found that such long zinc finger peptides, especially those having 11 or more (e.g. 11, 12 or 18) adjacent zinc finger domains preferentially repressed target genes with approximately 35 or more CAG-repeats over target sequences having lower repeat numbers. It was also shown that stable expression of these zinc finger proteins in a model HD cell line reduced chromosomal expression of the mutant htt gene (with 111 CAG-repeats), at both the protein and mRNA level. Meanwhile, the shorter wild-type htt gene (with 7 CAG-repeats in this particular mouse cell line) was unaffected, as were other wild-type genomic CAG repeat genes.

R6/2 mice are a well-established animal model for the study of HD and potential therapeutics. These mice express exon 1 of the human HD gene with approximately 150 CAG repeats. R6/2 mice have an early onset of HD symptoms and a fast progression of the disease, showing a life expectancy of 12 to 17 weeks (Gil & Rego (2009) Brain Res. Rev. 59: 410-431).

Using this model, the zinc finger proteins were assayed for their ability to reduce expression of mutant htt in a transgenic mouse model of HD, accordingly to the timeline shown below.

First, the ZF6xHunt-Kox-1, ZF11xHunt-Kox-1 and ZF12xHunt-Kox-1 repressor proteins were inserted into adeno-associated virus (AAV) vectors (AAV2/1 subtype; Molecular Therapy (2004) 10: 302-317). In parallel experiments, the zinc finger-AAV vectors were injected into the striatum of R6/2 mice in order to mediate expression of ZFP-Kox-1 fusion proteins in striatum cells. The ability of expressed ZFP-Kox-1 fusion proteins in striatum cells to reduce HD symptoms in R6/2 mice was assessed over a period of up to 12 weeks by periodically assessing the behaviour and symptoms of zinc finger-AAV infected R6/2 mice, as well as the expression levels of the mutant htt protein, in comparison to control R6/2 mice infected with a AAV-GFP control vector.

Timeline:
  Week 0: —New born R6/2 mice.
  Week 4: —Stereotaxic injection into the striatum of R6/2 mice with AAV—e.g. ZF6xHunt-Kox-1-ires-GFP and control AAV-GFP.
  Week 4 to 12: —Weekly behavioural test: accelerating rotarod test, hind-limb clasping and stride length analysis.
    —Every two weeks: sacrifice of mice for qRT-PCR to check for reduction of expression of mutant HD fragments and immunohistochemistry to show a reduction in polyQ aggregates and expression of other neuronal markers such as DARPP-32 and NeuN.

ZFP-Kox1 fusion proteins were shown to reduce mutant htt protein expression, and improve motor and neuropathological abnormalities of R6/2 mice in comparison to negative controls.

Example 9

Striatal Delivery of Zinc Fingers in R6/2 Mice Causes Dose-Dependent Repression of Mutant Huntingtin and Attenuates Disease Phenotypes The ZF11xHunt-Kox-1 peptide was shown to be effective in inhibiting mutant htt expression in the STHdh model cell line (Example 5). Therefore, to test the ability of these zinc finger peptides to treat/alleviate HD in vivo in an HD-mouse model AAV virus was used to deliver ZF11xHunt-Kox-1 to the affected brain area in R6/2 mice.

ZFxHunt Fused to Kox-1 Reduces Expression of Mutant Htt In Vivo

Female R6/2 mice were stereotaxically injected at 4 weeks of age with AAV2/1 virus expressing ZF11xHunt- Kox-1, under a CAG-promoter with WPRE elements (Garg et al. (2004) *J. Immunol.*, 173: 550-558). Injections were into the striatum of one brain hemisphere, with AAV2/1-GFP control injections into the other.

Figure 7:
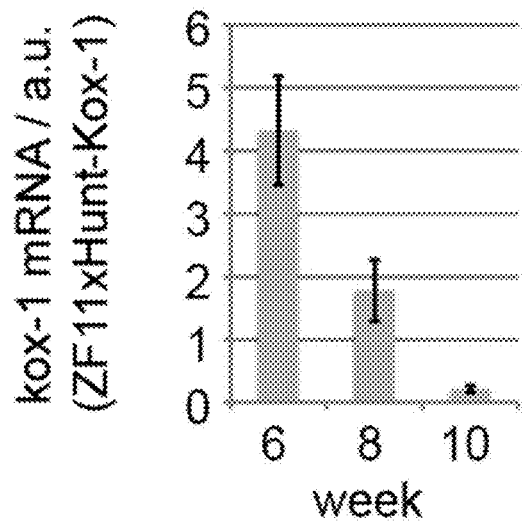
FIG. 7 Illustrates qRT-PCR data quantifying mRNA levels in mouse striatal samples injected with ZF11xHunt-Kox-1. (A) Measurement of Kox-1 levels reveals peak zinc finger expression at 6 weeks with a steady decline thereafter. (B) Mutant huntingtin repression (mut htt) was repressed most at week 6 and is no longer significantly repressed by week 10. (C) Zinc finger treatment has no significant effect on wild-type huntingtin levels (wt htt).
Figure 7:
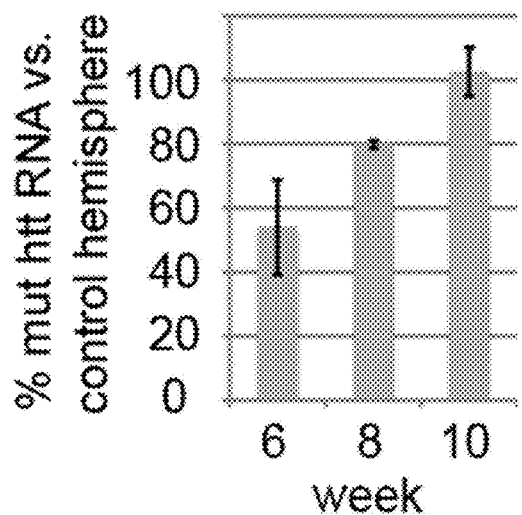
Figure 7:
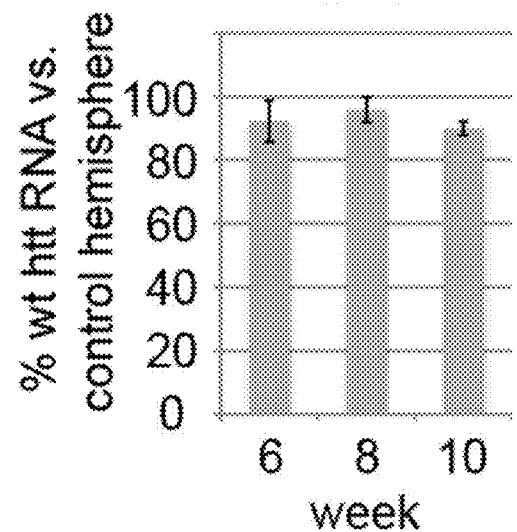

Analysis by qRT-PCR showed the highest expression levels of ZF11xHunt-Kox-1 in the injected striatum of 6-week-old mice (see FIG. 7A). At the same time, the levels of the mutant htt transgene mRNA in these portions of the brain were reduced by over 45% (on average), as compared to measured levels in the control hemisphere (see FIG. 7B).

Furthermore, in linear regression analysis, it was noted that ZF11xHunt-Kox-1 mRNA levels correlated negatively and closely with mutant htt mRNA levels (r-squared=0.79; p=0.0072), which is consistent with an in vivo dose-dependent repression of mutant htt by the zinc finger construct.

Repression levels of mutant htt mRNA reached up to 60% in some of the mice analysed at week 6. Notably, this repression was specific for mutant htt, since wt htt was unaltered at all time points analysed (see FIG. 7C). However, expression of the ZFP was significantly reduced by week 8, and concomitantly, repression levels of the htt gene, although still statistically-significant, dropped to 20% in comparison with the control hemisphere. By 10 weeks post-injection the ZFP expression levels were greatly reduced, and mutant htt levels were not reduced compared to the control hemisphere.

Similar results were obtained in mice injected in only one hemisphere with AAV-ZF11xHunt-Kox-1, when compared to non-injected control hemispheres (data not shown).

It is thought that immunological reactions to the heterologous expressed zinc finger peptides was responsible for the notable reduction in zinc finger expression in the brain of the mice, as well as the resulting reduction in repression of mutant htt protein. In this regard, significant cell death could be seen in injected brain sections, typically from 4 to 6 weeks post injection.

ZFxHunt-Kox-1 Delays the Expression of Behavioral Symptoms in R6/2 Mice

In a double blind experiment, male R6/2 mice and their wild-type littermates were treated in both hemispheres, at 4 weeks of age, with either AAV2/1-ZF11xHunt-Kox-1 or AAV2/1-GFP (i.e. lacking a zinc finger repression protein). The general condition of the mice (body weight, grip strength, clasping behavior), and their performance in different behavioural motor tests (accelerating rotarod, activity in an open field, paw print) were analysed twice a month, from week 3 of age (pre-surgery).

Figure 8A:
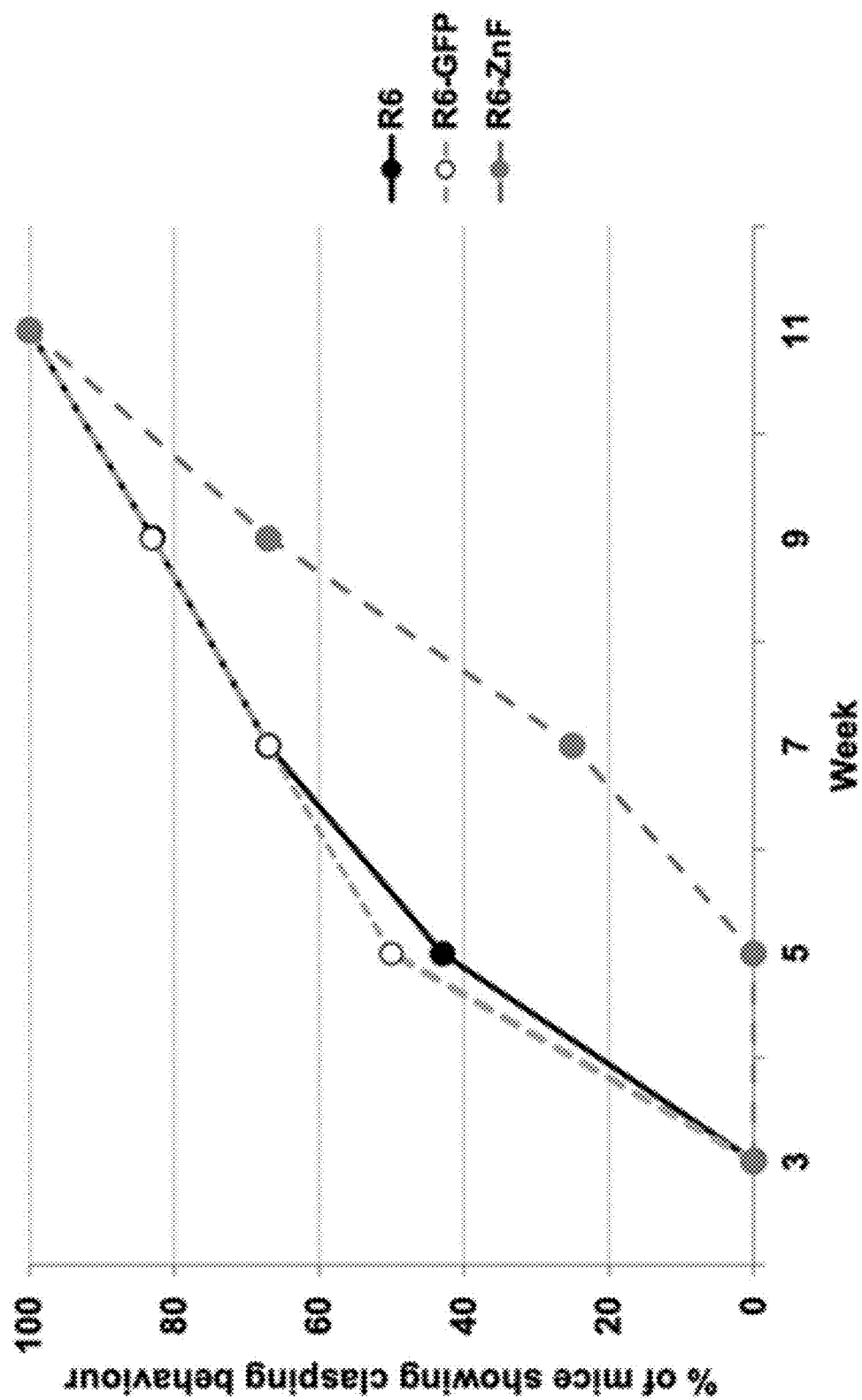
FIG. 8 Behavioural tests on the performance and general condition of R6/2 and wt male mice treated with either ZFP or GFP. (A) Graph showing results of clasping behavioural test. ZFP treatment resulted in a delay in the onset of clasping behaviour when compared with GFP-treated and non-operated R6/2 control mice. (B) Graph showing results of open field test. Increase of time spent in the centre of the open field was also delayed by the ZFP treatment at week 7. A significant difference was observed in R6/2-GFP mice at week 7 relative to all the other groups, but the effect had largely disappeared by week 9. (C) Graph showing results of rotarod test. The decline in the rotarod performance from pre-surgery levels was attenuated by ZFP. An ANOVA with repeated measures revealed that the R6/2-GFP group differed from WT-GFP, whereas R6/2-ZFP did not differ from its control WT-ZFP. (D) Graph showing body weight gain over the course of the experiment. Body weight gain was similar between both ZFP and GFP-treated mice, and started declining after week 7 of age, with no effect from the treatment. (E) Bar chart showing survival time. Survival was not significantly different between the groups of R6/2 mice. All data are presented as mean±S.E.M. *, p<0.01. **, p<0.001.

Consistent with the observed peak of repression at 6-weeks of age (FIG. 8B), the greatest improvements in HD symptoms were found between weeks 5 and 7. For example, ZF11xHunt-Kox-1 clearly delayed the onset of clasping behaviour in comparison to AAV2/1-GFP-treated or non-operated R6/2 control mice, as shown in FIG. 8A. Thus, whereas both GFP-treated and untreated R6/2 mice started clasping at week 5, this disease-behaviour was not detected at this time in any of the ZF11xHunt-Kox-1 treated mice at 5 weeks of age. Furthermore, by week 7, when 67% of the mice in the control groups exhibited clasping, only 25% of the treated mice exhibited such behaviour.

Figure 8B:
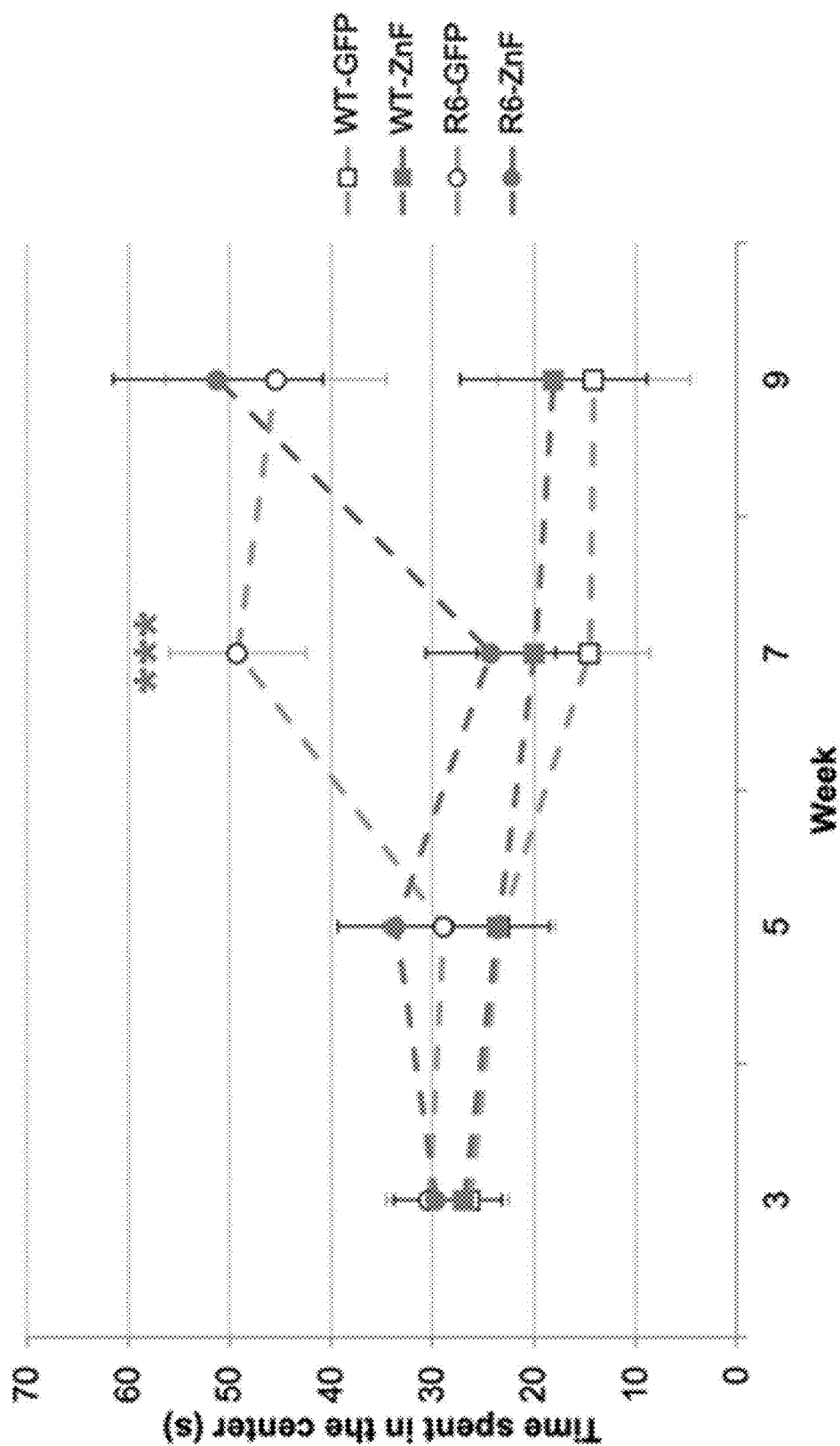

In the open field test, distance travelled and mean speed did not vary between treated and untreated R6/2 mice. However, the time spent in the centre of the open field at week 7 was increased in GFP-treated mice, with respect to both groups of wild-type mice, but not in ZF11xHunt-Kox-1 treated mice (Repeated Measures ANOVA: Group×Week significant interaction, $p<0.01$; post-hoc pair-wise comparisons at week 7: WT-GFP versus R6/2-GFP, $p<0.001$; WT-ZF versus R6/2-ZF, n.s.), as indicated in FIG. 8B. This effect might be due to the difficulty for untreated R6/2 mice in initiating the movement of escape towards the periphery of the open field, or simply due to a decreased reactivity.

Figure 8C:
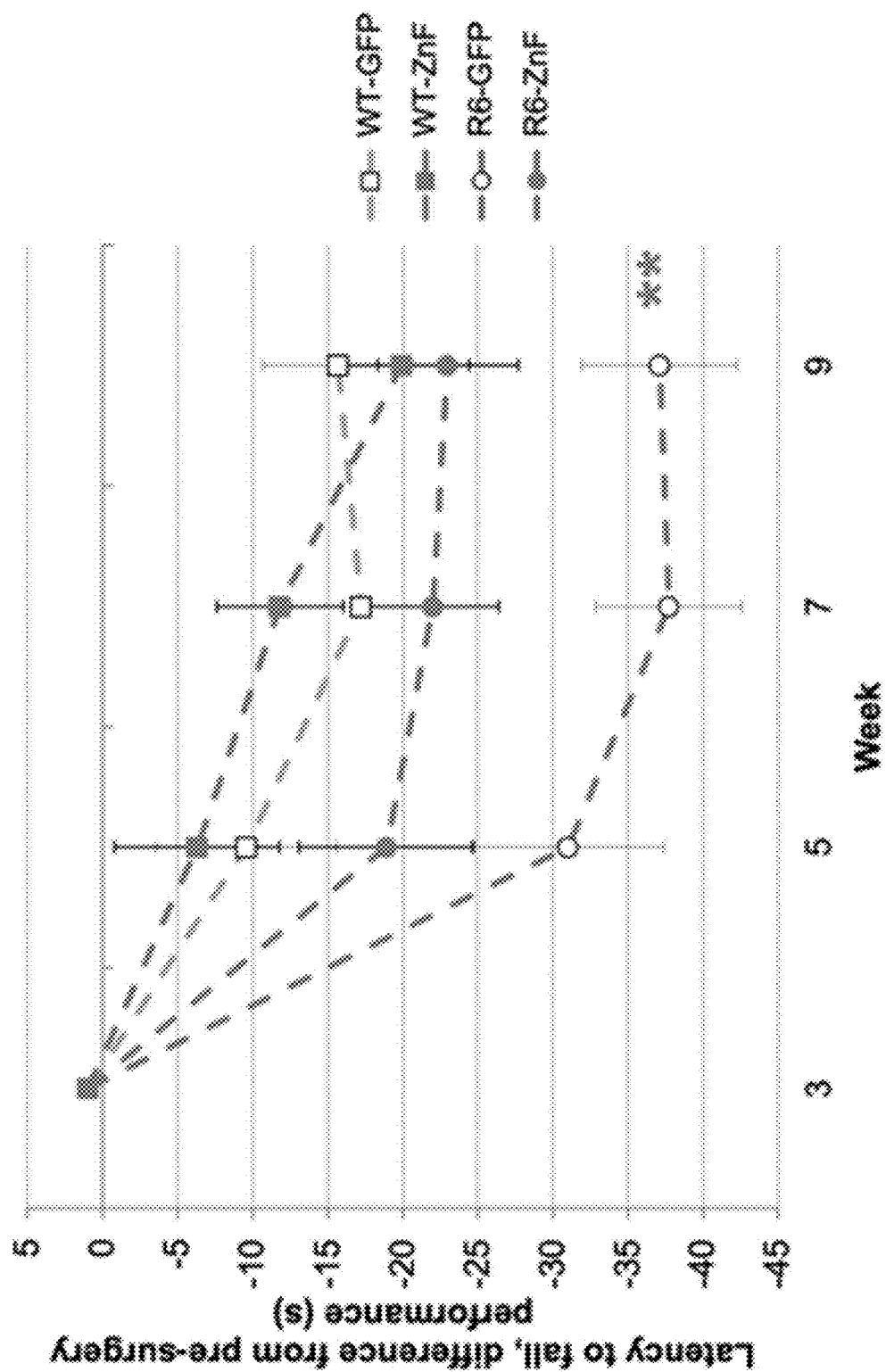

In the accelerating rotarod test, treatment with ZF11xHunt-Kox-1 was also found to attenuate the decline of performance with age, with respect to pre-surgery levels (Repeated measures ANOVA: significant main effect of Group, $p<0.05$; post-hoc comparisons between groups: WT-GFP vs R6/GFP, $p<0.05$; WT-ZF vs R6/2-ZF, n.s.), and the results are displayed in FIG. 8C.

Figure 8D:
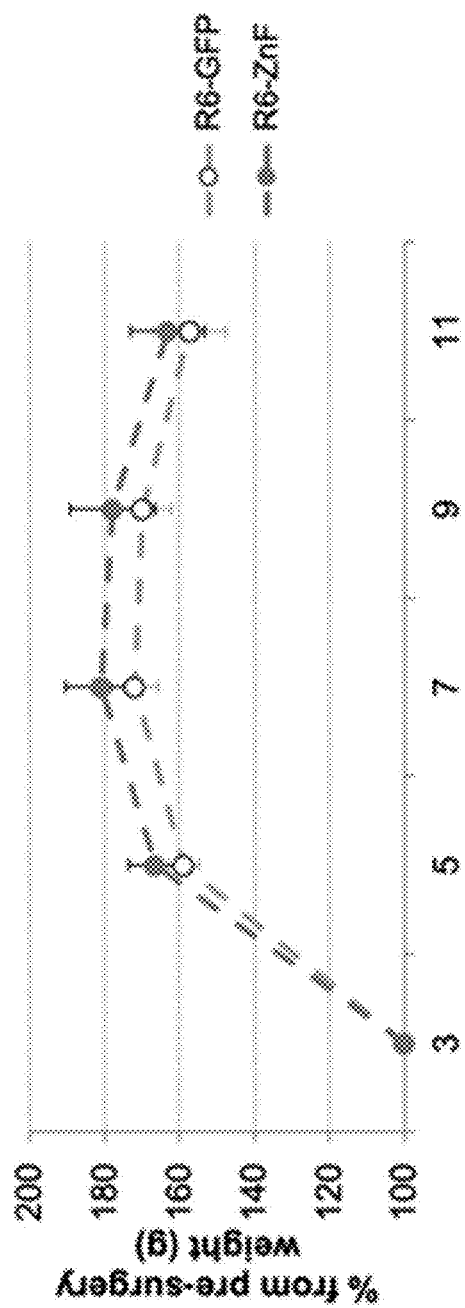
Figure 8E:
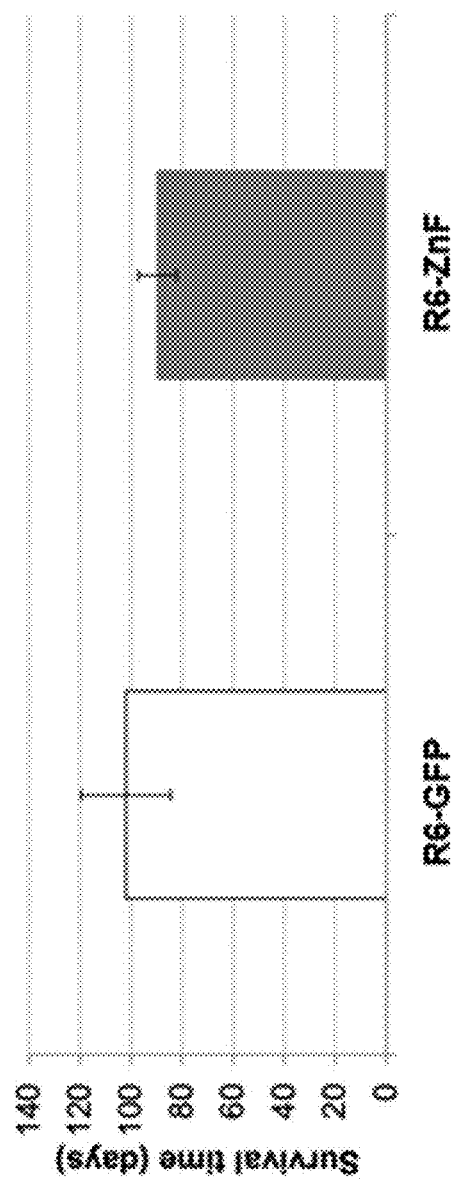

However, the grip strength and gait parameters measured in the paw print test did not reveal any notable difference between the groups, and neither did weight loss or survival time (see FIG. 8D).

Thus, the in vivo data in Huntington's disease models are consistent with a partial improvement in symptoms due to zinc finger repressor protein expression, which was coincident with a peak in zinc finger repression at approx. 6 weeks. However, the loss in ZFP expression over time (which is believed to be due to adverse toxicity and immunological effects which begin in about the fourth week post treatment), allowed the symptoms of HD to return in the treated mice, and indicated that control and treatment of symptoms in this model using these zinc finger constructs is transient: i.e. dependent on ZFP-repressor expression in these tests. Hence, the data provided here demonstrates both zinc finger-mediated repression of the htt gene in vivo, and partial disease phenotype amelioration.

Although the CAG-WPRE system is already designed to be an improvement on previous expression constructs (Garg et al. (2004) *J. Immunol.*, 173: 550-558), it is possible that further improvements might be achievable if zinc finger expression level and duration were increased.

Example 10

ZFxHunt Sequence Variants for Improved Viral Packaging

The QRATLQR (SEQ ID NO: 69) zinc finger helix was rationally designed, as described elsewhere in this document, and was demonstrated to bind htt DNA specifically with high affinity, when concatenated into long ZFP chains. However, this necessitates making highly-repetitive DNA and protein expression constructs, which in some cases may be suboptimal for viral packaging in AAV2 gene therapy applications.

Therefore, to devise a solution to this potential problem we decided to make a number of variants of the ZFP that conserve the desired nucleic acid recognition/DNA-binding functionality of the ZFPs described herein. Accordingly, the amino acid sequences of the nucleic acid recognition helices were varied while having regard to known zinc finger-nucleic acid recognition rules (e.g. as reviewed in Pabo et al. (2001), *Annu. Rev. Biochem.* 70: 313-340).

The present inventors also found that it was possible to vary ZFP backbone sequences conservatively without affecting zinc finger functionality. Therefore, in one or more zinc finger domains, the backbone residues forming the beta-beta-alpha-fold were varied to avoid undesirable repetition of sequences.

Furthermore, as already discussed above, in other embodiments the ZFP linker sequences between adjacent zinc finger domains may also be varied in sequence, if desired.

In this Example, in order to optimise viral packaging several 10 ZFxHunt variants were made, including the sequence exemplified below (SEQ ID NO: 141), which has altered zinc finger backbones and α-helices compared to ZFxHunt peptides having 6, 11, 12 and 18 zinc finger domains as described above, and tested for binding to the appropriate CAG-repeat target sequences. The altered backbones were designed having regard to different DNA-binding zinc finger sequences, including fingers from wild-type Zif268 and sp1. Furthermore, in order to reduce AAV2 construct size by approx. 240 bp, the FLAG&-epitope tag and one ZFxHunt domain were also removed, resulting in a viral package of optimum size encoding a 10-zinc finger peptide.

Figure 9:
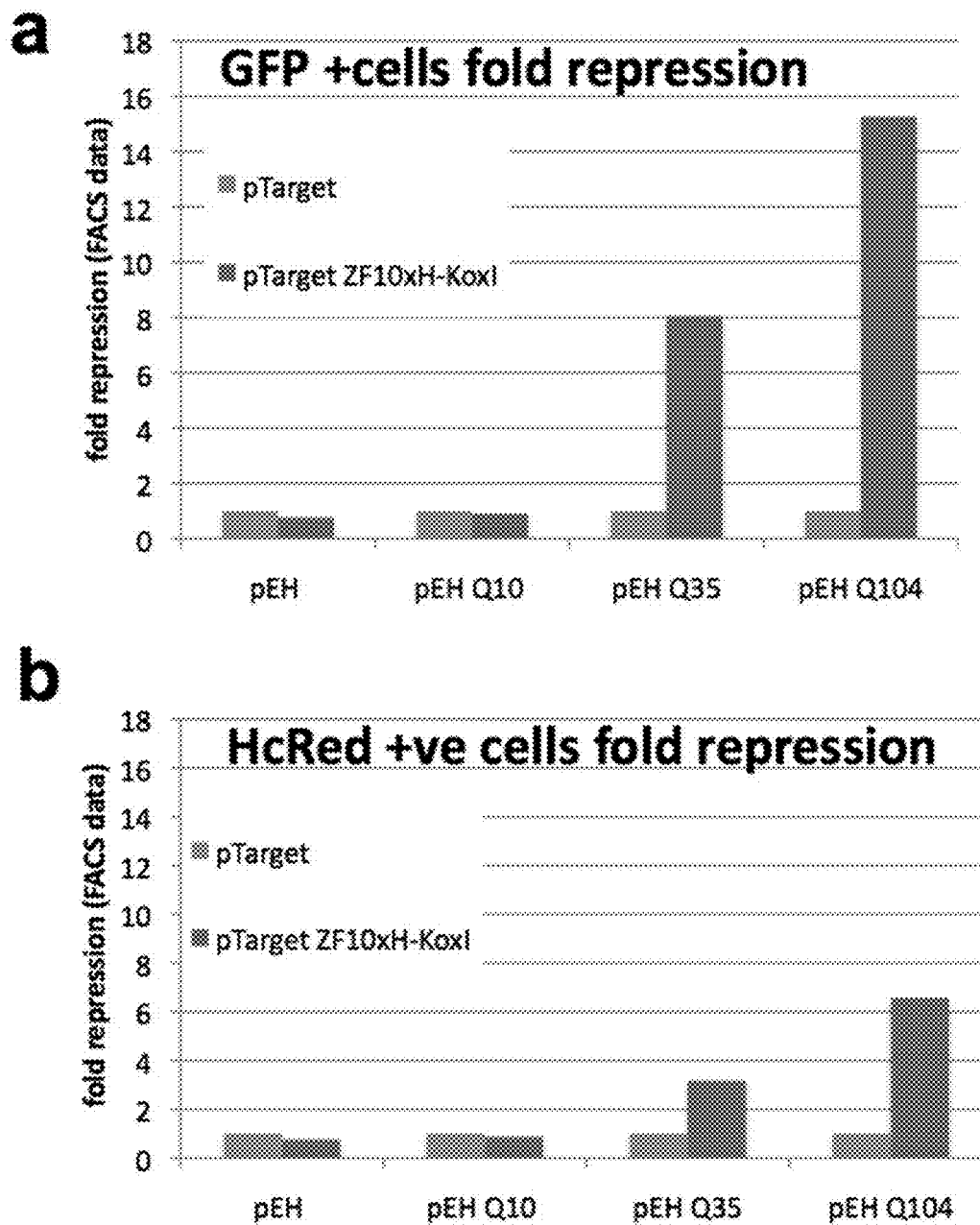
FIG. 9 Repression of poly-CAG constructs by ZF10xHunt containing conservative variant sequences in the nucleic acid recognition helix. An episomal assay was used including transient transfection followed by FACS for fluorescent cells. The poly-CAG-GFP reporter constructs code for 0 (pEH), 10 (Q10), 35 (Q35), and 104 (Q104) CAG-repeats, respectively. (a) ZF10xHunt-Kox-1 zinc fingers repress the fused GFP reporter gene. For comparison, the pTarget™ control contains no zinc fingers. (b) Kox-1-ZFP fusions also slightly repress a control HcRed gene on the same plasmid.

The resultant 10-zinc finger peptide (ZF10xHunt) targets and binds repetitive CAG sequences with high affinity and specificity, as do the previously described ZFPs. Moreover, the ZF10xHunt ZFP was shown to retain strong HTT-repression activity in episomal assays, as shown in FIG. 9. An episomal assay was used, which involved transient transfection followed by FACS for fluorescent cells. The poly-CAG-GFP reporter constructs code for 0 (pEH), 10 (Q10), 35 (Q35), and 104 (Q104) CAG-repeats, respectively. As shown in FIG. 9a ZF10xHunt-Kox-1 zinc fingers repress the fused GFP reporter gene. For comparison, the pTarget™ control contains no zinc fingers. However, as shown in FIG. 9b, the Kox-1-ZFP fusions also slightly repressed a control HcRed gene on the same plasmid, which effect is likely to be due to the recruitment of chromatin repression factors.

TABLE 8

ZF10xHunt amino acid sequences. In amino acid sequences recognition sequences are underlined and linker sequences are shown in bold. The mutated amino acids in the recognition sequences are shown in lowercase. The full repressor protein includes the linker and Kox-1 sequence at the C-terminus of the zinc finger peptide.

ZF10xHunt amino acid sequence (SEQ ID NO: 141)
YACPVESCDRRFSQRATLtRHIRTH TGQKP
FQCRI    CMRNFSQRATLsRHIRTH QNKKGS
HICHIQGCGKVYGQRATLQRHLRWH TGERP
FMCTWSYCGKRFTQRATLQRHKRTH LRQKDGERP
YACPVESCDRRFSQRATLsRHIRTH TGEKP
YKCPE  CGKSFSQRATLQRHQRTH TGSERP
FMCNWSYCGKRFTQRATLtRHKRTH TGEKP
FACPE  CPKRFMQRATLQRHIKTH TGSEKP
FQCRI    CMRNFSQRATLQRHIRTH TGERP
FACDI   CGRKFAQRATLQRHTKIH ZF10xHunt C-terminal linker and Kox-1 repressor peptide (SEQ ID NO: 142)
LRQKDA PKKKRKV GGS
LSPQHSAVTQGSIIKNKEGMDAKSLTAWSRTLVTFKDVFVDFTREEWKLL
DTAQQIVYRNVMLENYKNLVSLGYQLTKPDVILRLEKGEEPWLVEREIHQ
ETHPDSETAFEIKSSV*

Example 11

Zinc Finger Designs for Reduced Immunotoxicity

Whilst the zinc finger mutations/modifications described in Example 10 above may improve viral packaging, for example, in part by providing a less repetitive nucleic acid sequence for packaging within a virus; the resulting zinc finger peptide, when expressed, is necessarily also more diversified than previously.

Based on further investigations into heterologous zinc finger expression in vivo we have now discovered that this variability in peptide sequence may be disadvantageous for long term use in vivo due to zinc finger toxicity and immunogenicity (e.g. immunotoxicity). In this regard, we believe that the increased number of non-wild-type peptide sequences that result from the incorporation of sequence variability increasing the number of 'foreign' epitopes that may be detected by the animal body following administration of expression constructs, such as AAV vectors.

It was therefore decided to redesign the zinc finger peptides and repressor constructs described in the above Examples with the aim of reducing immunological reactions to the heterologous peptides when expressed in mice and humans.

In the first embodiments, the 11 zinc finger peptide ZF11xHunt-Kox-1 (see also Garriga et al., 2012), hereafter named ZF-Kox-1, was redesigned to create a series of 'mousified' and 'humanised' zinc finger peptides to reduce potential immunogenicity and toxicity in vivo. According to this embodiment, the main new design constraints were that the modified zinc finger peptide sequences should match host protein sequences as closely as possible, while maintaining poly(CAG) binding activity.

The aim of 'humanisation' or 'mousification' was to minimise the amino acid sequence differences between the artificial zinc finger peptide sequences designed to bind poly(CAG) DNA, and the naturally-occurring zinc finger peptide sequence of Zif268, which naturally binds GCG-TGG-GCG (Pavletich, 1991). As previously described, advantageously, the parent zinc finger scaffold proteins of Zif268 are almost identical in mouse and human (SEQ ID NO: 47 and SEQ ID NO: 48, respectively) and so one host optimised zinc finger design might have the potential to be used for both species. Herein, the notation mZF is used to denote the mousified zinc finger peptides and the notation hZF is used to denote humanised zinc finger peptides.

In this Example, in order to reduce the potential of the zinc finger peptides to create 'foreign' epitopes, the Kox-1 repressor domain of the hZF peptide was modified (see FIG. 10) by the removal of FLAGS epitope tags and the substitution of other effector domains, such as the nuclear localisation signal and KRAB repressors (previously from SV40), to human analogues. In addition, the zinc finger recognition helices and zinc finger linkers were modified to make them as close as possible to the human Zif268 transcription factor sequence (SEQ ID NO: 48; Pavletich, 1991). As previously described, these modifications were carried out within the constraint of retaining CAG-binding activity; and zinc finger ELISA experiments were used to monitor and guide this process (Isalan, 2001).

In the first instance, a human or mouse host-optimised peptide sequence was designed that retained the advantageous structure of the 11-zinc finger peptide described in Examples 1 to 10 as closely as possible so as to maintain the maximum possible DNA-binding affinity.

In one embodiment, in place of the zinc finger recognition sequence QRATLQR (SEQ ID NO: 69), the recognition sequence QSADLTR (SEQ ID NO: 2) was used for all 11 zinc finger domains of the protein. The resultant zinc finger peptide (11-zinc finger peptide 2) has the amino acid sequence of SEQ ID NO: 31, and the full zinc finger repressor protein has the sequence of SEQ ID NO: 49. SEQ ID NO: 31 has 33 out of 331 differences to the starting non-humanised starting peptide, which are indicated in bold and underlined in Table 9 below. As indicated, all highlighted differences were chosen to make the zinc finger peptide sequence closer to the wild-type human Zif268 (SEQ ID NO: 48) or mouse (SEQ ID NO: 47), while retaining poly(CAG) DNA binding.

In another embodiment (11-zinc finger peptide 3; SEQ ID NO: 33), further design changes were conducted to allow even closer host matching. In this embodiment, alpha helix recognition sequences were further modified along with linker sequences to be still closer to the natural human Zif268 sequence, while retaining effective binding to the target nucleic acid sequence poly(CAG) through the recognition alpha helices. In this embodiment, Fingers 1, 2, 4, 6, 8 and 10 had the recognition sequence of SEQ ID NO: 2, while Fingers 3, 5, 7, 9 and 11 had the recognition sequence of SEQ ID NO: 5 (QSADRKR). Furthermore, the linker sequences between Fingers 1 and 2, between Fingers 3 and 4, between Fingers 7 and 8 and between Fingers 9 and 10 are modified to the sequence TGSQKP (SEQ ID NO: 16), which better matches the wild-type sequence between Fingers 1 and 2 of natural Zif268. Finally, the long linker sequence between Fingers 5 and 6 was reduced in length and modified to the sequence LRQKDGGGGSGGGGSGGGGSQKP (SEQ ID NO: 24), to reduce the length of the non-wild-type sequence.

In a third embodiment (11-zinc finger peptide 1; SEQ ID NO: 29), modifications to the zinc finger recognition sequence were made so that each alanine residue in the sequence was replaced by glycine to result in the recognition sequences QSGDLTR (SEQ ID NO: 3) and QSGDRKR (SEQ ID NO: 4). The resultant zinc finger peptide has the sequence SEQ ID NO: 31. Linker sequences used in this peptide are the same as in SEQ ID NO: 33 above.

In order to demonstrate that some variability in sequence, within the confines of optimally host-matching the sequence to wild-type Zif268 was possible, yet another modified zinc finger peptide sequence was constructed (11-zinc finger peptide 4; SEQ ID NO: 35). This peptide incorporated the recognition sequence QSADLTR (SEQ ID NO: 2) in Finger 1, QSGDLTR (SEQ ID NO: 3) in Fingers 2, 4, 6, 8 and 10, and QSGDRKR (SEQ ID NO: 4) in Fingers 3, 5, 7, 9 and 11; while linker sequences remained the same as in SEQ ID NOs: 29 and 31.

The humanised and mousified zinc finger peptides therefore employed the same amino acid sequences. However, full repressor protein construct sequences varied between mouse and human versions as previously described. Thus, briefly, in the human version (hZF), human nuclear localisation signals and human Kox-1 was employed; whereas in the mouse version a mouse-derived nuclear localisation signal sequence was used and a KRAB repressor domain from a mouse protein (ZF87) was used as the repressor domain.

Figure 10:
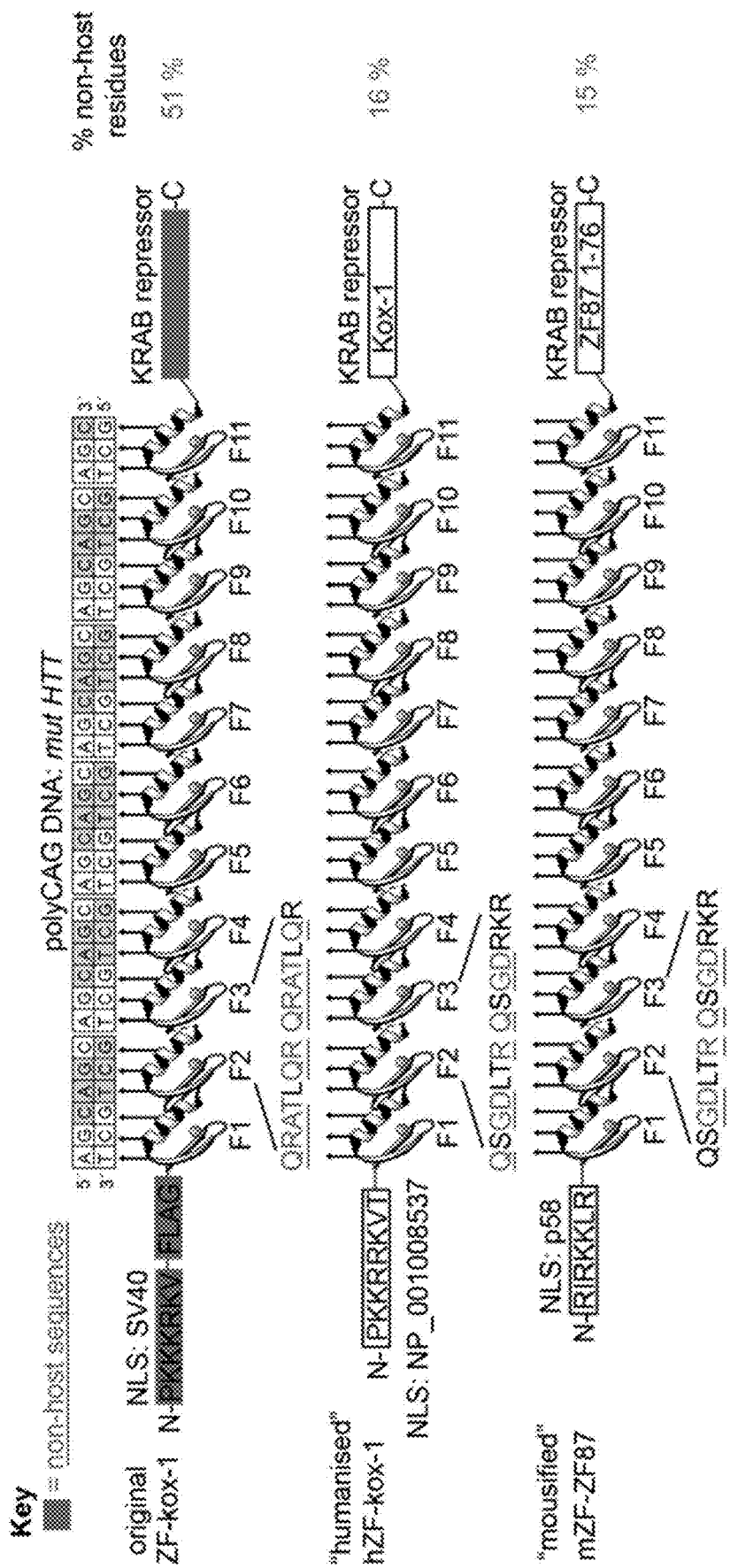
FIG. 10 Zinc finger (ZF) host optimisation designs: comparison of the ZF11-Kox-1, hZF11-Kox-1, and mZF11-ZF87 zinc finger repressor designs, showing the 11-finger constructs aligned to their target poly(CAG) DNA sequence (mut HTT). Protein domains containing non-host peptide sequences (containing potential foreign epitopes) are shaded in grey. For purposes of illustration, the sequences of representative DNA recognition helices from fingers 2 and 3 (F2, F3) are displayed below the ZF arrays, with foreign sequences in grey font and natural host sequences in black font. The percentage totals of non-host residues within the full-length peptide (which includes zinc finger and effector sequences) are given to show that the host-optimised designs reduce overall foreign sequences.

FIG. 10 shows the zinc finger (ZF) host optimisation designs for use in humans and in mice. A comparison of the original 11-finger construct (ZF-Kox-1) of Examples 1 to 10, with hZF-Kox-1 (SEQ ID NO: 54), and mZF-ZF87 (SEQ ID NO: 50) zinc finger repressor designs, showing the 11-finger constructs aligned to their target poly(CAG) DNA sequence (mut HTT). Protein domains containing non-host peptide sequences (containing potential foreign epitopes) are shaded in grey, and for purposes of illustration, the sequences of representative DNA recognition helices from Fingers 2 and 3 (F2, F3) are displayed below the zinc finger arrays, with 'foreign' sequences in grey font. The percentage totals of non-host residues within the full length protein repressor construct sequences are given to show that the host-optimised designs have significantly reduced overall foreign sequences.

TABLE 9

Zinc Finger Designs for Reduced Immunotoxicity.
Differences to the starting non-host matched starting peptide or from the
native human sequence are bold and underlined, as indicated.

```
Zinc finger peptide sequences of humanized ZF11xHunt design 1 with reduced
immunotoxicity (SEQ ID NO: 29):
YACPVESCDRRFS QSGDLTR HIRIH TGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH LRQKD GGGGSGGGGSGGGGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH Nucleic acid sequence coding for humanized ZF11xHunt design 1 (SEQ ID NO: 30):
TACGCCTGTCCTGTGGAATCCTGTGATAGACGGTTCAGCCAGAGCGGGGATCTGACAAGGCACATCAGAATTC
ATACTGGGTCCCAGAAGCCCTTCCAGTGCCGGATCTGTATGCGCAACTTTAGCCAGTCCGGAGACCTCACCCG
ACACATCCGAACCCATACAGGGGAGAAGCCTTTCGCCTGCGACATTTGTGGTCGGAAATTTGCTCAGAGCGGC
GATAGGAAGAGACACACAAAAATCCATACTGGCTCCCAGAAGCCATTCCAGTGCCGAATTTGTATGAGGAATT
TTTCTCAGAGTGGCGACCTGACTCGACACATCAGGACTCATACCGGCGAAAAGCCCTTCGCATGCGACATTTG
TGGAAGGAAATTTGCCCAGTCTGGGGATCGGAAGCGCCACACCAAAATCCATCTCAGACAGAAGGACGGAGGA
GGAGGTTCCGGAGGAGGAGGTAGTGGCGGAGGGGGTTCACAGAAGCCTTTCCAGTGCAGAATCTGTATGCGGA
ACTTTTCACAGAGCGGAGATCTGACCAGACACATCCGGACACATACTGGGGAGAAGCCATTCGCTTGCGACAT
TTGTGGTAGGAAATTTGCACAGTCTGGCGATCGAAAGAGGCACACCAAAATCCATACAGGAAGTCAGAAACCT
TTCCAGTGCCGCATTTGTATGCGAAATTTTTCCCAGTCTGGTGACCTGACACGCCATATTCGAACCCATACAG
GGGAAAAACCTTTCGCCTGTGACATTTGTGGAAGAAAATTTGCTCAGAGCGGGGATAGAAAGCGGCACACTAA
AATCCATACCGGCTCTCAGAAACCATTCCAGTGCCGGATTTGTATGCGCAACTTTAGTCAGTCAGGCGACCTG
ACCAGACACATCAGAACTCACACCGGAGAGAAACCCTTCGCATGTGATATCTGTGGTCGGAAATTCGCCCAGA
GCGGCGATCGCAAGCGACACACTAAAATCCAC Zinc finger peptide sequences of humanized ZF11xHunt design 2 (SEQ ID NO: 31):
  FQCRICMRNFSQSADLTRHTKIH TGSERP
  FQCRICMRNFSQSADLTRHIRTH TGEKP
  FACDICGRKFAQSADLTRHTKIH TGSERP
  FQCRICMRNFSQSADLTRHIRTH TGEKP
  FACDICGRKFAQSADLTRHTKIH LRQKDGGGGSGGGGSGGGGSQLVGTAERP
```

TABLE 9-continued

Zinc Finger Designs for Reduced Immunotoxicity.
Differences to the starting non-host matched starting peptide or from the
native human sequence are bold and underlined, as indicated.

```
FQCRICMRNFSQSADLTRHIRTH TGEKP
FACDICGRKFAQSADLTRHTKIH TGSERP
FQCRICMRNFSQSADLTRHIRTH TGEKP
FACDICGRKFAQSADLTRHTKIH TGSERP
FQCRICMRNFSQSADLTRHIRTH TGEKP
FACDICGRKFAQSADLTRHTKIH
```

Nucleic acid sequence coding for humanized ZF11xHunt design 2 (SEQ ID NO: 32):
```
TTCCAGTGCCGCATTTGTATGCGCAACTTTAGCCAGAGCGCGGACCTGACCCGCCATACCAAAATTCACACCG
GATCCGAACGGCCGTTTCAGTGCCGTATTTGCATGCGTAATTTTAGCCAGTCCGCGGACCTGACCCGCCATAT
TCGTACCCATACCGGTGAAAAACCGTTTGCCTGCGATATTTGTGGCCGTAAATTTGCCCAGAGCGCGGACCTG
ACCCGCCATACCAAAATTCATACCGGTTCTGAACGGCCGTTTCAGTGCAGGATTTGCATGCGTAATTTTTCCC
AGAGCGCGGACCTGACCCGCCATATTCGCACCCATACTGGTGAAAAACCGTTTGCCTGCGATATTTGCGGTCG
TAAATTTGCGCAGTCCGCTGACTTAACCCGCCATACCAAAATTCATCTGCGCCAGAAAGATGGTGGCGGCGGC
TCAGGTGGCGGCGGTAGTGGTGGCGGCGGCTCACAACTAGTCGGTACCGCCGAGCGCCCCTTCCAGTGCCGCA
TTTGTATGCGCAACTTTAGCCAGAGCGCGGACCTGACCCGTCATATTCGCACCCATACCGGTGAAAAACCGTT
TGCCTGCGATATTTGCGGTCGTAAATTTGCGCAGAGCGCGGACCTGACCCGCCATACCAAAATTCACACCGGA
TCCGAACGGCCGTTTCAGTGCCGTATTTGCATGCGTAATTTTAGCCAGTCCGCGGACCTGACCCGCCATATTC
GTACCCATACCGGTGAAAAACCGTTTGCCTGCGATATTTGTGGCCGTAAATTTGCCCAGagcGCGGACCTGAC
CCGCCATACCAAAATTCATACCGGTTCTGAACGGCCGTTTCAGTGCAGGATTTGCATGCGTAATTTTTCCCAG
AGCGCGGACCTGACCCGCCATATTCGCACCCATACTGGTGAAAAACCGTTTGCCTGCGATATTTGCGGTCGTA
AATTTGCGCAGAGCGCTGACTTAACCCGCCATACCAAAATTCAT
```

Zinc finger peptide sequences of humanized ZF11xHunt design 3 (SEQ ID NO: 33):
```
YACPVESCDRRFS QSADLTR HIRIH TGSQKP
  FQCRICMRNFS QSADLTR HIRTH TGEKP
  FACDICGRKFA QSADRKR HTKIH TGSQKP
  FQCRICMRNFS QSADLTR HIRTH TGEKP
  FACDICGRKFA QSADRKR HTKIH LRQKD GGGGSGGGGSGGGGSQKP
  FQCRICMRNFS QSADLTR HIRTH TGEKP
  FACDICGRKFA QSADRKR HTKIH TGSQKP
  FQCRICMRNFS QSADLTR HIRTH TGEKP
  FACDICGRKFA QSADRKR HTKIH TGSQKP
  FQCRICMRNFS QSADLTR HIRTH TGEKP
  FACDICGRKFA QSADRKR HTKIH
```

Nucleic acid sequence coding for humanized ZF11xHunt design 3 (SEQ ID NO: 34):
```
TACGCCTGTCCTGTGGAATCCTGTGATAGACGGTTCAGCCAGCAGAGCGCCGATCTGACAAGGCACATCAGAATTC
ATACTGGGTCCCAGAAGCCCTTCCAGTGCCGGATCTGTATGCGCAACTTTAGCCAGTCCGCCGACCTCACCCG
ACACATCCGAACCCATACAGGGGAGAAGCCTTTCGCCTGCGACATTTGTGGTCGGAAATTTGCTCAGAGCGCC
GATAGGAAGAGACACACAAAAATCCATACTGGCTCCCAGAAGCCATTCCAGTGCCGAATTTGTATGAGGAATT
TTTCTCAGAGTGCCGACCTGACTCGACACATCAGGACTCATACCGGCGAAAAGCCCTTCGCATGCGACATTTG
TGGAAGGAAATTTGCCCAGTCTGCCGATCGGAAGCGCCACACCAAAATCCATCTCAGACAGAAGGACGGAGGA
GGAGGTTCCGGAGGAGGAGGTAGTGGCGGAGGGGGTTCACAGAAGCCTTTCCAGTGCAGAATCTGTATGCGGA
ACTTTTCACAGAGCGCCGATCTGACCAGACACATCCGGACACATACTGGGGAGAAGCCATTCGCTTGCGACAT
TTGTGGTAGGAAATTTGCACAGTCTGCCGATCGAAAGAGGCACACCAAAATCCATACAGGAAGTCAGAAACCT
TTCCAGTGCCGCATTTGTATGCGAAATTTTTCCCAGTCTGCCGACCTGACACGCCATATTCGAACCCATACAG
GGGAAAAACCTTTCGCCTGTGACATTTGTGGAAGAAATTTGCTCAGAGCGCCGATAGAAAGCGGCACACTAA
AATCCATACCGGCTCTCAGAAACCATTCCAGTGCCGGATTTGTATGCGCAACTTTAGTCAGTCAGCCGACCTG
ACCAGACACATCAGAACTCACACCGGAGAGAAACCCTTCGCATGTGATATCTGTGGTCGGAAATTCGCCCAGA
GCGCCGATCGCAAGCGACACACTAAAATCCAC
```

Zinc finger peptide sequences of humanized ZF11xHunt design 4 (SEQ ID NO: 35):
```
YACPVESCDRRFS QSADLTR HIRIH TGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH LRQKD GGGGSGGGGSGGGGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH
```

Nucleic acid sequence coding for humanized ZF11xHunt design 4 (SEQ ID NO: 36):
```
TACGCCTGTCCTGTGGAATCCTGTGATAGACGGTTCAGCCAGCAGAGCGCCGATCTGACAAGGCACATCAGAATTC
ATACTGGGTCCCAGAAGCCCTTCCAGTGCCGGATCTGTATGCGCAACTTTAGCCAGTCCGGAGACCTCACCCG
ACACATCCGAACCCATACAGGGGAGAAGCCTTTCGCCTGCGACATTTGTGGTCGGAAATTTGCTCAGAGCGGC
GATAGGAAGAGACACACAAAAATCCATACTGGCTCCCAGAAGCCATTCCAGTGCCGAATTTGTATGAGGAATT
TTTCTCAGAGTGGCGACCTGACTCGACACATCAGGACTCATACCGGCGAAAAGCCCTTCGCATGCGACATTTG
TGGAAGGAAATTTGCCCAGTCTGGGGATCGGAAGCGCCACACCAAAATCCATCTCAGACAGAAGGACGGAGGA
GGAGGTTCCGGAGGAGGAGGTAGTGGCGGAGGGGGTTCACAGAAGCCTTTCCAGTGCAGAATCTGTATGCGGA
ACTTTTCACAGAGCGGAGATCTGACCAGACACATCCGGACACATACTGGGGAGAAGCCATTCGCTTGCGACAT
TTGTGGTAGGAAATTTGCACAGTCTGGCGATCGAAAGAGGCACACCAAAATCCATACAGGAAGTCAGAAACCT
TTCCAGTGCCGCATTTGTATGCGAAATTTTTCCCAGTCTGGTGACCTGACACGCCATATTCGAACCCATACAG
```

TABLE 9-continued

Zinc Finger Designs for Reduced Immunotoxicity.
Differences to the starting non-host matched starting peptide or from the
native human sequence are bold and underlined, as indicated.

```
GGGAAAAACCTTTCGCCTGTGACATTTGTGGAAGAAAATTTGCTCAGAGCGGGGATAGAAAGCGGCACACTAA
AATCCATACCGGCTCTCAGAAACCATTCCAGTGCCGGATTTGTATGCGCAACTTTAGTCAGTCAGGCGACCTG
ACCAGACACATCAGAACTCACACCGGAGAGAAACCCTTCGCATGTGATATCTGTGGTCGGAAATTCGCCCAGA
GCGGCGATCGCAAGCGACACACTAAAATCCAC

----

Peptide sequences of full construct (NLS-ZF11xHunt-KRAB-domain design 1) with
reduced immunotoxicity in mouse (SEQ ID NO: 50):
MG RIRKKLR LAERP
YACPVESCDRRFS QSGDLTR HIRIH TGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH LRQKDGGGGSGGGGSGGGGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH LRQKDGGGSGGGGS
EEMLSFRDVAIDFSAEEWECLEPAQWNLYRDVMLENYSHLVFLGLASCKPYLVTFLEQRQEPSVVKRPAAATV
HP Nucleic acid sequence coding for full construct (NLS-ZF11xHunt-KRAB-domain
design 1) with reduced immunotoxicity in mouse (SEQ ID NO: 57):
ATGGGCCGCATTAGAAAGAAACTCAGACTCGCAGAAAGACCTTACGCCTGTCCTGTGGAATCCTGTGATAGAC
GGTTCAGCCAGAGCGGGGATCTGACAAGGCACATCAGAATTCATACTGGGTCCCAGAAGCCCTTCCAGTGCCG
GATCTGTATGCGCAACTTTAGCCAGTCCGGAGACCTCACCCGACACATCCGAACCCATACAGGGGAGAAGCCT
TTCGCCTGCGACATTTGTGGTCGGAAATTTGCTCAGAGCGGCGATAGGAAGAGACACACAAAAATCCATACTG
GCTCCCAGAAGCCATTCCAGTGCCGAATTTGTATGAGGAATTTTTCTCAGAGTGGCGACCTGACTCGACACAT
CAGGACTCATACCGGCGAAAAGCCCTTCGCATGCGACATTTGTGGAAGGAAATTTGCCCAGTCTGGGGATCGG
AAGCGCCACACCAAAATCCATCTCAGACAGAAGGACGGAGGAGGAGGTTCCGGAGGAGGAGGTAGTGGCGGAG
GGGGTTCACAGAAGCCTTTCCAGTGCAGAATCTGTATGCGGAACTTTTCACGAGCGGAGATCTGACCAGACA
CATCCGGACACATACTGGGGAGAAGCCATTCGCTTGCGACATTTGTGGTAGGAAATTTGCACAGTCTGGCGAT
CGAAAGAGGCACACCAAAATCCATACAGGAAGTCAGAAACCTTTCCAGTGCCGCATTTGTATGCGAAATTTTT
CCCAGTCTGGTGACCTGACACGCCATATTCGAACCCATACAGGGGAAAAACCTTTCGCCTGTGACATTTGTGG
AAGAAAATTTGCTCAGAGCGGGGATAGAAAGCGGCACACTAAAATCCATACCGGCTCTCAGAAACCATTCCAG
TGCCGGATTTGTATGCGCAACTTTAGTCAGTCAGGCGACCTGACCAGACACATCAGAACTCACACCGGAGAGA
AACCCTTCGCATGTGATATCTGTGGTCGGAAATTCGCCCAGAGCGGCGATCGCAAGCGACACACTAAAATCCA
CCTCCGCCAGAAGGACGGCGGAGGATCCGGAGGGGGTGGGTCCGAAGAGATGCTCAGTTTTAGAGATGTCGCT
ATTGACTTTTCAGCCGAGGAATGGGAGTGCCTGGAACCTGCCCAGTGGAACCTGTACAGGGACGTGATGCTGG
AGAATTATAGCCACCTGGTCTTCCTGGGCCTCGCCTCCTGCAAGCCCTACCTCGTGACCTTTCTCGAACAGAG
GCAGGAGCCAAGCGTCGTCAAGAGACCAGCAGCAGCAACCGTCCATCCA Peptide sequences of full construct (NLS-ZF11xHunt-KRAB-domain design 1) with
reduced immunotoxicity in human (SEQ ID NO: 54):
MG PKKRRKVT GERP
YACPVESCDRRFS QSGDLTR HIRIH TGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH LRQKDGGGGSGGGGSGGGGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH TGSQKP
  FQCRICMRNFS QSGDLTR HIRTH TGEKP
  FACDICGRKFA QSGDRKR HTKIH LRQKDGGGSGGGGSS
LSPQHSAVTQGSIIKNKEGMTAKSLTAWSRTLVTFKDVFVDFTREEWKLLDTAQQIVYRNVMLENYKNLVSLG
YQLTKPDVILRLEKGEEPWLVEREIHQETHPDSETAFEIKSSV Nucleic acid sequence coding for full construct (NLS-ZF11xHunt-KRAB-domain
design 1) with reduced immunotoxicity in human (SEQ ID NO: 58):
ATGGGCCCGAAGAAACGCCGTAAAGTGACCGGCGAGCGCCCCTACGCCTGTCCTGTGGAATCCTGTGATAGAC
GGTTCAGCCAGAGCGGGGATCTGACAAGGCACATCAGAATTCATACTGGGTCCCAGAAGCCCTTCCAGTGCCG
GATCTGTATGCGCAACTTTAGCCAGTCCGGAGACCTCACCCGACACATCCGAACCCATACAGGGGAGAAGCCT
TTCGCCTGCGACATTTGTGGTCGGAAATTTGCTCAGAGCGGCGATAGGAAGAGACACACAAAAATCCATACTG
GCTCCCAGAAGCCATTCCAGTGCCGAATTTGTATGAGGAATTTTTCTCAGAGTGGCGACCTGACTCGACACAT
CAGGACTCATACCGGCGAAAAGCCCTTCGCATGCGACATTTGTGGAAGGAAATTTGCCCAGTCTGGGGATCGG
AAGCGCCACACCAAAATCCATCTCAGACAGAAGGACGGAGGAGGAGGTTCCGGAGGAGGAGGTAGTGGCGGAG
GGGGTTCACAGAAGCCTTTCCAGTGCAGAATCTGTATGCGGAACTTTTCACAGAGCGGAGATCTGACCAGACA
CATCCGGACACATACTGGGGAGAAGCCATTCGCTTGCGACATTTGTGGTAGGAAATTTGCACAGTCTGGCGAT
CGAAAGAGGCACACCAAAATCCATACAGGAAGTCAGAAACCTTTCCAGTGCCGCATTTGTATGCGAAATTTTT
CCCAGTCTGGTGACCTGACACGCCATATTCGAACCCATACAGGGGAAAAACCTTTCGCCTGTGACATTTGTGG
AAGAAAATTTGCTCAGAGCGGGGATAGAAAGCGGCACACTAAAATCCATACCGGCTCTCAGAAACCATTCCAG
```

TABLE 9-continued

Zinc Finger Designs for Reduced Immunotoxicity.
Differences to the starting non-host matched starting peptide or from the
native human sequence are bold and underlined, as indicated.

```
TGCCGGATTTGTATGCGCAACTTTAGTCAGTCAGGCGACCTGACCAGACACATCAGAACTCACACCGGAGAGA
AACCCTTCGCATGTGATATCTGTGGTCGGAAATTCGCCCAGAGCGGCGATCGCAAGCGACACACTAAAATCCA
CCTCCGCCAGAAGGACGGCGGAGGATCCGGAGGGGGTGGGTCCAGCTTGTCTCCTCAGCACTCTGCTGTCACT
CAAGGAAGTATCATCAAGAACAAGGAGGGCATGGATGCTAAGTCACTAACTGCCTGGTCCCGGACACTGGTGA
CCTTCAAGGATGTATTTGTGGACTTCACCAGGGAGGAGTGGAAGCTGCTGGACACTGCTCAGCAGATCGTGTA
CAGAAATGTGATGCTGGAGAACTATAAGAACCTGGTTTCCTTGGGTTATCAGCTTACTAAGCCAGATGTGATC
CTCCGGTTGGAGAAGGGAGAAGAGCCCTGGCTGGTGGAGAGAGAAATTCACCAAGAGACCCATCCTGATTCAG
AGACTGCATTTGAAATCAAATCATCAGTT
```

Peptide sequences of ZF10xHunt-kox-1 construct (NLS-ZF10xHunt-KRAB-domain)
with more sequence complexity and reduced immunotoxicity in human (SEQ ID NO:
59):
MG PKKRRKVT GERP
YACPVESCDRRFSQSGDLTRHIRIH TGQKP
FQCRI CMRNFSQSGDRKRHIRTH QNKKGS
HICHIQGCGKVYGQSGDLTRHLRWH TGERP
FMCTWSYCGKRFTQSGDRKRHKRTH LRQKDGERP
YACPVESCDRRFSQSGDLTRHIRIH TGEKP
YKCPE CGKSFSQSGDRKRHQRTH TGSERP
FMCNWSYCGKRFTQSGDLTRHKRTH TGEKP
FACPE CPKRFMQSGDRKRHIKTH TGSEKP
FQCRI CMRNFSQSGDLTRHIRTH TGERP
FACDI CGRKFAQSGDRKRHTKIH LRQKDGGGSGGGGSS
LSPQHSAVTQGSIIKNKEGMDAKSLTAWSRTLVTFKDVFVDFTREEWKLLDTAQQIVYRNVMLENYKNLVSLG
YQLTKPDVILRLEKGEEPWLVEREIHQETHPDSETAFEIKSSV Nucleic acid sequences of ZF10xHunt-kox-1 construct (NLS-ZF10xHunt-KRAB-
domain) with reduced immunotoxicity in human (SEQ ID NO: 60):
ATGGGCCCGAAGAAACGCCGTAAAGTGACCGGCGAGCGCCCCTACGCCTGCCCTGTGGAGTCCTGCGATAGAAGATTTTCC
CAGAGCGGCGACCTGACCAGACATATTCGGATTCACACCGGCCAGAAGCCATTCCAGTGCAGAATCTGTATGCGGAACTTT
TCCCAGAGCGGCGACCGCAAGCGGCACATTCGCACTCATCAGAATAAGAAAGGGTCTCACATCTGCCATATTCAGGGGTGT
GGCAAAGTGTATGGACAGAGCGGCGACCTGACCCGACACCTGAGGTGGCATACCGGAGAGAGGCCCTTCATGTGCACATGG
AGTTACTGTGGCAAGAGGTTCACCCAGAGCGGCGACCGCAAGAGACACAAACGGACACATCTGCGACAGAAGGACGGAGAG
CGACCATATGCATGCCCAGTCGAAAGTTGTGATAGGAGATTCTCACAGAGCGGCGACCTGACCCGCCACATCCGAATTCAT
ACCGGCGAGAAACCTTACAAGTGCCCAGAATGTGGAAAGAGCTTTTCCCAGAGCGGCGACCGCAAGAGGCACCAGAGAACC
CATACAGGCAGTGAGCGGCCCTTCATGTGCAACTGGTCATATTGTGGAAAAAGGTTTACCCAGAGCGGCGACCTGACCCGG
CACAAACGCACACATACTGGCGAGAAGCCTTTCGCTTGCCCCGAATGTCCTAAGCGGTTTATGCAGAGCGGCGACCGCAAG
CGGCACATCAAAACCCATACAGGAAGCGAGAAGCCTTTCCAGTGCCGAATTTGTATGAGGAATTTTTCCCAGAGCGGCGAC
CTGACCCGACACATCAGGACTCATACCGGGGAACGGCCATTCGCCTGCGACATTTGTGGCAGAAAATTTGCACAGAGCGGC
GACCGCAAGCGACACACCAAAATCCACCTCCGCCAGAAGGACGGCGGAGGATCCGGAGGGGGTGGGTCCAGCTTGTCTCCT
CAGCACTCTGCTGTCACTCAAGGAAGTATCATCAAGAACAAGGAGGGCATGGATGCTAAGTCACTAACTGCCTGGTCCCGG
ACACTGGTGACCTTCAAGGATGTATTTGTGGACTTCACCAGGGAGGAGTGGAAGCTGCTGGACACTGCTCAGCAGATCGTG
TACAGAAATGTGATGCTGGAGAACTATAAGAACCTGGTTTCCTTGGGTTATCAGCTTACTAAGCCAGATGTGATCCTCCGG
TTGGAGAAGGGAGAAGAGCCCTGGCTGGTGGAGAGAGAAATTCACCAAGAGACCCATCCTGATTCAGAGACTGCATTTGAA
ATCAAATCATCAGTT Peptide sequences of ZF12xHunt-kox-1 construct (NLS-ZF12xHunt-KRAB-domain)
with reduced immunotoxicity in human (SEQ ID NO: 61):
MG PKKRRKVT GERP
YACPVESCDRRFS QSGDLTR HIRIH TGQKP
   FACDICGRKFA QSGDRKR HTKIH TGSQKP
   FQCRICMRNFS QSGDLTR HIRTH TGEKP
   FACDICGRKFA QSGDRKR HTKIH TGSQKP
   FQCRICMRNFS QSGDLTR HIRTH TGEKP
   FACDICGRKFA QSGDRKR HTKIH LRQKDGGGGSGGGGSGGGGSQKP
   FQCRICMRNFS QSGDLTR HIRTH TGEKP
   FACDICGRKFA QSGDRKR HTKIH TGSQKP
   FQCRICMRNFS QSGDLTR HIRTH TGEKP
   FACDICGRKFA QSGDRKR HTKIH TGSQKP
   FQCRICMRNFS QSGDLTR HIRTH TGEKP
   FACDICGRKFA QSGDRKR HTKIH LRQKDGGGSGGGGSS
LSPQHSAVTQGSIIKNKEGMDAKSLTAWSRTLVTFKDVFVDFTREEWKLLDTAQQIVYRNVMLENYKNLVSLG
YQLTKPDVILRLEKGEEPWLVEREIHQETHPDSETAFEIKSSV Nucleic acid sequences of ZF12xHunt-kox-1 construct (NLS-ZF12xHunt-KRAB-
domain) with reduced immunotoxicity in human (SEQ ID NO: 62):
ATGGGCCCGAAGAAACGCCGTAAAGTGACCGGCGAGCGCCCCTACGCCTGTCCTGTGGAATCCTGTGATAGACGGT
TCAGCCAGAGCGGGGATCTGACAAGGCACATCAGAATTCATACTGGGCAGAAGCCCTTCGCCTGCGACATTTGTGGTCGGA
AATTTGCTCAGAGCGGCGATAGGAAGAGACACACAAAAATCCATACTGGCTCCCAGAAGCCATTCCAGTGCCGGATCTGTA
TGCGCAACTTTAGCCAGTCCGGAGACCTCACCCGACACATCCGAACCCATACAGGGGAGAAGCCTTTCGCCTGCGACATTT
GTGGTCGGAAATTTGCTCAGAGCGGCGATAGGAAGAGACACACAAAATCCATACTGGCTCCCAGAAGCCATTCCAGTGCC
GAATTTGTATGAGGAATTTTTCTCAGAGTGGCGACCTGACTCGACACATCAGGACTCATACCGGCGAAAAGCCCTTCGCAT
GCGACATTTGTGGAAGGAAATTTGCCCAGTCTGGGGATCGGAAGCGCCACACCAAAATCCATCTCAGACAGAAGGACGGAG
GAGGAGGTTCCGGAGGAGGAGGTAGTGGCGGAGGGGGTTCACAGAAGCCTTTCCAGTGCAGAATCTGTATGCGGAACTTTT
CACAGAGCGGAGATCTGACCAGACACATCCGGACACATACTGGGGAGAAGCCATTCGCTTGCGACATTGTGGTAGGAAAT
TTGCACAGTCTGGCGATCGAAAGAGGCACACCAAAATCCATACAGGAAGTCAGAAACCTTTCCAGTGCCGCATTTGTATGC
```

TABLE 9-continued

Zinc Finger Designs for Reduced Immunotoxicity.
Differences to the starting non-host matched starting peptide or from the
native human sequence are bold and underlined, as indicated.

```
GAAATTTTTCCCAGTCTGGTGACCTGACACGCCATATTCGAACCCATACAGGGGAAAAACCTTTCGCCTGTGACATTTGTG
GAAGAAAATTTGCTCAGAGCGGGGATAGAAAGCGGCACACTAAAATCCATACCGGCTCTCAGAAACCATTCCAGTGCCGGA
TTTGTATGCGCAACTTTAGTCAGTCAGGCGACCTGACCAGACACATCAGAACTCACACCGGAGAGAAACCCTTCGCATGTG
ATATCTGTGGTCGGAAATTCGCCCAGAGCGGCGATCGCAAGCGACACACTAAAATCCACCTCCGCCAGAAGGACGGCGGAG
GATCCGGAGGGGGTGGGTCCAGCTTGTCTCCTCAGCACTCTGCTGTCACTCAAGGAAGTATCATCAAGAACAAGGAGGCA
TGGATGCTAAGTCACTAACTGCCTGGTCCCGGACACTGGTGACCTTCAAGGATGTATTTGTGGACTTCACCAGGGAGGAGT
GGAAGCTGCTGGACACTGCTCAGCAGATCGTGTACAGAAATGTGATGCTGGAGAACTATAAGAACCTGGTTTCCTTGGGTT
ATCAGCTTACTAAGCCAGATGTGATCCTCCGGTTGGAGAAGGGAGAAGAGCCCTGGCTGGTGGAGAGAGAAATTCACCAAG
AGACCCATCCTGATTCAGAGACTGCATTTGAAATCAAATCATCAGTT
```

Peptide sequences of ZF18xHunt-kox-1 construct (NLS-ZF18xHunt-KRAB-domain)
with reduced immunotoxicity in human (SEQ ID NO: 63):

```
MG PKKRRKVT GERP
YACPVESCDRRFS QSGDLTR HIRIH TGQKP
   FACDICGRKFA QSGDRKR HTKIH TGSQKP
   FQCRICMRNFS QSGDLTR HIRTH TGEKP
   FACDICGRKFA QSGDRKR HTKIH TGSQKP
   FQCRICMRNFS QSGDLTR HIRTH TGEKP
   FACDICGRKFA QSGDRKR HTKIH LRQKDGGGGSGGGGSGGGGSQKP
YACPVESCDRRFS QSGDLTR HIRIH TGQKP
   FACDICGRKFA QSGDRKR HTKIH TGSQKP
   FQCRICMRNFS QSGDLTR HIRTH TGEKP
   FACDICGRKFA QSGDRKR HTKIH TGSQKP
   FQCRICMRNFS QSGDLTR HIRTH TGEKP
   FACDICGRKFA QSGDRKR HTKIH LRQKDGGGGSGGGGSGGGGSQKP
   FQCRICMRNFS QSGDLTR HIRTH TGEKP
   FACDICGRKFA QSGDRKR HTKIH TGSQKP
   FQCRICMRNFS QSGDLTR HIRTH TGEKP
   FACDICGRKFA QSGDRKR HTKIH TGSQKP
   FQCRICMRNFS QSGDLTR HIRTH TGEKP
   FACDICGRKFA QSGDRKR HTKIH LRQKDGGGSGGGGSS
LSPQHSAVTQGSIIKNKEGMDAKSLTAWSRTLVTFKDVFVDFTREEWKLLDTAQQIVYRNVMLENYKNLVSLG
YQLTKPDVILRLEKGEEPWLVEREIHQETHPDSETAFEIKSSV
```

Nucleic acid sequences of ZF18xHunt-kox-1 construct (NLS-ZF18xHunt-KRAB-
domain) with reduced immunotoxicity in human (SEQ ID NO: 64):

```
ATGGGCCCGAAGAAACGCCGTAAAGTGACCGGCGAGCGCCCCTACGCCTGTCCTGTGGAATCCTGTGATAGACGGT
TCAGCCAGAGCGGGGATCTGACAAGGCACATCAGAATTCATACTGGGCAGAAGCCCTTCGCCTGCGACATTTGTGGTCGGA
AATTTGCTCAGAGCGGCGATAGGAAGAGACACACAAAAATCCATACTGGCTCCCAGAAGCCATTCCAGTGCCGGATCTGTA
TGCGCAACTTTAGCCAGTCCGGAGACCTCACCCGACACATCCGAACCCATACAGGGGAGAAGCCTTTCGCCTGCGACATTT
GTGGTCGGAAATTTGCTCAGAGCGGCGATAGGAAGAGACACACAAAAATCCATACTGGCTCCCAGAAGCCATTCCAGTGCC
GAATTTGTATGAGGAATTTTTCTCAGAGTGGCGACCTGACTCGACACATCAGGACTCATACCGGCGAAAAGCCCTTCGCAT
GCGACATTTGTGGAAGGAAATTTGCCCAGTCTGGGGATCGGAAGCGCCACACCAAAATCCATCTCAGACAGAAGGACGGAG
GAGGAGGTTCCGGAGGAGGAGGTAGTGGCGGAGGGGGTTCACAGAAGCCTTACGCCTGTCCTGTGGAATCCTGTGATAGAC
GGTTCAGCCAGAGCGGGGATCTGACAAGGCACATCAGAATTCATACTGGGCAGAAGCCCTTCGCCTGCGACATTTGTGGTC
GGAAATTTGCTCAGAGCGGCGATAGGAAGAGACACACAAAAATCCATACTGGCTCCCAGAAGCCATTCCAGTGCCGGATCT
GTATGCGCAACTTTAGCCAGTCCGGAGACCTCACCCGACACATCCGAACCCATACAGGGGAGAAGCCTTTCGCCTGCGACA
TTTGTGGTCGGAAATTTGCTCAGAGCGGCGATAGGAAGAGACACACAAAAATCCATACTGGCTCCCAGAAGCCATTCCAGT
GCCGAATTTGTATGAGGAATTTTTCTCAGAGTGGCGACCTGACTCGACACATCAGGACTCATACCGGCGAAAAGCCCTTCG
CATGCGACATTTGTGGAAGGAAATTTGCCCAGTCTGGGGATCGGAAGCGCCACACCAAAATCCATCTCAGACAGAAGGACG
GAGGAGGAGGTTCCGGAGGAGGAGGTAGTGGCGGAGGGGGTTCACAGAAGCCTTTCCAGTGCAGAATCTGTATGCGGAACT
TTTCACAGAGCGGAGATCTGACCAGACACATCCGGACACATACTGGGGAGAAGCCATTCGCTTGCGACATTTGTGGTAGGA
AATTTGCACAGTCTGGCGATCGAAAGAGGCACACCAAAATCCATACAGGAAGTCAGAAACCTTTCCAGTGCCGCATTTGTA
TGCGAAATTTTTCCCAGTCTGGTGACCTGACACGCCATATTCGAACCCATACAGGGGAAAAACCTTTCGCCTGTGACATTT
GTGGAAGAAAATTTGCTCAGAGCGGGGATAGAAAGCGGCACACTAAAATCCATACCGGCTCTCAGAAACCATTCCAGTGCC
GGATTTGTATGCGCAACTTTAGTCAGTCAGGCGACCTGACCAGACACATCAGAACTCACACCGGAGAGAAACCCTTCGCAT
GTGATATCTGTGGTCGGAAATTCGCCCAGAGCGGCGATCGCAAGCGACACACTAAAATCCACCTCCGCCAGAAGGACGGCG
GAGGATCCGGAGGGGTGGGTCCAGCTTGTCTCCTCAGCACTCTGCTGTCACTCAAGGAAGTATCATCAAGAACAAGGAGGAG
GCATGGATGCTAAGTCACTAACTGCCTGGTCCCGGACACTGGTGACCTTCAAGGATGTATTTGTGGACTTCACCAGGGAGG
AGTGGAAGCTGCTGGACACTGCTCAGCAGATCGTGTACAGAAATGTGATGCTGGAGAACTATAAGAACCTGGTTTCCTTGG
GTTATCAGCTTACTAAGCCAGATGTGATCCTCCGGTTGGAGAAGGGAGAAGAGCCCTGGCTGGTGGAGAGAGAAATTCACC
AAGAGACCCATCCTGATTCAGAGACTGCATTTGAAATCAAATCATCAGTT
```

Example 12

Host-matching Reduces Microglial Proliferation

Microglial cells have a significant involvement in brain innate immune responses, so we sought to test whether the administration of various zinc finger constructs described herein might have undesirable effects in upregulating microglia.

To test this, unilateral injections of recombinant AAV constructs (rAAV2/1-ZF-Kox-1, rAAV2/1-mZF-ZF87 and rAAV2/1-GFP), or PBS were given in the striata of wild-type (WT) mice. WT mice were used in these investigations to avoid any confounding effects that might otherwise have occurred by use of the previously described mice that develop the HD phenotype.

To check the infection region covered by the injection procedure, the volume covered by GFP fluorescence in GFP-injected samples was measured. This revealed a consistent average of ~50% infection, both at 4 and 6 weeks post-injection (data not shown). Significantly, no GFP fluorescence was apparent outside of the injected striatum.

Since the number of viral copies and the vector amount used was the same for GFP, ZF-Kox-1 and mZF-ZF87, it was assumed that the efficiency of transduction would be similar in all groups.

Figure 11:
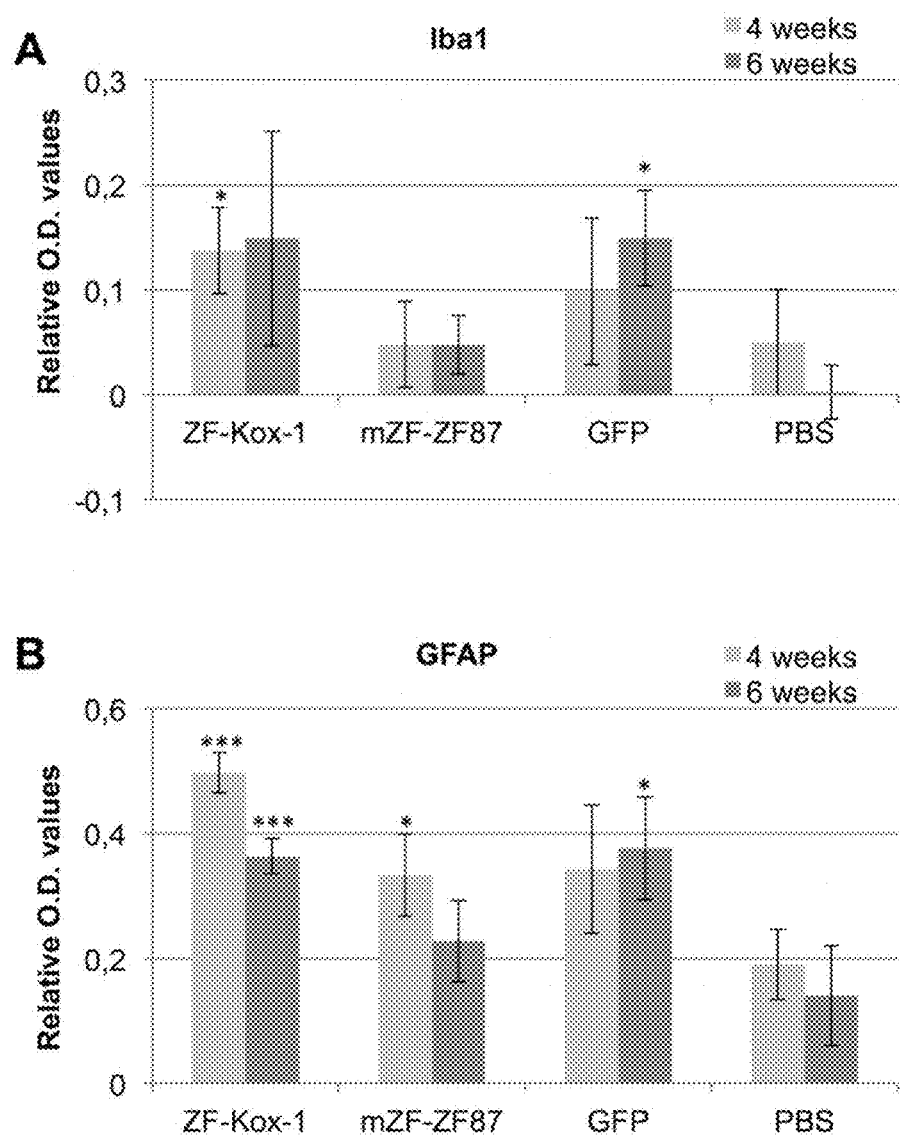
FIG. 11 Relative O.D. values of the striatal samples immunostained for glial markers: relative O.D. values, representing inflammatory responses to various treatments, were calculated for the microglial marker Iba1 and the reactive astroglial marker GFAP, at 4 and 6 weeks after injection. Non-optimised ZF11-Kox-1 treatment was compared to expression of a host optimised mZF11-ZF87, GFP or a control PBS injection. Relative O.D. is calculated as the mean O.D. of four coronal slices, separated by 240 μm in the injected hemisphere, minus the average O.D. in the contralateral control hemisphere. Data are displayed as Relative O.D.±S.E.M,  P<0.001, P<0.01, *P<0.05.

To measure microglial upregulation, immunostaining with a marker for the ionised calcium-binding adapter molecule 1 (Iba1) was used. Similarly, to measure astroglial upregulation, immunostaining with a marker for the reactive astroglial marker, GFAP was used (see Example 13 below). The sample tissues were then analysed by quantifying the O.D. following a similar procedure as in (Ciesielska et al. (2013) Mol. Ther. 21: 158-166). A Student's t-test, compared the O.D. value of the injected hemispheres against the background O.D. of the contralateral, non-injected hemisphere (FIG. 11A). This revealed that ZF-Kox-1 and GFP provoked significant increases in microglia, at 4 and 6 weeks post-injection, respectively, as further demonstrated in FIGS. 12A and 12F). For ZF-Kox-1, the average values of O.D. at 6 weeks were similar to 4 weeks post-injection, but the increased variability in the samples prevented the result from reaching statistical significance.

Figure 12:
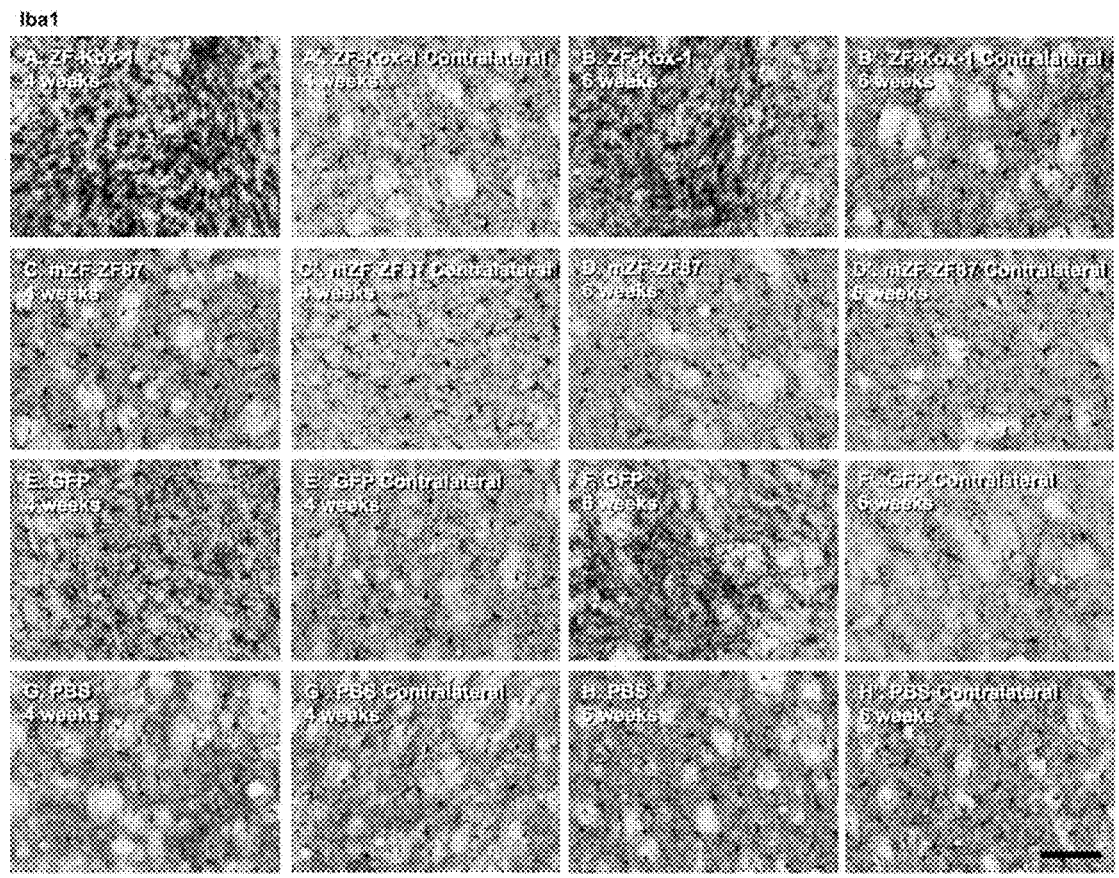
FIG. 12 Microglial activation (Iba1+ cells) in the striatum after various treatments: representative micrographs of Iba1 immunostained striatal coronal slices, for the control and injected hemispheres, for each treatment at 4 or 6 weeks. ZF11-Kox-1 samples at 4 and 6 weeks after treatment (A, B) in comparison to the corresponding contralateral hemispheres (A', B'). Hemispheres treated with mZF-ZF87 at 4 and 6 weeks post injection compared with their contralateral non-injected hemispheres (C, C'; D, D'). GFP-treated samples 4 weeks after injection (E) and 6 weeks after GFP injection (F), compared with the contralateral hemispheres (E', F'). PBS-injected at both time points (G, G'; H, H'). Scale bar 100 μm.

FIG. 12 provides representative micrographs of Iba1 immunostained striatal coronal slices, for the control and injected hemispheres, for each treatment at 4 or 6 weeks. ZF-Kox-1 samples displayed an apparent increase in Iba1 immunoreactivity in the injected hemispheres, at 4 and 6 weeks after treatment (A, B). This was not observed in the contralateral hemispheres (A', B'). By contrast, hemispheres treated with mZF-ZF87 showed similar levels of Iba1+ cells compared with their contralateral non-injected hemispheres (C, C', D, D').

As can be seen, certain GFP-treated samples showed a slight increase in Iba1 immunoreactivity 4 weeks after treatment (E), whereas Iba1 immunoreactivity was significantly increased 6 weeks after GFP injections, compared with the contralateral hemispheres (F, F').

PBS-injected samples show similar Iba1 immunoreactivity between hemispheres at both time points (G, G', H, H').

As can be seen from these data, mZF-ZF87 and PBS injections did not significantly increase the amount of microglial staining (see FIGS. 12C, 12D, 12G and 12H). Only scattered enlarged microglial cells could be detected in the tissue, mainly surrounding the needle tract, in both the mZF-87 and PBS-injected hemispheres.

Thus, the injection of the foreign proteins, ZF-Kox-1 and GFP, induced a strong proliferation of microglial cells in WT mice, at different time points, which was not present in the case of the host-matched mZF-ZF87 zinc finger repressor protein. Accordingly, it can be concluded that ZF-Kox-1 treatment is inflammatory at both 4 and 6 weeks after injection (see FIGS. 12A and 12B), whereas treatment with a mousified equivalent protein is not.

Example 13

Host-matching Reduces Astroglial Proliferation

Following on from Example 12, above, next it was assayed whether the various treatments provoked an increase in reactive astroglia by immunostaining the mouse brain slices for glial fibrillary acidic protein (GFAP), and measuring resulting O.D., as in the previous experiment.

The O.D. value of the injected hemispheres was compared against the basal O.D. of the contralateral, non-injected hemisphere by means of a Student's t test and the results are depicted in FIG. 11B).

Figure 13:
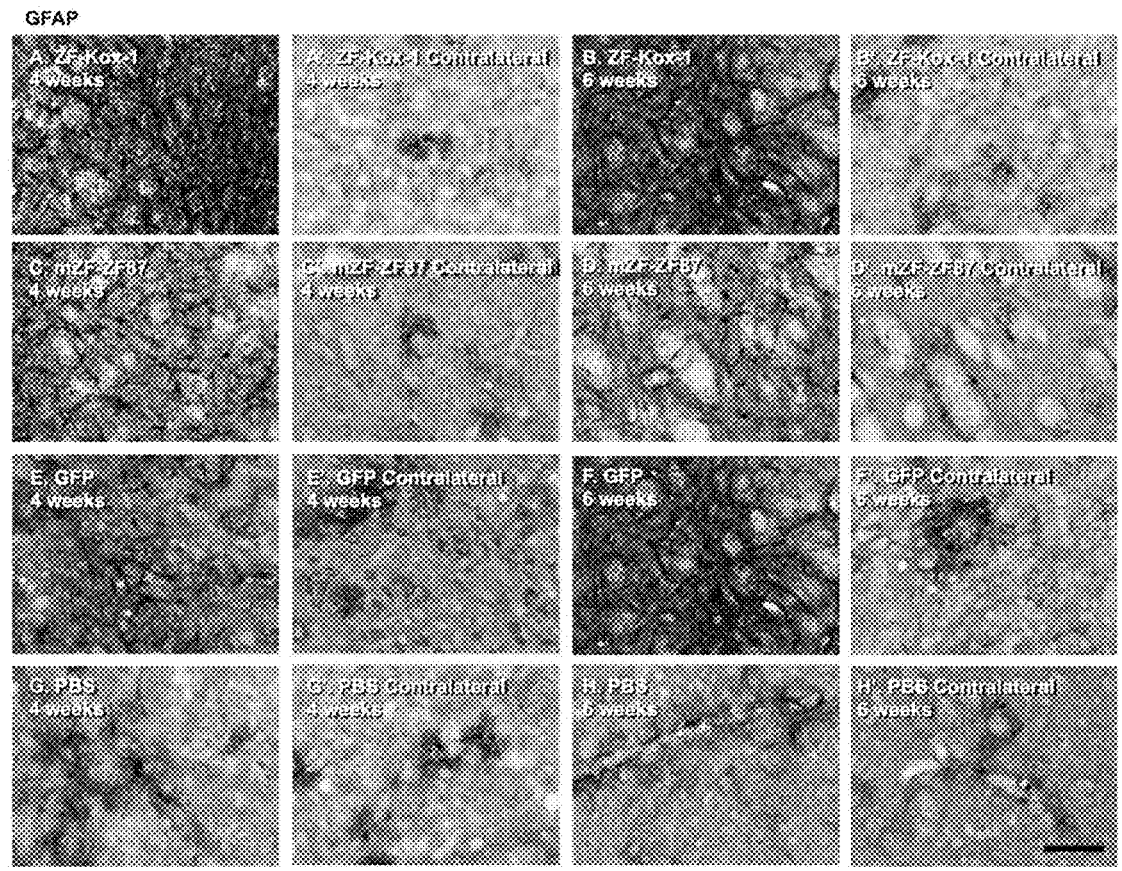
FIG. 13 Astroglial activation (GFAP+ cells) in the striatum and cortex after various treatments: representative micrographs of GFAP immunostained striatal coronal slices for the control and injected hemispheres, for each treatment at each time point. ZF11-Kox-1 samples at 4 and 6 weeks after treatment (A, B) in comparison to the non-injected contralateral hemispheres, respectively (A', B'). mZF11-ZF87 treatment at 4 and 6 weeks post injection compared with their contralateral non-injected hemispheres (C, C'; D, D'). GFP-treated samples 4 weeks after injection (E) and 6 weeks after GFP injection (F), compared with the contralateral hemispheres (E', F'). PBS-injected at both time points (G, G'; H, H'). Scale bar 100 μm. Experiments carried out using mfZF11-ZF87 of SEQ ID NOs: 49, 50, 51 and 52. Results shown for modulator polypeptide of SEQ ID NO: 49.

Turning to FIG. 13, which provides representative micrographs of GFAP immunostained striatal coronal slices, the results clearly show that GFAP was significantly upregulated in the injected hemispheres, at both time points, in the ZF-Kox-1 samples (FIGS. 13A and 13B); whereas, by contrast, the mZF-ZF87 injected samples showed a lower and transient GFAP upregulation, and this was mainly restricted to areas surrounding the needle tract. Moreover, this mild activation was only notable at around 4 weeks post injection (FIGS. 13C and 13D). In contrast, GFP caused a delayed reactivity, reaching a significant increase (with respect to the control hemisphere) at 6 weeks post-injection (FIG. 13F). As expected, the PBS control injection did not induce a significant increase in reactive astroglia (FIGS. 13G and 13H). Isolated, non-reactive astrocytes were found in all contralateral, non-injected hemispheres (as shown in FIG. 13).

Overall, it can be seen from the data that ZF-Kox-1 and GFP caused a persistent reaction of astroglial cells in WT mice, whereas for mZF-ZF87 and PBS this reaction was weaker and was already reduced at week 6 post-injection.

In general, therefore, GFAP staining patterns through upregulation of astroglial cells largely mirrored that of Iba1 staining in upregulation of microglial cells.

Example 14

Reduction in Toxicity and Resulting Neuronal Death

To verify whether the observed inflammatory responses were accompanied by neuronal loss, immunohistochemical detection of the neuronal marker NeuN was used.

Figure 14:
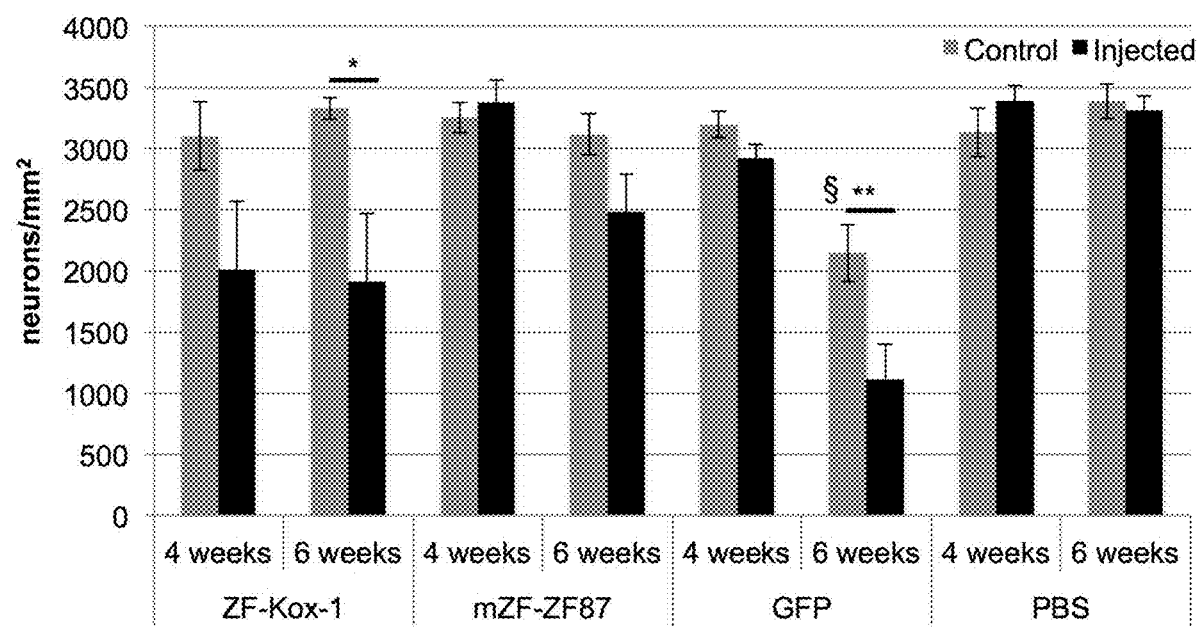
FIG. 14 Bar chart illustrating striatal neuronal density after various treatments. The estimated neuronal density in the striata of mice after the different treatments is illustrated. Data are expressed as mean±S.E.M. *P<0.05; **P<0.01; § P<0.01 (§ compares cell counts in the contralateral hemispheres of the 6-week GFP and PBS samples.

First, neuronal density was estimated in each hemisphere of the various treated animals (FIG. 14). A Student's t test between the injected and the non-injected hemispheres revealed that the number of neurons showed a trend to reduction by ZF-Kox-1 by week 4 after injection (p=0.08). This reduction reached significance by 6 weeks post-injection (p=0.014).

Figure 15:
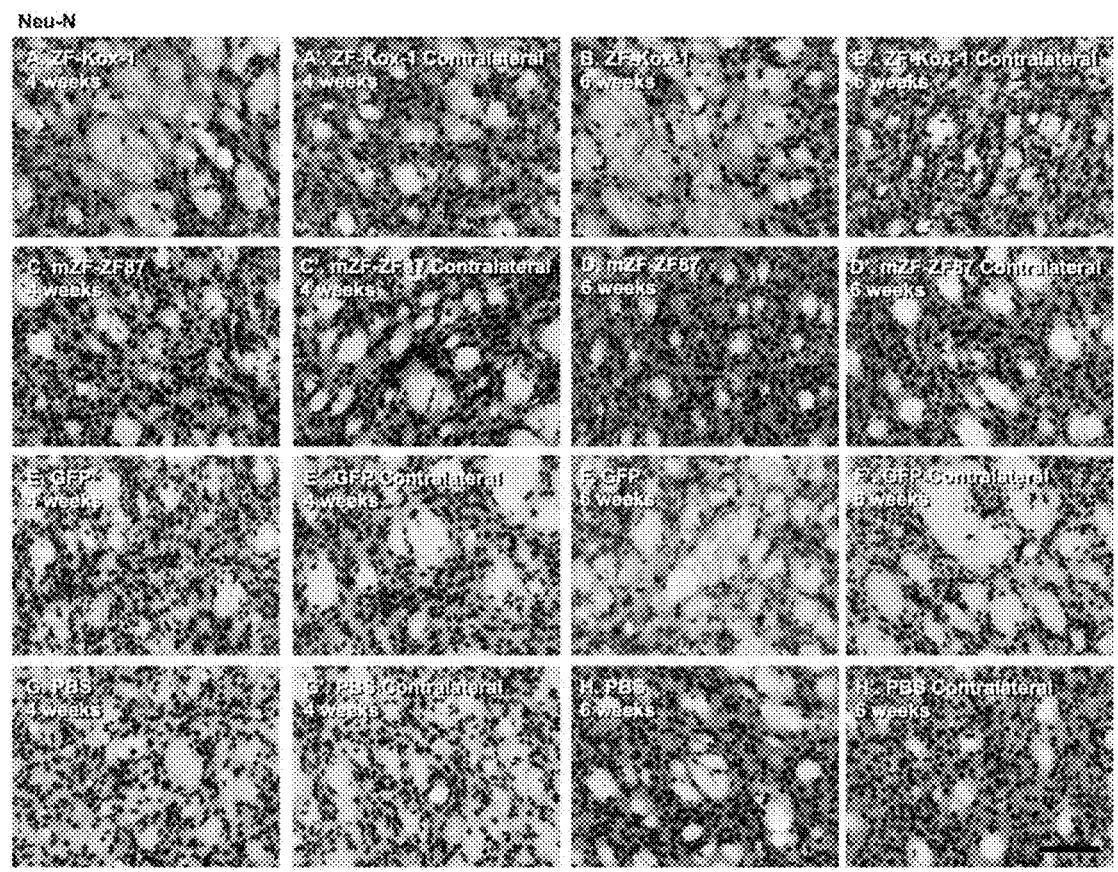
FIG. 15 Visualising striatal neuronal density after various treatments: representative micrographs of Neu-N immunostained striatal coronal slices for the control and injected hemisphere of each treatment at each time point. ZF-Kox-1 toxicity is observed in areas of the injected striata that are devoid of marked neurons, 4 and 6 weeks after treatment (A, B), whereas the contralateral hemispheres (A', B') show neuronal densities similar to PBS injected (G, H) and untreated hemispheres (G', H'). Conversely, mZF-ZF87 treatment did not significantly affect neuronal density (C, C', D, D') at either time point. Strikingly, GFP injections did not affect neuronal density at 4 weeks after treatment (E, E'), but caused a delayed strong toxic response that reduced neuronal density both in the injected (F) and the contralateral hemisphere (F'), 6 weeks post-injection. Scale bar 100 μm.

With reference to FIG. 15, which quantitates neuronal density after the various treatments used in the study, it can also be seen that injection of ZF-Kox-1-expressing AAV resulted in extensive neuronal death in some samples after 6 weeks. This meant that no effective detection of NeuN was possible in the area surrounding the injection site (see FIGS. 15A and 15B). In fact, no NeuN could be observed at all in some of the slices, which displayed only high background staining.

Notably, GFP treatment in this study resulted in cell numbers being reduced in the contralateral, non-injected hemisphere also.

Turning to FIG. 15, striatal neuronal density after various treatments was also visualised by staining, as shown in the representative micrographs of NeuN immunostained striatal coronal slices for the control and injected hemisphere of each treatment at each time point.

As demonstrated by the micrographs of FIG. 15, ZF-Kox-1 toxicity was observed in areas of the injected striata that are devoid of marked neurons, 4 and 6 weeks after treatment (A, B), whereas the contralateral hemispheres (A', B') show neuronal densities similar to PBS injected (G, H) and untreated hemispheres (G', H'). Conversely, mZF-ZF87 treatment did not significantly affect neuronal density (C, C', D, D') either at 4 or 6 weeks post injection. Strikingly, GFP injections did not affect neuronal density at 4 weeks after treatment (E, E'), but caused a delayed strong toxic response that reduced neuronal density both in the injected (F) and the contralateral hemisphere (F') at 6 weeks post-injection.

In the case of mZF-ZF87 treated samples neuronal density at either 4 or 6 weeks after treatment (see FIGS. 15C and 15D) was unaffected; although, a limited reduction in the number of neurons near the needle tract in two out of four animals at week 6 post-injection was observed, but did not reach significance (p=0.13). Indeed, in general, most of the mZF-ZF87 treated samples were similar to PBS injected hemispheres (see FIGS. 15G and 15H).

Finally, in agreement with the previous observations in Iba1+ and GFAP immunodetection, neuron density was not affected by GFP at 4 weeks post-treatment (see FIG. 14 and FIG. 15E), with only some areas showing scarcely-distributed neurons close to the needle tract. However, GFP significantly reduced neuronal density by week 6 post-injection (p=0.018). The cytotoxicity of GFP was thus observed after a delay and was the strongest toxic effect observed in this study.

Example 15

Long-Term Repression of Mut HTT polyCAG Target In Vivo

As reported in Examples 1 to 10, it had previously been demonstrated that the ZF-Kox-1 repressor protein was capable of functionally repressing its target mutant HTT gene, in vivo, in R6/2 HD model mice for up to 3 weeks after bilateral injection. During the time while this repression was active, pathological clasping symptoms in mice were virtually abolished (Garriga-Canut et al. (2012), *Proc. Natl. Acad. Sci.;* 109, E3136-3145).

Following this study, we further investigated whether repression of the target mutant HTT gene could be sustained for a longer period, e.g. up to 6 weeks, when mice were treated with either the ZF-Kox-1 zinc finger construct or the mousified mZF-ZF87 zinc finger repressor construct.

To this end, rAAV2/1-ZF-Kox-1 was injected into R6/2 mice. Test injections were performed only in one hemisphere so that the contralateral hemisphere was left untreated for the purpose of having a baseline comparison. Brain samples from sacrificed animals were taken at 2, 4 and 6 weeks post-injection, and RNA levels were analysed via quantitative real-time PCR (Garriga-Canut et al. (2012), *Proc. Natl. Acad. Sci.,* 109, E3136-3145).

Figure 16:
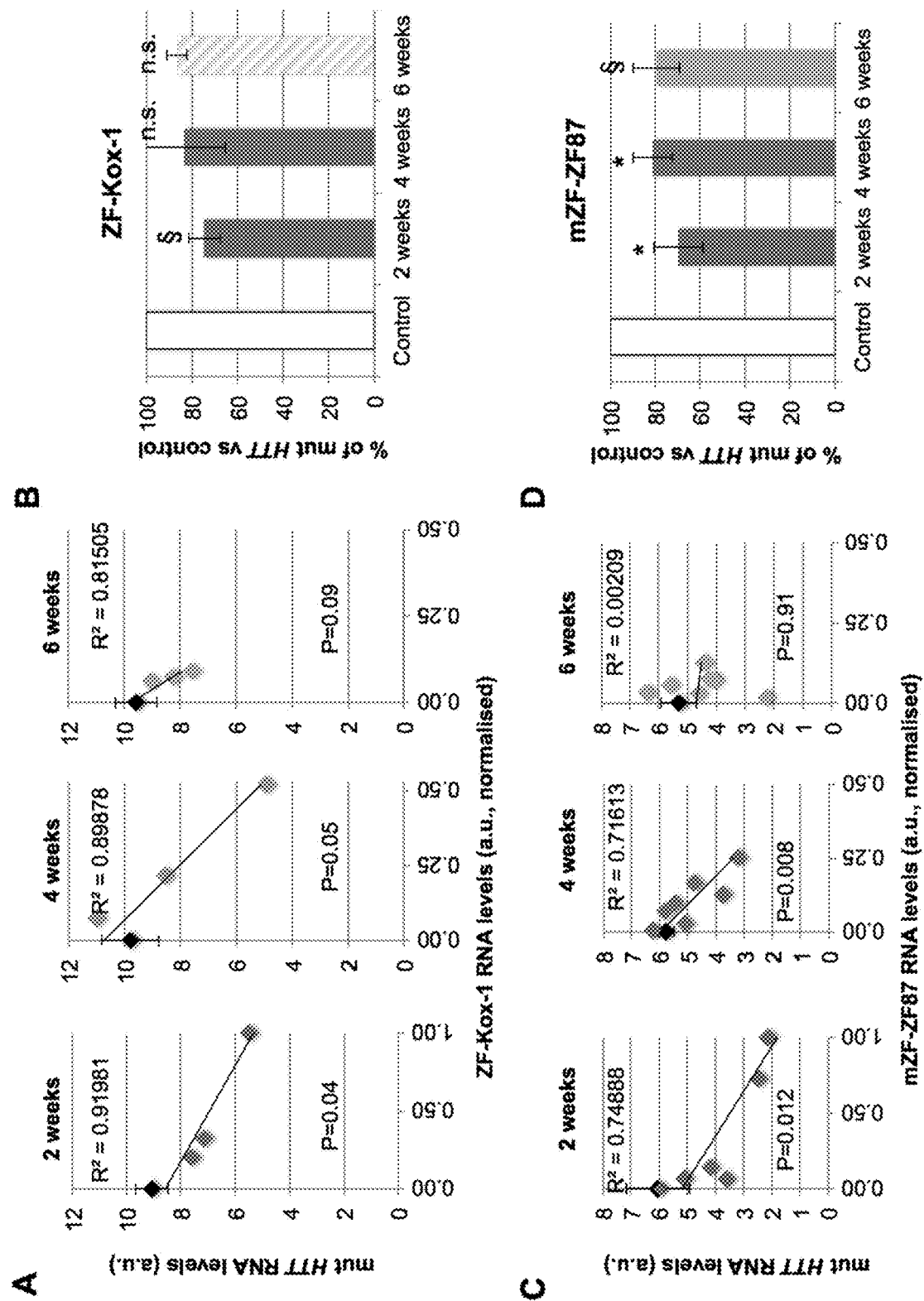
FIG. 16 Mutant huntingtin gene expression analysis after treatment with zinc finger peptides: A. Linear regression showing negative correlations of mut HTT RNA levels and ZF11-Kox-1 expression 2, 4, and 6 weeks after treatment. Black diamonds show mean mut HTT expression values (±1 S.E.M.) in the control hemispheres of each group. ZF11-Kox-1 expression levels are in arbitrary units (a.u), normalised to the maximum ZF11-Kox-1 qRT-PCR signal across all samples; B. Percentage of mut HTT with respect to the average value in the control hemispheres, over the same period; C. Linear regression analysis testing for negative correlations between mut HTT RNA levels and mZF11-ZF87 expression, at 2, 4 and 6 weeks after treatment. mZF11-ZF87 expression levels are in arbitrary units (a.u), normalised to the maximum mZF11-ZF87 qRT-PCR signal across all samples; D. Percentage of mut HTT with respect to the average value in the control hemispheres over the same period. The columns show mean RNA expression levels; error bars: ±1 S.E.M. *P<0.05; § P<=0.06.
Figure 17A:
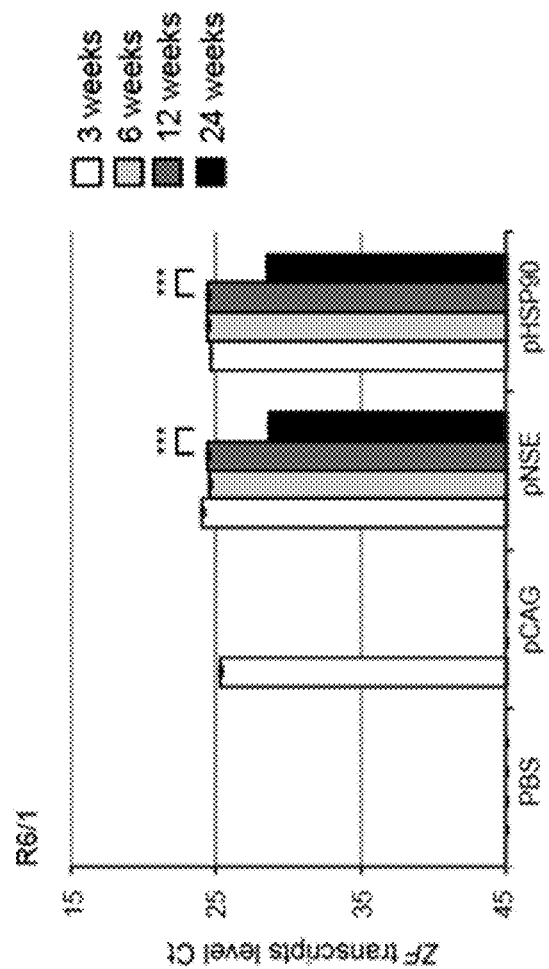
FIG. 17 Long-term effects of bilateral intraventricular injection of AAV (10 virions) expressing zinc fingers mZF-KRAB (Mol. Neurodegeneration 11(1):64, 2016) under pCAG, pNSE or pHSP promoters. A. Zinc finger repression of mutant Huntingtin in R6/1 mice. mut HTT (exon 1) expression levels in the whole brain samples from the various treatments were compared to transcript levels in PBS controls by qRT-PCR. B. Zinc finger expression over time measured by qRT-PCR Ct (threshold cycle value; log scale). mZF-KRAB transcript levels from whole brains were assayed by qRT-PCR at 3, 6, 12 and 24 weeks after viral (or PBS control) injections in R6/1 neonates. pCAG loses detectable expression by 6 weeks, whereas pNSE and pHSP90 maintain detectable expression up to at least 24 weeks. C. The same data for zinc finger expression over time, normalised to control CAG levels in R6/1. D. Zinc finger expression over time, normalised to control CAG levels in WT neonates. E. Verification of lack of cross-reactivity of mZF-KRAB with short WT Htt alleles in WT mice. WT Htt (exon 1) expression levels were quantified in the same treatment samples as above. F. Verification of lack of cross-reactivity of mZF-KRAB in R6/1 mice. Error bars are S.E.M (n=3). * p<0.01, ** p<0.001, n.s.=not significant.
Figure 17B:
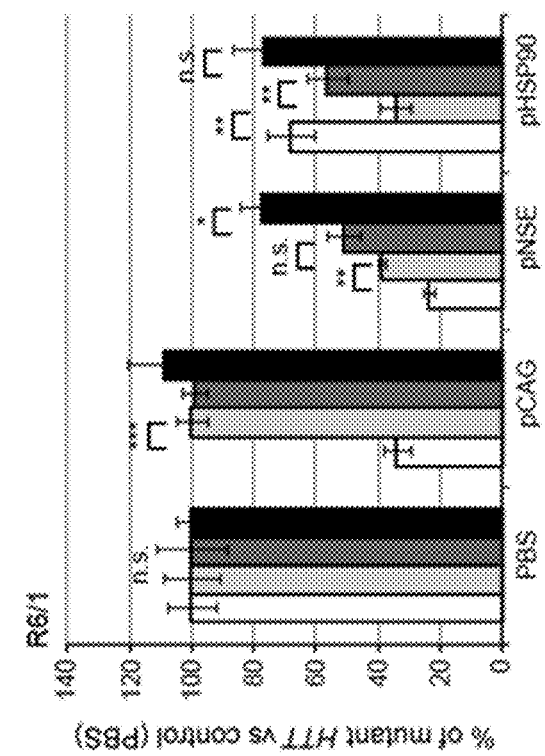
Figure 17C:
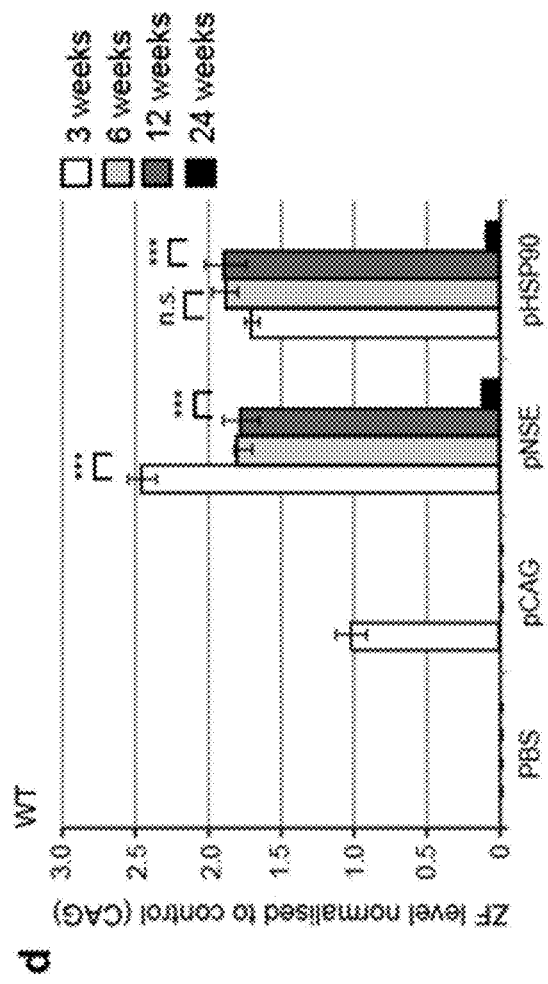
Figure 17D:
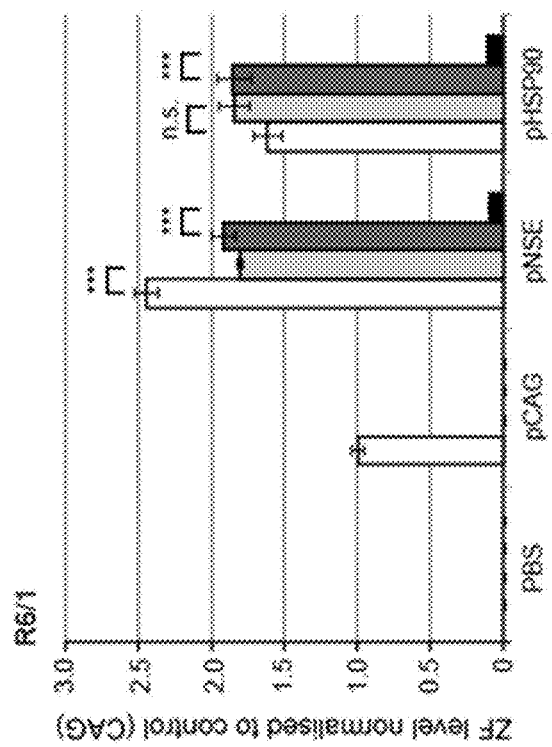
Figures 17E, 17F:
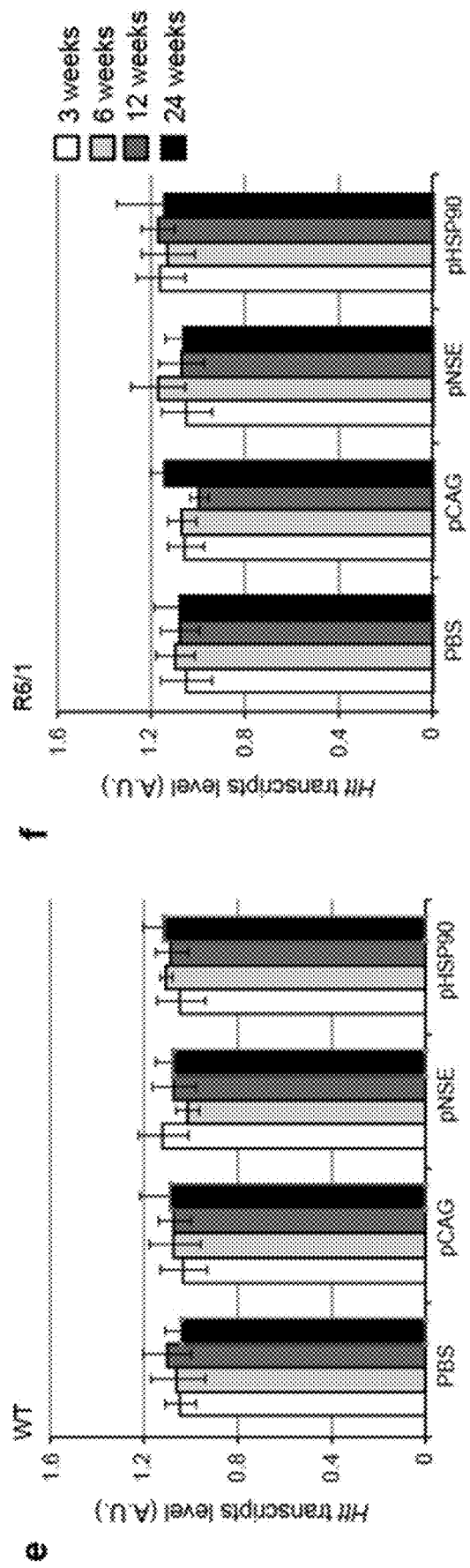

FIG. 16 shows mutant HTT gene expression analysis after treatment with zinc finger constructs. In (A) a linear regression analysis shows negative correlations of mut HTT RNA levels and ZF-Kox-1 expression at 2, 4 and 6 weeks after treatment, suggesting an effective repression of mut HTT by virtue of the treatment. Black diamonds show the mean mut HTT expression values (±1 S.E.M.) of the control hemispheres of each group.

By carrying out a linear regression of the RNA levels of mut HTT versus ZF-Kox-1, for each time point (FIG. 7A), it is possible to verify whether ZF-Kox-1 is able to repress its target gene (mut HTT) in a dose-dependent manner. In this regard, the data show a significant and negative correlation between these RNA levels 2 weeks after treatment (p=0.04). There were also trends approaching significance at 4 and 6 weeks (p=0.05, p=0.09). These results indicate that, although there is variability in individual injected mice, generally, higher expression of the ZF-Kox-1 results in lower levels of mut HTT, which is consistent with previous results (Garriga-Canut et al. (2012), *Proc. Natl. Acad. Sci.;* 109, E3136-3145).

FIG. 16B shows the percentage of mut HTT with respect to the average value in the control hemispheres, over the same period. The data show an average of approx. 25% reduction of mut HTT, 2 weeks post-treatment (previously reported in (Garriga-Canut et al. (2012), *Proc. Natl. Acad. Sci.;* 109, E3136-3145)), with an individual mouse showing up to approx. 40% reduction. While the data show that the average percentage increases with time, later values should be interpreted with some caution because of ZF-Kox-1 expression leakage to the contralateral hemisphere and the significant neuronal loss that could be observed.

By comparing the mut HTT levels in the ZF-Kox-1-injected hemisphere to the baseline in the uninjected hemisphere (FIG. 16B), we saw that ZF-Kox-1 yielded a mean reduction in mut HTT of approx. 35% after 2 weeks, which is in the therapeutic range (Garriga-Canut et al. (2012), *Proc. Natl. Acad. Sci.;* 109, E3136-3145). Repression was maintained at approx. 20% at 4 and 6 weeks after injection. However, ZF-Kox-1 expression was accompanied by significant cell loss (as demonstrated above—see FIGS. 14 and 15).

We next explored whether host-matched mZF-ZF87 was a more suitable candidate for long-term repression of mutant HTT. The early-onset R6/2 phenotype (as used in the above Example) is useful for phenotyping trials but, as a result of Ethical Review (see Materials and Methods), we refined the procedure for collecting zinc finger expression and repression data at 6 weeks, and switched to the later-onset HD mouse model, R6/1. Ethically, the use of R6/1 is preferred over R6/2 because the data can be collected before any HD symptoms are detected, maximising animal welfare. In fact, both R6/1 and R6/2 bear the same transgene, although the CAG repeats are longer in R6/2 (approx. 250 repeats versus approx. 150 repeats in R6/1). It was not thought that this repeat number difference would matter for quantifying repression, since we have seen comparable zinc finger repression in StHdh cells with 111 repeats (Garriga-Canut et al. (2012), *Proc. Natl. Acad. Sci.;* 109, E3136-3145).

Although R6/1 is thus a valid model for testing zinc finger repression, the data should not be formally compared to the results with R6/2 mice described in this Example above, because of the phenotypic differences.

rAAV2/1-mZF-ZF87 vector was injected into R6/1 mice and the mice were sacrificed at 2, 4 and 6 weeks post-injection to obtain samples for RNA level analysis via quantitative real-time PCR.

FIG. 16C shows a linear regression analysis which demonstrates a negative correlation between mut HTT RNA levels and mZF-ZF87 expression at 2, 4 and 6 weeks post-treatment. Again, mZF-ZF87 expression levels are in arbitrary units (a.u), normalised to the maximum mZF-ZF87 qRT-PCR signal across all samples. The data show that mZF-ZF87 RNA levels were negatively correlated with mut HTT at 2 and 4 weeks post-injection (p<0.05). This indicates that mZF-ZF87 target repression is functioning. The linear correlation was lost by week 6 post-injection, although the majority of mice still had reduced mut HTT levels in the injected hemisphere, with respect to control levels. Interestingly, studies in mice have shown that transient repression of mut HTT with modified oligonucleotides can persist for 8 weeks after treatment (Kordasiewicz et al. (2012), *Neuron,* 74: 1031-1044). Therefore it is likely that we are observing persistent repression of mut HTT at 6 weeks, which is no longer correlated to mZF-ZF87 expression, because of a trend to reduction in zinc finger expression over time. Furthermore, in this regard, it should be appreciated that KRAB domains lay down heterochromatin across genetic loci and thus cause strong long-term repression which can outlast their expression (Groner et al. (2010), *PLoS Genet.,* 6.).

The bar graph in FIG. 16D shows the percentage of mut HTT with respect to the average value in the control hemispheres over the same period. By comparing the mut HTT levels in the mZF-ZF87-injected hemisphere to the baseline in the non-injected hemisphere we saw that repression was on average approx. 30% at 2 weeks (p=0.04) and stabilised around approx. 20% at 4 and 6 weeks (p=0.04, p=0.05, respectively). Although these repression levels are very similar to those seen for ZF-Kox-1 (and are thus likely to be in the established therapeutic range (Garriga-Canut et al. (2012), *Proc. Natl. Acad. Sci.,* 109, E3136-3145)), the apparent, significant reduction in toxicity over ZF-Kox-1 makes this mousified construct preferable.

Example 16

Specific Repression of mut HTT by mZF-ZF87

Since the mouse genome contains seven potential polyQ expansion genes (Garriga-Canut et al. (2012), *Proc. Natl. Acad. Sci.;* 109, E3136-3145), it was important to understand whether the transcriptional repression of mut HTT was specific or whether the test repressor proteins might also affect one or more of the other potential polyCAG-targets.

Thus, the effects of ZF-Kox-1 and mZF-ZF87 on the expression of four of these genes (wild-type wt HTT, ATN1, ATXN2, TBP; Table 10), were tested.

Example 17

A. Alternative Promoter Design for Long Term (Therapeutic) Transgene Expression: Neuron Specific Expression We have previously described (PNAS 109: E3136-E3145, 2012; WO 2012/049332) the use of the strong viral promoter, pCAG (CMV-enhanced chicken beta-actin) to express zinc fingers transcription factors and thus repress transcription of the mutant huntingtin gene (HTT) over a period of several weeks. However, it has been found that the pCAG promoter can (appear to) lose activity by 6 weeks after the start of expression; as demonstrated in FIG. 17, (see panels a, b, c and d) for expression of the target HTT gene (panel a) and expression of of transgene (panels b, c and d) with pCAG at 3 weeks compared to expression levels at 6, 12 and 24 weeks. This reduction in expression of the transgene/transcriptional effect is likely due to cellular DNA methylation of the CMV DNA, as has been reported in the literature (e.g. see *Gene Ther.,* 2001, 8: 1323-1332). Therefore, the present inventors set out to achieve a longer-term single-treatment therapy and investigated alternative promoters for such purpose.

The NSE promoter-enhancer region(s) was considered to have potential application in this respect, but has not previously been characterised in either mice or humans. Since most HD models are based in mice, the inventors therefore identified and chemically synthesised a rat version of the pNSE promoter for use in mouse and vectorised it to express mZF-KRAB-WPRE from the rAAV2/1 viral vector.

TABLE 10

Expression of mouse endogenous CAG-containing genes after treatment with ZF-Kox1 and mZF-ZF87.

| Treatment | Time[1] | LR[2] | HTT (4, 7) % | LR[2] | ATN1 (3, 10) % | LR[2] | ATXN2 (6, 10) % | LR[2] | TBP (3, 13) % |
|---|---|---|---|---|---|---|---|---|---|
| ZF-Kox-1 | 2 | $R^2 = 0.97$[§] | 92.1 ± 0.4\* | $R^2 = 0.03$ | 101.2 ± 13.8 | $R^2 = 0.09$ | 95.5 ± 3.9 | $R^2 = 0.98$[§] | 94.5 ± 5.0 |
|  | 4 | $R^2 = 0.99$[§] | 89.6 ± 2.4\* | $R^2 = 0.64$ | 91.7 ± 13.7 | $R^2 = 0.57$ | 96.1 ± 6.8 | $R^2 = 0.98$ | 91.5 ± 1.7 |
|  | 6 | $R^2 = 0.99$\* | 90.6 ± 9.6 | $R^2 = 0.09$ | 106.3 ± 4.9 | $R^2 = 0.96$ | 98.4 ± 2.9 | $R^2 = 0.65$ | 98.1 ± 3.3 |
| mZF-ZF87 | 2 | $R^2 = 0.53$ | 98.3 ± 3.3 | $R^2 = 0.02$ | 109.4 ± 10.6 | $R^2 = 0.00$ | 103.3 ± 11.8 | $R^2 = 0.08$ | 99.1 ± 7.9 |
|  | 4 | $R^2 = 0.14$ | 88.4 ± 6.7 | $R^2 = 0.19$ | 88.6 ± 7.3 | $R^2 = 0.36$ | 89.6 ± 5.4 | $R^2 = 0.43$ | 90.5 ± 10.4 |
|  | 6 | $R^2 = 0.43$ | 92.5 ± 11.35 | $R^2 = 0.16$ | 91.4 ± 6.5 | $R^2 = 0.00$ | 96.7 ± 4.4 | $R^2 = 0.07$ | 94.7 ± 4.8 |

The first number (in brackets after the name of the gene) represents the number of CAG repeats, the second the number of glutamines in the coding stretch (CAG + CAA). Values are given as the percentage expression of the gene of interest, with respect to the average values in the control hemispheres. The result of ZF-Kox-1 at 6 weeks post-injection should be read with caution, since at this time point there was significant neuronal loss and leakage of the vector to the contralateral hemisphere.
In bold: [§]$P < 0.1$; \*$P < 0.05$.
ATN1: atrophin 1;
ATXN2: ataxin 2;
HTT: huntingtin (mouse);
TBP: TATA binding protein.
[1]Weeks post-injection
[2]LR = Linear Regression The results of this study show that the RNA levels of the four tested genes were not negatively correlated with the expression of either zinc finger construct; except, strikingly, in the case of wt HTT with ZF-Kox-1, at all time points. In particular, ZF-Kox-1 significantly repressed approx. 10% of mouse HTT at 2 and 4 weeks after treatment, in a dose-dependent manner.

Conversely, the expression of none of the genes was negatively correlated with mZF-ZF87 at any timed point. Overall, the results thus demonstrate that not only is mZF-ZF87 less toxic than ZFKox-1 (or GFP), it seems also to be more specific for repressing mut HTT in vivo.

Therefore, several design variants—as discussed above— are possible to retain poly(CAG) binding, while maximising host matching properties and minimising toxicity in vivo.

In in vivo studies, it was found that the rat pNSE promoter was able to achieve transgene expression in mice over a longer time period than corresponding pCAG-based viral vectors: see FIG. 17, panels b, c and d, for comparison between pCAG and pNSE expression levels over the period of 3 to 24 weeks post infection. Specifically, it was found that whereas pCAG promoter activity was lost by 6 weeks, the pNSE promoter displayed relatively stable expression up to approximately 12 weeks (74-78% of the maximum expression level), and zinc finger peptide was still detectable after 24 weeks (albeit at a reduced level of 4-5% of maximum pNSE levels and 10-12% of maximum pCAG levels in WT and R6/1). The sequence of the synthetic pNSE used in these experiments is provided as SEQ ID NO: 152, whose sequence without restriction cloning sites is SEQ ID NO: 153.

It should be noted that the detection of zinc finger peptide is based on a relative scale and that even approximately 5-10% of the maximum expression may still indicate an absolute concentration of zinc finger peptide that could be functionally active and (therapeutically) effective; this can only be determined by examining the repression of target mutant HTT (see FIG. 17, panel a).

When looking at repression of mutant HTT, pCAG-driven repression was only detected at 3 weeks post infection and was apparently lost by the 6 week time point assay, as shown in FIG. 17, panel a for pCAG. This finding is consistent with the complete loss of detectable zinc finger transgene expression from this promoter at all assayed time points post 3 weeks. By contrast, pNSE-driven repression of the HTT gene was maintained over the entire 24-week period, albeit with a trend to reduction over time (again, see FIG. 17, panel a; pNSE). Importantly, at 3, 6, 12 and 24 weeks, respectively, the expression of zinc finger repressor peptide was sufficient to result in 77%, 61%, 48% and 23% repression of mutant HTT in whole brain samples from mice.

Notably, pNSE-ZF still repressed mutant HTT expression levels by nearly a quarter after 24 weeks, which is close to the repression levels previously found to be in the therapeutic range (see PNAS 109: E3136-E3145, 2012).

As expected, the short wild-type Htt allele was unaffected in all samples, indicating a lack of off-target activity (see FIG. 17, panels e and f); demonstrating the selectivity of the zinc finger peptides/modulators of the invention.

Overall, the results show that combining the mouse host-adapted mZF-KRAB zinc finger peptide (mZF11-ZF87) with the rat pNSE promoter allows target mut HTT repression in the whole brain, for an extended 6 month period. This is a considerable improvement over the 3 weeks reported repression previously demonstrated (PNAS 109: E3136-E3145, 2012).

pNSE promoter activity is relatively specific to neurons (*Gene Ther*. (2001), 8: 1323-1332). Thus, when used in combination with rAAV2/1 viral vectors that show a strong tropism towards neurons, the targeting of pNSE is expected to be more neuron specific and advantageously provide long-term therapeutic benefits for the treatment of neurological disorders, such as HD, in animals (e.g. humans).

B. Alternative Promoter Design for Long Term Therapeutic Transgene Expression: Ubiquitous Expression The pNSE promoter described above (see also SEQ ID NOs: 148, 151, 152 and 153), particularly when in combination with rAAV2/1 vectors, may allow the therapeutic targeting of a large proportion of the brain over an extended time period.

However, there are many other cells types in the brain which are thought to play a role in HD, such as glia cells. Additionally, it may be advantageous to have the ability to target other organs or tissues of a subject, such as the heart. Therefore, the inventors sought to identify new promoter sequences that might target alternative cell types, such as in the brain or other potential target organs or tissues. In particular, it was desirable to be able to target such alternative cell types in a ubiquitous manner.

Accordingly, the inventors searched for new endogenous promoters/enhancers that may allow the targeting of a range of cell types beyond only neurons. For instance, a recent RNA-seq study explored gene expression in the striatum and cortex, in WT and R6/2 mice, and found many genes consistently-upregulated in all four sample types (Vashishtha et al. 10.1073/pnas.1311323110). The promoters/enhancer regions from some of these genes might potentially be good candidates to drive therapeutic gene expression. Unfortunately, the functional promoter/enhancer regions in these genes remain to be characterised.

Therefore, in accordance with this example, the inventors selected and screened potential promoters/enhancers in silico and then engineered the new promoter/enhancer sequences by de novo gene synthesis for in vitro and in vivo testing. Since the location of any potentially functional DNA fragments was not known and the length of any potentially effective sequences also was not known, a number of different construct sequences and sequence lengths were studied to identify effective and/or optimal promoter-enhancer sequences.

Selected sequences were then vectorised and tested, and edits were made to determine appropriate lengths of DNA sequences to include in the potential promoter-enhancer sequences before and after the transcriptional start site of the wild-type genes in order to capture suitable functionality.

The inventors thereby surprisingly identified a new promoter-enhancer sequence that was able to achieve potentially therapeutic zinc finger transgene expression levels in a sustained manner, i.e. for periods of over 24 weeks, and potentially longer (see FIG. 17, as described further below).

A preliminary analysis was carried out in silico for alternative promoter candidates and 8 were identified that were in the top 20 most-expressed genes in all conditions according to Vashishtha et al. (10.1073/pnas.1311323110: conditions: cortex & striatum, 8 & 12 week-old mice, R6/2 & WT; Table S3). In order of expression level, these highly-expressed genes were: Tmsb4x (NCBI Gene ID: 19241), Snap25 (20614), Fth1 (14319), Cst3 (13010), Cpe (12876), Hsp90ab1 (15516), Calm1 (12313) and Rtn1 (104001).

From these 8 promoters the ubiquitous gene promoter Hsp90ab1 was selected for further testing because its endogenous gene product has been reported as being strongly expressed in a variety of cell types in a number of different organisms. This gene promoter is naturally associated with the heat shock protein HSP90. Notably, the Hsp90beta isoform appears to be constitutively expressed, whereas the Hsp90alpha isoform is expressed under cellular stress.

The Hsp90 promoter/enhancer has not been previously characterised and so it was not possible to identify a hybrid promoter/enhancer construct, based on literature, for use in driving zinc finger peptide gene expression in the HD mouse model described herein. In this regard, whereas the non-homologous stress-dependent Hsp90beta minimal promoter had been previously studied (Gene, (1996), 172, 279-284), as has a 2.0 kb sequence in the Silkworm *Bombyx mori* (doi: 10.1534/g3.114.011643), these promoter/enhancer sequences of the prior art show no evident homology to the mouse promoter region of Hsp90 by sequence alignment.

Therefore, the present inventors set out to test potential regions in the mouse promoter (SEQ ID NO: 143) for activity in the mouse expression models described herein. The mouse promoter of SEQ ID NO: 143 is slightly homologous to the human promoter SEQ ID NO:144.

First, potential transcription factor binding sites and TATA boxes were identified using a 20 kbp genome region (SEQ ID NO: 145) to search for distal enhancers, using the TSSW algorithm on the world wide at linux1.softberry.com/berry.phtml?topic=tssw&group=programs&subgroup=promoter).

Seven potential promoter/enhancer regions were identified within the 20 kbp sequence region, as listed below, with the identified binding sites in each described as "Position (strand)Species$Transcription factor—Sequence". Transcription factor binding sites for human (HS), mouse and rat;

enhancer regions and TATA boxes identified below are greyed out in the relevant sections (SEQ ID NO: 154 to 160) of sequence SEQ ID NO: 145 reproduced below.

```
1. Promoter Pos: 820 LDF-1.19 TATA box at 786 19.41
                                            (SEQ ID NO: 154)
Ggagggagagtgcaggctcatggcaggcctcaggagacctgtgttccttac agggtctgtttgctctctcactctttctccttttccctctgtctgtct cctcccttgcctgctctgtcactgttgtcactgtccctgacccttttct cttttctgtcttctttgactgtctttccctgcctctcaatcatccgtcctcc tcctcctcctcgattgctcccaccttcggtttccaagcttataaactgct tctgctgctggataaaaatagcggtggcagcggccaggctggca
```

Annotation:

Position (DNA strand+ or −) Species$Transcription factor-SEQUENCE (complement): 523(−)HS$NPY_04-CCCCTCC(ggagggg); 531(−) MOUSE$MT1-TGCAC (gtgca); 534(−) HS$EGFR_19-GCCTGC (gcaggc); 538(+) HS$ALBU_03-TGGCA; 545(−)HS$EGFR_19-GCCTGC (gcaggc); 558(−)HS$APOB_04-CAGGTC (gacctg); 561(+) HS$CDC2_02-TTCCTT; 566(−)HS$CDC2_01-AAGGAA (ttcctt); 612(−) RAT$POMC_0-CAGAG (ctctg); 615 (+)HS$GG_12-CTGTC; 617(−) RAT$POMC_0-CAGAG (ctctg); 631(+)HS$EGFR_19-GCCTGC; 638(+) HS$GG_12-CTGTC; 640(−) RAT$POMC_0-CAGAG (ctctg); 640(+) HS$CLASE_0-GTCAC; 649(+) HS$CLASE_0-GTCAC; 650(−) MOUSE$RAS1-ACAACA (tgttgt); 653(+)HS$GG_12-CTGTC; 654(+) RAT$A2UG_1-TGTCCC; 659(−) RAT$A2UG_1-GGGACA (tgtccc); 663(−) RAT$EAI_09-GTCAG (ctgac); 678(+)HS$GG_12-CTGTC; 681(+) MOUSE$RAS1-TCTTCT; 691(+)HS$GG_12-CTGTC; 703(+) MOUSE$AACRGCCTCTC; 708 (+)HS$EGFR_15-TCAAT; 745(+) HS$BG_18-CCACC; 746(+)HS$GG_13-CACCC; 747(−) MOUSE$M1H2-TGGGGA (tcccca); 749(−)HS$BG_17-GGTGGGG (ccccacc); 749(−) HS$BG_22-GGTGG (ccacc); 756(+)HS$IGKL_01-TTTCCA; 786(+) TATA-GA-TAAAAA; 796(−)HS$GMCSF_0-TATTT (aaata); 799(+) HS$BG_22-GGTGG; 801(+)HS$ALBU_03-TGGCA; 803 (−)HS$BG_18-CCACC (ggtgg); 816(+)HS$ALBU_03-TGGCA.

```
2. Promoter Pos: 9004 LDF-12.67
                                            (SEQ ID NO: 155)
tgccagacttcctggagaacaacgggcctatgtgtcctcatgttggcgtt ggacctccccgttcttcagccatactgtggtctgaggaagggtgtgttgg tatgggatgtgagactccctcggtggagggggcgctgatgctccagctca ggactgactggaactgagaggaacactctggtcctaagtgcccttgtcc ccagccctgggagacagaagcttttgccccgcccatctcccaagccccc tcccccaaggctgcatgttctctcatcctctaccagctgatggctacagg ggtgg
```

Annotation:

Position (DNA strand+ or −) Species$Transcription factor-SEQUENCE (complement): 8704(−)HS$ALBU_03-TGGCA (tgcca); 8732(+) RAT$AFEP_0-TGTCCT; 8735(−) RAT$A2UG_1-GACACA (tgtgtc); 8754(−)HS$HH4_02-GGTCC (ggacc); 8763(+) RAT$INS2_0-CTTCAGCC; 8793(−)HS$GG_13-CACCC (gggtg); 8795(−) MOUSE$GATA-CACACCC (gggtgtg); 8801(+) MOUSE$AAMY-ATGGGA; 8821(+)HS$BG_22-GGTGG; 8825(−) HS$BG_18-CCACC; 8830(−)HS$NPY_04-CCCCTCC (ggagggg); 8857(−) RAT$EAI_09-GTCAG (ctgac); 8879(+) HS$HH4_02-GGTCC; 8879(−) RAT$POMC_0-CAGAG (ctctg); 8892(−) RAT$NF1_01-GGGCA (tgccc); 8902(−) MOUSE$M1H2-TGGGGA (tcccca); 8913(−)HS$A11COL-TCTCCCA (tgggaga); 8913(−)HS$LCK_01-TCTCCCAGG (cctgggata); 8916(−)HS$GG_12-CTGTC (gacag); 8925(+) HS$A11COL-GCCCCGCCCC (SEQ ID NO: 182); 8927(+) MOUSE$JUND-CCCGCCCC; 8928(−) RAT$NF1_01-GGGCA (tgccc); 8788(−) MOUSE$FCGR-TTCCTC (gaggaa); 8872(−) MOUSE$FCGR-TTCCTC (gaggaa); 8933(−) HS$APOE_08-GGGCGG (ccgccc); 8934(−) MOUSE$DHFR-GGGGCGGGGC (SEQ ID NO: 183) (gccccgcccc (SEQ ID NO: 182)); 8934(−)HS$MT2A_10-GGGGCGGGG (ccccgcccc;)8936(+)HS$A11COL-TCTCCCA; 8944(+)HS$AAC_13-GCCCCCTCCCC (SEQ ID NO: 184); 8946(+)HS$NPY_04-CCCCTCC; 8953(−) MOUSE$CMYC-GGGAGGG (ccctccc;)8955(−) HS$AAC_10-GGGGGAGGGG SEQ ID NO: 185 (ccctcccc (SEQ ID NO: 186)); 8895(+) RAT$A2UG_1-TGTCCC; 8900(−) RAT$A2UG_1-GGGACA; 9000(+) HS$BG_22-GGTGG; 9003(−)HS$GG_13-CACCC (gggtg); 9004(−) MOUSE$THY1-CCACCCCTG (caggggtgg); 9004(−)HS$BG_18-CCACC (ggtgg)

```
3. Promoter Pos: 9707 LDF-3.70
                                            (SEQ ID NO: 156)
gatccacctgcctctgcttcctgagtgctgggatttaaaggtgtatacaac catagcctgggttgttttcaattcttttcttcttcttctttttttttttt taaaattaatgtgcattggtgttttgcttacatatatgtctgtgtcagag catctgaccctctgggactggagttaaagacagttgtgagctgccacgtgg ctcctgggaattgaacccaggtttcctggaagagcagccaatgctcttaac cactgagccatccctccctccattccccagttgcttgttatcaatccttac taaggt
```

Annotation:

Position (DNA strand+ or −) Species$Transcription factor-SEQUENCE (complement): 9413(+) MOUSE$TDT-CCACCTG; 9413(+)HS$BG_18-CCACC; 9417(−) HS$BG_22-GGTGG (ccacc); 9425(−) RAT$POMC_0-CAGAG (ctctg); 9443(+) MOUSE$WAP-TTTAAA; 9446 (−)HS$GRH_03-TAAAT (attta); 9448(−) MOUSE$WAP-TTTAAA (tttaaa); 9478(+) HS$EGFR_15-TCAAT; 9481(−) HS$CDC2_10-TTGAA (ttcaa); 9482(−)HS$CMYB_01-ATTGAA (ttcaat)9489(+) MOUSE$RAS1-TCTTCT9492 (+) MOUSE$RAS1-TCTTCT; 9495(+) MOUSE$RAS1-TCTTCT; 9510(+) MOUSE$WAP-TTTAAA; 9512(+)

RAT$PL_15-TAAAAT; 9513(-) MOUSE$ADA-TAAAAAA (tttttta); 9515(-) MOUSE$WAP-TTTAAA (tttaaa); 9522(-)HS$GMCSF_0-CATTA (taatg); 9526(+) MOUSE$A21C-ATTGG; 9526(-) MOUSE$MT1-TGCAC (gtgca); 9530(-)HS$BAC_03-CCAAT (attgg); 9545(+) RAT$GLU_04-TATAT; 9548(-) RAT$GLU_04-TATAT (atata); 9556(+) RAT$EAI_09-GTCAG; 9558(+) RAT$POMC_0-CAGAG; 9558(-) RAT$A2UG_1-GACACA (tgtgtc); 9563(+)HS$IGKL_11-CATCTG; 9570(-) RAT$EAI_09-GTCAG (ctgac); 9576(-) RAT$POMC_0-CAGAG (ctctg); 9593(+)HS$NEU_01-CAGTTG; 9595(-) HS$GG_12-CTGTC (gacag); 9608(-)HS$ALBU_03-TGGCA (tgcca); 9623(+)HS$CMYB_01-ATTGAA; 9624 (+)HS$CDC2_10-TTGAA; 9627(-) HS$EGFR_15-TCAAT (attga); 9640(-) MOUSE$UPA-AGGAAA (tttcct); 9649(+)HS$BG_02-AGCCAAT; 9649(+) MOUSE$NCAM-AGCCAA; 9650(+)HS$CJUN_02-GCCAATG; 9650 (+) MOUSE$JUND-GCCAAT; 9651(+)HS$BAC_03-CCAAT; 9655(-) MOUSE$A21C-ATTGG (ccaat); 9682(-) MOUSE$CMYC-GGGAGGG (ccctccc); 9692(+)HS$NEU_01-CAGTTG; 9693(-) MOUSE$M1H2-TGGGGA (tcccca); 9705(+)HS$EGFR_15-TCAAT; 9707 (-)HS$GP2B_02-TGATAA (ttatca)

4. Promoter Pos: 14700 LDF-1.71 TATA box at 14673 21.01

(SEQ ID NO: 157)

Tggaagagcagatagtgctcttaacctctgggctggccttgaactcaga aatcctcctgcctctacctcccgagtgctgggattaaaggcgtgcgcca ccactgcctggccctgagctttacttgagcatactaagtgcatagaac ctccagcccacttgggcccttaacaacccaaggatgaacctgggtggcc taaggaaacagacaggcttaggacccatggagtcagggtagtacacagc tctgctctcagaagattaaaaaagaaaaaaaaaaaaaagccaggtgact cccagtgacctagaaaggaagcccttcaggaagggaggagtgtgggcac agaaagcagccctgcaggctggggctgggttataaaaggctgcgggtgc catgctgagctctatcctgaagagtgggaaaggcccctagagacagcct taaaacccctagg Annotation:

Position (DNA strand+ or -) Species$Transcription factor-SEQUENCE (complement): 14400(-)HS$BG_22-GGTGG (ccacc); 14403(+) MOUSE$ACRD-TGCCTGG; 14413(-) HS$GG_36-GGGGCC (ggcccc); 14441(-) MOUSE$MT1-TGCAC (gtgca); 14490(+) HS$BG_22-GGTGG; 14493(-)HS$GG_13-CACCC (gggtg); 14494(-) HS$BG_18-CCACC (ggtgg); 14498(+)HS$CDC2_01-AAGGAA; 14499(+) MOUSE$UPA-AGGAAA; 14502(+) HS$APOA2_1-AAACAGAC; 14503(-)HS$CDC2_02-TTCCTT (aaggaa); 14511(-) HS$GG_12-CTGTC (gacag); 14521(-)HS$HH4_02-GGTCC (ggacc); 14523(-) HS$GG_40-TGGGTC (gaccca); 14528(+) RAT$EAI_09-GTCAG; 14537(-) RAT$EAI_07-CTACCC (gggtag); 14549(-) RAT$POMC_0-CAGAG (ctctg); 14560(-) MOUSE$RAS1-TCTTCT (agaaga); 14562(+) MOUSE$ADA-TAAAAAA; 14593(-)HS$APOA2_0-GTCACCTG (caggtgac); 14593(-)HS$CLASE_0-GTCAC (gtgac); 14603(-)HS$CLASE_0-GTCAC (gtgac); 14609(+) HS$CDC2_01-AAGGAA; 14614(-)HS$CDC2_02-TTCCTT (aaggaa); 14638(+) RAT$NF1_01-GGGCA; 14644(-) RAT$A2UG_0-TGTGCC (ggcaca); 14662(-) HS$EGFR_19-GCCTGC (gcaggc)14673(+) TATA-TATAAAAG; 14691(-)HS$GG_13-CACCC (gggtg); 14694(-)HS$ALBU_03-TGGCA (tgcca); 14694(-) RAT$OMP_07-TGGCAC (gtgcca).

5. Promoter Pos: 17266 LDF-0.75 TATA box at 17238 20.29

(SEQ ID NO: 158)

Ggatgagaagttcaaggtcaaaccaggcactggaggcacatgcctttaat cccagcatttgggagactaaggcaggctgatttctgagttcaaggccagc ctggtctataaagttccaggacacagagaaacctgcaaaaaaaaaaaaa aaaaaaaaaaaaaaaaaaaagaaagaaataccataaaaactaatattc attattaaacgttcgtgtgtgcgtatttcctggaggagctggagttacag tggctgtgagctggcagaggtgcccgggtggaacttcggccctcaagacc agttagtgctggaccttctctctaaccccaggcctttataaaaggaa tcttatcatcttatcacccgggtgtgaaggtgcgccttcaatcccagcac tctggaggtagtgacacacctactccaacaaggccatacttcctaatagt gccac Annotation:

Position (DNA strand+ or -) Species$Transcription factor-SEQUENCE (complement): 16966(-)HS$A11COL-TCTCCCA (tgggaga); 16977(-)HS$EGFR_19-GCCTGC (gcaggc); 16979(+)HS$HH4_01-GATTTC; 16992(-) RAT$POMC_0-TGAACT (agttca); 16993(-) HS$CDC2_10-TTGAA (ttcaa); 17020(+) RAT$A2UG_1-GACACA; 17023 (-) RAT$AFEP_0-TGTCCT (aggaca); 17024(+) RAT$POMC_0-CAGAG; 17082(-)HS$GMCSF_0-TATTT (aaata); 17092(+)HS$GG_22-CTAAT; 17096(+) HS$PL_09-TATTCAT; 17100(+) HS$GMCSF_0-CATTA; 17102(-)HS$PL_05-ATGAATA (tattcat); 17108(-) HS$ALBU_04-TTAATAAT (attattaa); 17124(+) HS$GMCSF_0-TATTT; 17130(-)HS$INS_05-GGAAAT (atttcc); 17131(-) MOUSE$UPA-AGGAAA (tttcct); 17155 (-) RAT$GF_04-AGCCACT (agtggct); 17162(+) HS$ALBU_03-TGGCA; 17165(+) RAT$POMC_0-CAGAG; 17175 (-) RAT$NF1_01-GGGCA (tgccc); 17177 (+)HS$BG_22-GGTGG; 17180(-)HS$GG_13-CACCC (gggtg); 17181(-)HS$BG_18-CCACC; 17215(-) HS$HH4_02-GGTCC (ggacc); 7238 (+) TATA-TATAAAAA; 17245(+)HS$CDC2_01-AAGGAA; 17250 (-)HS$CDC2_02-TTCCTT (aaggaa); 17252(+)HS$BG_06-CTTATCAT; 17257(-) MOUSE$AAG-GATAAG (cttatc); 17258(-)HS$GP2B_02-TGATAA (ttatca); 17265(-) MOUSE$AAG-GATAAG (cttatc); 17265(+)HS$GG_13-CACCC; 17266(-)HS$GP2B_02-TGATAA (ttatca).

6. Enhancer Pos: 19922 LDF-42.00:

(SEQ ID NO: 159)

Ccacctccattctctttcagtcccctgagttctggactcttgggggtgg ggggtggaagcgcctaccttgagttttctgaggcagtccgtagggtatt cgcccgcagatacatccctaattgcatatgcatgctccctgctcatcttg aggggggacatgtcctactcctgcagaaatggggatgtgcaaaacgata ttgaattggccttgactcaggaaccaggcccggggtcccgctcctcccg cccctccacgatctgctaccatgacgtcaaggtgggcgggcg Annotation:

Position (DNA strand+ or -) Species$Transcription factor-SEQUENCE (complement): 19622(+) RAT$A12COL- CACCTCC; 19625(−)HS$BG_22-GGTGG (ccacc); 19648 (+) MOUSE$RAS1-AGTTCT; 19666(+)HS$BG_17-GGTGGGG; 19666(+)HS$BG_22-GGTGG; 19669(−)HS$GG_13-CACCC (gggtg); 19670(−)HS$BG_18-CCACC (ggtgg); 19672 (−) MOUSE$PERI-CCCCACCCCC (SEQ ID NO: 187) (ggggtgggg (SEQ ID NO: 188); 19674(+) HS$BG_22-GGTGG; 19677(−)HS$GG_13-CACCC (gggtg); 19678(−)HS$BG_18-CCACC (ggtgg); 19738(+)HS$GG_22-CTAAT; 19742(+)HS$PL_01-TTGCATA; 19775(+) RAT$A2UG_1-GGGACA; 19780(−) RAT$A2UG_1-TGTCCC (gggaca); 19781(+) RAT$AFEP_0-TGTCCT; 19789(+)HS$EGFR_20-TCCTGC; 19795(+)HS$HH4_07-AGAAATG; 19801(−)HS$GMCSF_0-CATTT (aaatg); 19812(−) MOUSE$MT1-TGCAC (gtgca); 19820(+) HS$CMYB_01-ATTGAA; 19821(+)HS$CDC2_10-TTGAA; 19824(−)HS$EGFR_15 TCAAT (attga); 19825(+) MOUSE$A21C-ATTGG; 19830(−) MOUSE$JUND-GCCAAT (attggc); 19833(+)HS$MT2A_08-TGACTCA; 19839(−) MOUSE$NGF-TGAGTCA (tgactca); 19854(+) HS$HH4_02-GGTCC; 19867(+) MOUSE$JUND-CCCGCCCC; 19868(+)HS$TGFB1_0-CCGCCCCC; 19872(+)HS$NPY_04-CCCCTCC; 19872(−)HS$CDC25C-GGCGG (ccgcc); 19873(−)HS$APOE_08-GGGCGG (ccgccc); 19874 (−)HS$MT2A_10-GGGGCGGGG (ccccgcccc); 19875(−) RAT$MT1_01-GGGGGCGG (ccgccccc); 19893(+)HS$FN_03-TGACGTCA; 19893(+)HS$VIP_04-TGACGT; 19893(+) HS$INS_04-TGACG; 19900(−)HS$INS_04-TGACG (cgtca); 19900(−) HS$VIP_04-TGACGT (acgtca); 19900(−)HS$FN_03-TGACGTCA (tgacgtca); 19902(+)HS$BG_22-GGTGG; 19905 (+)HS$APOE_08-GGGCGG; 19906(−)HS$BG_18-CCACC (ggtgg); 19906(+)HS$CDC25C-GGCGG; 19909 (+)HS$APOE_08-GGGCGG; 19910(+)HS$CDC25C-GGCGG; 19912(−) HS$APOE_09-GCCCGCCC (gggcgggc); 19913(+)HS$CDC25C-GGCGG; 19914(−) MOUSE$MT1-CCGCCCG (cgggcgg).

7. Promoter Pos: 20018 LDF-2.88 TATA box at 19989 18.87

(SEQ ID NO: 160)
ctaattgcatatgcatgctccctgctcatcttgagggggacatgtccta ctcctgcagaaatgggggatgtgcaaaacgatattgaattggccttgact caggaaccaggcccggggtcccgctcctccccgcccccctccacgatctgc taccatgacgtcaaggtgggcgggcggcggcaggtgcgtggcccgcagcc actcctttaaggcggagggatccaagggcggggcccgggctgtgcttcgc cttatatagggcggtcggggcgt Annotation:
Position (DNA strand+ or −) Species$Transcription factor-SEQUENCE (complement): 19738(+)HS$GG_22-CTAAT; 19742(+)HS$PL_01-TTGCATA; 19775(+) RAT$A2UG_1-GGGACA; 19780(−) RAT$A2UG_1-TGTCCC (gggaca); 19781(+) RAT$AFEP_0-TGTCCT; 19789(+)HS$EGFR_20-CCTGC; 19795(+)HS$HH4_07-AGAAATG; 19801(−) HS$GMCSF_0-CATTT (aaatg); 19812(−) MOUSE$MT1-TGCAC (gtgca); 19914(−) MOUSE$MT1-CCGCCCG (cgggcgg); 19820(+) HS$CMYB_01-ATTGAA; 19821(+) HS$CDC2_10-TTGAA; 19824(−)HS$EGFR_15-TCAAT (attga); 19825(+) MOUSE$A21C-ATTGG; 19829(−)HS$BAC_03-CCAAT (attgg); 19830(−) MOUSE$JUND-GCCAAT (attggc); 19833(+)HS$MT2A_08-TGACTCA19839(−) MOUSE$NGF-TGAGTCA (tgactca)19854(+)HS$HH4_02-GGTCC; 19867(+) MOUSE$JUND-CCCGCCCC; 19868(+)HS$TGFB1_0-CCGCCCCC; 19872(+)HS$NPY_04-CCCCTCC; 19872(−)HS$CDC25C-GGCGG (ccgcc); 19873(−)HS$APOE_08-GGGCGG (ccgccc); 19874(−) HS$MT2A_10-GGGGCGGGG (ccccgcccc); 19875(−) RAT$MT1_01-GGGGGCGG (ccgccccc); 19893(+) HS$FN_03-TGACGTCA; 19893(+)HS$VIP_04-TGACGT; 19893(+)HS$INS_04-TGACG; 19900(−) HS$INS_04-TGACG (cgtca); 19900(−) HS$VIP_04-TGACGT (acgtca); 19900(−)HS$FN_03-TGACGTCA (tgacgtca); 19990(+) RAT$GLU_04-TATAT; 19902(+) HS$BG_22-GGTGG; 19905(+)HS$APOE_08-GGGCGG; 19906(−)HS$BG_18-CCACC (ggtgg); 19906(+) HS$CDC25C-GGCGG; 19909(+) HS$APOE_08-GGGCGG; 19910(+)HS$CDC25C-GGCGG; 19912(−) HS$APOE_09-GCCCGCCC (gggcgggc); 19913(+) HS$CDC25C-GGCGG; 19934(+) RAT$GF_04-AGCCACT; 19947(+)HS$TPI_04-AGGCGG; 19948(+) HS$CDC25C-GGCGG; 19962(+) HS$WAF1_03-AGGGCGG; 19963(+)HS$APOE_08-GGGCGG; 19964(+) HS$CDC25C-GGCGG; 19967(+)HS$GG_36-GGGGCC; 19989(+) TATA box-TTATATAG; 19995(−) RAT$GLU_04-TATAT (atata); 19995(+)HS$WAF1_03-AGGGCGG; 19996(+)HS$APOE_08-GGGCGG; 19997(+) HS$CDC25C-GGCGG; 20005(+) MOUSE$GLUT-GGGGCGT; 20006(+) MOUSE$GLUT-GGGCGT; 20011 (−)HS$U2SN_04-ACGCCC (gggcgt)

Thereafter, since the AAV-ZF vector has an insert packaging limit of approx. 1810 bp, we designed a potentially enhanced, minimal hsp90ab1 constitutive promoter, by using potential enhancer regions from a region of approx. 1.7 k upstream of the transcription start site (small caps in the sequence shown below), plus 95 bp of exon 1 (big caps in the sequence shown below), thus resulting in a 1810 bp insert size that is ideal for an optimally-packaged AAV vector in the present expression system. Optimal packaging sizes are essential for high AAV titres (>10 virions/ml), which may in turn be essential for effective gene therapy. The final synthetic hsp90ab1 design (SEQ ID NO: 146) was further designed to also contain flanking NheI sites (see bold), which were added for cloning into the AAV vector. A cryptic NheI site (underlined in the sequence below) was mutated from the original sequence (c>a).

gctagcaacaccctagggccttctgagcaatcctacccagtgtctcctcat atattgatttctttatgggcttcacacacacacacacacacacacacac acacacacacacacacagaattaaggagaggctaacagacagtgcagga tgggatgataacagacgaagtagacagaggcaaggagaaagcaactactgt ttaacaatgaatgcacattagacagactgcaggcaagcaccgggaacaaag gtgtgggcggtggtgtggggacacaagccagcatgagctaagatagcagag cactgagtgcccatcctctactggagggctcatcagtccaacaagcttcca gatgcagccttggaaaaaggcaaggctagattgccagctgaaggacatggc aggccacctttagaacagaggcactggcacaacttggttttctggctcctg gaactgggccaacctgtgaccagcaccttcatgcggatgcctagaactcca gcttctctgaaaagactgggacctgctcctctctaggtccaaagagctgca tgcagtagggaagaggctagagaagcgaaaccagcttgagaaacagcttgt gctcacatagggagggcgcacgtacccgcgcgctgtgtacgtgggagaccg -continued
```
gggaggctgaggggtggggagtgttctacccagtagcgcaagctgatagct cggttctctgttcactagaaggtgtccgcagtcactcaccccacagcccc cgtgccctgtgaccgatccaggtcagctatccctccctctgcgctccactc ccccactgttatgtgggcctcttagggccacgcgtggagggtcgttcaacc ctggcccacggtaggcagacttggggaaaatttcttcccagggtaagatca aggtaggggaaaaaaaaaaaaaaaaaaagccacccagccaagcggcgacga agacactgccccgccgcagcagggaggtggagcctaggggggaggggtg gagaccgccgagacaggcctagaaactgctggaagaaatcgcagcaccacc gctgctgatccttccgccgcaggccgccaaagagtccctaccagcccaggc ccgtgcccctccctcggggaaagcggctcccagcctgaagctgtgctgta cccgggagggtggggatgggggaatcgggggcctccttaaagttggacaag gaatttatcatccttttctcttgatgtgcgatttgtagggaacattctagt aagatcgggtctggaaatggcagccgagttggccacctccattctctttca gtcccctgagttctggactcttgggggtgggggggtggaagcgcctacct tgagttttctgaggcagtccgtagggtattcgcccgcagatacatccctaa ttgcatatgcatgctccctgctcatcttgagggggacatgtcctactcct gcagaaatggggatgtgcaaaacgatattgaattggccttgactcaggaa ccaggcccggggtcccgctcctcccgccccctccacgatctgctaccatg acgtcaaggtgggcgggcggcggcaggtgcgtggcccgcagccactcctt aaggcggagggatccaagggcggggccogggctgtgottcgccttatatag ggcggtoggggcgttcgggagctCTCTTGAGTCACCCCCGCGCAGCCTAG

GCTTGCCGTGCGAGTCGGACTTGGTCCGGGCCCACCACCCTGCTCTGTACT

ACTACTCGGCTTTCCCGTCAAGgctagc
```

The above designed potential pHSP promoter was synthesised chemically and vectorised to express mZF11-KRAB-WPRE.

In one example, the expression construct was inserted into an rAAV2/9 viral vector, similarly to that described previously for the equivalent pNSE construct in rAAV2/1, for a broader expression profile than for rAAV2/1 which is relatively specific for neuronal expression (*Expert Opin. Biol. Ther.*, (2012), Jun.; 12(6): 757-766.). In this way, it was possible to assay for both neuron-specific and potential ubiquitous expression of peptide-encoding constructs. Similarly, the expression construct can be inserted into an rAAV2/1 viral vector for expression in cell types preferentially targeted by AAV2/1.

To administer viral expression constructs, bilateral intraventricular injection on neonatal R6/1 mice was performed, with the maximum volume of AAV possible (4 μl, ~10 virions).

In these studies, it was found that pHSP controlled expression constructs (based on SEQ ID NO: 146) were expressed for a significantly longer period of time than pCAG (see FIG. 17, panels b, c and d; pHSP data for 3, 6, 12 and 24 weeks post administration).

As previously indicated, the data of FIG. 17 clearly demonstrates that, when considering the functional repression of mutant HTT, pCAG-driven repression was only detected at 3 weeks and was lost by 6 weeks (FIG. 17, panel a; pCAG), which matched the complete loss of detectable zinc finger peptide expression from this viral promoter. By contrast, pHSP-driven repression was maintained over the entire 24-week period, albeit with slightly less repression at 3 weeks and a slight trend to reduction in expression over time (FIG. 17, panel a; pHSP).

Beneficially, the short wild-type Htt allele was unaffected in all samples, indicating a lack of off-target activity (see FIG. 17, panels e and f) for the 11-finger zinc finger peptide of the invention.

In summary, these results clearly demonstrate that the combination of mZF11-KRAB design with a ubiquitous promoter (pHSP) results in similar levels of repression of target gene to those based on the neuron-specific promoter (pNSE).

It should be further noted that long-term expression of transcription factors (TFs) is very challenging and, to our knowledge, has never been attempted before. Indeed, it is far more difficult to express functional levels of a synthetic transcription factor for months on end compared to a secreted enzymatic reporter, such as luciferase (*Gene Ther.* 2001; 8:1323-32), which amplifies any gene expression signal. Hence, the expression of zinc finger transcription factor observed at 24 weeks post infection in the present examples sets a new benchmark.

Overall, the pHSP construct described herein achieved mut HTT repression of approx. 25% in the whole brain for at least 24 weeks. Furthermore, it has previously been found that approx. 25% repression of mutant HTT is in the therapeutic range (PNAS (2012), 109: E3136-E3145). Thus, the promoter designs of the present invention hold great promise for therapy.

While the present beneficial results in long-term endogenous gene expression have been demonstrated in the context of zinc finger-dependent repression of mutant HTT, these results indicate that the pHSP promoter/enhance sequence identified herein may also prove useful for ubiquitous expression of any sequence (e.g. transgene) of interest: for example, for therapeutic applications, such as in gene therapies, and in particular for the expression of transcription factors.

C. Alternative Promoter Design for Long Term Therapeutic Transgene Expression: Human Use The novel pNSE and pHSP promoter/enhancer sequences described above for expression of genes in mouse were used to derive corresponding promoter/enhancer sequences for expression of genes in human cells in two ways.

First, the mouse versions (e.g. SEQ ID NO: 146 for pHSP) used and tested as described in relation to FIG. 17 are studied in different human cell types in tissue culture. In view of the sequence conservation of many promoter sequences and binding sites for transcription factors between different species, promoter constructs are often functional in more than one species. It is therefore possible to identify mouse promoter/enhancer constructs that achieve suitable transgene expression levels for therapeutic (gene therapy) applications in a variety of human cell/tissue types.

Secondly, humanised versions of the human hsp90ab1 and pNSE promoter fragments can be designed based on similar choices of DNA sequence start and end points in order to achieve an optimal 1.8 kb DNA promoter fragment suitable for AAV viral packaging. NheI flanking restriction sites may be added to each of these sequences, e.g. resulting in the human promoter/enhancer sequences of SEQ ID NOs: 147 and 148. Thus SEQ ID NO: 147 corresponds to the sequence extending 1.6 kbps upstream of the transcription start site of human hsp90ab1 and 179 bps of exon 1 of the gene, with additional NheI flanking sites. SEQ ID NO: 148 corresponds to the sequence extending 1.6 kbps upstream of the transcription start site of human enolase 2 plus 210 bps of exon 1 of the gene, with the addition of flanking NheI restriction sites.

DISCUSSION

In these Examples, zinc finger peptides have been designed that are able to recognise and bind both DNA strands of a stretch of CAG repeats, by recognising both poly-GCA and poly-GCT triplets; and shown that such proteins are able to induce transcription repression of target genes both in vitro and in vivo.

It has been demonstrated that naked zinc finger peptides (i.e. lacking additional effector domains) can be highly efficient inhibitors of target gene expression (polyQ-EGFP expression was reduced by up to 90%), particularly when the number of CAG-repeats is equal or superior to 35. This is a significant finding, since the number of CAG-repeats in wild-type genes in the human genome (including the htt gene), is less than 35. Without being bound by theory, it is likely that the mechanism of repression in these cases is due to steric hindrance of RNA polymerase complex progression, as reported by Choo et al. for a synthetic ZFP against the Bcr-Abl oncogene (Choo et al. (1994) Nature, 372 (6507): 642-645).

Fusing the Kox-1 repression domain to the zinc finger peptides of the invention was found to further reduce expression of targeted genes. In these experiments, it was demonstrated that repression required binding to CAG repeats, since control vectors lacking CAG repeats were not affected.

Although partial reduction of the shorter wild-type htt protein has been shown to be tolerated for up to 4 months in animal models (Boudreau et al. (2009), Mol. Ther. 17(6): 1053-1063), it is generally considered that a safe and effective therapy for HD should preferentially target the mutant htt allele. Using a competition assay, it has been shown that the zinc finger peptides of the invention preferentially repress the expression of reporter genes containing over 35 CAG repeats, which suggests that they hold significant promise for a therapeutic strategy to reduce the levels of mutant huntingtin protein in heterozygous patients.

After 20 days (approx. 3 weeks) of stable expression of the zinc finger peptides, the 11-finger protein was found to exhibit the strongest repression of the target mutant HTT allele. In fact, when fused to the Kox-I repression domain, the most active zinc finger peptides of the invention were able to dramatically reduce the levels of the endogenous mutant protein by 95%, and the levels of the mutant mRNA by approximately 80%, with negligible effect on the expression of the wild-type allele, or on any other genes containing a wild-type number of CAG repeats. However, sustained, mid to long term, expression of therapeutic zinc finger proteins would likely be required for an effective therapy.

Gene therapy is an attractive therapeutic strategy for various neurodegenerative diseases. For example, lentiviral vectors have been used to mediate the widespread and long-term expression of transgenes in non-dividing cells such as mature neurons (Dreyer, Methods Mol. Biol. 614: 3-35). An rAAV vector was also used by Rodriguez-Lebron et al. (2005) Mol. Ther. 12(4): 618-633, to deliver anti-mutant Htt shRNAs in HD model mice; thereby reducing striatal mHtt levels and slowing progression of the HD-like phenotype. Moreover, as RNAi (van Bilsen et al. (2008), Hum. Gene Ther. 19(7): 710-719; Zhang et al. (2009), J. Neurochem. 108(1): 82-90; Pfister et al. (2009), Curr. Biol. 19(9): 774-778), and LNAs (Hu et al. (2009), Nat. Biotechnol. 27(5): 478-484; and Hu et al. (2009), Ann. NY Acad. Sci. 1175: 24-31) have recently shown promise for treating HD, suitable delivery vehicles are likely to be optimised in the years ahead, and the complementary zinc finger peptide approach described here would likely benefit from such advances.

Accordingly, a model cell line derived from striatal cells of a knock-in HD mouse model (Trettel et al. (2000), Hum. Mol. Genet. 9(19): 2799-2809) has been developed and used to demonstrate the effects of the zinc finger peptides of the invention under likely therapeutic conditions (i.e. single-copy alleles in chromosomal loci).

rAAV appeared as a promising delivery system, and so we used it to deliver the zinc finger peptide modulators of the invention to the striatum of the R6/2 and the R6/1 mouse models of HD. We observed a significant repression of the mutant htt transgene in R6/2 and R6/1 brain striatum compared to control striatum, while expression of the wt gene was unaltered. Co-incident with the reduced mutant htt expression levels, mice showed a delay in the onset of many HD-like symptoms characteristic of the R6/2 model line. Specifically, we found a delay in the onset of clasping behaviour, as well as an attenuation of the deficits in the accelerating rotarod (Menalled et al. (2009), Neurobiol. Dis. 35: 319-336).

However, even with the improved rAAV expression construct, for some zinc finger peptide modulators we observed a significant reduction in expression of the zinc finger peptides over time (4 to 6 weeks post-injection), with a concomitant reduction in mutant htt repression. Decreased expression of the zinc finger peptide over time could be due to a number of reasons (e.g. promoter silencing, or to instability of the zinc finger peptide DNA that remains as extra-chromosomal DNA in quiescent striatal cells).

Further studies indicated that the reduction in expression of zinc finger peptides from about 4 weeks post-injection coincides with an upregulation in the host immune system (microglial and astroglial cells are significantly activated in vivo), suggesting that the expression of these heterologous peptides might be prevented by a severe and targeted host immune response to cells expressing the zinc finger peptides. Thus, it was decided to try to improve the mid- to long-term expression of the potentially therapeutic peptides in vivo by reducing their immunogenicity in mouse and human cells. In this way, it was hoped to create zinc finger repressor proteins capable of long-term therapeutic activity against the mutant HTT gene and other pathogenic genes associated with expanded CAG-trinucleotide repeat sequences.

Mousification versus Humanizaton In Therapy Development

The humanisation of biologics, such as engineered antibodies, is long established as a way of reducing immunoreactivity in therapy (Carter et al. (1992), Proc. Natl. Acad. Sci. USA, 89: 4285-4289; and Presta et al. (1997), Cancer Res., 57: 4593-4599). Adapting synthetic gene therapy constructs for their hosts is relatively more challenging because they can have more components, and longer functional regions have to be considered. For example, multiple zinc finger binding helices usually require several non-wild-type amino acids to bind desired target sequences (see e.g. FIG. 10). Nonetheless, it was considered in this work that these differences should be minimised to maximise the chances of developing successful therapeutic candidate peptides.

In this study, we have shown that "mousifying" a zinc finger repressor construct for therapy in mouse brains significantly reduced in vivo toxicity, while maintaining similar repression efficiency against the target gene when compared to the original (non-mousified) peptide in expression and repression studies. The reduction of inflammatory responses following host-matching of the zinc finger construct suggests an immune response against non-self proteins as the most likely explanation for the detected medium-term toxicity. Indirect evidence supporting this hypothesis is the lack of apparent toxicity of ZF-Kox-1, both in cell culture and in short-term in vivo assays. Indeed, we were able to generate stable cell lines expressing ZF-Kox-1 in vitro, and a cell viability assay showed no toxic effects (Garriga-Canut et al. (2012), *Proc. Natl. Acad. Sci.;* 109, E3136-3145).

One objective in this study was to replace all associated effector domains expressed as part of the therapeutic protein with host homologues, while another objection was to re-engineer the functional DNA-binding domain of the zinc finger peptide to retain their intended binding activity. The latter required using the fewest possible amino acid changes, relative to the host organism protein scaffold (in this case, the mouse zinc finger domain, Zif268). In principle, epitope scanning (Parker et al. (2010), *BMC Bioinformatics,* 11: 180) can also help to guide the final choice of amino acid design changes, with the aim being to reduce potential epitopes.

In subsequent studies, it was shown that the protein sequence changes introduced were sufficient to reduce neuronal cell loss in vivo, making the potential gene therapy construct significantly less toxic than even a GFP expression vector. In fact, the mousified construct behaved more like a control PBS injection than a heterologous protein treatment.

Functional mut HTT Repression and Sustained Zinc Finger Expression This study has demonstrated that reduced toxicity levels of zinc finger peptide modulators of the invention correlates with mut HTT repression activity. As individual ZF-expressing cells of the invention achieve 95% mut HTT repression with the strong promoters used here, slight improvements in transduction efficiency may be a target for future research so as to further improve the therapeutic effect in HD phenotype reversal. One approach may be to increase the effective dosage of the zinc finger peptide modulators of the invention. For example, repression of mut HTT throughout the whole brain might be enhanced by increasing the viral dosage, while monitoring potential toxicity.

Previous studies with modified antisense oligonucleotides have shown that transiently lowering mut HTT levels to approx. 50% is sufficient for a sustained phenotypic reversal over a two-month period (Kordasiewicz et al. (2012), *Neuron,* 74: 1031-1044). Such levels of repression are within the range achieved in the present study.

It is also possible to alter zinc finger expression levels and persistence by altering promoter designs. Here, the effectiveness of a strong expression construct has been demonstrated, which contains the CMV early enhancer element and chicken β-actin promoter, with the Woodchuck hepatitis virus post-transcriptional regulatory element (pCAG-WPRE). However, use of a 1.8 kb rat neuron specific enolase promoter (pNSE) sequence, which has been shown to give persistent expression that is several 100-fold greater than the CMV promoter in rodent brains (Peel et al. (1997), *Gene Ther.,* 4: 16-24; Forss-Petter et al. (1990), *Neuron,* 5: 187-197), has been demonstrated to provide prolonged expression of zinc finger peptide transgenes. In combination with a WPRE, pNSE has been shown to give strong stable luciferase expression in the rat striatum, even after 15 months (Xu et al. (2001), *Gene Ther.,* 8: 1323-1332). Interestingly, pNSE appears to be specific to neurons (which do not present antigens). In combination with rAAV2/1 vectors, which show a strong tropism towards neurons, the targeting may thus beneficially avoid expression in glia and astrocytes (which do present antigens). The reduced antigen presentation may account for how foreign luciferase gene expression is sustained for at least 15 months. It has been demonstrated here that zinc finger constructs of the invention in combination with WPRE and NSE (e.g. rAAV2/1-pNSE-mZF-ZF87-WPRE) can yield strong stable repression of mut HTT primarily in neurons, rather than also in glia and astrocytes. It is possible that since pNSE restricts expression to neurons, this potential therapeutic route could reduce inflammation and toxicity even further, enabling very long term expression of therapeutic zinc finger constructs. Overall, the results presented here demonstrate that combining the mouse host-adapted mZF-KRAB construct of the invention with the mouse pNSE promoter allows target mut HTT repression in the whole brain, for an extended 6 month period, which is clearly significantly longer than the 3 weeks reported previously. Similar effects can be expected in human, using either the mouse promoter or the human equivalent of the synthetic pNSE promoter used in this study, as described above.

Additionally, further benefits associated with the use of a newly characterised ubiquitous promoter, pHSP (based on Hsp90) have been shown. In particular, these benefits of the invention are enhanced when the novel promoter is used in combination with rAAV2/9 vectors, based on a virus that infects a wide variety of cell types. Thus, it has been demonstrated that pHSP-driven repression of mutant HTT can be maintained over long periods of time (e.g. for at least 24 weeks).

In other words, the results presented herein show that combining the mZF11-KRAB construct with the ubiquitous promoter (pHSP) according to the invention, may allow similar levels of repression of target gene (e.g. of mutant HTT) in the brain as compared to when the neuron-specific promoter (pNSE) is used. Similar effects can be expected in human subjects using either the mouse promoter or the human equivalent of the synthetic pHSP promoter used in this study. Similarly, beneficial effects are expected with the other zinc finger modulator peptides disclosed herein, which may contain 6, 8, 10, 11, 12, 18 or more adjacent zinc finger domains.

As described above, the inventors have developed a formulation for a promoter-enhancer (derived from Hsp90ab1) that functions ubiquitously and long term in vivo. However, the use of ubiquitous promoters goes beyond applications to gene therapy in the brain, and have particular significance in Huntington's and other poly-glutamine diseases where injection and expression of therapeutic zinc fingers in peripheral tissue may become increasingly important.

Although HD is widely thought of as primarily a neurological disease, it is in fact a complex disease that has a peripheral component to its pathophysiology, including effects in the heart, skeletal muscle, kidney and liver. In fact, heart failure is the second most common cause of death in HD patients (Zielonka, D et al., (2014), *Exp. Clin. Cardiol.* 20, 2547-2554).

The inventors have previously established a number of molecular and physiological events leading to HD-related cardiomyopathy in two widely used HD mouse models, namely R6/2 and HdhQ150 (Mielcarek, M. et al., (2014), Dysfunction of the CNS-Heart Axis in Mouse Models of Huntington's Disease. *PLoS Genetics,* 10(8): e1004550). Following on from this, the inventors have recently obtained a striking new technical effect in two HD mouse models (as well as in clinical HD settings), which suggests a metabolic remodelling typical of failing hearts (Toczek, M. et al. (2016), An impaired metabolism of nucleotides underpins a novel mechanism of cardiac remodelling leading to Huntington's disease related cardiomyopathy. *BBA Molecular basis of disease*, 1862, 2147-2157). Indeed, it was found that heart dysfunction in HD appears to be associated with cellular energy imbalances, changes in catabolism of adenine nucleotides, steady-state internal redox derangements and an activation of AMPK, leading to a shift in the cardiac substrate preference. These changes were accompanied by increased concentrations of adenine nucleotide catabolites (inosine, hypoxanthine, xanthine and uric acid) and uridine, in both HD mouse models and HD patients' plasma. These metabolites represent the first identified biomarkers related to heart dysfunction in HD.

In this context, the new ubiquitous promoter (pHSP) for mouse and human use as described herein, and alternative multi-cell type-targeting AAV tropisms (e.g. rAAV2/9) can be advantageously used in methods and treatments described herein. For example, it would prove particularly useful if HD morbidity and mortality could be rescued using zinc finger repression of mutant HTT in peripheral tissues such as the heart. Additionally, in the brain, using rAAV2/9 (broad infectivity), rAAV2/1 (more neuron-specific), or a mixture of both could be used to tune the target cell range, particularly in combination with advantageously-chosen promoter-enhancers.

CONCLUSION

This study demonstrates that host-matching synthetic gene constructs can reduce immunotoxicity damage to the brain. This could be applied to many other gene therapy constructs, including ones that are promising but show a degree of toxicity. Developing constructs that function for the lifetime of an organism is an important aim of gene therapy and host optimisation brings us one step closer towards this goal.

Overall, the results presented in this study establish that the zinc finger peptides of the invention can specifically and effectively repress mutant htt in vivo (via striatal injection), in a dose-dependent manner; and that, as a result, there are some clear behavioural improvements and reduction in Huntington's disease symptoms. The constructs of the present invention demonstrate improved host-compatibility and do not induce the strong immunological responses when expressed in mouse brain that caused the expression of previous constructs to be shut down. The improved therapeutic zinc finger constructs disclosed here have demonstrated great potential for the treatment of Huntington's disease due to the ability to maintain heterologous protein expression over the mid- to long-term without obvious toxicity issues. Improved delivery and expression systems will further enhance the potential of these therapeutic peptides.

The protein constructs of the invention also have great potential for the treatment of other diseases known to be associated with pathogenic expanded polyglutamine repeat sequences.

Acknowledgements

The work leading to this invention has received funding from the European Union Seventh Framework Programme H2020 (ERC-2014-PoC 641232-Fingers4Cure) under grant agreement number 641232. The work leading to this invention has also received funding from the European Research Council under the European Union's Seventh Framework Programme (FP72007-2013)/ERC grant agreement number 201249.

Sequences

TABLE 11

Peptide and Nucleic Acid Sequences.

| SEQ ID NO: | Sequence Type | Sequence |
|---|---|---|
| 1 | Recognition sequence (prt) | $QS^A/_GD^L/R^T/_KR$ |
| 2 | Recognition sequence (prt) | QSADLTR |
| 3 | Recognition sequence (prt) | QSGDLTR |
| 4 | Recognition sequence (prt) | QSGDRKR |
| 5 | Recognition sequence (prt) | QSADRKR |
| 6 | Linker (prt) | TGEKP |
| 7 | Linker (prt) | $TG^E/Q^K/_RP$ |
| 8 | Linker (prt) | $TG^G/_S^E/_Q^K/_RP$ |
| 9 | Linker (prt) | TGGERP |
| 10 | Linker (prt) | TGSERP |
| 11 | Linker (prt) | TGGQRP |
| 12 | Linker (prt) | TGSQRP |

TABLE 11-continued

Peptide and Nucleic Acid Sequences.

| SEQ ID NO: | Sequence Type | Sequence |
|---|---|---|
| 13 | Linker (prt) | TGGEKP |
| 14 | Linker (prt) | TGSEKP |
| 15 | Linker (prt) | TGGQKP |
| 16 | Linker (prt) | TGSQKP |
| 17 | Linker (prt) | $TG(^G/_S)_{0-2}{^E/_Q}{^K/_R}P$ |
| 18 | Linker (prt) | $T(^G/_S)_{0-2}G{^E/_Q}{^K/_R}P$ |
| 19 | Linker (prt) | $TG(^G/_S)_{3}{^E/_Q}{^K/_R}P$ |
| 20 | Linker (prt) | $T(^G/_S)_{3}G{^E/_Q}{^K/_R}P$ |
| 21 | Linker (prt) | LRQKD(GGGGS)$_{1-4}$QLVGTAERP |
| 22 | Linker (prt) | LRQKD(GGGGS)$_{1-4}$QKP |
| 23 | Linker (prt) | LRQKDGGGGSGGGGSGGGGSQLVGTAERP |
| 24 | Linker (prt) | LRQKDGGGGSGGGGSGGGGSQKP |
| 25 | Poly-zinc finger peptide (prt) | [(Formula 2)-X$_6$]$_{n0}$-{[(Formula 2)-X$_5$-(Formula 2)-X$_6$]$_{n1}$-[(Formula 2)-X$_5$-(Formula 2)-X$_L$]}$_{n2}$-[(Formula 2)-X$_5$-(Formula 2)-X$_6$]$_{n3}$-[(Formula 2)-X$_5$-(Formula 2)]-[X$_6$-(Formula 2)-]$_{n4}$ |
| 26 | Poly-zinc finger peptide (prt) | [(Formula 1-6)-L3]$_{n0}$-{[(Formula 1-6)-L2-(Formula 1-6)-L3]$_{n1}$-[(Formula 1-6)-L2-(Formula 1-6)-X$_L$]}$_{n2}$-[(Formula 1-6)-L2-(Formula 1-6)-L3]$_{n3}$-[(Formula 1-6)-L2-(Formula 1-6)]-[L3-(Formula 1-6)]$_{n4}$ |
| 27 | Poly-zinc finger peptide (prt) | [(Formula 1-6)-L4]$_{n0}$-{[(Formula 1-6)-L1-(Formula 1-6)-L4]$_{n1}$-[(Formula 1-6)-L1-(Formula 1-6)-X$_L$]}$_{n2}$-[(Formula 1-6)-L1-(Formula 1-6)-L4]$_{n3}$-[(Formula 1-6)-L1-(Formula 1-6)]-[L4-(Formula 1-6)]$_{n4}$ |
| 28 | Poly-zinc finger peptide (prt) | [(Formula 1-6)-L5]$_{n0}$-{[(Formula 1-6)-L1-(Formula 1-6)-L5]$_{n1}$-[(Formula 1-6)-L1-(Formula 1-6)-X$_L$]}$_{n2}$-[(Formula 1-6)-L1-(Formula 1-6)-L5]$_{n3}$-[(Formula 1-6)-L1-(Formula 1-6)]-[L5-(Formula 1-6)]$_{n4}$ |
| 29 | 11-zinc finger peptide 1 (prt) | YACPVESCDRRFSQSGDLTRHIRIHTGSQKPFQCRICMRNFSQSGDLTRHIRT HTGEKPFACDICGRKFAQSGDRKRHTKIHTGSQKPFQCRICMRNFSQSGDLTR HIRTHTGEKPFACDICGRKFAQSGDRKRHTKIHLRQKDGGGGSGGGGSGGGGS QKPFQCRICMRNFSQSGDLTRHIRTHTGEKPFACDICGRKFAQSGDRKRHTKI HTGSQKPFQCRICMRNFSQSGDLTRHIRTHTGEKPFACDICGRKFAQSGDRKR HTKIHTGSQKPFQCRICMRNFSQSGDLTRHIRTHTGEKPFACDICGRKFAQSG DRKRHTKIH |
| 30 | 11-zinc finger peptide 1 (DNA) | TACGCCTGTCCTGTGGAATCCTGTGATAGACGGTTCAGCCAGAGCGGGGATCT GACAAGGCACATCAGAATTCATACTGGGTCCCAGAAGCCCTTCCAGTGCCGGA TCTGTATGCGCAACTTTAGCCAGTCCGGAGACCTCACCCGACACATCCGAACC CATACAGGGGAGAAGCCTTTCGCCTGCGACATTTGTGGTCGGAAATTTGCTCA GAGCGGCGATAGGAAGAGACACACAAAAATCCATACTGGCTCCCAGAAGCCAT TCCAGTGCCGAATTTGTATGAGGAATTTTTCTCAGAGTGGCGACCTGACTCGA CACATCAGGACTCATACCGGCGAAAAGCCCTTCGCATGCGACATTTGTGGAAG GAAATTTGCCCAGTCTGGGGATCGGAAGCGCCACACCAAAATCCATCTCAGAC AGAAGGACGGAGGAGGAGGTTCCGGAGGAGGAGGTAGTGGCGAGGGGGTTCA CAGAAGCCTTTCAGTGCAGAATCTGTATGCGGAACTTTTCACAGAGCGGAGA TCTGACCAGACACATCCGGACACATACTGGGGAGAAGCCATTCGCTTGCGACA TTTGTGGTAGGAAATTTGCACAGTCTGGCGATCGAAAGAGGCACACCAAAATC CATACAGGAAGTCAGAAACCTTTCCAGTGCCGCATTTGTATGCGAAATTTTTC CCAGTCTGGTGACCTGACACGCCATATTCGAACCCATACAGGGGAAAAACCTT TCGCCTGTGACATTTGTGGAAGAAAATTTGCTCAGAGCGGGGATAGAAGCGG CACACTAAAATCCATACCGGCTCTCAGAAACCATTCCAGTGCCGGATTTGTAT GCGCAACTTTAGTCAGTCAGGCGACCTGACCAGACACATCAGAACTCACACCG GAGAGAAACCCTTCGCATGTGATATCTGTGGTCGGAAATTCGCCCAGAGCGGC GATCGCAAGCGACACACTAAAATCCAC |

TABLE 11-continued

Peptide and Nucleic Acid Sequences.

| SEQ ID NO: | Sequence Type | Sequence |
|---|---|---|
| 31 | 11-zinc finger 2 peptide (prt) | FQCRICMRNFSQSADLTRHTKIHTGSERPFQCRICMRNFSQSADLTRHIRTHT GEKPFACDICGRKFAQSADLTRHTKIHTGSERPFQCRICMRNFSQSADLTRHI RTHTGEKPFACDICGRKFAQSADLTRHTKIHLRQKDGGGGSGGGGSGGGGSQL VGTAERPFQCRICMRNFSQSADLTRHIRTHTGEKPFACDICGRKFAQSADLTR HTKIHTGSERPFQCRICMRNFSQSADLTRHIRTHTGEKPFACDICGRKFAQSA DLTRHTKIHTGSERPFQCRICMRNFSQSADLTRHIRTHTGEKPFACDICGRKF AQSADLTRHTKIH |
| 32 | 11-zinc finger peptide 2 (DNA) | TTCCAGTGCCGCATTTGTATGCGCAACTTTAGCCAGAGCGCGGACCTGACCCG CCATACCAAAATTCACACCGGATCCGAACGGCCGTTTCAGTGCCGTATTTGCA TGCGTAATTTTAGCCAGTCCGCGGACCTGACCCGCCATATTCGTACCCATACC GGTGAAAAACCGTTTGCCTGCGATATTTGTGGCCGTAAATTTGCCCAGAGCGC GGACCTGACCCGCCATACCAAAATTCATACCGGTTCTGAACGGCCGTTTCAGT GCAGGATTTGCATGCGTAATTTTTCCCAGAGCGCGGACCTGACCCGCCATATT CGCACCCATACTGGTGAAAAACCGTTTGCCTGCGATATTTGCGGTCGTAAATT TGCGCAGTCCGCTGACTTAACCCGCCATACCAAAATTCATCTGCGCCAGAAAG ATGGTGGCGGCGGCTCAGGTGGCGGCGGTAGTGGTGGCGGCGGCTCACAACTA GTCGGTACCGCCGAGCGCCCCTTCCAGTGCCGCATTTGTATGCGCAACTTTAG CCAGAGCGCGGACCTGACCCGTCATATTCGCACCCATACCGGTGAAAAACCGT TTGCGTGCGATATTTGCGGTCGTAAATTTGCGCAGAGCGCGGACCTGACCCGC CATACCAAAATTCACACCGGATCCGAACGGCCGTTTCAGTGCCGTATTTGCAT GCGTAATTTTAGCCAGTCCGCGGACCTGACCCGCCATATTCGTACCCATACCG GTGAAAAACCGTTTGCCTGCGATATTTGTGGCCGTAAATTTGCCCAGagcGCG GACCTGACCCGCCATACCAAAATTCATACCGGTTCTGAACGGCCGTTTCAGTG CAGGATTTGCATGCGTAATTTTTCCCAGAGCGCGGACCTGACCCGCCATATTC GCACCCATACTGGTGAAAAACCGTTTGCCTGCGATATTTGCGGTCGTAAATTT GCGCAGAGCGCTGACTTAACCCGCCATACCAAAATTCAT |
| 33 | 11-zinc finger peptide 3 (prt) | YACPVESCDRRFSQSADLTRHIRIHTGSQKPFQCRICMRNFSQSADLTRHIRT HTGEKPFACDICGRKFAQSADRKRHTKIHTGSQKPFQCRICMRNFSQSADLTR HIRTHTGEKPFACDICGRKFAQSADRKRHTKIHLRQKDGGGGSGGGGSGGGGS QKPFQCRICMRNFSQSADLTRHIRTHTGEKPFACDICGRKFAQSADRKRHTKI HTGSQKPFQCRICMRNFSQSADLTRHIRTHTGEKPFACDICGRKFAQSADRKR HTKIHTGSQKPFQCRICMRNFSQSADLTRHIRTHTGEKPFACDICGRKFAQSA DRKRHTKIH |
| 34 | 11-zinc finger peptide 3 (DNA) | TACGCCTGTCCTGTGGAATCCTGTGATAGACGGTTCAGCCAGAGCGCCGATCT GACAAGGCACATCAGAATTCATACTGGGTCCCAGAAGCCCTTCCAGTGCCGGA TCTGTATGCGCAACTTTAGCCAGTCCGCCGACCTCACCCGACACATCCGAACC CATACAGGGGAGAAGCCTTTCGCCTGCGACATTTGTGGTCGGAAATTTGCTCA GAGCGCCGATAGGAAGAGACACACAAAAATCCATACTGGCTCCCAGAAGCCAT TCCAGTGCCGAATTTGTATGAGGAATTTTTCTCAGAGTGCCGACCTGACTCGA CACATCAGGACTCATACCGGCGAAAAGCCCTTCGCATGCGACATTTGTGGAAG GAAATTTGCCCAGTCTGCCGATCGGAAGCGCCACACCAAAATCCATCTCAGAC AGAAGGACGGAGGAGGAGGTTCCGGAGGAGGAGGTAGTGGCGGAGGGGGTTCA CAGAAGCCTTTCCAGTGCAGAATCTGTATGCGGAACTTTTCACAGAGCGCCGA TCTGACCAGACACATCCGGACACATACTGGGGAGAAGCCATTCGCTTGCGACA TTTGTGGTAGGAAATTTGCACAGTCTGCCGATCGAAAGAGGCACACCAAAATC CATACAGGAAGTCAGAAACCTTTCCAGTGCCGCATTTGTATGCGAAATTTTTC CCAGTCTGCCGACCTGACACGCCATATTCGAACCCATACAGGGGAAAAACCTT TCGCCTGTGACATTTGTGGAAGAAAATTTGCTCAGAGCGCCGATAGAAAGCGG CACACTAAAATCCATACCGGCTCTCAGAAACCATTCCAGTGCCGGATTTGTAT GCGCAACTTTAGTCAGTCAGCCGACCTGACCAGACACATCAGAACTCACACCG GAGAGAAACCCTTCGCATGTGATATCTGTGGTCGGAAATTCGCCCAGAGCGCC GATCGCAAGCGACACACTAAAATCCAC |
| 35 | 11-zinc finger peptide 4 (prt) | YACPVESCDRRFSQSADLTRHIRIHTGSQKPFQCRICMRNFSQSGDLTRHIRT HTGEKPFACDICGRKFAQSGDRKRHTKIHTGSQKPFQCRICMRNFSQSGDLTR HIRTHTGEKPFACDICGRKFAQSGDRKRHTKIHLRQKDGGGGSGGGGSGGGGS QKPFQCRICMRNFSQSGDLTRHIRTHTGEKPFACDICGRKFAQSGDRKRHTKI HTGSQKPFQCRICMRNFSQSGDLTRHIRTHTGEKPFACDICGRKFAQSGDRKR HTKIHTGSQKPFQCRICMRNFSQSGDLTRHIRTHTGEKPFACDICGRKFAQSG DRKRHTKIH |
| 36 | 11-zinc finger peptide 4 (DNA) | TACGCCTGTCCTGTGGAATCCTGTGATAGACGGTTCAGCCAGAGCGCCGATCT GACAAGGCACATCAGAATTCATACTGGGTCCCAGAAGCCCTTCCAGTGCCGGA TCTGTATGCGCAACTTTAGCCAGTCCGGAGACCTCACCCGACACATCCGAACC CATACAGGGGAGAAGCCTTTCGCCTGCGACATTTGTGGTCGGAAATTTGCTCA GAGCGGCGATAGGAAGAGACACACAAAAATCCATACTGGCTCCCAGAAGCCAT TCCAGTGCCGAATTTGTATGAGGAATTTTTCTCAGAGTGCCGACCTGACTCGA CACATCAGGACTCATACCGGCGAAAAGCCCTTCGCATGCGACATTTGTGGAAG GAAATTTGCCCAGTCTGGGGATCGGAAGCGCCACACCAAAATCCATCTCAGAC AGAAGGACGGAGGAGGAGGTTCCGGAGGAGGAGGTAGTGGCGGAGGGGGTTCA CAGAAGCCTTTCCAGTGCAGAATCTGTATGCGGAACTTTTCACAGAGCGGAGA TCTGACCAGACACATCCGGACACATACTGGGGAGAAGCCATTCGCTTGCGACA |

TABLE 11-continued

Peptide and Nucleic Acid Sequences.

| SEQ ID NO: | Sequence Type | Sequence |
|---|---|---|
| | | TTTGTGGTAGGAAATTTGCACAGTCTGGCGATCGAAAGAGGCACACCAAAATC<br>CATACAGGAAGTCAGAAACCTTTCCAGTGCCGCATTTGTATGCGAAATTTTTC<br>CCAGTCTGGTGACCTGACACGCCATATTCGAACCCATACAGGGGAAAAACCTT<br>TCGCCTGTGACATTTGTGGAAGAAAATTTGCTCAGAGCGGGGATAGAAAGCGG<br>CACACTAAAATCCATACCGGCTCTCAGAAACCATTCCAGTGCCGGATTTGTAT<br>GCGCAACTTTAGTCAGTCAGGCGACCTGACCAGACACATCAGAACTCACACCG<br>GAGAGAAACCCTTCGCATGTGATATCTGTGGTCGGAAATTCGCCCAGAGCGGC<br>GATCGCAAGCGACACACTAAAATCCAC |
| 37 | SV40 nuclear localisation (prt) | PKKKRKV |
| 38 | Mouse primase p58 nuclear localisation (prt) | RIRKKLR |
| 39 | Human Kox-1 KRAB domain (prt) | LSPQHSAVTQGSIIKNKEGMDAKSLTAWSRTLVTFKDVFVDFTREEWKLLDTA<br>QQIVYRNVMLENYKNLVSLGYQLTKPDVILRLEKGEEPWLVEREIHQETHPDS<br>ETAFEIKSSV |
| 40 | Mouse ZF87 KRAB domain (prt) | EEMLSFRDVAIDFSAEEWECLEPAQWNLYRDVMLENYSHLVFLGLASCKPYLV<br>TFLEQRQEPSVVKRPAAATVHP |
| 41 | Linker (prt) | LRQKDGGGGSGGGGSGGGGSQLVSS |
| 42 | Linker (prt) | LRQKDGGGGSGGGGSS |
| 43 | Linker (prt) | LRQKDGGGSGGGGS |
| 44 | Human N-terminal leader (prt) | MGPKKRRKVTGERP |
| 45 | Mouse N-terminal leader (prt) | MGRIRKKLRLAERP |
| 46 | Human KIAA2022 nuclear localisation (prt) | PKKRRKVT |
| 47 | Mouse Zif268 (prt) | ERPYACPVESCDRRFSRSDELTRHIRIHTGQKPFQCRICMRNFSRSDHLTTHI<br>RTHTGEKPFACDICGRKFARSDERKRHTKIHLRQKD |
| 48 | Human Zif268 (prt) | ERPYACPVESCDRRFSRSDELTRHIRIHTGQKPFQCRICMRNFSRSDHLTTHI<br>RTHTGEKPFACDICGRKFARSDERKGHTKIHLRQKD |
| 49 | Mousified 11-zinc finger modulator 2 mZF-ZF87 (prt) | MGRIRKKLRLAERPFQCRICMRNFSQSADLTRHTKIHTGSERPFQCRICMRNF<br>SQSADLTRHIRTHTGEKPFACDICGRKFAQSADLTRHTKIHTGSERPFQCRIC<br>MRNFSQSADLTRHIRTHTGEKPFACDICGRKFAQSADLTRHTKIHTGSERPFQCRIC<br>GSGGGGSGGGGSQLVGTAERPFQCRICMRNFSQSADLTRHIRTHTGEKPFACD<br>ICGRKFAQSADLTRHTKIHTGSERPFQCRICMRNFSQSADLTRHIRTHTGEKP<br>FACDICGRKFAQSADLTRHTKIHTGSERPFQCRICMRNFSQSADLTRHIRTHT<br>GEKPFACDICGRKFAQSADLTRHTKIHLRQKDGGGSGGGGSEEMLSFRDVAID<br>FSAEEWECLEPAQWNLYRDVMLENYSHLVFLGLASCKPYLVTFLEQRQEPSVV<br>KRPAAATVHP |
| 50 | Mousified 11-zinc finger modulator 1 mZF-ZF87 (prt) | MGRIRKKLRLAERPYACPVESCDRRFSQSGDLTRHIRIHTGSQKPFQCRICMR<br>NFSQSGDLTRHIRTHTGEKPFACDICGRKFAQSGDRKRHTKIHTGSQKPFQCR<br>ICMRNFSQSGDLTRHIRTHTGEKPFACDICGRKFAQSGDRKRHTKIHLRQKDG<br>GGSGGGGSGGGGSQKPFQCRICMRNFSQSGDLTRHIRTHTGEKPFACDICGR<br>KFAQSGDRKRHTKIHTGSQKPFQCRICMRNFSQSGDLTRHIRTHTGEKPFACD<br>ICGRKFAQSGDRKRHTKIHTGSQKPFQCRICMRNFSQSGDLTRHIRTHTGEKP<br>FACDICGRKFAQSGDRKRHTKIHLRQKDGGGSGGGGSEEMLSFRDVAIDFSAE<br>EWECLEPAQWNLYRDVMLENYSHLVFLGLASCKPYLVTFLEQRQEPSVVKRPA<br>AATVHP |

TABLE 11-continued

Peptide and Nucleic Acid Sequences.

| SEQ ID NO: | Sequence Type | Sequence |
|---|---|---|
| 51 | Mousified 11-zinc finger modulator 3 mZF-ZF87 (prt) | MGRIRKKLRLAERPYACPVESCDRRFSQSADLTRHIRIHTGSQKPFQCRICMR NFSQSADLTRHIRTHTGEKPFACDICGRKFAQSADRKRHTKIHTGSQKPFQCR ICMRNFSQSADLTRHIRTHTGEKPFACDICGRKFAQSADRKRHTKIHLRQKDG GGGSGGGGSGGGGSQKPFQCRICMRNFSQSADLTRHIRTHTGEKPFACDICGR KFAQSADRKRHTKIHTGSQKPFQCRICMRNFSQSADLTRHIRTHTGEKPFACD ICGRKFAQSADRKRHTKIHTGSQKPFQCRICMRNFSQSADLTRHIRTHTGEKP FACDICGRKFAQSADRKRHTKIHLRQKDGGGSGGGGSEEMLSFRDVAIDFSAE EWECLEPAQWNLYRDVMLENYSHLVFLGLASCKPYLVTFLEQRQEPSVVKRPA AATVHP |
| 52 | Mousified 11-zinc finger modulator 4 mZF-ZF87 (prt) | MGRIRKKLRLAERPYACPVESCDRRFSQSADLTRHIRIHTGSQKPFQCRICMR NFSQSGDLTRHIRTHTGEKPFACDICGRKFAQSGDRKRHTKIHTGSQKPFQCR ICMRNFSQSGDLTRHIRTHTGEKPFACDICGRKFAQSGDRKRHTKIHLRQKDG GGGSGGGGSGGGGSQKPFQCRICMRNFSQSGDLTRHIRTHTGEKPFACDICGR KFAQSGDRKRHTKIHTGSQKPFQCRICMRNFSQSGDLTRHIRTHTGEKPFACD ICGRKFAQSGDRKRHTKIHTGSQKPFQCRICMRNFSQSGDLTRHIRTHTGEKP FACDICGRKFAQSGDRKRHTKIHLRQKDGGGSGGGGSEEMLSFRDVAIDFSAE EWECLEPAQWNLYRDVMLENYSHLVFLGLASCKPYLVTFLEQRQEPSVVKRPA AATVHP |
| 53 | Humanised 11-zinc finger modulator 2 hZF-ZF-kox1 (prt) | MGPKKRRKVTGERPFQCRICMRNFSQSADLTRHTKIHTGSERPFQCRICMRNF SQSADLTRHIRTHTGEKPFACDICGRKFAQSADLTRHTKIHTGSERPFQCRIC MRNFSQSADLTRHIRTHTGEKPFACDICGRKFAQSADLTRHIRTHTGEKPFACD ICGRKFAQSADLTRHTKIHTGSERPFQCRICMRNFSQSADLTRHIRTHTGEKP FACDICGRKFAQSADLTRHTKIHTGSERPFQCRICMRNFSQSADLTRHIRTHT GEKPFACDICGRKFAQSADLTRHTKIHLRQKDGGGGSGGGGSSLSPQHSAVTQ GSIIKNKEGMDAKSLTAWSRTLVTFKDVFVDFTREEWKLLDTAQQIVYRNVML ENYKNLVSLGYQLTKPDVILRLEKGEEPWLVEREIHQETHPDSETAFEIKSSV |
| 54 | Humanised 11-zinc finger modulator 1 hZF-ZF-kox1 (prt) | MGPKKRRKVTGERPYACPVESCDRRFSQSGDLTRHIRIHTGSQKPFQCRICMR NFSQSGDLTRHIRTHTGEKPFACDICGRKFAQSGDRKRHTKIHTGSQKPFQCR ICMRNFSQSGDLTRHIRTHTGEKPFACDICGRKFAQSGDRKRHTKIHLRQKDG GGGSGGGGSGGGGSQKPFQCRICMRNFSQSGDLTRHIRTHTGEKPFACDICGR KFAQSGDRKRHTKIHTGSQKPFQCRICMRNFSQSGDLTRHIRTHTGEKPFACD ICGRKFAQSGDRKRHTKIHTGSQKPFQCRICMRNFSQSGDLTRHIRTHTGEKP FACDICGRKFAQSGDRKRHTKIHLRQKDGGGGSGGGGSSLSPQHSAVTQGSII KNKEGMDAKSLTAWSRTLVTFKDVFVDFTREEWKLLDTAQQIVYRNVMLENYK NLVSLGYQLTKPDVILRLEKGEEPWLVEREIHQETHPDSETAFEIKSSV |
| 55 | Humanised 11-zinc finger modulator 3 hZF-ZF-kox1 (prt) | MGPKKRRKVTGERPYACPVESCDRRFSQSADLTRHIRIHTGSQKPFQCRICMR NFSQSADLTRHIRTHTGEKPFACDICGRKFAQSADRKRHTKIHTGSQKPFQCR ICMRNFSQSADLTRHIRTHTGEKPFACDICGRKFAQSADRKRHTKIHLRQKDG GGGSGGGGSGGGGSQKPFQCRICMRNFSQSADLTRHIRTHTGEKPFACDICGR KFAQSADRKRHTKIHTGSQKPFQCRICMRNFSQSADLTRHIRTHTGEKPFACD ICGRKFAQSADRKRHTKIHTGSQKPFQCRICMRNFSQSADLTRHIRTHTGEKP FACDICGRKFAQSADRKRHTKIHLRQKDGGGGSGGGGSSLSPQHSAVTQGSII KNKEGMDAKSLTAWSRTLVTFKDVFVDFTREEWKLLDTAQQIVYRNVMLENYK NLVSLGYQLTKPDVILRLEKGEEPWLVEREIHQETHPDSETAFEIKSSV |
| 56 | Humanised 11-zinc finger modulator 4 hZF-ZF-kox1 (prt) | MGPKKRRKVTGERPYACPVESCDRRFSQSADLTRHIRIHTGSQKPFQCRICMR NFSQSGDLTRHIRTHTGEKPFACDICGRKFAQSGDRKRHTKIHTGSQKPFQCR ICMRNFSQSGDLTRHIRTHTGEKPFACDICGRKFAQSGDRKRHTKIHLRQKDG GGGSGGGGSGGGGSQKPFQCRICMRNFSQSGDLTRHIRTHTGEKPFACDICGR KFAQSGDRKRHTKIHTGSQKPFQCRICMRNFSQSGDLTRHIRTHTGEKPFACD ICGRKFAQSGDRKRHTKIHTGSQKPFQCRICMRNFSQSGDLTRHIRTHTGEKP FACDICGRKFAQSGDRKRHTKIHLRQKDGGGGSGGGGSSLSPQHSAVTQGSII KNKEGMDAKSLTAWSRTLVTFKDVFVDFTREEWKLLDTAQQIVYRNVMLENYK NLVSLGYQLTKPDVILRLEKGEEPWLVEREIHQETHPDSETAFEIKSSV |
| 57 | Mousified 11-zinc finger modulator 1 mZF-ZF87 (DNA) | ATGGGCCGCATTAGAAAGAAACTCAGACTCGCAGAAAGACCTTACGCCTGTCC TGTGGAATCCTGTGATAGACGGTTCAGCCAGAGCGGGGATCTGACAAGGCACA TCAGAATTCTATACTGGGTCCCAGAAGCCCTTCCAGTGCCGGATCTGTATGCGC AACTTTAGCCAGTCCGGAGACCTCACCCGACACATCCGAACCCATACAGGGGA GAAGCCTTTCGCCTGCGACATTTGTGGTCGGAAATTTGCTCAGAGCGGCGATA GGAAGAGACACACAAAAATCCATACTGGCTCCCAGAAGCCATTCCAGTGCCGA ATTTGTATGAGGAATTTTTCTCAGAGTGGCGACCTGACTCGACACATCAGGAC TCATACCGGCGAAAAGCCCTTCGCATGCGACATTTGTGGAAGGAAATTTGCCC AGTCTGGGGATCGGAAGCGCCACACCAAAATCCATCTCAGACAGAAGGACGGA GGAGGAGGTTCCGGAGGAGGAGGTAGTGGCGGAGGGGGTTCACAGAAGCCTTT CCAGTGCAGAATCTGTATGCGGAACTTTTCACAGAGCGGAGATCTGACCAGAC ACATCCGGACACATACTGGGGAGAAGCCATTCGCTTGCGACATTTGTGGTAGG AAATTTGCACAGTCTGGCGATCGAAAGAGGCACACCAAAATCCATACAGGAAG TCAGAAACCTTTCCAGTGCCGCATTTGTATGCGAAATTTTTCCCAGTCTGGTG |

TABLE 11-continued

Peptide and Nucleic Acid Sequences.

| SEQ ID NO: | Sequence Type | Sequence |
|---|---|---|
| | | ACCTGACACGCCATATTCGAACCCATACAGGGGAAAAACCTTTCGCCTGTGAC<br>ATTTGTGGAAGAAAATTTGCTCAGAGCGGGGATAGAAAGCGGCACACTAAAT<br>CCATACCGGCTCTCAGAAACCATTCCAGTGCCGGATTTGTATGCGCAACTTTA<br>GTCAGTCAGGCGACCTGACCAGACACATCAGAACTCACACCGGAGAGAAACCC<br>TTCGCATGTGATATCTGTGGTCGGAAATTCGCCCAGAGCGGCGATCGCAAGCG<br>ACACACTAAAATCCACCTCCGCCAGAAGGACGGCGGAGGATCCGGAGGGGGTG<br>GGTCCGAAGAGATGCTCAGTTTTAGAGATGTCGCTATTGACTTTTCAGCCGAG<br>GAATGGGAGTGCCTGGAACCTGCCCAGTGGAACCTGTACAGGGACGTGATGCT<br>GGAGAATTATAGCCACCTGGTCTTCCTGGGCCTCGCCTCCTGCAAGCCCTACC<br>TCGTGACCTTTCTCGAACAGAGGCAGGAGCCAAGCGTCGTCAAGAGACCAGCA<br>GCAGCAACCGTCCATCCA |
| 58 | Humanised<br>11-zinc finger<br>modulator 1<br>hZF-ZF-kox1<br>(DNA) | ATGGGCCCGAAGAAACGCCGTAAAGTGACCGGCGAGCGCCCCTACGCCTGTCC<br>TGTGGAATCCTGTGATAGACGGTTCAGCCAGAGCGGGGATCTGACAAGGCACA<br>TCAGAATTCATACTGGGTCCCAGAAGCCCTTCCAGTGCCGGATCTGTATGCGC<br>AACTTTAGCCAGTCCGGAGACCTCACCCGACACATCCGAACCCATACAGGGGA<br>GAAGCCTTTCGCCTGCGACATTTGTGGTCGGAAATTTGCTCAGAGCGGCGATA<br>GGAAGAGACACACAAAAATCCATACTGGCTCCCAGAAGCCATTCCAGTGCCGA<br>ATTTGTATGAGGAATTTTTCTCAGAGTGGCGACCTGACTCGACACATCAGGAC<br>TCATACCGGCGAAAAGCCCTTCGCATGCGACATTTGTGGAAGGAAATTTGCCC<br>AGTCTGGGGATCGGAAGCGCCACACCAAAATCCATCTCAGACAGAAGGACGGA<br>GGAGGAGGTTCCGGAGGAGGAGGTAGTGGCGGAGGGGGTTCACAGAAGCCTTT<br>CCAGTGCAGAATCTGTATGCGGAACTTTTCACAGAGCGGAGATCTGACCAGAC<br>ACATCCGGACACATACTGGGGAGAAGCCATTCGCTTGCGCACATTTGTGGTAGG<br>AAATTTGCACAGTCTGGCGATCGAAAGAGGCACACCAAAATCCATACAGGAAG<br>TCAGAAACCTTTCCAGTGCCGCATTTGTATGCGAATTTTTTCCCAGTCTGGTG<br>ACCTGACACGCCATATTCGAACCCATACAGGGGAAAAACCTTTCGCCTGTGAC<br>ATTTGTGGAAGAAAATTTGCTCAGAGCGGGGATAGAAAGCGGCACACTAAAT<br>CCATACCGGCTCTCAGAAACCATTCCAGTGCCGGATTTGTATGCGCAACTTTA<br>GTCAGTCAGGCGACCTGACCAGACACATCAGAACTCACACCGGAGAGAAACCC<br>TTCGCATGTGATATCTGTGGTCGGAAATTCGCCCAGAGCGGCGATCGCAAGCG<br>ACACACTAAAATCCACCTCCGCCAGAAGGACGGCGGAGGATCCGGAGGGGGTG<br>GGTCCAGCTTGTCTCCTCAGCACTCTGCTGTCACTCAAGGAAGTATCATCAAG<br>AACAAGGAGGGCATGGATGCTAAGTCACTAACTGCCTGGTCCCGGACACTGGT<br>GACCTTCAAGGATGTATTTGTGGACTTCACCAGGGAGGAGTGGAAGCTGCTGG<br>ACACTGCTCAGCAGATCGTGTACAGAAATGTGATGCTGGAGAACTATAAGAAC<br>CTGGTTTCCTTGGGTTATCAGCTTACTAAGCCAGATGTGATCCTCCGGTTGGA<br>GAAGGGAGAAGAGCCCTGGCTGGTGGAGAGAGAAATTCACCAAGAGACCCATC<br>CTGATTCAGAGACTGCATTTGAAATCAAATCATCAGTT |
| 59 | Humanised<br>10-zinc finger<br>modulator<br>hZF-ZF-kox1<br>(prt) | MGPKKRRKVTGERPYACPVESCDRRFSQSGDLTRHIRIHTGQKPFQCRICMRN<br>FSQSGDRKRHIRTHQNKKGSHICHIQGCGKVYGQSGDLTRHLRWHTGERPFMC<br>TWSYCGKRFTQSGDRKRHKRTHLRQKDGERPYACPVESCDRRFSQSGDLTRHI<br>RIHTGEKPYKCPECGKSFSQSGDRKRHQRTHTGSERPFMCNWSYCGKRFTQSG<br>DLTRHKRTHTGEKPFACPECPKRFMQSGDRKRHIKTHTGSEKPFQCRICMRNF<br>SQSGDLTRHIRTHTGERPPACDICGRKFAQSGDRKRHTKIHLRQKDGGGSGGG<br>GSSLSPQHSAVTQGSIIKNKEGMDAKSLTAWSRTLVTFKDVFVDFTREEWKLL<br>DTAQQIVYRNVMLENYKNLVSLGYQLTKPDVILRLEKGEEPWLVEREIHQETH<br>PDSETAFEIKSSV |
| 60 | Humanised<br>10-zinc finger<br>modulator<br>hZF-ZF-kox1<br>(DNA) | ATGGGCCCGAAGAAACGCCGTAAAGTGACCGGCGAGCGCCCCTACGCCTGCCCTGTGGA<br>GTCCTGCGATAGAAGATTTTCCCAGAGCGGCGACCTGACCAGACATATTCGGATTCACA<br>CCGGCCAGAAGCCATTCCAGTGCAGAATCTGTATGCGGAACTTTTCCCAGAGCGGCGAC<br>CGCAAGCGGCACATTCGCACTCATCAGAATAAGAAAGGGTCTCACATCTGCCATATTCA<br>GGGGTGTGGCAAAGTGTATGGACAGAGCGGCGACCTGACCCGACACCTGAGGTGGCATA<br>CCGGAGAGAGGCCCTTCATGTGCACATGGAGTTACTGTGGCAAGAGGTTCACCCAGAGC<br>GGCGACCGCAAGAGACACAAACGGACACATCTGCGACAGAAGGACGGAGAGCGACCATA<br>TGCATGCCCAGTCGAAAGTTGTGATAGGAGATTCTCACAGAGCGGCGACCTGACCCGCC<br>ACATCCGAATTCATACCGGCGAGAAACCTTACAAGTGCCCAGAATGTGGAAAGAGCTTT<br>TCCCAGAGCGGCGACCGCAAGAGGCACCAGAGAACCCATACAGGCAGTGAGCGGCCCTT<br>CATGTGCAACTGGTCATATTGTGGAAAAAGGTTTACCCAGAGCGGCGACCTGACCCGGC<br>ACAAACGCACACATACTGGCGAGAAGCCTTTCGCTTGCCCCGAATGTCCTAAGCGGTTT<br>ATGCAGAGCGGCGACCGCAAGCGGCACATCAAAACCCATACAGGAAGCGAGAAGCCTTT<br>CCAGTGCCGAATTTGTATGAGGAATTTTTCCCAGAGCGGCGACCTGACCCGACACATCA<br>GGACTCATACCGGGGAACGGCCATTCGCCTGCGACATTTGTGGCAGAAATTTGCACAG<br>AGCGGCGACCGCAAGCGACACACCAAAATCCACCTCCGCCAGAAGGACGGCGGAGGATC<br>CGGAGGGGGTGGGTCCAGCTTGTCTCCTCAGCACTCTGCTGTCACTCAAGGAAGTATCA<br>TCAAGAACAAGGAGGGCATGGATGCTAAGTCACTAACTGCCTGGTCCCGGACACTGGTG<br>ACCTTCAAGGATGTATTTGTGGACTTCACCAGGGAGGAGTGGAAGCTGCTGGACACTGC<br>TCAGCAGATCGTGTACAGAAATGTGATGCTGGAGAACTATAAGAACCTGGTTTCCTTGG<br>GTTATCAGCTTACTAAGCCAGATGTGATCCTCCGGTTGGAGAAGGGAGAAGAGCCCTGG<br>CTGGTGGAGAGAGAAATTCACCAAGAGACCCATCCTGATTCAGAGACTGCATTTGAAAT<br>cAAATcATcAGTT |

TABLE 11-continued

Peptide and Nucleic Acid Sequences.

| SEQ ID NO: | Sequence Type | Sequence |
|---|---|---|
| 61 | Humanised 12-zinc finger modulator hZF-ZF-kox1 (prt) | MGPKKRRKVTGERPYACPVESCDRRFSQSGDLTRHIRIHTGQKPFACDICGRK FAQSGDRKRHTKIHTGSQKPFQCRICMRNFSQSGDLTRHIRTHTGEKPFACDI CGRKFAQSGDRKRHTKIHTGSQKPFQCRICMRNFSQSGDLTRHIRTHTGEKPF ACDICGRKFAQSGDRKRHTKIHLRQKDGGGSGGGGSGGGGSQKPFQCRICMR NFSQSGDLTRHIRTHTGEKPFACDICGRKFAQSGDRKRHTKIHTGSQKPFQCR ICMRNFSQSGDLTRHIRTHTGEKPFACDICGRKFAQSGDRKRHTKIHTGSQKP FQCRICMRNFSQSGDLTRHIRTHTGEKPFACDICGRKFAQSGDRKRHTKIHLR QKDGGGSGGGGSSLSPQHSAVTQGSIIKNKEGMDAKSLTAWSRTLVTFKDVFV DFTREEWKLLDTAQQIVYRNVMLENYKNLVSLGYQLTKPDVILRLEKGEEPWL VEREIHQETHPDSETAFEIKSSV |
| 62 | Humanised 12-zinc finger modulator hZF-ZF-kox1 (DNA) | ATGGGCCCGAAGAAACGCCGTAAAGTGACCGGCGAGCGCCCCTACGCCTGTCC TGTGGAATCCTGTGATAGACGGTTCAGCCAGAGCGGGGATCTGACAAGGCACA TCAGAATTCATACTGGGCAGAAGCCCTTCGCCTGCGACATTTGTGGTCGGAAA TTTGCTCAGAGCGGCGATAGGAAGAGACACACAAAAATCCATACTGGCTCCCA GAAGCCATTCCAGTGCCGGATCTGTATGCGCAACTTTAGCCAGTCCGGAGACC TCACCCGACACATCCGAACCCATACAGGGGAGAAGCCTTTCGCCTGCGACATT TGTGGTCGGAAATTTGCTCAGAGCGGCGATAGGAAGAGACACACAAAAATCCA TACTGGCTCCCAGAAGCCATTCCAGTGCCGAATTTGTATGAGGAATTTTTCTC AGAGTGGCGACCTGACTCGACACATCAGGACTCATACCGGCGAAAAGCCCTTC GCATGCGACATTTGTGGAAGGAAATTTGCCCAGTCTGGGGATCGGAAGCGCCA CACCAAAATCCATCTCAGACAGAAGGACGGAGGAGGAGGTTCCGGAGGAGGAG GTAGTGGCGGAGGGGGTTCACAGAAGCCTTTCCAGTGCAGAATCTGTATGCGG AACTTTTCACAGAGCGGAGATCTGACCAGACACATCCGGACACATACTGGGGA GAAGCCATTCGCTTGCGACATTTGTGGTAGGAAATTTGCACAGTCTGGCGATC GAAAGAGGCACACCAAAATCCATACAGGAAGTCAGAAACCTTTCCAGTGCCGC ATTTGTATGCGAAATTTTTCCCAGTCTGGTGACCTGACACGCCATATTCGAAC CCATACAGGGGAAAAACCTTTCGCCTGTGACATTTGTGGAAGAAAATTTGCTC AGAGCGGGGATAGAAAGCGGCACACTAAAATCCATACCGGCTCTCAGAAACCA TTCCAGTGCCGGATTTGTATGCGCAACTTTAGTCAGTCAGGCGACCTGACCAG ACACATCAGAACTCACACCGGAGAGAAACCCTTCGCATGTGATATCTGTGGTC GGAAATTCGCCCAGAGCGGCGATCGCAAGCGACACACTAAAATCCACCTCCGC CAGAAGGACGGCGGAGGATCCGGAGGGGGTGGGTCCAGCTTGTCTCCTCAGCA CTCTGCTGTCACTCAAGGAAGTATCATCAAGAACAAGGAGGGCATGGATGCTA AGTCACTAACTGCCTGGTCCCGGACACTGGTGACCTTCAAGGATGTATTTGTG GACTTCACCAGGGAGGAGTGGAAGCTGCTGGACACTGCTCAGCAGATCGTGTA CAGAAATGTGATGCTGGAGAACTATAAGAACCTGGTTTCCTTGGGTTATCAGC TTACTAAGCCAGATGTGATCCTCCGGTTGGAGAAGGGAGAAGAGCCCTGGCTG GTGGAGAGAGAAATTCACCAAGAGACCCATCCTGATTCAGAGACTGCATTTGA AATCAAATCATCAGTT |
| 63 | Humanised 18-zinc finger modulator hZF-ZF-kox1 (prt) | MGPKKRRKVTGERPYACPVESCDRRFSQSGDLTRHIRIHTGQKPFACDICGRK FAQSGDRKRHTKIHTGSQKPFQCRICMRNFSQSGDLTRHIRTHTGEKPFACDI CGRKFAQSGDRKRHTKIHTGSQKPFQCRICMRNFSQSGDLTRHIRTHTGEKPF ACDICGRKFAQSGDRKRHTKIHLRQKDGGGSGGGGSGGGGSQKPYACPVESC DRRFSQSGDLTRHIRIHTGQKPFACDICGRKFAQSGDRKRHTKIHTGSQKPFQ CRICMRNFSQSGDLTRHIRTHTGEKPFACDICGRKFAQSGDRKRHTKIHTGSQ KPFQCRICMRNFSQSGDLTRHIRTHTGEKPFACDICGRKFAQSGDRKRHTKIH LRQKDGGGSGGGGSGGGGSQKPFQCRICMRNFSQSGDLTRHIRTHTGEKPFA CDICGRKFAQSGDRKRHTKIHTGSQKPFQCRICMRNFSQSGDLTRHIRTHTGE KPFACDICGRKFAQSGDRKRHTKIHTGSQKPFQCRICMRNFSQSGDLTRHIRT HTGEKPFACDICGRKFAQSGDRKRHTKIHLRQKDGGGSGGGGSSLSPQHSAVT QGSIIKNKEGMDAKSLTAWSRTLVTFKDVFVDFTREEWKLLDTAQQIVYRNVM LENYKNLVSLGYQLTKPDVILRLEKGEEPWLVEREIHQETHPDSETAFEIKSS V |
| 64 | Humanised 18-zinc finger modulator hZF-ZF-kox1 (DNA) | ATGGGCCCGAAGAAACGCCGTAAAGTGACCGGCGAGCGCCCCTACGCCTGTCC TGTGGAATCCTGTGATAGACGGTTCAGCCAGAGCGGGGATCTGACAAGGCACA TCAGAATTCATACTGGGCAGAAGCCCTTCGCCTGCGACATTTGTGGTCGGAAA TTTGCTCAGAGCGGCGATAGGAAGAGACACACAAAAATCCATACTGGCTCCCA GAAGCCATTCCAGTGCCGGATCTGTATGCGCAACTTTAGCCAGTCCGGAGACC TCACCCGACACATCCGAACCCATACAGGGGAGAAGCCTTTCGCCTGCGACATT TGTGGTCGGAAATTTGCTCAGAGCGGCGATAGGAAGAGACACACAAAAATCCA TACTGGCTCCCAGAAGCCATTCCAGTGCCGAATTTGTATGAGGAATTTTTCTC AGAGTGGCGACCTGACTCGACACATCAGGACTCATACCGGCGAAAAGCCCTTC GCATGCGACATTTGTGGAAGGAAATTTGCCCAGTCTGGGGATCGGAAGCGCCA CACCAAAATCCATCTCAGACAGAAGGACGGAGGAGGAGGTTCCGGAGGAGGAG GTAGTGGCGGAGGGGGTTCACAGAAGCCTTACGCCTGTCCTGTGGAATCCTGT GATAGACGGTTCAGCCAGAGCGGGGATCTGACAAGGCACATCAGAATTCATAC TGGGCAGAAGCCCTTCGCCTGCGACATTTGTGGTCGGAAATTTGCTCAGAGCG GCGATAGGAAGAGACACACAAAAATCCATACTGGCTCCCAGAAGCCATTCCAG TGCCGGATCTGTATGCGCAACTTTAGCCAGTCCGGAGACCTCACCCGACACAT CCGAACCCATACAGGGGAGAAGCCTTTCGCCTGCGACATTTGTGGTCGGAAAT TTGCTCAGAGCGGCGATAGGAAGAGACACACAAAAATCCATACTGGCTCCCAG |

TABLE 11-continued

Peptide and Nucleic Acid Sequences.

| SEQ ID NO: | Sequence Type | Sequence |
|---|---|---|
| | | AAGCCATTCCAGTGCCGAATTTGTATGAGGAATTTTTCTCAGAGTGGCGACCT
GACTCGACACATCAGGACTCATACCGGCGAAAAGCCCTTCGCATGCGACATTT
GTGGAAGGAAATTTGCCCAGTCTGGGGATCGGAAGCGCCACACCAAAATCCAT
CTCAGACAGAAGGACGGAGGAGGAGGTTCCGGAGGAGGAGGTAGTGGCGGAGG
GGGTTCACAGAAGCCTTTCCAGTGCAGAATCTGTATGCGGAACTTTTCACAGA
GCGGAGATCTGACCAGACACATCCGGACACATACTGGGGAGAAGCCATTCGCT
TGCGACATTTGTGGTAGGAAATTTGCACAGTCTGGCGATCGAAAGAGGCACAC
CAAAATCCATACAGGAAGTCAGAAACCTTTCCAGTGCCGCATTTGTATGCGAA
ATTTTTCCCAGTCTGGTGACCTGACACGCCATATTCGAACCCATACAGGGGAA
AAACCTTTCGCCTGTGACATTTGTGGAAGAAAATTTGCTCAGAGCGGGGATAG
AAAGCGGCACACTAAAATCCATACCGGCTCTCAGAAACCATTCCAGTGCCGGA
TTTGTATGCGCAACTTTAGTCAGTCAGGCGACCTGACCAGACACATCAGAACT
CACACCGGAGAGAAACCCTTCGCATGTGATATCTGTGGTCGGAAATTCGCCCA
GAGCGGCGATCGCAAGCGACACACTAAAATCCACCTCCGCCAGAAGGACGGCG
GAGGATCCGGAGGGGGTGGGTCCAGCTTGTCTCCTCAGCACTCTGCTGTCACT
CAAGGAAGTATCATCAAGAACAAGGAGGGCATGGATGCTAAGTCACTAACTGC
CTGGTCCCGGACACTGGTGACCTTCAAGGATGTATTTGTGGACTTCACCAGGG
AGGAGTGGAAGCTGCTGGACACTGCTCAGCAGATCGTATACAGAAATGTGATG
CTGGAGAACTATAAGAACCTGGTTTCCTTGGGTTATCAGCTTACTAAGCCAGA
TGTGATCCTCCGGTTGGAGAAGGGAGAAGAGCCCTGGCTGGTGGAGAGAGAAA
TTCACCAAGAGACCCATCCTGATTCAGAGACTGCATTTGAAATCAAATCATCA
GTT |
| 65 | Linker (prt) | TGQKP |
| 66 | Linker (prt) | TGERP |
| 67 | dodecamer repeat sequence (DNA) | CCCCGCCCCGCG |
| 68 | ZF11-Kox-1 (prt) | MADYKDHDGDYKDHDIDYKDDDDKPKKKRKVTGAERPFQCRICMRNFSQRATL
QRHTKIHTGSERPFQCRICMRNFSQRATLQRHIRTHTGEKPFACDICGRKFAQ
RATLQRHTKIHTGSERPFQCRICMRNFSQRATLQRHIRTHTGEKPFACDICGR
KFAQRATLQRHTKIHLRQKDGGGSGGGGSGGGGSQLVGTAERPFQCRICMRN
FSQRATLQRHIRTHTGEKPFACDICGRKFAQRATLQRHTKIHTGSERPFQCRI
CMRNFSQRATLQRHIRTHTGEKPFACDICGRKFAQRATLQRHTKIHTGSERPF
QCRICMRNFSQRATLQRHIRTHTGEKPFACDICGRKFAQRATLQRHTKIHLRQ
KDGGGSGGGGSGGGGSQLVSSLSPQHSAVTQGSIIKNKEGMDAKSLTAWSRT
LVTFKDVFVDFTREEWKLLDTAQQIVYRNVMLENYKNLVSLGYQLTKPDVILR
LEKGEEPWLVEREIHQETHPDSETAFEIKSSV |
| 69 | Recognition sequence | QRATLQR |
| 70 | Primer | GTGGAAGCTGCTGGACACT |
| 71 | Primer | AACGTAAAGTGACCGGGGCCG |
| 72 | Primer | GGTCCGAAGAGATGCTCAGT |
| 73 | Primer | CAGGAAGACCAGGTGGCTAT |
| 74 | Primer | GCTGCACCGACCGTGAGT |
| 75 | Primer | CGCAGGCTGCAGGGTTAC |
| 76 | Primer | CAGATGTCAGAATGGTGGCT |
| 77 | Primer | GCCTTGGAAGATTAGAATCCA |
| 78 | Primer | CACCTGCCTCCACCTCATGGC |
| 79 | Primer | ATGCTCCTTGGGGGCCCTGG |
| 80 | Primer | ATCCCAATGCAAAGGAGTTC |
| 81 | Primer | CTGCTGATGACCCACCATAG |
| 82 | Primer | ACTTCGTGCAAGAAATGCTG |
| 83 | Primer | GCTCATAGCTCTTGGCTCCT |
| 84 | Primer | GGTTAAGCAGTACAGCCCCA |

TABLE 11-continued

Peptide and Nucleic Acid Sequences.

| SEQ ID NO: | Sequence Type | Sequence |
|---|---|---|
| 85 | Primer | AGAGGTCCTTTTCACCAGCA |
| 86 | Primer | GCTTCTTTGCAGCTCCTTCGT |
| 87 | Primer | CCAGCGCAGCGATATCG |
| 88 | Primer | CCACCGACATGGGCACAATGCA |
| 89 | Primer | ATGGGCAAAGGTGGTTGCAGGG |
| 90 | ZF4xHunt (prt) | FQCRICMRNFSQRATLQRHIRTHTGEKPFACDICGRKFAQRATLQRHTKIHTGS ERPFQCRICMRNFSQRATLQRHIRTHTGEKPFACDICGRKFAQRATLQRHTKIH |
| 91 | ZF6xHunt (prt) | FQCRICMRNFSQRATLQRHIRTHTGEKPFACDICGRKFAQRATLQRHTKIHTGS ERPFQCRICMRNFSQRATLQRHIRTHTGEKPFACDICGRKFAQRATLQRHTKIH TGSERPFQCRICMRNFSQRATLQRHIRTHTGEKPFACDICGRKFAQRATLQRHT KIH |
| 92 | ZF11xHunt (prt) | FQCRICMRNFSQRATLQRHTKIHTGSERPFQCRICMRNFSQRATLQRHIRTHTG EKPFACDICGRKFAQRATLQRHTKIHTGSERPFQCRICMRNFSQRATLQRHIRT HTGEKPFACDICGRKFAQRATLQRHTKIHLRQKDGGGGSGGGGSGGGGSQLVGT AERPFQCRICMRNFSQRATLQRHIRTHTGEKPFACDICGRKFAQRATLQRHTKI HTGSERPFQCRICMRNFSQRATLQRHIRTHTGEKPFACDICGRKFAQRATLQRH TKIHTGSERPFQCRICMRNFSQRATLQRHIRTHTGEKPFACDICGRKFAQRATL QRHTKIH |
| 93 | ZF12xHunt (prt) | FQCRICMRNFSQRATLQRHIRTHTGEKPFACDICGRKFAQRATLQRHTKIHTGS ERPFQCRICMRNFSQRATLQRHIRTHTGEKPFACDICGRKFAQRATLQRHTKIH TGSERPFQCRICMRNFSQRATLQRHIRTHTGEKPFACDICGRKFAQRATLQRHT KIHLRQKDGGGSGGGGSGGGGSQLVGTAERPFQCRICMRNFSQRATLQRHIRT HTGEKPFACDICGRKFAQRATLQRHTKIHTGSERPFQCRICMRNFSQRATLQRH IRTHTGEKPFACDICGRKFAQRATLQRHTKIHTGSERPFQCRICMRNFSQRATL QRHIRTHTGEKPFACDICGRKFAQRATLQRHTKIH |
| 94 | ZF18xHunt (prt) | FQCRICMRNFSQRATLQRHIRTHTGEKPFACDICGRKFAQRATLQRHTKIHTGS ERPFQCRICMRNFSQRATLQRHIRTHTGEKPFACDICGRKFAQRATLQRHTKIH TGSERPFQCRICMRNFSQRATLQRHIRTHTGEKPFACDICGRKFAQRATLQRHT KIHLRQKDGGGSQLVGTAERPFQCRICMRNFSQRATLQRHIRTHTGEKPFACDI CGRKFAQRATLQRHTKIHTGSERPFQCRICMRNFSQRATLQRHIRTHTGEKPFA CDICGRKFAQRATLQRHTKIHTGSERPFQCRICMRNFSQRATLQRHIRTHTGEK PFACDICGRKFAQRATLQRHTKIHLRQKDGGGSGTAERPFQCRICMRNFSQRAT LQRHIRTHTGEKPFACDICGRKFAQRATLQRHTKIHTGSERPFQCRICMRNFSQ RATLQRHIRTHTGEKPFACDICGRKFAQRATLQRHTKIHTGSERPFQCRICMRN FSQRATLQRHIRTHTGEKPFACDICGRKFAQRATLQRHTKIH |
| 95 | Primer | CCTGAAGTTCATCTGCACCA |
| 96 | Primer | AAGTCGTGCTGCTTCATGTG |
| 97 | Primer | AGATGCTGCGGAAGAAGAAG |
| 98 | Primer | GGTACCGTCGACTGCAGAA |
| 99 | Primer | CTTTGCTTTCCTTGGTCAGG |
| 100 | Primer | TATCCAACACTTCGTGGGGT |
| 101 | Primer | GTCTCCCTCCGATCTGGATA |
| 102 | Primer | CACACTTCCAGGGCTGTAGA |
| 103 | Primer | CCAGCACCGTAGAGAGGATT |
| 104 | Primer | AGCCCTGTCCAAACACAAA |
| 105 | Primer | GACGCAGCTGAGCAAGTTAG |
| 106 | Primer | GAAGGAACGTGGGTTGAACT |
| 107 | Primer | AGAGCTTCGGAAGAGACGAG |
| 108 | Primer | ACTCCCAAGTGCTCCTGAAC |
| 109 | Primer | AACTGTGTGGCTCACTCTGG |

TABLE 11-continued

Peptide and Nucleic Acid Sequences.

| SEQ ID NO: | Sequence Type | Sequence |
|---|---|---|
| 110 | Primer | TGGGAAGATGTTACCGTTGA |
| 111 | Primer | GGGAACTACACCCTCCTGAA |
| 112 | Primer | CGCTGCTTCTTCTTCCTCTT |
| 113 | Primer | ACGCCGAATATAATCCCAAG |
| 114 | Primer | CTTCACTCTTGGCTCCTGTG |
| 115 | Primer | CAGATGTCAGAATGGTGGCT |
| 116 | Primer | GCCTTGGAAGATTAGAATCCA |
| 117 | Primer | CACCTGCCTCCACCTCATGGC |
| 118 | Primer | ATGCTCCTTGGGGGCCCTGG |
| 119 | Primer | TGTGGAGAGAATCGAGGAGA |
| 120 | Primer | CAGCCCTGTCCAAATACAAA |
| 121 | Primer | ATCCCAATGCAAAGGAGTTC |
| 122 | Primer | CTGCTGATGACCCACCATAG |
| 123 | Primer | ACCTCGCACTATTCTTGGCT |
| 124 | Primer | TGCATCTGTTGGACCTTGAT |
| 125 | Primer | TGCCCGTGTTCCTCACCGGA |
| 126 | Primer | GCGCGGAGACAGTGGTTGCT |
| 127 | Primer | CACTGGCAATAGCAAAGGAA |
| 128 | Primer | TTCTTGAGCGAGTTCACCAC |
| 129 | Primer | ACTTCGTGCAAGAAATGCTG |
| 130 | Primer | GCTCATAGCTCTTGGCTCCT |
| 131 | Primer | TCCTGGCTTTGAGGAGCCGA |
| 132 | Primer | CCACAGCACAGCTCTGCAGCAT |
| 133 | Primer | GGGGGCTCAAGCAGGCATGG |
| 134 | Primer | GGGAGCCAGCCTCCGAGTCA |
| 135 | Primer | CAGATGTCAGAATGGTGGCT |
| 136 | Primer | GCCTTGGAAGATTAGAATCCA |
| 137 | Primer | GGTTAAGCAGTACAGCCCCA |
| 138 | Primer | AGAGGTCCTTTTCACCAGCA |
| 139 | Primer | GTAAAACGACGGCCAG |
| 140 | Primer | CAGGAAACAGCTATGAC |
| 141 | ZF10xHunt (prt) | YACPVESCDRRESQRATLtRHIRIHTGQKPFQCRICMRNESQRATLsRHIRTHQNKKGSHICHIQGCGKVYGQRATLQRHLRWHTGERPFMCTWSYCGKRFTQRATLQRHKRTHLRQKDGERPYACPVESCDRRESQRATLsRHIRIHTGEKPYKCPECGKSFSQRATLQRHQRTHTGSERPFMCNWSYCGKRFTQRATLtRHKRTHTGEKPFACPECPKREMQRATLQRHIKTHTGSEKPFQCRICMRNESQRATLQRHIRTHTGERPFACDICGRKFAQRATLQRHTKIH |
| 142 | ZNF10xHunt C-terminal linker and repressor domain (prt) | LRQKDAPKKKRKVGGSLSPQHSAVTQGSIIKNEGMDAKSLTAWSRTLVTEKDVFVDETREEWKLLDTAQQIVYRNVMLENYKNLVSLGYQLTKPDVILRLEKGEEPWLVEREIHQETHPDSETAFEIKSSV |

TABLE 11-continued

Peptide and Nucleic Acid Sequences.

| SEQ ID NO: | Sequence Type | Sequence |
|---|---|---|
| 143 | Mouse hsp90ab1 promoter 2k plus exon 1 95 bp (mouse NCBI 15516 NC_000083.6) | agtacactcctgtccccattctactttcagaacaggaatggccctgggtttagtg accccattattcacagagaccttcattttcctgtccatgaaatatacagagtagc tttcaaccattcagaggccaaggagaggtagtcagtgctgtttgtgaactaggga atccaggattggtgggtcttagggaaacactaccctggagctaaatgtccagccc agggatcagctaggctcctttttgctgagagggtttgagtgttgaagtttctggtt tcagattaggaatcaatgcaacaccctagggccttctgagcaatcctacccagtg tctcctcatatattgattttotttatgggcttcacacacacacacacacacacaca cacacacacacacacacacacacacagaattaaggagaggctaacagacagtgcagg atgggatgataacagacgaagtagacagaggcaaggagaaagcaactactgttta acaatgaatgcacattagacagactgcaggcaagcaccgggaacaaaggtgtggg cggtggtgtggggacacaagccagcatgagctaagatagcagagcactgagtgcc catcctctactggagggctcatcagtccaacaagcttccagatgcagccttggaa aaaggcaaggctagattgccagctgaaggacatggcaggccacctttagaacaga ggcactggcacaacttggttttctggctcctgaactgggccaacctgtgaccag caccttcatgcggatgcctagaactccagcttctctgaaaagactgggacctgct cctctctaggtccaaagagctgcatgcagtagggaagaggctagagaagcgaaac cagcttgagaaacagcttgtgctcacatagggagggcgcacgtacccgcgcgctg tgtacgtgggagaccggggaggctgagggggtgggagtgttctacccagtagcgc aagctgctagctcggttctctgttcactagaaggtgtccgcagtcactcaccccc acagcccccgtgccctgtgaccgatccaggtcagctatccctccctctgcgctcc actccccactgttatgtgggcctcttagggccacgcgtggagggtcgttcaacc ctggcccacggtaggcagacttggggaaaatttcttcccagggtaagatcaaggt aggggaaaaaaaaaaaaaaaaaagccacccagccaagcggcgacgaagacactg ccccccgccgcagcaggggaggtggagcctaggggggaggggtggagaccgccgag acaggcctagaaactgctggaagaaatcgcagcaccaccgctgctgatccttccg ccgcaggccgccaaagagtccctaccagccccaggcccgtgcccctccctcgggg aaagcggctcccagcctgaagctgtgctgtacccgggagggtggggatgggggaa tcggggggcctccttaaagttggacaaggaatttatcatccttttctcttgatgtg cgatttgtagggaacattctagtaagatcgggtctggaaatggcagccgagttgg ccacctccattctctttcagtcccctgagttctggactcttgggggggtgggggg tggaagcgcctaccttgagttttctgaggcagtccgtagggtattcgcccgcaga tacatccctaattgcatatgcatgctccctgctcatcttgaggggggacatgtcc tactcctgcagaaatgggggatgtgcaaaacgatattgaattggccttgactcag gaaccaggcccggggtcccgctcctccccgcccctccacgatctgctaccatga cgtcaaggtgggcgggcggcggcaggtgcgtggcccgcagccactccttaaggc ggagggatccaagggcggggcccgggctgtgcttcgccttatataggcggtcgg gggcgttcgggagctctcttGAGTCACCCCCGCGCAGCCTAGGCTTGCCGTGCGA GTCGGACTTGGTCCGGGCCCACCACCCTGCTCTGTACTACTACTCGGCTTTCCCG TCAAG |
| 144 | Human hsp90ab1 promoter 2k plus exon 1 179 bp (human NCBI 3326 NC_000006.12) | gcctggctaggcatggtcctaagactgctccctttcccaagctgagctgagggcc tctgcggcttctcccatcctcctatggttcacacttggctgctgcagcctccagt gggttaagggctcccagtcctgtgtatgcatctctgcatccccaggatctccaca cagtggaggcttagtgagtgtcaatgagtggaaaacgatggcgttgtggacaca ggtaggcggtctcctgaaaggcttcctggaagagaaagtggaatttcttttttt ttttcttttttgagacagagtctcactgtgtcgctcaggctggagtgcagtggcg tgatctcggctcacggcaacctctgccgcccgggttcaagtgattctcctgcttc agcctcccaagtagcggggactataggcgcgctaccacgcccggctaattttgt attttagtagagacaaggtttcaccagagtggccaggctggtcttgaactcctg acctggtgatccgctggactcggcctcccaaagtgctggaattacaggcatgagc caccgcgcccagccccctttttttttttttttttttgagacggagttctctct tttgttgcccaggctggagtgcaatggcatggtctcagctcactgcagcctctgc ctccagagttcaagcaatcttcctgcctcagcctcccaagtagctgggattacag gcatgtgccaccacgcccagctaattttttagtagagacgaggttttttcaccatgt tggccaggctggttgtgaactactgacctcgggtgatccacccacctcggccttc caaagtgctgggattacaggtatgagccactgtgcccagcagagaaagtggaatt tctatgctggtgtaacatttgagattttcccatttagaaagttcttcaggaagccg tcgagtcttgacacagaaaggatccagctcaggggaagcccatccacaggagtga ttcctgctttggatttaggtcctaggggtgagatcacatccctgctccatttctg gagcagaaagggagctagtgcagcaaggactctgagtagacgggccttgggagtc actgaagccacttccctgttgacagaatgtgcacactgacttcatccgctcaca ggagagtgagagtttgtgaatgctctctgtgaactggggagcagattttttaatga gctctgcttagaaggagaggacacgttaagggatcacgctcccactggtttgcgg ttttggtcaggaatagagcacccaacgcccttcttatagacttctcccagccat aggcttttgcagaccataatgaaagggagaaaggatatccaatcgggatggtga tggcaggcatggcgaagtggacagggacaaagaagaggaaagcaagggacaccct ttgttctttggtattcaacacatgaacaaaacttgttaacgaatcgtagactggg taacaacagggctggtgagggaggacgatgtgggtggctgtggaaactcttcc caagcatcccaggggtgggccaggaagggggagcagatggacatctacagggcaca gagcagggagtggctattctctcctggagggtttgtgggtccagcaggctttcgg atgaggccttggaaaggcaaggacagcttgccaactggagggcaggcaaaacggc tgagccaggccagacacggcagctcactggccaggggcatggcctaggggctctg gtgccaaggctgaaggggaacaacttggccagccgctctgtggccggcatcgtca cgcggcctccaagagctccggctgccctgcactggttcccagagactccctcctt |

TABLE 11-continued

Peptide and Nucleic Acid Sequences.

| SEQ ID NO: | Sequence Type | Sequence |
|---|---|---|
| | | cccaggtccaaatggctgcaggagcgaagtgggcggaaaaaaagcgaaccagctt gagaaagggcttgacgtgcctgcgtagggagggcgcatgtcccgtgctccgtgt acgtggcggccgcaggggctAGAGGGGGGTCCCCCCCGCAGGTACTCCACTCTCA GTCTGCAAAAGTGTACGCCCGCAGAGCCGCCCCAGGTGCCTGGGTGTTGTGTGAT TGACGCGGGGAAGGAGGGGTCAGCCGATCCCTCCCCAACCCTCCATCCCATCCCT GAGGATTGGGCTGGTACCCGCGTCTCTCGGACAG |
| 145 | Mouse Hsp90ab1- 20 kb to 100b | ctcttgagtcctcttgagtcgggtgtcccttgaatatgcttcttccttacaggac tagcccactggtgctgttatctcctcttttgagagtgaggcacagggcagcatgtc aagggtttggttaggagctctgggagcacgatgctagctttccaaatttcccttc aaagccactgtcagacacgggaagaggatagttagtggccttggactgagaaagg aactgggggtgggggggaagaaaggaacattctggaactggaggtcaaggaaa ggaacttgctgtggagaagtctgtgtccctcccacagttatgaaatatattcctg gagaactcaggaagcccctaggcagcagctggaaaggcgtagaggctggctccag cagaggctggctccagcagaggctggctccagcagaggctggagggagtcccgat tactctaggaagcagtctgcgaagggaaggccctccctgccacagtcttgattgg gtgatggggtgggggcacccaggaggggagagtgcaggctcatggcaggcctcag gagacctgtgttcctacagggtctgtttgctctctcactcttttctccctttttc ccctctgctctgtctcctccccttttgcctgctctgtcactgttgtcactgtcct gacccctttctcttttctgtcttcttttgactgtcttttccctgcctctcaatcat ccgtcctcctcctcctcctcgattgctccccacccttcggtttccaagcttataa actgcttctgctgctggataaaaatagcggtggcagcggccaggctggcagccag gtgcagcccaatcaggcagagagacgacaggaaggccttcctggggccaaaggcc agatggggctgagttgagtggtcctgagtctgcagaggcttcccttgcctactct gtgtccagctctaccccccccccccaagagaaaggcccagggcagtgtggaagca gagccagacagggctcgatattcctttaccccccagcaagagccagagggagggag ctgccagccaggcacagccgagaacactggagccatgacaaccagtcaccagcct caggacaggtactgggtggccaaggggtgtgacggagggtggttgcagggagggg ggagccggtctggagatctggggagtgagtctctaggggtaagggtgggacggagg gaggtgcggtgtttgggacttgagggaggggacctcaggactaactgtgttccca gcctggtggttctgagtcagttctgcatgggggtagggtggagaacatgcatgccc tggctgggtgctggctagcatgcccgcagggctaggtgagcagtaggtccctatt ggagtgtctcagtctttccactgttatgcgcagctagacagcagcttccagctcc tcccaccatcactgtggggagacacttggctgcttccctcattccagaacacatc tggcaggactaccctgtccctgggggtcgccttgcatgacctcagcccacgct gctctctggcctgaccctctcagccttctagctccggagcttgggatcttcctca agctagttaaggtccggaatgcgtgctaggatggaaaaggagcttgagtctagtc cttcagaggggctgggagcttgtggaagtttatgaagcgcatgatacactctttcca gatggcccctctgtcctgttgggtctctgaacctctcacggctcccctgcccacc attttcctcttgtgctatgtaactaggcccattctgactggagagttagctgcat ctttctgggaccatttctccatcctgtaaagtctggtgagaacaccagccttctg tgactgttttctgaggggaagaattgtcattgtcattgtaggttccagcttcctg cctcctttccttcccaggctgcctggtgccctggcctcttcaacaatctaccat ttcactgctgcctggctcagcagctcttctctgacctcctgtcttgtataacct tccctcggaattttaccttccatctgagccttttgaaccaagccttgagcatcttg acctcaagggaatggatgagggctttgaaggctgtggtgtggccatggcttaga ctggcgaatttggttgctcttctggctgtcccatttcaggcttgcaagaggcctg ttccactgagttgggtctctgctaccatctctgtgcagcctgtagatgccggcta aggggaaggtattttaccaggcataggcaactgtaatggaagggaccagggccac taagcttacaggcaaagactgtccgaagtcatgctcagaaccagatggcagccat aagtcctaatctatctgccctgccgtaggtagtttggactataaaactggttctg tctgtctaatatctaataagggaaaaaaaaattctatagctctctacttcctagt ccccaccccctacccccagccatgtgacccactgggtctagaattgtctgggtgt tgttttttgacctcaagagttcttgagagaactggcgttcccgcttagacagctt aactacttccagctggtgtggtggggctggggcttgtgcccactgccctttaccc gcccacctttaacagaggttccaacaccagctctgaagtgtgggtcatcacact gcttccccgatcacccagccccctgaaccttctaggacttgggaacaaaggttct gtctcccgtgtcattcagaactgccaccagcccttttccttcaaccatcttaca gcctgtcctgtacccaggacctacacatccctcacacctctgcaggagggcgcct acttgtggatacacacagctgggaccgctgggtagacggagggaggggaggtgg gctgactgatcactttgccttttcctacgcaggtataaggcagtatggcttatc ttctttgtgctgggcctggggacactgctcccctggaatttttttatgaccgcaa ccaaggtgaggttggagtgggggtcaggtactaggctccagaggacatgttcctt aggctttcaaggcctggttctgtgcctctgggcacagagagggacagaggtccca acactcaacctctgcaaaccccacagtatttcacaaaccgcctggacgtgtccca gaatgtgtcctcggacactgatcaatcatgcgaaagcaccaaggccttggctgac cccacagtggccttgccagcccggagttctctcagtgccatcttcaacaatgtca tgaccctggtgccatgctgcccttgctggtcttcacctgcctcaactcgtttct gcatcagcggtgagcctcccgtccatgatgcccagccagctcctgcttcctcag ccccaggctgaccttcctgacaccccaccaccaccaccccctgcctctccta ggatctctcaatctgttcggatcttgggcagcctgctggcaatcctgctggtatt ccttgtcactgccgcctggtgaaggtggagatggatgctctgatcttctttgtc atcaccatgatcaagattgtgctcatcaattgtaatcgggaggggacgggatgga cagccatgggcctgggttgagatcagggtggggtggttcaggttaaagcttcct gggaagccctgattgccagcctctgctgacaagctgtctttgctactccccagca |

TABLE 11-continued

Peptide and Nucleic Acid Sequences.

| SEQ ID NO: | Sequence Type | Sequence |
|---|---|---|
| | | tttggtgccattttgcaagccagccttttggtctggcaggtgtcctgccagcca
actacacagcccccatcatgagtggccagggcctggctggcttcttcacctctgt
cgccatgatctgtgccattgccagtgagtccaactgcgcgcgcactgccctgctt
tgctggttgtggggaggcagggtagggtgatttggaagggtggagcgtatctgag
cttgtgcactgtctgcgccaggtggttctgagctgtcagaaagcgcctttggcta
cttcatcacagcctgtgcagttgtcattttggccatcctgtgctacctggctctg
cctcggacggtgagcaaatggggggatttggggaggcctcggggtttcaaagcaa
gggtgtctggaaactaaaggatggcaagctcggatgcctagagctgccctgactc
tacttacttctcccatctcccttgctgaacaggaattctatcgccattacctgca
gctcaaccttgcggggcctgcagagcaggagaccaagttggatctcataagtaaa
ggtcttaattactaaaggaagtctggtagggcggtaggatgggagtggagagggtt
gtgggcatgttgtgttaactggcagctgggagccaaaggaggacactcgggccgt
gagtgggtagggagaggggaaaagaggggtgagccagggaagatagcgcagatgc
cttgcagggtcttggcgtgttgctcggttggtaagagtgggtgcacaaaggcctg
agtttgattcctgcactgggcaaggtggtgcacatgtaaccttagcgtttgggaa
ggagaggcaggaggactgtattcaaggtcatccttggctatacagtgagttcaag
gccagcctgacctacatgacatcttgatgaagaaagaagggaaacttgggtcacc
ctgaatgtctcgggcattcggacagaggtcagcggcttcagagggaacagagaat
gacaggagcctcctggggaagggtcagtccccaggggctcgagtcaagggttat
tagggtagaactgcggactagccagttaagggaggtgcccacctccagctcattc
tacctgttgttctgtcctccccaaaacttaaagatccttttacaacctctcaccc
gacaggagaggagccaaaaggaagaagagaggaatctgggtgccaggcccccaac
tctccacccaccaacagaaaccagtctatcaaagccatacttaagagtgtacgtg
ggcccggggtgtcctgcctaccctcctcacccttcttctctcctttttgctgtttc
taccttataccacttcccttctgatctaagactgggctttctcctgtcttccta
tgaatgctgtgtgtgtgtctgtctgtctgtctgtctgtgagattaaaaaa
aaaagatttatttatttattatacataagtacattgtagttgtcttcagacacca
cagaagagggcaacagatctcattacagatggttgtgagccaccatgtaattgct
gggaattgaactcaggaccttcaaaagagcagtccgtgcttttaactgctgagcc
atctctccagccccatctctgagatttatttattttattatttatttattt
atttattgttttttcaagaacagggttttgatgtagccctggttgtcttggaact
cactctgtagaccaggctggccttgaactcagagatcagcctgcctctgcctcct
gagttctgggattaaaaaggggtatggtaccagtgtctggctctttggtcttttg
tacacagagccatgacaacctagggccctgtatgaatctctcttctcttctctct
ctccagatctgtgtcccggctctgtctgtctgcttcatcttcacggttaccattg
ggttgttccctgctgtgactgctgaggtggaatccagcatcgcaggcacaagtcc
ctggagtatgtgtcccttgcccctcccagcccccccccagccccgcact
tccctcctaggacggattcacccagagtctaaagtggaatcatgggtggggtatg
ggcaacctctggggctccctctgcccagctggatctacaacgggcctactagacac
cctgccattggatggaaacctctgaggcagaatgaagagtcctaggcccagagag
ggccagttgctaagtcttaagtctctttcctagaaagtcacttcattcccgtggc
ctgtttcttgaatttcaatgtctttgactggctaggccggagcctcactgctgtc
tgcatgtgggtgagtacagcatgggcggcagggctgtggggttcaggtgtccagc
tgaggccaagagggaacccaagaaagtatggtggctgcagtgtggctctgtgact
gatagagggcttgctagcatgcatggcccctgggtcccatctgtaaaactgcaag
aagggaaaatggaggggtggggcagtggctcaacaggttaagagcactgactgc
tcttccagagatcctgagttcaattcccagcagccacaacggggctcacaacca
tctgtaatgggatctgatgcctcttctggtgcatctgaagacagctaccagtgt
actcatcaaaaacaaaaaacctgcaagaagggaaaaaataccgtgtactactcata
acttatgtgtaactctgtgtacaagttcattcgtttgttttatctgtctgtagagg
cagggtctctgtgtgttgctatctgggaatttactctgtagaccaggctggcctg
gaactcagatctcttttactccctgcttcccaagtgcatgtgccaccagctaagac
tttcaaattatgtgtgtgtgcatgtgaatgcaatgcccacagaggccagaagagg
gcaccagatccctggagctggagttagaggagcttgtgaggactggaaactaaa
cctgggtcttccgcaagagcaggactcttaactattgagccattcctggcccatg
cgtacagttcttaggtgtgtagcctggcagaggtgtgcatgtcatggctcccacc
tagatggaaagatacatctcgacatatcataggcaccactgcgcccctagcaatc
agcaccccaaaggcacccaggcctagtggttttatccaagtccccagggccc
aggagaccgggaggactgacatgcgtgctgaagccttgcctgtgtccgcagcctg
gccaggatagccgctggctgccggtttggtcgcctcgaggattgtgtttattcc
cctgctgatgctctgcaacgtgaaggctcgccactgcggcgcgcagcggcaccac
ttcgtcttttaagcatgacgcctggttcatcgccttcatggctgccttttgccttct
ccaatggctacctcgccagcctctgcatgtgcttcgggcccaagtgagtcgggcc
atgaggggatttggtgacatcaggcaggacttacagggagatggcagtaggagag
tccctccccatctcatagctgcacggagttggagttgctgggggtttaaggggg
cagtggaggtaagggcttgctaatgtgctcctgctgagctgtgtgggaaggg att
aagacagggtggaggatggtccctagacacagtctcccaagaagtgggctgggat
tgggagtgttggaaggtttgggggtgggggacagggctgggctcagcttgccta
agattaccctgcctttccttttaggaaagtcaaaccagctgaggcggagacagca
ggaaacatcatgtccttctttctgtgtctgggcctggctctgggagctgtgttgt
ccttcttgttaagggcacttgtgtgaccctgtggggacagaagaactacactgcc
tgcttcctgctcacttccttccctgccagggacgagcaggggtcgagagggggctg
ttcttctagctgacttctgctttcctctggactgtgcttcgcccagctgtccagg
agccagcgatggcctgcgggtggacttggaattcagggtcagaatggcaagggct
caatggcctctgactgacagctccgactgatgcccgcttactccaagcacaagag |

TABLE 11-continued

Peptide and Nucleic Acid Sequences.

| SEQ ID NO: | Sequence Type | Sequence |
|---|---|---|
| | | actccagggccaagagagatctgtccgcctgcctatcacaggatagggcggaggc
ggatggctgattggtgtcgtgtgacctgatgtccctcccttgccttcttcctt
ctgtgcctgttccatgtccccagcccttgtcattttactgcctttttttatactga
cagaaaccaggtgccttcagaggccatctgattaaataaacatttttttctcca
tagctctgtgcatccttccaaggtttaactaactccttggagaggagagaaggct
ggcagcctgagtctaggtttctgcaatgacccaagcctgggcctgggtataaggg
ggaggatgcagtccttcagtctcagaggggctgcagcgcccctactggggacac
agggaagagacaggcctggagccaagacgccacccagactgtggcccagatttag
aaagatgtagcccgagtggtcttcacattccataagtacctgaaggtggccttga
accgcttcctatgtgctggtactgcagctgtgtaccaccatgtcctggatctagg
gatcaagtccagggctttgtgcatgctaggcaagcgctctgctagccgagctatg
ccccagccctctttctcatttcaagggcctggaaatggaggcagctttgtcttc
cccgctaccttcccctcccccaccacgctgtcctcagctcctggaatgaactctg
ccaaactggccagccccaccccagctcctggccatactcccacatccctgggca
ggaaaaggctgaggcctgggctctcccttaccttggctccaggccctgacaccaa
agcccaggctgccagacttcctggagaacaacgggcctatgtgtcctcatgttgg
cgttggacctccccgttcttcagccatactgtggtctgaggaagggtgtgttggt
atgggatgtgagactccctcggtggaggggcgctgatgctccagctcaggactg
actggaactgagaggaacactctggtcctaagtgcccttgtcccagccctggg
agacagaagcttttgccccgcccatctcccaagcccctcccccaaggctgcat
gttctctcatcctctaccagctgatggctacaggggtggccctactgttgggact
tccttttttcacagaaatttcatttaaaactagtggttctcaaacttcctagtgct
tcaacactttaacacagttcctcatggggtgagcccaaccataaaattatttt
cgttgctgtttcataactgcaattctgctgctgttatgagtcgttctataaatat
ctgtttcccatggtcttgggtgaccctgtgaaagggtccttagacccaccca
aagggtcacaatccacaggtggagaactgatttaaacaaaggcttcagactttc
gtgagaagtagtgtattttcttttgtttttgtttttttattgagacagagtttc
tctctaaccttggctgtcctggaactctatatatagatcatgctggccttaaact
cagagatccacctgcctctgcttcctgagtgctgggattaaaggtgtatacaac
catagcctgggttgttttcaattcttttcttcttcttcttttttttttttaaa
attaatgtgcattggtgttttttgcttacatatatgtctgtgtcagagcatctgac
cctctgggactggagttaaagacagttgtgagctgccacgtggctcctgggaatt
gaacccaggtttcctggaagagcagccaatgctcttaaccactgagccatccctc
cctccattccccagttgcttgttatcaatccttactaaggtcaagcttggtggtg
ggttggaggttaaacgcatcactgtaccaagcacgggtgtccatgactagtttgt
caaaactgcatacatgcctcagcagtggtagctcacacctttaatgctggcgctt
gggaggcagaggcaggcagatctgtgagttcaaggctgttctggtggtctacagt
tcaagttccaggaaagcagggctatacagagaaaccatgtttcaaacaaccaaac
caatcaaccaacaaacaccccccagcatacatctgctctgttagaaatggccttcc
tatgctatctggttcaaactgcctgttccctaactaggaggcaagctaaaaaata
caaacaaagtctctcctgcttgcccttagctccaatgacttgacttcctcctcgt
actgaaattcacgagagggtttagcagctttctttttcaacactggtagcctctgg
ggaacccgaatttttttcccaaactctaacttcctacctacagtctggctcctgg
gttccctctaatccaccccgtgtgtggccacaaggaactggtgagagtgtaatt
actcattttccaaagattttattttatgtatgtgagtacactgtagctgtcctcag
acataccagaagagggcaccagaccccactacagatgcttgtgagccaccttgtg
gttgctgagagttgaactcaggacctctgggagagcagtcagtgttctcaccgct
gagccatctctccagccctcccctttccccgccctcccccttttttttgagtcag
tttttctgtgtagccctgactgtcttggaacttgctctctagagatcctcctgtc
tctgcctcctgagcactaggaagtaaggtatgtgccaccgctgtcctgcctgtaa
ctacttttttactggtcttagcttttccgaagagtgttgaagattcagcaagatg
gctgtgcatcctggctggcatggtactcactatggctactctcccgagggctagg
attgaggcatggcaccatcacaagggaattttttgtgcagtgattacaagggtgtc
tctcccttcccaaagttccctgatgtttgactctctaccattggcttgtgaaag
tctctccccgttctgcgccctagggcgttggtgatatgacttatctcctgtcaca
ctttgagctgaaagtgctccctggttcctaggggtgatctgaagatattcatgag
catgtgacgcttgtcaagtttacccatctcatgtcccacccacctatgtggtga
cattcattgcttgaatgtccttgaatgttagtaggctcttaactctggcactgac
ctgaatgggtgtcggagggggcatttatgattctgccaccagtgttgaagaaaa
tatctggaatataatcgttttctcccaaagtctttttaaaaaaaaaaacaatt
tatgtacattggtgttttgcttgcatatacatctagttgcagacagttgtgaact
accatgtgggtcctgggaattgaaccagg tgctctgtaagaggagccagtgctc
ttaagaaccactgagatctctcttcagcctcccccacctcaaactcttctaatgc
atagccttgtccctgagtaactacactgatggcttctgaccacaagtgagctctg
taggcaccaccttgaaggtcaaggagagtcaggacccactgcaggttacttcctc
ctcctggggagggaggaagcttgagcaagggactgccaggtatccttcctgccac
aatgttgtacatcacttcctgacgtctctggtctctgttcaaagcagtctactga
actgctgttttctggatggctgccactgatgtaaaagtcctttactgtgtgggtc
aatatggtgaagattgcagagcacccccttgtggtcataatccaccactgcaatt
gagcagaccagtgactgcaaggatgtctgcttttttccggtgtttacatgagaaga
ctggtaaattctacctttgtttaaaaacctctaggtataaaaggaggagatgtg
aaaacaagggtacaaggaagtggagagacaggagaacctcaattctcacctaaac
taaattgttcgtagaattaagttgatagcaactaggaatggatgtgagcagagaa
ctgtgctgtctggctgtgcaaacaggaaagtgtgacggcaggagattggcagaa
tgatgtcacagctaggctggcagtccatacaggtccctggggaccgtagtgttcc |

TABLE 11-continued

Peptide and Nucleic Acid Sequences.

| SEQ ID NO: | Sequence Type | Sequence |
|---|---|---|
| | | tagggtgggaatggccagagtcctcaactccttaacccatcgatgactgtgttct
agccaggctagaaaaacaggcttaccctgtttgttttcatggtgtgcccattcag
ccctctacccctcccggtagtcccgagcacgcggcttctgggtcctagctgtgg
ggaagtgctaagtgtggatcagcagggcccgagacagcagcacgctcttccttgg
ccttttcaggggggtagggccacttggcttgaattcagacccacagagtcatctgt
cttgggcccagctgttcaaaccaggaaaagccattctctgtggctccggtttctc
gccagggagtgggaacatcgggcaggctctgctaagggaattaaaccacgtgcct
agagttggtacagggtaagaagatactatttatttatttatttatttatttattt
atttattagagttggtacagggtaagaagatactatttatttatttatttattta
ttggttttcgagacagggtttctccgtgtagccctggctgtcctgaaactcact
ctgtagaccaggctggcctcaaactcagaaatctgcctgcctttgcctcccaaat
gctgggattaaaggtgtgcaccaccactgaacagcaagaagatacttcttaatgct
gctgcccgtaaggtcccctggtaaccaggatgagtctcggcatcctggggtggt
ccacctaagctacctgctccctcccccacacctctgggcgctgggagcttgaga
accaagccatacttacctagttacctcttccagtgtggattactgcttgggctct
tgctgtcagtcagtcagctaggaatcccaagacttttggagacgggatgcacctg
ggtttggggtaggggctgctggagctaagcaaagtatgtgatgtcacaggttccc
tgcccccaccctcaatgggagcaccttctccacttgcttgtgaggaagtcagact
gtgggacctataccactgcacctcgtgcccaggtcaccttacaccaggtactcag
agtctctcatgtgtaaagcagggaaggtaacaggtggagagccacagagatcatg
aatgactcagctctcccatagctggggactgggactcctcgatgcgtgcctggtt
tactctggaaaacagaaaggctaaaggatgaaaagggattctgtaggcaggcat
gacgatgcggtgcgtgcctttaatcccaggactcaggaagcagaggcagggggat
ttctgtgagtttgaggccagcctggtctaacagagttgagttcgaggacagccaa
ggaaggctacactgtgaaaccctgactcaaaacaaaaacaaaacaacagcaacaa
aaagattctgtcagtaaactacagtggaacgaaaggcttgggtccttgatgtgta
tctctgccacccagtcccagagctaaggacacaggcacagagcacagcaaacaga
gatccagtcagctgagacccgtgtgcagaaagggagtcgccagtgcctggggcag
aacaggaggcaggcagaacccaggacaggtgtgtgtatggcgccagcctgcccc
tccctgaccagtcaggtccagaataaattctgttcaggctactctttagtttcc
cttgaaggggctgggagcactggaggtcaagtctgagaggactgtggtagaagag
aaggcagggctggttagttagttacatacctttagagacacaggtcttcagaacac
ggaaaaatggtcccgagtgtgttaatggggtaccctgatgaggtcccgtttacat
tttgagaatagggtcagtcacaaatcctgtccttttttttttttttttttggtttt
tcgagacagggtttctctgtgtagccctggctgtcctggcattcactttgtagac
caggctggcctggaactcagaaatgcctctgcctcccgagggctgggattaaagg
catgcgccaccacgcccggctctcttttttacatttcttttttaatcctgtccctt
ttataaccattctgcctttagcgattctgttcttgtccataactttagctatcgg
cttggttaggcctgggtcttcaatccaaatccagtctggatcgcccctcccatc
cctctgcctgttggatagctgtttttgtcttgttttatgatttgcttattatgt
atacagtgttctgcctgcatgtacacatgcaagtcagaagagggcgccagatctc
attacagatggtcatgagccaccatgtggttgttggggattgaactcaggacctc
tggaagagcagatagtgctcttaacctctgggctggccttgaactcagaaatcct
cctgcctctacctcccgagtgctgggattaaaggcgtgcgccaccactgcctggc
ccctgagctttacttgagcatactaagtgcatagaacctccagcccacttgggcc
cttaacaacccaaggatgaacctgggtggcctaaggaaacagacaggcttaggac
ccatggagtcagggtagtacacagctctgctctcagaagattaaaaaagaaaaaa
aaaaaaagccaggtgactcccagtgacctagaaaggaagcccttcaggaaggga
ggagtgtgggcacagaaagcagccctgcaggctggggctgggttataaaaggctg
cgggtgccatgctgagctctatcctgaagagtgggaaaggcccctagagacagcc
ttaaaaccccctaggcctggaggggcctgagtcccagtagtaggctgcaaccacc
attgttcctaagatagggtttatacttgatccggcagaagctgttggagagtggc
cagctaacacagctcgtaacaggtcactacttgccgctgctgggcccacgcttg
gttatctacaccctgtaggcaaagaattctccttacaattggtagtgaattgggg
gtaaaatcaactccttcactctccacaccttgcttttttttctttgtttttaacc
attttccccaatgttgtccagactactctgcttcagtgtccagaatgctgggaca
aacaaatgccaccattcctgagttaaagatagtgtattgataagggaaatgtta
catttgaattttagcccctataaagttttgaatgtgccttgccagcctgcctgtg
cgttgtgtacacataatacctttgggggcaggagaggtgaatatttctctagaac
tggagttacaggtagttgtgagccacacccacaccccggctctgggaatcttac
ccccatcttctgcaggagcaagtgttgttttttttttttttttttttttga
gacagagtctctgtatagccctggctgtcctggaactccttttgtagaccaggctg
gcctcaaactcaggaatctgcctgcgtctgcctcccaagtgctgggattaaaggc
gtgcgccaccatgctcggcaagacagagtctttgtatgtagtcctcgatgtcctg
gaacttaccatgtagacgaagctggcctcacactcagagacccaccctcctttgc
ctcctgggtgctggcatcaaaggtgcttacaaccacccgagcctgtctacaggt
gtcttgcttccatgtgtgtgtgccatgtgtgctccggaagggcagccagtgattt
tagcccctgattcatctctctagccccatcatcgtttttttttttttgtttgttta
tttattttattttttttgttttcgagacagggtttctctgtgtagccctg
gctgtcctggaactcactctgtagaccaggctggcctcgaactcagaaatcctcc
tgcctctgcctcccgagtgctgggattaaaggcgtgcgccaccactgcccggcat
catcgttgttttaaggcagggtctcactccatagaccaggctagcctgcagaaca
ctgcatagcctaggctgccctggaactcatggtaatcctctaccccaaattctaa
atgccggaaaagtaaatatgagctactaaacccagactcgagactatgaatattt
gaaaattttctgggtaagcgtgagaagataaattacctagccattgggtttacta |

TABLE 11-continued

Peptide and Nucleic Acid Sequences.

| SEQ ID NO: | Sequence Type | Sequence |
|---|---|---|
| | | aatcaagcctgataagtgccttattaaaaaaggcaaacggaaaggtggagggacg |
| | | gctcagcggttaagaccacatactgctcttgcagaggacccagcctttattttt |
| | | tatttttattttttttgtttttttttttttgagacagggtttctctgtatagct |
| | | ctggctgtcgtaactcactctgtagatcaggctggcctagaactcaaatcggcct |
| | | gcctctgcctcccagtgctgggattaaaggcatgtgctaccactgcccggcttg |
| | | gacccagcctttagttcccagctcccacatccacctggaactccatatctgacct |
| | | ttggcatcacatgcacatacacataattgagaataaaataaatactatggggctg |
| | | gagagatggctccgtggttaagaacactggctgttgttcttccagaggacctggg |
| | | ttgaattcctggcacccacatggggctcagaaccatttgtaatttccaattccg |
| | | ggggatctgaagaccttcatctgacctctgtgggtaccaggttagcatacagggt |
| | | gtacttacatacatgcagccaaaatactacacatagtgtatgtgtacatgcct |
| | | ttaaaatgcaacacagctgatatggtgatacatgtattgtgatcagaaataggag |
| | | gatgagaagcaggcggatttctgagtttgaggccagcctggtctacaaagtgagt |
| | | accaggacagccagggctatagagagaaaccctgtctcgaaaaacaaaacaaaca |
| | | aaaaaagaaataggaggatgagaagttcaaggtcaaaccaggcactggaggcaca |
| | | tgcctttaatcccagcatttgggagactaaggcaggctgatttctgagttcaagg |
| | | ccagcctggtctataaagttccaggacacagagaaaccctgcaaaaaaaaaaaa |
| | | aaaaaaaaaaaaaaaaaaaagaaagaaataccataaaaactaatattcattat |
| | | taaacgttcgtgtgtgcgtatttcctggaggagctggagttacagtggctgtgag |
| | | ctggcagaggtgccgggtggaacttcggccctcaagaccagttagtgctggacc |
| | | ttctctctaaccccccaggccttttataaaaaggaatcttatcatcttatcacccg |
| | | ggtgtgaaggtgcgccttcaatcccagcactctggaggtagtgacacacctactc |
| | | caacaaggccatacttcctaatagtgccactccctaggcatatacaaaccatcac |
| | | ccccccccccaaaaaagagaacttatctgtgtgtgtgtgtgtgtgtgtaag |
| | | tatgggcacaaggacacaatcaatgcacatgaagaagtccaaggacaacttgagg |
| | | agtcagtttgtccctttcaccatgggatctgtcatcaaattgaggtctgggctgt |
| | | cctgcttggaggaccagggtaaatgcttttacccatggagtgagtcatcgtgctc |
| | | cctagccctcctcctccttggttgttgagatagagtctgttagtataaccttag |
| | | ctggtctggtaccatgtacttggaattacaagcatcctcttgtctcaaccaccct |
| | | aatactgacacagacatgtgctgccacagcaaggtaaaaggtatctctaggttga |
| | | tataaaatgattttttccactttatgcaacaggatttcactcctagcccacgctgg |
| | | cctgtaatacgcgctcctctcctctcctccgagctgggatcgaagctgtgccccc |
| | | cacccccatgcctggtgcccgttccccaactgagaacgtcccaggaagctgctgt |
| | | ggagccttggtcctgtcattgctgggggacagccaaagggaaactgcagaggaga |
| | | ggttcctggcctgcttcagactagggttccagcaagagagagtacactcctgtcc |
| | | ccattctactttcagaacaggaatggccctgggtttagtgacccccattattcaca |
| | | gagaccttcattttcctgtccatgaaatatacagagtagcttcaaccattcaga |
| | | ggccaaggagaggtagtcagtgctgtttgtgaactagggaatccaggattggtgg |
| | | gtcttagggaaacactaccctggagctaaatgtccagcccagggatcagctaggc |
| | | tccttttgctgagagggtttgagtgttgaagtttctggtttcagattaggaatca |
| | | atgcaacaccctagggccttctgagcaatcctaccagtgtctcctcatatattg |
| | | atttctttatgggcttcacacacacacacacacacacacacacacacacacac |
| | | acacacacagaattaaggagaggctaacagacagtgcaggatgggatgataacag |
| | | acgaagtagacagaggcaaggagaaagcaactactgtttaacaatgaatgcacat |
| | | tagacagactgcaggcaagcaccgggaacaaaggtgtgggcggtggtgtggggac |
| | | acaagccagcatgagctaagatagcagagcactgagtgcccatcctctactggag |
| | | ggctcatcagtccaacaagcttccagatgcagccttggaaaaaggcaaggctaga |
| | | ttgccagctgaaggacatggcaggccacctttagaacagaggcactggcacaact |
| | | tggttttctggctcctggaactgggccaacctgtgaccagcaccttcatgcggat |
| | | gcctagaactccagcttctctgaaaagactgggacctgctcctctctaggtccaa |
| | | agagctgcatgcagtagggaagaggctagagaagcgaaaccagcttgagaaacag |
| | | cttgtgctcacatagggagggcgcacgtacccgcgcgctgtgtacgtgggagacc |
| | | ggggaggctgaggggtggggagtgttctacccagtagcgcaagctgctagctcgg |
| | | ttctctgttcactagaaggtgtccgcagtcactcaccccccacagccccgtgccc |
| | | tgtgaccgatccaggtcagctatccctccctctgcgctccactcccccactgtta |
| | | tgtgggcctcttagggccacgcgtggagggtcgttcaaccctggcccacggtagg |
| | | cagactttgggaaaatttcttcccagggtaagatcaaggtaggggaaaaaaaaa |
| | | aaaaaaaagccacccagccaagcggcgacgaagacactgcccccgccgcagcag |
| | | ggggaggtggagcctagggggagggtggagaccgccgagacaggcctagaaact |
| | | gctggaagaaatcgcagcaccaccgctgctgatccttccgccgcaggccgccaaa |
| | | gagtccctaccagcccagcccgtgcccctcccctcggggaaagcggctcccagc |
| | | ctgaagctgtgctgtacccgggaggtggggatggggaatcgggggcctcctta |
| | | aagttggacaaggaatttatcatccttttctcttgatgtgcgatttgtagggaac |
| | | attctagtaagatcgggtctggaaatggcagccgagttggccacctccattctct |
| | | ttcagtccctgagttctggactcttgggggtgggggggtggaagcgcctacct |
| | | tgagttttctgaggcagtccgtagggtattcgcccgcagatacatccctaattgc |
| | | atatgcatgctccctgctcatcttgaggggggacatgtcctactcctgcagaaat |
| | | ggggatgtgcaaaacgatattgaattggcttgactcaggaaccaggcccgggg |
| | | tcccgctcctccccgcccctccacgatctgctaccatgacgtcaaggtgggcgg |
| | | gcggcggcaggtgcgtggcccgcagccactcctttaaggcggagggatccaaggg |
| | | cggggcccgggctgtgcttcgccttatataggggcggtcggggggcgttcgggagct |
| | | CTCTTGAGTCACCCCCGCGCAGCCTAGGCTTGCCGTGCGAGTCGGACTTGGTCCG |
| | | GGCCCACCACCCTGCTCTGTACTACTACTCGGCTTTCCCGTCAAGG |

TABLE 11-continued

Peptide and Nucleic Acid Sequences.

| SEQ ID NO: | Sequence Type | Sequence |
|---|---|---|
| 146 | Synthetic mouse 1.8 kb hsp90ab1 promoter-enhancer design | gctagcaacaccctagggccttctgagcaatcctacccagtgtctcctcatatat<br>tgatttctttatgggcttcacacacacacacacacacacacacacacacacac<br>acacacacacagaattaaggagaggctaacagacagtgcaggatgggatgataac<br>agacgaagtagacagaggcaaggagaaagcaactactgtttaacaatgaatgcac<br>attagacagactgcaggcaagcaccgggaacaaaggtgtgggcggtggtgtgggg<br>acacaagccagcatgagctaagatagcagagcactgagtgcccatcctctactgg<br>agggctcatcagtccaacaagcttccagatgcagccttggaaaaaggcaaggcta<br>gattgccagctgaaggacatggcaggccacctttagaacagaggcactggcacaa<br>cttggttttctggctcctggaactgggccaacctgtgaccagcaccttcatgcgg<br>atgcctagaactccagcttctctgaaaagactgggacctgctcctctctaggtcc<br>aaagagctgcatgcagtagggaagaggctagagaagcgaaaccagcttgagaaac<br>agcttgtgctcacatagggagggcgcacgtacccgcgcgctgtgtacgtgggaga<br>ccggggaggctgaggggtggggagtgttctacccagtagcgcaagctgatagctc<br>ggttctctgttcactagaaggtgtccgcagtcactcaccccacagccccgtgc<br>cctgtgaccgatccaggtcagctatccctccctctgcgctccactccccactgt<br>tatgtgggcctcttagggccacgcgtggagggtcgttcaaccctggcccacggta<br>ggcagactggggaaaatttcttcccagggtaagatcaaggtaggggaaaaaaaa<br>aaaaaaaaaagccacccagccaagcggcgacgaagacactgcccccgccgcagc<br>aggggaggtggagcctaggggggaggggtggagaccgccgagacaggcctagaaa<br>ctgctggaagaaatcgcagcaccacgctgctgatccttccgccgcaggccgcca<br>aagagtccctaccagcccaggcccgtgcccctcccctcggggaaagcggctccca<br>gcctgaagctgtgctgtacccgggagggtggggatgggggaatcgggggcctcct<br>taaagttggacaaggaatttatcatccttttctcttgatgtgcgatttgtaggga<br>acattctagtaagatcgggtctggaaatggcagccgagttggccacctccattct<br>ctttcagtcccctgagttctggactcttggggggtgggggggtggaagcgcctac<br>cttgagttttctgaggcagtccgtagggtattcgcccgcagatacatccctaatt<br>gcatatgcatgctccctgctcatcttgagggggacatgtcctactcctgcagaa<br>atggggatgtgcaaaacgatattgaattggccttgactcaggaaccaggcccgg<br>ggtcccgctcctccccgcccctccacgatctgctaccatgacgtcaaggtgggc<br>gggcggcggcaggtgcgtggcccgcagccactcctttaaggcggagggatccaag<br>ggcggggcccgggctgtgcttcgccttatatagggcggtcgggggcgttcgggag<br>ctCTCTTGAGTCACCCCCGCGCAGCCTAGGCTTGCCGTGCGAGTCGGACTTGGTC<br>CGGGCCCACCACCCTGCTCTGTACTACTACTCGGCTTTCCCGTCAAGgctagc |
| 147 | Synthetic human 1.8 kb hsp90ab1 promoter-enhancer design | gctagcctgcttcagcctcccaagtagcggggactataggcgcgctaccacgccc<br>ggctaattttttgtatttttagtagagacaaggtttcaccagagtgcaggcttgg<br>tcttgaactcctgacctggtgatccgctggactcggcctcccaaagtgctggaat<br>tacaggcatgagccaccgcgcccagcccccttttttttttttttttttttttgag<br>acggagttttctcttttgttgcccaggctggagtgcaatggcatggtctcagctca<br>ctgcagcctctgcctccagagttcaagcaatcttcctgcctcagcctcccaagta<br>gctgggattacaggcatgtgccaccacgcccagctaatttttagtagagacgagg<br>tttttccaccatgttggccaggctggttgtgaactactgacctcgggtgatccacc<br>cacctcggccttccaaagtgctgggattacaggtatgagccactgtgcccagcag<br>agaaagtggaatttctatgctggtgtaacatttgagattttcccatttagaaagt<br>cttcaggaagccgtcgagtcttgacacagaaaggatccagctcaggggaagccca<br>tccacaggagtgattcctgctttggatttaggtcctaggggtgagatcacatccc<br>tgctccatttctggagcagaaagggagctagtgcagcaaggactctgagtagacg<br>ggccttgggagtcactgaagccacttccctgttgacagaatgtgcacactgactt<br>tcatccgctcacaggagagtgagagtttgtgaatgctctctgtgaactggggagc<br>agattttaatgagctctgcttagaaggagaggacacgttaagggatcacgctcc<br>cactggtttgcggttttggtcaggaatagagcacccaacgccccttcttatagac<br>ttctcccagccataggctttttgcagaccataatgaaagggagaaaggatatcca<br>atcggatggtgatggcaggcatggcgaagtggacagggacaaagaagaggaaag<br>caagggacacccttgttctttggtattcaacacatgaacaaaaacttgttaacga<br>atcgtagactgggtaacaacagggctggtgagggaggacgatgtgggtggctgtg<br>gggaaactcttcccaagcatcccaggggtgggccaggaaggggagcagatggaca<br>tctacagggcacagagcagggagtggctattctctcctggagggggttgtgggtcc<br>agcaggctttcggatgaggccttggaaaggcaaggacagcttgccaactggaggg<br>caggcaaaacggctgagccaggccagacacggcagctcactggccaggggcatgg<br>cctaggggctctggtgccaaggctgaaggggaacaacttggccagccgctctgtg<br>gccggcatcgtcacgcggcctccaagagctccggctgccctgcactggttcccag<br>agactccctccttcccaggtccaaatggctgcaggagcgaagtgggcggaaaaaa<br>agcgaaccagcttgagaaagggcttgacgtgcctgcgtagggagggcgcatgtcc<br>ccgtgctccgtgtacgtggcggccgcaggggctAGAGGGGGGTCCCCCCCGCAGG<br>TACTCCACTCTCAGTCTGCAAAAGTGTACGCCCGCAGAGCCGCCCCAGGTGCCTG<br>GGTGTTGTGTGATTGACGCGGGGAAGGAGGGGTCAGCCGATCCCTCCCCAACCCT<br>CCATCCCATCCCTGAGGATTGGGCTGGTACCCGCGTCTCTCGGACAGgctagc |
| 148 | Synthetic human 1.8 kb eno2 (pNSE) promoter-enhancer design | gctagccataccttgaacgcctggacaaggaattctatgaggaggaggaacgggc<br>tgaggctgatgtgattcgacagaggctgaaggaagaaaaggagcaggagcctgag<br>ccccagcgtgacctggaacccgaacagtcattgatctagcagcagttctagcctc<br>taaagatagtaaggaagcctgcagggaggcagtgggaggaggccaagggctgggc<br>aggtaggggaagaggcaagaggggaagctgctgcagaaggaggtgggagaggaaa<br>gcatcagacaagcaggaccctttaaagagaggagggttaggagtcagggagaggaa |

TABLE 11-continued

Peptide and Nucleic Acid Sequences.

| SEQ ID NO: | Sequence Type | Sequence |
|---|---|---|
| | | aagggacccaaggggcctgggaccagctgagaaagacttaggaggccagaagagt<br>aagtgaaaagaattgggtggcaggcagaggagttggtgggggtggggcagcca<br>tacctgacacagagtgaagtcggctaggaaaggacaggtgtgggtgcatggtagg<br>ggctgcagggaaagttggtggtgtatgcagctggacctaggagagaagcaggag<br>aggaagatccagcacaaaaaatctgaagctaaaaacaggacacagagatggggga<br>agaaaagagggcagagtgaggcaaaaagagactgaagagatgagggtggccgcca<br>ggcactttagatagggggagaggctttatttacctctgtttgttttttttttttt<br>ttttttttttttttgcgaggtagtcttgcttagtctccaggctggagtgcagtgg<br>cacaatctcagctcactgcaacttccacctcctgggttcaagcaattctcctgcc<br>tcagcctcccgagtagctgggactacaggcgcatgcaaccgcgcctggctaattt<br>ttgtattttagtagaaacggggtttcaccacgttagccaggatggtctggatct<br>cctgacctcgtgatctgcccgcctccgccttccaaagtgctgggattacagggt<br>gagccacagcgcctggtccctatttacttctgtcttctacctccaggagatcaaa<br>gacgctggccttcagacctgatcagactcccaggggcagccaccacatgtatgac<br>agagaacagaggatgcctgttttgccccaaagctggaaattcatcacaacctga<br>gggccaggatctgctctgtgccggtcctctgggcagtgtggggtgcagaatgggg<br>tgcctaggcctgagcgttgcctggagcctaggccgggggccgccctcgggcaggc<br>gtgggtgagagccaagaccgcgtgggccgcggggtgctggtaggagtggttggag<br>agacttgcgaaggcggctggggtgttcggatttccaataaagaaacagagtgatg<br>ctcctgtgtctgacccgggtttgtgagacattgaggctgtcttgggcttcactggc<br>agtgtgggccttcgtacccgggctacaggggtgcggctctgcctgttactgtcga<br>gtgggtcgggccgtgggtatgagcgcttgtgtgcgctggggccaggtcgtgggtg<br>ccccaccttccccatcctcctcccttcccactccaccctcgtcggtccccc<br>aACCCGCGCTCGTACGTGCGCCTCCGCCGGCAGCTCCTGACTCATCGGGGGCTCC<br>GGGTCACATGCGCCCGCGCGGCCCTATAGGCGCCTCCTCCGCCCGCCGCCCGGGA<br>GCCGCAGCCGCCGCCGCCACTGCCACTCCCGCTCTCTCAGCGCCGCCGTCGCCAC<br>CGCCACCGCCACCGCCACTACCACCGTCTGAGTCTGCAGTCCCGAGGGCTAGC |
| 149 | Synthetic mouse 1.8 kb hsp90ab1 promoter-enhancer design-without flanking restriction sites | aacaccctagggccttctgagcaatcctacccagtgtctcctcatatattgattt<br>ctttatgggcttcacacacacacacacacacacacacacacacacacacacacac<br>acacagaattaaggagaggctaacagacagtgcaggatgggatgataacagacga<br>agtagacagaggcaaggagaaagcaactactgtttaacaatgaatgcacattaga<br>cagactgcaggcaagcaccgggaacaaaggtgtgggcggtggtgtggggacacaa<br>gccagcatgagctaagatagcagagcactgagtgcccatcctctactggagggct<br>catcagtccaacaagcttccagatgcagccttggaaaaaggcaaggctagattgc<br>cagctgaaggacatggcaggccacctttagaacagaggcactggcacaacttggt<br>tttctggctcctggaactgggccaacctgtgaccagcaccttcatgcggatgcct<br>agaactccagcttctctgaaaagactgggacctgctcctctctaggtccaaagag<br>ctgcatgcagtagggaagaggctagagaagcgaaaccagcttgagaaacagcttg<br>tgctcacatagggagggcgcacgtacccgcgcgctgtgtacgtgggagaccgggg<br>aggctgaggggtgggagtgttctacccagtagcgcaagctgctagctcggttct<br>ctgttcactagaaggtgtccgcagtcactcacccccacagcccccgtgccctgtg<br>accgatccaggtcagctatccctccctctgcgctccactcccccactgttatgtg<br>ggcctcttagggccacgcgtggagggtcgttcaaccctggcccacggtaggcaga<br>cttggggaaaatttcttcccagggtaagatcaaggtagggggaaaaaaaaaaaaa<br>aaaaagccaccagccaagcggcggcgacgaagacactgcccccgccgcagcagggga<br>ggtggagcctaggggggagggtggagaccgccgagacaggcctagaaactgctg<br>gaagaaatcgcagcaccaccgctgctgatccttccgccgcaggccgccaaagagt<br>ccctaccagcccaggcccgtgcccctccctcggggaaagcggctcccagcctga<br>agctgtgctgtacccggagggtggggatgggggaatcgggggcctccttaaagt<br>tggacaaggaatttatcatccttttctcttgatgtgcgatttgtagggaacattc<br>tagtaagatcgggtctggaaatggcagccgagttggccacctccattctctttca<br>gtcccctgagttctggactcttgggggggtggggggtggaagcgcctaccttgag<br>ttttctgaggcagtccgtagggtattcgcccgcagatacatccctaattgcatat<br>gcatgctccctgctcatcttgagggggggacatgtcctactcctgcagaaatgggg<br>gatgtgcaaaacgatattgaattggccttgactcaggaaccaggccccgggtccc<br>gctcctccccgcccctccacgatctgctaccatgacgtcaaggtgggcgggcgg<br>cggcaggtgcgtggcccgcagccactccttaaggcggagggatccaagggcggg<br>gcccgggctgtgcttcgccttatataggcgtggtggggcgttcgggagctCTCT<br>TGAGTCACCCCCGCGCAGCCTAGGCTTGCCGTGCGAGTCGGACTTGGTCCGGGCC<br>CACCACCCTGCTCTGTACTACTACTCGGCTTTCCCGTCAAG |
| 150 | Synthetic human 1.8 kb hsp90ab1 promoter-enhancer design-without flanking restriction sites | ctgcttcagcctcccaagtagcggggactataggcgcgctaccacgcccggctaa<br>ttttttgtattttagtagagacaaggttcaccagagtggccaggctggtcttga<br>actcctgacctggtgatccgctggactcggcctcccaaagtgctggaattacagg<br>catgagccaccgcgcccagccccctttttttttttttttttttgagacggag<br>tttctcttttgttgcccaggctggagtgcaatggcatggtctcagctcactgcag<br>cctctgcctcccagagttcaagcaatcttcctgcctcagcctcccaagtagctggg<br>attacaggcatgtgccaccacgcccagctaattttagtagagacgaggttttc<br>accatgttggccaggctggtttgtgaactactgaccctcgggtgatccacccactc<br>ggccttccaaagtgctgggattacaggtatgagccactgttgcccagcagagaaag<br>tggaatttctatgctggtgtaacatttgagattttcccatttagaaagtcttcag<br>gaagccgtcgagtcttgacacagaaaggatccagctcaggggaagcccatccaca<br>ggagtgattcctgctttggatttaggtcctaggggtgagatcacatccctgctcc<br>atttctggagcagaaaggggagctagtgcagcaaggactctgagtagacgggcctt |

TABLE 11-continued

Peptide and Nucleic Acid Sequences.

| SEQ ID NO: | Sequence Type | Sequence |
|---|---|---|
| | | gggagtcactgaagccacttccctgttgacagaatgtgcacactgactttcatcc
gctcacaggagagtgagagtttgtgaatgctctctgtgaactggggagcagattt
ttaatgagctctgcttagaaggagaggacacgttaagggatcacgctcccactgg
tttgcggttttggtcaggaatagagcacccaacgcccccttcttatagacttctcc
cagccataggcttttttgcagaccataatgaaagggagaaaggatatccaatcggg
atggtgatggcaggcatggcgaagtggacagggacaaagaagaggaaagcaaggg
acacccttttgttctttggtattcaacacatgaacaaaacttgttaacgaatcgta
gactgggtaacaacagggctggtgagggaggacgatgtgggtggctgtggggaaa
ctcttcccaagcatcccaggggtgggccaggaaggggagcagatggacatctaca
gggcacagagcagggagtggctattctctcctggaggggtttgtgggtccagcagg
ctttcggatgaggccttggaaaggcaaggacagcttgccaactggagggcaggca
aaacggctgagccaggccagacacggcagctcactggccaggggcatggcctagg
ggctctggtgccaaggctgaaggggaacaacttggccagccgctctgtggccggc
atcgtcacgcggcctccaagagctccggctgccctgcactggttcccagagactc
cctccttcccaggtccaaatggctgcaggagcgaagtgggcggaaaaaaagcgaa
ccagcttgagaaagggcttgacgtgcctgcgtagggagggcgcatgtccccgtgc
tccgtgtacgtggcggccgcaggggctAGAGGGGGGTCCCCCCCGCAGGTACTCC
ACTCTCAGTCTGCAAAAGTGTACGCCCGCAGAGCCGCCCCAGGTGCCTGGGTGTT
GTGTGATTGACGCGGGGAAGGAGGGGTCAGCCGATCCCTCCCCAACCCTCCATCC
CATCCCTGAGGATTGGGCTGGTACCCGCGTCTCTCGGACAG |
| 151 | Synthetic human 1.8 kb en02 (pNSE) promoter-enhancer design-without flanking restriction sites | cataccttgaacgcctggacaaggaattctatgaggaggaggaacgggctgaggc
tgatgtgattcgacagaggctgaaggaagaaaaggagcaggagcctgagcccag
cgtgacctggaacccgaacagtcattgatctagcagcagttctagcctctaaaga
tagtaaggaagcctgcagggaggcagtgggaggaggccaaggggctgggcaggtag
gggaagaggcaagagggggaagctgctgcagaaggaggtgggagaggaaagcatca
gacaagcaggaccccttaaagagaggagggttaggagtcagggagaggaaaaggga
cccaaggggcctgggaccagctgagaaagacttaggaggccagaagagtaagtga
aaagaattggggtggcaggcagaggagttggtggggggtggggcagccatacctg
acacagagtgaagtcggctaggaaaggacaggtgtgggtgcatggtagggctgc
agggggaaagttggtggtgtatgcagctggacctaggagagaagcaggagaggaag
atccagcacaaaaatctgaagctaaaaacaggacacagagatgggggaagaaaa
gagggcagagtgaggcaaaaagagactgaagagatgagggtggccgccaggcact
ttagataggggagaggctttatttacctctgtttgttttttttttttttttttttt
ttttttttgcgaggtagtcttgcttagtctccaggctggagtgcagtggcacaat
ctcagctcactgcaacttccacctcctgggttcaagcaattctcctgcctcagcc
tcccgagtagctgggactacaggcgcatgcaaccgcgccttggctaattttttgtat
ttttagtagaaacggggttttcaccacgttagccaggatggtctggatctcctgac
ctcgtgatctgcccgcctccgccttccaaagtgctgggattacaggggtgagcca
cagcgcctggtccctatttacttctgtcttctacctccaggagatcaaagacgct
ggccttcagacctgatcagactcccaggggcagccaccacatgtatgacagagaa
cagaggatgcctgttttttgccccaaagctggaaattcatcacaacctgaggccca
ggatctgctctgtgccggtcctctgggcagtgtggggtgcagaatggggtgccta
ggcctgagcgttgcctggagcctaggccggggggccgccctcgggcaggcgtgggt
gagagccaagaccgcgtgggccgcggggtgctggtaggagtggttggagagactt
gcgaaggcggctgggtgttcggatttccaataaagaaacagagtgatgctcctg
tgtctgacccgggtttgtgagacattgaggctgtcttgggcttcactggcagtgtg
ggccttcgtacccggctacaggggtgcggctctgcctgttactgtcgagtgggt
cgggccgtgggtatgagcgcttgtgtgcgctggggccaggtcgtgggtgccccca
cccttccccatcctcctccttcccactccaccctcgtcggtccccaACCCG
CGCTCGTACGTGCGCCTCCGCCGGCAGCTCCTGACTCATCGGGGGCTCCGGGTCA
CATGCGCCCGCGCGGCCCTATAGGCGCCTCCTCCGCCCGCCGCCCGGGAGCCGCA
GCCGCCGCCGCCACTGCCACTCCCGCTCTCTCAGCGCCGCCGTCGCCACCGCCAC
CGCCACCGCCACTACCACCGTCTGAGTCTGCAGTCCCGAGG |
| 152 | Synthetic rat 1.8 kb en02 (pNSE) promoter-enhancer design | gctagcctcctctgctcgcccaatccttccaacccccatggtggtatggctgac
acagaaaatgtctgctcctgtatgggacatttgcccctcttctccaaatataaga
caggatgaggcctagcttttgctgctccaaagttttaaaagaacacattgcacgg
catttagggactctaaagggtggaggaggaatgagggaattgcatcatgccaagg
ctggtcctcatccatcactgcttccagggcccagagtggcttccaggaggtattc
ttacaaaggaagcccgatctgtagctaacactcagagcccattttcctgcgttaa
cccctcccgacctcatatacaggagtaacatgatcagtgacctggggaggctggc
caaactgcgggacctgcccaagctgagggccttggtgctgctggacaacccctgt
gccgatgagactgactaccgccaggaggccctggtgcagatggcacacctagagc
gcctagacaaagagtactatgaggacgaggaccgggcagaagctgaggagatccg
acagaggctgaaggaggaacaggagcaagaactcgacccggaccaacagcatggaa
ccgtacctcccgccaacttagtggcacctctagcctgcagggacagtaaaggtga
tggcaggaaggcagcccccggaggtcaaaggctgggcacgcgggaggagaggcca
gagtcagaggctgcgggtatctcagatatgaaggaaagatgagagaggctcagga
agaggtaagaaaagacacaagagaccagagaagggagaagaattagagagggagg
cagaggaccgctgtctctacagacatagctggtagagactgggaggaagggatga
accctgagcgcatgaagggaaggaggtggctggtggtatatggaggatgtagctg
ggccagggaaaagatcctgcactaaaaatctgaagctaaaaataacaggacacgg
ggtggagaggcgaaaggagggcagagtgaggcagagagactgagaggcctgggga
tgtgggcattccggtagggcacacagttcacttgtcttctcttttttccaggaggc |

TABLE 11-continued

Peptide and Nucleic Acid Sequences.

| SEQ ID NO: | Sequence Type | Sequence |
|---|---|---|
| | | caaagatgctgacctcaagaactcataatacccccagtggggaccaccgcattcat<br>agccctgttacaagaagtgggagatgttccttttttgtcccagactggaaatccgt<br>tacatcccgaggctcaggttctgtggtggtcatctctgtgtggcttgttctgtgg<br>gcctacctaaagtcctaagcacagctctcaagcagatccgaggcgactaagatgc<br>tagtagggggttgtctggagagaagagccgaggaggtgggctgtgatggatcagtt<br>cagctttcaaataaaaaggcgtttttatattctgtgtcgagttcgtgaacccctg<br>tggtgggcttctccatctgtctgggttagtacctgccactatactggaataaggg<br>gacgcctgcttccctcgagttggctggacaaggttatgagcatccgtgtacttat<br>gggggttgccagcttggtcctggatcgcccgggcccttcccccacccgttcggttc<br>cccaccacccccgcgctcgtacgtgcgtctccgcctgcagctcttgactcatcg<br>gggcccccgggtcacatgcgctcgctcggctctataggcgccgcccctgccca<br>cCCCCCGCCCGCGCTGGGAGCCGCAGCCGCCGCCACTCCTGCTCTCTCTGCGCCG<br>CCGCCGTCACCACCGCCACCGCCACCGGCTGAGTCTGCAGTCgctagc |
| 153 | Synthetic rat 1.8 kb en02 (pNSE) promoter-enhancer design-without flanking restriction sites | ctcctctgctcgcccaatccttccaacccctatggtggtatggctgacacagaa<br>aatgtctgctcctgtatgggacatttgcccctcttctccaaatataagacaggat<br>gaggcctagcttttgctgctccaaagttttaaaagaacacattgcacggcattta<br>gggactctaaaggggtggaggaggaatgagggaattgcatcatgccaaggctggtc<br>ctcatccatcactgcttccagggcccagagtggcttccaggaggtattcttacaa<br>aggaagcccgatctgtagctaacactcagagcccattttcctgcgttaaccctc<br>ccgacctcatatacaggagtaacatgatcagtgacctgggggagctggccaaact<br>gcgggacctgcccaagctgagggccttggtgctgctggacaaccctgtgccgat<br>gagactgactaccgccaggaggccctggtgcagatggcacacctagagcgcctag<br>acaaagagtactatgaggacgaggacccgggcagaagctgaggagatccgacagag<br>gctgaaggaggaacaggagcaagaactcgacccggaccaagacatggaaccgtac<br>ctcccgccaacttagtggcacctctagcctgcagggacagtaaaggtgatggcag<br>gaaggcagcccccggaggtcaaaggctgggcacgcggggaggagaggccagagtca<br>gaggctgcgggtatctcagatatgaaggaaagatgagagaggctcaggaagaggt<br>aagaaaagacacaagagaccagagaagggagaagaattagagagggaggcagagg<br>accgctgtctctacagacatagctggtagagactgggaggaagggatgaaccctg<br>agcgcatgaagggaaggaggtggctggtggtatatggaggatgtagctgggccag<br>ggaaaagatcctgcactaaaaatctgaagctaaaaataacaggacacggggtgga<br>gaggcgaaaggagggcagagtgaggcagagagactgagaggcctggggatgtggg<br>cattccggtagggcacacagttcacttgtcttctctttttccaggaggccaaaga<br>tgctgacctcaagaactcataatacccccagtggggaccaccgcattcatagccct<br>gttacaagaagtgggagatgttccttttttgtcccagactggaaatccgttacatc<br>ccgaggctcaggttctgtggtggtcatctctgtgtggcttgttctgtgggcctac<br>ctaaagtcctaagcacagctctcaagcagatccgaggcgactaagatgctagtag<br>gggttgtctggagagaagagccgaggaggtgggctgtgatggatcagttcagctt<br>tcaaataaaaaggcgtttttatattctgtgtcgagttcgtgaacccctgtggtgg<br>gcttctccatctgtctgggttagtacctgccactatactggaataaggggacgcc<br>tgcttccctcgagttggctggacaaggttatgagcatccgtgtacttatggggtt<br>gccagcttggtcctggatcgcccgggcccttcccccacccgttcggttcccccacc<br>accaccccgcgctcgtacgtgcgtctccgcctgcagctcttgactcatcggggccc<br>cccgggtcacatgcgctcgctcggctctataggcgccgcccctgcccacCCCC<br>GCCCGCGCTGGGAGCCGCAGCCGCCGCCACTCCTGCTCTCTCTGCGCCGCCGCCG<br>TCACCACCGCCACCGCCACCGGCTGAGTCTGCAGTC |
| 154 | | Ggaggggagagtgcaggctcatggcaggcctcaggagacctgtgttccttacagg<br>gtctgtttgctctctcactctttctccctttttccccctctgctctgtctcctccc<br>ctttgcctgctctgtcactgttgtcactgtccctgacccctttctcttttctgt<br>cttctttgactgtctttccctgcctctcaatcatccgtcctcctcctcctcctcg<br>attgctccccaccccttcggtttccaagcttataaactgcttctgctgctggataa<br>aaatagcggtggcagcggccaggctggca |
| 155 | | tgccagacttcctggagaacaacgggcctatgtgtcctcatgttggcgttggacc<br>tccccgttcttcagccatactgtggtctgaggaagggtgtgttggtatgggatgt<br>gagactccctcggtggaggggggcgctgatgctccagctcaggactgactggaact<br>gagaggaacactctggtcctaagtgccccttgtccccagccctgggagacagaag<br>cttttgccccgccccatctcccaagccccctcccccaaggctgcatgttctctca<br>tcctctaccagctgatggctacaggggtgg |
| 156 | | gatccacctgcctctgcttcctgagtgctgggatttaaaggtgtatacaaccata<br>gcctgggttgttttcaattcttttttcttcttcttctttttttttttttaaaatta<br>atgtgcattggtgtttttgcttacatatatgtctgtgtcagagcatctgaccctc<br>tgggactggagttaaagacagttgtgagctgccacgtggctcctgggaattgaac<br>ccaggtttcctggaagagcagccaatgctcttaaccactgagccatccctccctc<br>cattcccccagttgcttgttatcaatccttactaaggt |
| 157 | | tggaagagcagatagtgctcttaacctctgggctggccttgaactcagaaatcct<br>cctgcctctacctcccgagtgctgggattaaaggcgtgcgccaccactgcctggc<br>ccctgagctttacttgagcatactaagtgcatagaacctccagcccacttgggcc<br>cttaacaacccaaggatgaacctgggtggcctaaggaaacagacaggcttaggac<br>ccatggagtcagggtagtacacagctctgctctcagaagattaaaaagaaaaaa<br>aaaaaaagccaggtgactcccagtgacctagaaaggaagcccttcaggaaggga |

TABLE 11-continued

Peptide and Nucleic Acid Sequences.

| SEQ ID NO: | Sequence Type | Sequence |
|---|---|---|
| | | ggagtgtgggcacagaaagcagccctgcaggctggggctgggttataaaaggctg cgggtgccatgctgagctctatcctgaagagtgggaaaggcccctagagacagcc ttaaaaccccctagg |
| 158 | | ggatgagaagttcaaggtcaaaccaggcactggaggcacatgcctttaatcccag catttgggagactaaggcaggctgatttctgagttcaaggccagcctggtctata aagttccaggacacagagaaaccctgcaaaaaaaaaaaaaaaaaaaaaaaaaaa aaaaaaagaaagaaataccataaaaactaatattcattattaaacgttcgtgtgt gcgtatttcctggaggagctggagttacagtggctgtgagctggcagaggtgccc gggtggaacttcggccctcaagaccagttagtgctggaccttctctctaacccc aggccttttataaaaaggaatcttatcatcttcatcccgggtgtgaaggtgcgc cttcaatcccagcactctggaggtagtgacacacctactccaacaaggccatact tcctaatagtgccac |
| 159 | | ccacctccattctctttcagtccctgagttctggactcttgggggtgggggg tggaagcgcctaccttgagttttctgaggcagtccgtagggtattcgcccgcaga tacatccctaattgcatatgcatgctccctgctcatcttgagggggacatgtcc tactcctgcagaaatgggggatgtgcaaaacgatattgaattggccttgactcag gaaccaggcccggggtcccgctcctccccgcccctccacgatctgctaccatga cgtcaaggtgggcgggcg |
| 160 | | ctaattgcatatgcatgctccctgctcatcttgagggggacatgtcctactcct gcagaaatgggggatgtgcaaaacgatattgaattggccttgactcaggaaccag gcccggggtcccgctcctccccgcccctccacgatctgctaccatgacgtcaag gtgggcgggcggcggcaggtgcgtggcccgcagccactccttttaaggcggaggga tccaagggcggggcccgggctgtgcttcgccttatatagggcggtcgggggcgt |

---

SEQUENCE LISTING

<160> NUMBER OF SEQ ID NOS: 188

<210> SEQ ID NO 1
<211> LENGTH: 7
<212> TYPE: PRT
<213> ORGANISM: Artificial Sequence
<220> FEATURE:
<223> OTHER INFORMATION: Synthetic recognition sequence of zinc finger
      domain
<220> FEATURE:
<221> NAME/KEY: misc_feature
<222> LOCATION: (3)..(3)
<223> OTHER INFORMATION: Ala or Gly
<220> FEATURE:
<221> NAME/KEY: misc_feature
<222> LOCATION: (5)..(5)
<223> OTHER INFORMATION: Leu or Arg
<220> FEATURE:
<221> NAME/KEY: misc_feature
<222> LOCATION: (6)..(6)
<223> OTHER INFORMATION: Thr or Lys

<400> SEQUENCE: 1

Gln Ser Xaa Asp Xaa Xaa Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic recognition sequence of zinc finger
      domain

<400> SEQUENCE: 2

Gln Ser Ala Asp Leu Thr Arg
1               5

```
<210> SEQ ID NO 3
<211> LENGTH: 7
<212> TYPE: PRT
<213> ORGANISM: Artificial Sequence
<220> FEATURE:
<223> OTHER INFORMATION: Synthetic recognition sequence of zinc finger
      domain

<400> SEQUENCE: 3

Gln Ser Gly Asp Leu Thr Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic recognition sequence of zinc finger
      domain

<400> SEQUENCE: 4

Gln Ser Gly Asp Arg Lys Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Recognition sequence

<400> SEQUENCE: 5

Gln Ser Ala Asp Arg Lys Arg
1               5

<210> SEQ ID NO 6
<211> LENGTH: 5
<212> TYPE: PRT
<213> ORGANISM: Artificial Sequence
<220> FEATURE:
<223> OTHER INFORMATION: Linker

<400> SEQUENCE: 6

Thr Gly Glu Lys Pro
1               5

<210> SEQ ID NO 7
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (3)..(3)
<223> OTHER INFORMATION: Glu or Gln
<220> FEATURE:
<221> NAME/KEY: misc_feature
<222> LOCATION: (4)..(4)
<223> OTHER INFORMATION: Lys or Arg

<400> SEQUENCE: 7

Thr Gly Xaa Xaa Pro
1               5

<210> SEQ ID NO 8
<211> LENGTH: 6
<212> TYPE: PRT
```

```
<213> ORGANISM: Artificial Sequence
<220> FEATURE:
<223> OTHER INFORMATION: Linker
<220> FEATURE:
<221> NAME/KEY: misc_feature
<222> LOCATION: (3)..(3)
<223> OTHER INFORMATION: Gly or Ser
<220> FEATURE:
<221> NAME/KEY: misc_feature
<222> LOCATION: (4)..(4)
<223> OTHER INFORMATION: Glu or Gln
<220> FEATURE:
<221> NAME/KEY: misc_feature
<222> LOCATION: (5)..(5)
<223> OTHER INFORMATION: Lys or Arg

<400> SEQUENCE: 8

Thr Gly Xaa Xaa Xaa Pro
1               5

<210> SEQ ID NO 9
<211> LENGTH: 6
<212> TYPE: PRT
<213> ORGANISM: Artificial Sequence
<220> FEATURE:
<223> OTHER INFORMATION: Linker

<400> SEQUENCE: 9

Thr Gly Gly Glu Arg Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Linker

<400> SEQUENCE: 10

Thr Gly Ser Glu Arg Pro
1               5

<210> SEQ ID NO 11
<211> LENGTH: 6
<212> TYPE: PRT
<213> ORGANISM: Artificial Sequence
<220> FEATURE:
<223> OTHER INFORMATION: Linker

<400> SEQUENCE: 11

Thr Gly Gly Gln Arg Pro
1               5

<210> SEQ ID NO 12
<211> LENGTH: 6
<212> TYPE: PRT
<213> ORGANISM: Artificial Sequence
<220> FEATURE:
<223> OTHER INFORMATION: Linker

<400> SEQUENCE: 12

Thr Gly Ser Gln Arg Pro
1               5

<210> SEQ ID NO 13
<211> LENGTH: 6
<212> TYPE: PRT
<213> ORGANISM: Artificial Sequence
<220> FEATURE:
```

```
<223> OTHER INFORMATION: Linker

<400> SEQUENCE: 13

Thr Gly Gly Glu Lys Pro
1               5

<210> SEQ ID NO 14
<211> LENGTH: 6
<212> TYPE: PRT
<213> ORGANISM: Artificial Sequence
<220> FEATURE:
<223> OTHER INFORMATION: Linker

<400> SEQUENCE: 14

Thr Gly Ser Glu Lys Pro
1               5

<210> SEQ ID NO 15
<211> LENGTH: 6
<212> TYPE: PRT
<213> ORGANISM: Artificial Sequence
<220> FEATURE:
<223> OTHER INFORMATION: Linker

<400> SEQUENCE: 15

Thr Gly Gly Gln Lys Pro
1               5

<210> SEQ ID NO 16
<211> LENGTH: 6
<212> TYPE: PRT
<213> ORGANISM: Artificial Sequence
<220> FEATURE:
<223> OTHER INFORMATION: Linker

<400> SEQUENCE: 16

Thr Gly Ser Gln Lys Pro
1               5

<210> SEQ ID NO 17
<211> LENGTH: 7
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (3)..(3)
<223> OTHER INFORMATION: Gly or Ser
<220> FEATURE:
<221> NAME/KEY: misc_feature
<222> LOCATION: (4)..(4)
<223> OTHER INFORMATION: Gly or Ser
<220> FEATURE:
<221> NAME/KEY: misc_feature
<222> LOCATION: (3)..(4)
<223> OTHER INFORMATION: Any one or all of amino acids 3-4 can either be
      present or absent
<220> FEATURE:
<221> NAME/KEY: misc_feature
<222> LOCATION: (5)..(5)
<223> OTHER INFORMATION: Glu or Gln
<220> FEATURE:
<221> NAME/KEY: misc_feature
<222> LOCATION: (6)..(6)
<223> OTHER INFORMATION: Lys or Arg

<400> SEQUENCE: 17

Thr Gly Xaa Xaa Xaa Xaa Pro
1               5
```

```
<210> SEQ ID NO 18
<211> LENGTH: 7
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (2)..(2)
<223> OTHER INFORMATION: Gly or Ser
<220> FEATURE:
<221> NAME/KEY: misc_feature
<222> LOCATION: (3)..(3)
<223> OTHER INFORMATION: Gly or Ser
<220> FEATURE:
<221> NAME/KEY: misc_feature
<222> LOCATION: (2)..(3)
<223> OTHER INFORMATION: Any one or all of amino acids 2-3 can either be
      present or absent
<220> FEATURE:
<221> NAME/KEY: misc_feature
<222> LOCATION: (5)..(5)
<223> OTHER INFORMATION: Glu or Gln
<220> FEATURE:
<221> NAME/KEY: misc_feature
<222> LOCATION: (6)..(6)
<223> OTHER INFORMATION: Lys or Arg

<400> SEQUENCE: 18

Thr Xaa Xaa Gly Xaa Xaa Pro
1               5

<210> SEQ ID NO 19
<211> LENGTH: 8
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (3)..(5)
<223> OTHER INFORMATION: Gly or Ser
<220> FEATURE:
<221> NAME/KEY: misc_feature
<222> LOCATION: (6)..(6)
<223> OTHER INFORMATION: Glu or Gln
<220> FEATURE:
<221> NAME/KEY: misc_feature
<222> LOCATION: (7)..(7)
<223> OTHER INFORMATION: Lys or Arg

<400> SEQUENCE: 19

Thr Gly Xaa Xaa Xaa Xaa Xaa Pro
1               5

<210> SEQ ID NO 20
<211> LENGTH: 8
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (2)..(4)
<223> OTHER INFORMATION: Gly or Ser
<220> FEATURE:
<221> NAME/KEY: misc_feature
<222> LOCATION: (6)..(6)
<223> OTHER INFORMATION: Glu or Gln
<220> FEATURE:
<221> NAME/KEY: misc_feature
<222> LOCATION: (7)..(7)
<223> OTHER INFORMATION: Lys or Arg
```

```
<400> SEQUENCE: 20

Thr Xaa Xaa Xaa Gly Xaa Xaa Pro
1               5

<210> SEQ ID NO 21
<211> LENGTH: 19
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (6)..(10)
<223> OTHER INFORMATION: This region may encompass 5, 10, 15 or 20
      residues

<400> SEQUENCE: 21

Leu Arg Gln Lys Asp Gly Gly Gly Gly Ser Gln Leu Val Gly Thr Ala
1               5                   10                  15

Glu Arg Pro

<210> SEQ ID NO 22
<211> LENGTH: 13
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (6)..(10)
<223> OTHER INFORMATION: This region may encompass 5, 10, 15 or 20
      residues

<400> SEQUENCE: 22

Leu Arg Gln Lys Asp Gly Gly Gly Gly Ser Gln Lys Pro
1               5                   10

<210> SEQ ID NO 23
<211> LENGTH: 29
<212> TYPE: PRT
<213> ORGANISM: Artificial Sequence
<220> FEATURE:
<223> OTHER INFORMATION: Linker

<400> SEQUENCE: 23

Leu Arg Gln Lys Asp Gly Gly Gly Gly Ser Gly Gly Gly Gly Ser Gly
1               5                   10                  15

Gly Gly Ser Gln Leu Val Gly Thr Ala Glu Arg Pro
            20                  25

<210> SEQ ID NO 24
<211> LENGTH: 23
<212> TYPE: PRT
<213> ORGANISM: Artificial Sequence
<220> FEATURE:
<223> OTHER INFORMATION: Linker

<400> SEQUENCE: 24

Leu Arg Gln Lys Asp Gly Gly Gly Gly Ser Gly Gly Gly Gly Ser Gly
1               5                   10                  15

Gly Gly Ser Gln Lys Pro
            20

<210> SEQ ID NO 25
```

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29
<211> LENGTH: 327
<212> TYPE: PRT
<213> ORGANISM: Artificial Sequence
<220> FEATURE:
<223> OTHER INFORMATION: 11-zinc finger peptide 1

<400> SEQUENCE: 29

```
Tyr Ala Cys Pro Val Glu Ser Cys Asp Arg Arg Phe Ser Gln Ser Gly
1               5                   10                  15

Asp Leu Thr Arg His Ile Arg Ile His Thr Gly Ser Gln Lys Pro Phe
            20                  25                  30

Gln Cys Arg Ile Cys Met Arg Asn Phe Ser Gln Ser Gly Asp Leu Thr
        35                  40                  45

Arg His Ile Arg Thr His Thr Gly Glu Lys Pro Phe Ala Cys Asp Ile
    50                  55                  60

Cys Gly Arg Lys Phe Ala Gln Ser Gly Asp Arg Lys Arg His Thr Lys
65                  70                  75                  80

Ile His Thr Gly Ser Gln Lys Pro Phe Gln Cys Arg Ile Cys Met Arg
                85                  90                  95

Asn Phe Ser Gln Ser Gly Asp Leu Thr Arg His Ile Arg Thr His Thr
            100                 105                 110

Gly Glu Lys Pro Phe Ala Cys Asp Ile Cys Gly Arg Lys Phe Ala Gln
        115                 120                 125

Ser Gly Asp Arg Lys Arg His Thr Lys Ile His Leu Arg Gln Lys Asp
    130                 135                 140

Gly Gly Gly Gly Ser Gly Gly Gly Ser Gly Gly Gly Ser Gln
145                 150                 155                 160

Lys Pro Phe Gln Cys Arg Ile Cys Met Arg Asn Phe Ser Gln Ser Gly
                165                 170                 175

Asp Leu Thr Arg His Ile Arg Thr His Thr Gly Glu Lys Pro Phe Ala
            180                 185                 190

Cys Asp Ile Cys Gly Arg Lys Phe Ala Gln Ser Gly Asp Arg Lys Arg
        195                 200                 205

His Thr Lys Ile His Thr Gly Ser Gln Lys Pro Phe Gln Cys Arg Ile
    210                 215                 220

Cys Met Arg Asn Phe Ser Gln Ser Gly Asp Leu Thr Arg His Ile Arg
225                 230                 235                 240
```

```
Thr His Thr Gly Glu Lys Pro Phe Ala Cys Asp Ile Cys Gly Arg Lys
            245                 250                 255

Phe Ala Gln Ser Gly Asp Arg Lys Arg His Thr Lys Ile His Thr Gly
        260                 265                 270

Ser Gln Lys Pro Phe Gln Cys Arg Ile Cys Met Arg Asn Phe Ser Gln
    275                 280                 285

Ser Gly Asp Leu Thr Arg His Ile Arg Thr His Thr Gly Glu Lys Pro
    290                 295                 300

Phe Ala Cys Asp Ile Cys Gly Arg Lys Phe Ala Gln Ser Gly Asp Arg
305                 310                 315                 320

Lys Arg His Thr Lys Ile His
            325
```

<210> SEQ ID NO 30
<211> LENGTH: 981
<212> TYPE: DNA
<213> ORGANISM: Artificial Sequence
<220> FEATURE:
<223> OTHER INFORMATION: 11-zinc finger peptide 1

<400> SEQUENCE: 30

```
tacgcctgtc ctgtggaatc ctgtgataga cggttcagcc agagcgggga tctgacaagg      60
cacatcagaa ttcatactgg gtcccagaag cccttccagt gccggatctg tatgcgcaac     120
tttagccagt ccggagacct cacccgacac atccgaaccc atacagggga gaagcctttc     180
gcctgcgaca tttgtggtcg gaaatttgct cagagcggcg ataggaagag acacacaaaa     240
atccatactg gctcccagaa gccattccag tgccgaattt gtatgaggaa ttttctcag     300
agtggcgacc tgactcgaca catcaggact cataccggcg aaaagccctt cgcatgcgac     360
atttgtggaa ggaaatttgc ccagtctggg gatcggaagc gccacaccaa atccatctc      420
agacagaagg acggaggagg aggttccgga ggaggaggta gtggcggagg gggttcacag      480
aagcctttcc agtgcagaat ctgtatgcgg aacttttcac agagcggaga tctgaccaga      540
cacatccgga cacatactgg ggagaagcca ttcgcttgcg acatttgtgg taggaaattt      600
gcacagtctg gcgatcgaaa gaggcacacc aaaatccata caggaagtca gaaccttc       660
cagtgccgca tttgtatgcg aaatttttcc cagtctggtg acctgacacg ccatattcga      720
acccatacag gggaaaaacc tttcgcctgt gacatttgtg gaagaaaatt tgctcagagc      780
ggggatagaa agcggcacac taaaatccat accggctctc agaaaccatt ccagtgccgg      840
atttgtatgc gcaactttag tcagtcaggc gacctgacca gacacatcag aactcacacc      900
ggagagaaac ccttcgcatg tgatatctgt ggtcggaaat tcgcccagag cggcgatcgc      960
aagcgacaca ctaaaatcca c                                                981
```

<210> SEQ ID NO 31
<211> LENGTH: 331
<212> TYPE: PRT
<213> ORGANISM: Artificial Sequence
<220> FEATURE:
<223> OTHER INFORMATION: 11-zinc finger peptide 2

<400> SEQUENCE: 31

```
Phe Gln Cys Arg Ile Cys Met Arg Asn Phe Ser Gln Ser Ala Asp Leu
1               5                   10                  15

Thr Arg His Thr Lys Ile His Thr Gly Ser Glu Arg Pro Phe Gln Cys
            20                  25                  30
```

```
Arg Ile Cys Met Arg Asn Phe Ser Gln Ser Ala Asp Leu Thr Arg His
             35                  40                  45

Ile Arg Thr His Thr Gly Glu Lys Pro Phe Ala Cys Asp Ile Cys Gly
 50                  55                  60

Arg Lys Phe Ala Gln Ser Ala Asp Leu Thr Arg His Thr Lys Ile His
 65                  70                  75                  80

Thr Gly Ser Glu Arg Pro Phe Gln Cys Arg Ile Cys Met Arg Asn Phe
                 85                  90                  95

Ser Gln Ser Ala Asp Leu Thr Arg His Ile Arg Thr His Thr Gly Glu
            100                 105                 110

Lys Pro Phe Ala Cys Asp Ile Cys Gly Arg Lys Phe Ala Gln Ser Ala
        115                 120                 125

Asp Leu Thr Arg His Thr Lys Ile His Leu Arg Gln Lys Asp Gly Gly
130                 135                 140

Gly Gly Ser Gly Gly Gly Gly Ser Gly Gly Gly Ser Gln Leu Val
145                 150                 155                 160

Gly Thr Ala Glu Arg Pro Phe Gln Cys Arg Ile Cys Met Arg Asn Phe
                165                 170                 175

Ser Gln Ser Ala Asp Leu Thr Arg His Ile Arg Thr His Thr Gly Glu
            180                 185                 190

Lys Pro Phe Ala Cys Asp Ile Cys Gly Arg Lys Phe Ala Gln Ser Ala
        195                 200                 205

Asp Leu Thr Arg His Thr Lys Ile His Thr Gly Ser Glu Arg Pro Phe
210                 215                 220

Gln Cys Arg Ile Cys Met Arg Asn Phe Ser Gln Ser Ala Asp Leu Thr
225                 230                 235                 240

Arg His Ile Arg Thr His Thr Gly Glu Lys Pro Phe Ala Cys Asp Ile
                245                 250                 255

Cys Gly Arg Lys Phe Ala Gln Ser Ala Asp Leu Thr Arg His Thr Lys
            260                 265                 270

Ile His Thr Gly Ser Glu Arg Pro Phe Gln Cys Arg Ile Cys Met Arg
        275                 280                 285

Asn Phe Ser Gln Ser Ala Asp Leu Thr Arg His Ile Arg Thr His Thr
290                 295                 300

Gly Glu Lys Pro Phe Ala Cys Asp Ile Cys Gly Arg Lys Phe Ala Gln
305                 310                 315                 320

Ser Ala Asp Leu Thr Arg His Thr Lys Ile His
                325                 330
```

<210> SEQ ID NO 32
<211> LENGTH: 993
<212> TYPE: DNA
<213> ORGANISM: Artificial Sequence
<220> FEATURE:
<223> OTHER INFORMATION: 11-zinc finger peptide 2

<400> SEQUENCE: 32

```
ttccagtgcc gcatttgtat gcgcaacttt agccagagcg cggacctgac ccgccatacc      60
aaaattcaca ccggatccga acggccgttt cagtgccgta tttgcatgcg taattttagc     120
cagtccgcgg acctgacccg ccatattcgt acccataccg tgaaaaaacc gtttgcctgc     180
gatatttgtg gcgtaaaatt tgcccagagc gcggacctga cccgccatac caaaattcat     240
accggttctg aacggccgtt tcagtgcagg atttgcatgc gtaattttc ccagagcgcg     300 gacctgaccc gccatattcg cacccatact ggtgaaaaac cgtttgcctg cgatatttgc     360
```

-continued

```
ggtcgtaaat ttgcgcagtc cgctgactta acccgccata ccaaaattca tctgcgccag      420
aaagatggtg gcggcggctc aggtggcggc ggtagtggtg gcggcggctc acaactagtc      480
ggtaccgccg agcgccccttc ccagtgccgc atttgtatgc gcaactttag ccagagcgcg     540
gacctgaccc gtcatattcg cacccatacc ggtgaaaaac cgtttgcgtg cgatatttgc     600
ggtcgtaaat ttgcgcagag cgcggacctg acccgccata ccaaaattca caccggatcc     660
gaacggccgt ttcagtgccg tatttgcatg cgtaatttta gccagtccgc ggacctgacc     720
cgccatattc gtacccatac cggtgaaaaa ccgtttgcct gcgatatttg tggccgtaaa     780
tttgcccaga gcgcggacct gacccgccat accaaaattc ataccggttc tgaacggccg     840
tttcagtgca ggatttgcat gcgtaatttt tcccagagcg cggacctgac cgccatatt     900 cgcacccata ctggtgaaaa accgtttgcc tgcgatattt gcggtcgtaa atttgcgcag     960
agcgctgact taacccgcca taccaaaatt cat                                  993
```

<210> SEQ ID NO 33
<211> LENGTH: 327
<212> TYPE: PRT
<213> ORGANISM: Artificial Sequence
<220> FEATURE:
<223> OTHER INFORMATION: 11-zinc finger peptide 3

<400> SEQUENCE: 33

```
Tyr Ala Cys Pro Val Glu Ser Cys Asp Arg Arg Phe Ser Gln Ser Ala
1               5                   10                  15

Asp Leu Thr Arg His Ile Arg Ile His Thr Gly Ser Gln Lys Pro Phe
            20                  25                  30

Gln Cys Arg Ile Cys Met Arg Asn Phe Ser Gln Ser Ala Asp Leu Thr
        35                  40                  45

Arg His Ile Arg Thr His Thr Gly Glu Lys Pro Phe Ala Cys Asp Ile
    50                  55                  60

Cys Gly Arg Lys Phe Ala Gln Ser Ala Asp Arg Lys Arg His Thr Lys
65                  70                  75                  80

Ile His Thr Gly Ser Gln Lys Pro Phe Gln Cys Arg Ile Cys Met Arg
                85                  90                  95

Asn Phe Ser Gln Ser Ala Asp Leu Thr Arg His Ile Arg Thr His Thr
            100                 105                 110

Gly Glu Lys Pro Phe Ala Cys Asp Ile Cys Gly Arg Lys Phe Ala Gln
        115                 120                 125

Ser Ala Asp Arg Lys Arg His Thr Lys Ile His Leu Arg Gln Lys Asp
    130                 135                 140

Gly Gly Gly Gly Ser Gly Gly Gly Ser Gly Gly Gly Ser Gln
145                 150                 155                 160

Lys Pro Phe Gln Cys Arg Ile Cys Met Arg Asn Phe Ser Gln Ser Ala
                165                 170                 175

Asp Leu Thr Arg His Ile Arg Thr His Thr Gly Glu Lys Pro Phe Ala
            180                 185                 190

Cys Asp Ile Cys Gly Arg Lys Phe Ala Gln Ser Ala Asp Arg Lys Arg
        195                 200                 205

His Thr Lys Ile His Thr Gly Ser Gln Lys Pro Phe Gln Cys Arg Ile
    210                 215                 220

Cys Met Arg Asn Phe Ser Gln Ser Ala Asp Leu Thr Arg His Ile Arg
225                 230                 235                 240

Thr His Thr Gly Glu Lys Pro Phe Ala Cys Asp Ile Cys Gly Arg Lys
                245                 250                 255
```

```
Phe Ala Gln Ser Ala Asp Arg Lys Arg His Thr Lys Ile His Thr Gly
            260                 265                 270

Ser Gln Lys Pro Phe Gln Cys Arg Ile Cys Met Arg Asn Phe Ser Gln
        275                 280                 285

Ser Ala Asp Leu Thr Arg His Ile Arg Thr His Thr Gly Glu Lys Pro
    290                 295                 300

Phe Ala Cys Asp Ile Cys Gly Arg Lys Phe Ala Gln Ser Ala Asp Arg
305                 310                 315                 320

Lys Arg His Thr Lys Ile His
                325

<210> SEQ ID NO 34
<211> LENGTH: 981
<212> TYPE: DNA
<213> ORGANISM: Artificial Sequence
<220> FEATURE:
<223> OTHER INFORMATION: 11-zinc finger peptide 3

<400> SEQUENCE: 34
tacgcctgtc ctgtggaatc ctgtgataga cggttcagcc agagcgccga tctgacaagg      60
cacatcagaa ttcatactgg gtcccagaag cccttccagt gccggatctg tatgcgcaac     120
tttagccagt ccgccgacct cacccgacac atccgaaccc atacagggga gaagcctttc     180
gcctgcgaca tttgtggtcg gaaatttgct cagagcgccg ataggaagag acacacaaaa     240
atccatactg gctcccagaa gccattccag tgccgaattt gtatgaggaa ttttctcag     300
agtgccgacc tgactcgaca catcaggact cataccggcg aaaagccctt cgcatgcgac     360
atttgtggaa ggaaatttgc ccagtctgcc gatcggaagc gccacaccaa atccatctc     420
agacagaagg acggaggagg aggttccgga ggaggaggta gtggcggagg gggttcacag     480
aagccttttcc agtgcagaat ctgtatgcgg aactttttcac agagcgccga tctgaccaga     540
cacatccgga cacatactgg ggagaagcca ttcgcttgcg acatttgtgg taggaaattt     600
gcacagtctg ccgatcgaaa gaggcacacc aaaatccata caggaagtca gaaacctttc     660
cagtgccgca tttgtatgcg aaatttttcc cagtctgccg acctgacacg ccatattcga     720
acccatacag gggaaaaacc tttcgcctgt gacatttgtg gagaaaattt gctcagagc     780
gccgatagaa agcggcacac taaaatccat accggctctc agaaaccatt ccagtgccgg     840
atttgtatgc gcaactttag tcagtcagcc gacctgacca gacacatcag aactcacacc     900
ggagagaaac ccttcgcatg tgatatctgt ggtcggaaat tcgcccagag cgccgatcgc     960
aagcgacaca ctaaaatcca c                                              981

<210> SEQ ID NO 35
<211> LENGTH: 327
<212> TYPE: PRT
<213> ORGANISM: Artificial Sequence
<220> FEATURE:
<223> OTHER INFORMATION: 11-zinc finger peptide 4

<400> SEQUENCE: 35

Tyr Ala Cys Pro Val Glu Ser Cys Asp Arg Arg Phe Ser Gln Ser Ala
1               5                  10                  15

Asp Leu Thr Arg His Ile Arg Ile His Thr Gly Ser Gln Lys Pro Phe
            20                  25                  30

Gln Cys Arg Ile Cys Met Arg Asn Phe Ser Gln Ser Gly Asp Leu Thr
        35                  40                  45
```

-continued

```
Arg His Ile Arg Thr His Thr Gly Glu Lys Pro Phe Ala Cys Asp Ile
 50                  55                  60
Cys Gly Arg Lys Phe Ala Gln Ser Gly Asp Arg Lys Arg His Thr Lys
 65                  70                  75                  80
Ile His Thr Gly Ser Gln Lys Pro Phe Gln Cys Arg Ile Cys Met Arg
                 85                  90                  95
Asn Phe Ser Gln Ser Gly Asp Leu Thr Arg His Ile Arg Thr His Thr
            100                 105                 110
Gly Glu Lys Pro Phe Ala Cys Asp Ile Cys Gly Arg Lys Phe Ala Gln
        115                 120                 125
Ser Gly Asp Arg Lys Arg His Thr Lys Ile His Leu Arg Gln Lys Asp
130                 135                 140
Gly Gly Gly Gly Ser Gly Gly Gly Ser Gly Gly Gly Ser Gln
145                 150                 155                 160
Lys Pro Phe Gln Cys Arg Ile Cys Met Arg Asn Phe Ser Gln Ser Gly
                165                 170                 175
Asp Leu Thr Arg His Ile Arg Thr His Thr Gly Glu Lys Pro Phe Ala
            180                 185                 190
Cys Asp Ile Cys Gly Arg Lys Phe Ala Gln Ser Gly Asp Arg Lys Arg
        195                 200                 205
His Thr Lys Ile His Thr Gly Ser Gln Lys Pro Phe Gln Cys Arg Ile
210                 215                 220
Cys Met Arg Asn Phe Ser Gln Ser Gly Asp Leu Thr Arg His Ile Arg
225                 230                 235                 240
Thr His Thr Gly Glu Lys Pro Phe Ala Cys Asp Ile Cys Gly Arg Lys
                245                 250                 255
Phe Ala Gln Ser Gly Asp Arg Lys Arg His Thr Lys Ile His Thr Gly
            260                 265                 270
Ser Gln Lys Pro Phe Gln Cys Arg Ile Cys Met Arg Asn Phe Ser Gln
        275                 280                 285
Ser Gly Asp Leu Thr Arg His Ile Arg Thr His Thr Gly Glu Lys Pro
290                 295                 300
Phe Ala Cys Asp Ile Cys Gly Arg Lys Phe Ala Gln Ser Gly Asp Arg
305                 310                 315                 320
Lys Arg His Thr Lys Ile His
                325
```

<210> SEQ ID NO 36
<211> LENGTH: 981
<212> TYPE: DNA
<213> ORGANISM: Artificial Sequence
<220> FEATURE:
<223> OTHER INFORMATION: 11-zinc finger peptide 4

<400> SEQUENCE: 36

```
tacgcctgtc ctgtggaatc ctgtgataga cggttcagcc agagcgccga tctgacaagg    60
cacatcagaa ttcatactgg gtcccagaag cccttccagt gccggatctg tatgcgcaac   120
tttagccagt ccggagacct cacccgacac atccgaaccc atacagggga gaagcctttc   180
gcctgcgaca tttgtggtcg gaaatttgct cagagcggcg ataggaagag acacacaaaa   240
atccatactg gctcccagaa gccattccag tgccgaattt gtatgaggaa tttttctcag   300
agtggcgacc tgactcgaca catcaggact cataccggcg aaaagccctt cgcatgcgac   360
atttgtggaa ggaaatttgc ccagtctggg gatcggaagc gccacaccaa atccatctc    420
agacagaagg acggaggagg aggttccgga ggaggaggta gtggcggagg gggttcacag   480
```

```
aagcctttcc agtgcagaat ctgtatgcgg aacttttcac agagcggaga tctgaccaga    540
cacatccgga cacatactgg ggagaagcca ttcgcttgcg acatttgtgg taggaaattt    600
gcacagtctg gcgatcgaaa gaggcacacc aaaatccata caggaagtca gaaacctttc    660
cagtgccgca tttgtatgcg aaattttccc cagtctggtg acctgacacg ccatattcga    720
acccatacag gggaaaaacc tttcgcctgt gacatttgtg gaagaaaatt tgctcagagc    780
ggggatagaa agcggcacac taaaatccat accggctctc agaaaccatt ccagtgccgg    840
atttgtatgc gcaactttag tcagtcaggc gacctgacca gacacatcag aactcacacc    900
ggagagaaac ccttcgcatg tgatatctgt ggtcggaaat tcgcccagag cggcgatcgc    960
aagcgacaca ctaaaatcca c                                              981

<210> SEQ ID NO 37
<211> LENGTH: 7
<212> TYPE: PRT
<213> ORGANISM: Artificial Sequence
<220> FEATURE:
<223> OTHER INFORMATION: SV40 nuclear localisation

<400> SEQUENCE: 37

Pro Lys Lys Lys Arg Lys Val
1               5

<210> SEQ ID NO 38
<211> LENGTH: 7
<212> TYPE: PRT
<213> ORGANISM: Artificial Sequence
<220> FEATURE:
<223> OTHER INFORMATION: Mouse primase p58 nuclear localisation

<400> SEQUENCE: 38

Arg Ile Arg Lys Lys Leu Arg
1               5

<210> SEQ ID NO 39
<211> LENGTH: 116
<212> TYPE: PRT
<213> ORGANISM: Artificial Sequence
<220> FEATURE:
<223> OTHER INFORMATION: Human Kox-1 KRAB domain

<400> SEQUENCE: 39

Leu Ser Pro Gln His Ser Ala Val Thr Gln Gly Ser Ile Ile Lys Asn
1               5                   10                  15

Lys Glu Gly Met Asp Ala Lys Ser Leu Thr Ala Trp Ser Arg Thr Leu
            20                  25                  30

Val Thr Phe Lys Asp Val Phe Val Asp Phe Thr Arg Glu Glu Trp Lys
        35                  40                  45

Leu Leu Asp Thr Ala Gln Gln Ile Val Tyr Arg Asn Val Met Leu Glu
    50                  55                  60

Asn Tyr Lys Asn Leu Val Ser Leu Gly Tyr Gln Leu Thr Lys Pro Asp
65                  70                  75                  80

Val Ile Leu Arg Leu Glu Lys Gly Glu Glu Pro Trp Leu Val Glu Arg
                85                  90                  95

Glu Ile His Gln Glu Thr His Pro Asp Ser Glu Thr Ala Phe Glu Ile
            100                 105                 110

Lys Ser Ser Val
        115
```

```
<210> SEQ ID NO 40
<211> LENGTH: 75
<212> TYPE: PRT
<213> ORGANISM: Artificial Sequence
<220> FEATURE:
<223> OTHER INFORMATION: Mouse ZF87 KRAB domain

<400> SEQUENCE: 40

Glu Glu Met Leu Ser Phe Arg Asp Val Ala Ile Asp Phe Ser Ala Glu
1               5                   10                  15

Glu Trp Glu Cys Leu Glu Pro Ala Gln Trp Asn Leu Tyr Arg Asp Val
            20                  25                  30

Met Leu Glu Asn Tyr Ser His Leu Val Phe Leu Gly Leu Ala Ser Cys
        35                  40                  45

Lys Pro Tyr Leu Val Thr Phe Leu Glu Gln Arg Gln Glu Pro Ser Val
    50                  55                  60

Val Lys Arg Pro Ala Ala Ala Thr Val His Pro
65                  70                  75

<210> SEQ ID NO 41
<211> LENGTH: 25
<212> TYPE: PRT
<213> ORGANISM: Artificial Sequence
<220> FEATURE:
<223> OTHER INFORMATION: Linker

<400> SEQUENCE: 41

Leu Arg Gln Lys Asp Gly Gly Gly Ser Gly Gly Gly Gly Ser Gly
1               5                   10                  15

Gly Gly Gly Ser Gln Leu Val Ser Ser
            20                  25

<210> SEQ ID NO 42
<211> LENGTH: 16
<212> TYPE: PRT
<213> ORGANISM: Artificial Sequence
<220> FEATURE:
<223> OTHER INFORMATION: Linker

<400> SEQUENCE: 42

Leu Arg Gln Lys Asp Gly Gly Gly Ser Gly Gly Gly Gly Ser Ser
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: Linker

<400> SEQUENCE: 43

Leu Arg Gln Lys Asp Gly Gly Gly Ser Gly Gly Gly Gly Ser
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Human N-terminal leader

<400> SEQUENCE: 44

Met Gly Pro Lys Lys Arg Arg Lys Val Thr Gly Glu Arg Pro
1               5                   10
```

<210> SEQ ID NO 45
<211> LENGTH: 14
<212> TYPE: PRT
<213> ORGANISM: Artificial Sequence
<220> FEATURE:
<223> OTHER INFORMATION: Mouse N-terminal leader

<400> SEQUENCE: 45

Met Gly Arg Ile Arg Lys Lys Leu Arg Leu Ala Glu Arg Pro
1               5                   10

<210> SEQ ID NO 46
<211> LENGTH: 8
<212> TYPE: PRT
<213> ORGANISM: Artificial Sequence
<220> FEATURE:
<223> OTHER INFORMATION: Human KIAA2022 nuclear localisation

<400> SEQUENCE: 46

Pro Lys Lys Arg Arg Lys Val Thr
1               5

<210> SEQ ID NO 47
<211> LENGTH: 89
<212> TYPE: PRT
<213> ORGANISM: Artificial Sequence
<220> FEATURE:
<223> OTHER INFORMATION: Mouse Zif268

<400> SEQUENCE: 47

Glu Arg Pro Tyr Ala Cys Pro Val Glu Ser Cys Asp Arg Arg Phe Ser
1               5                   10                  15

Arg Ser Asp Glu Leu Thr Arg His Ile Arg Ile His Thr Gly Gln Lys
            20                  25                  30

Pro Phe Gln Cys Arg Ile Cys Met Arg Asn Phe Ser Arg Ser Asp His
        35                  40                  45

Leu Thr Thr His Ile Arg Thr His Thr Gly Glu Lys Pro Phe Ala Cys
    50                  55                  60

Asp Ile Cys Gly Arg Lys Phe Ala Arg Ser Asp Glu Lys Arg His
65                  70                  75                  80

Thr Lys Ile His Leu Arg Gln Lys Asp
                85

<210> SEQ ID NO 48
<211> LENGTH: 89
<212> TYPE: PRT
<213> ORGANISM: Artificial Sequence
<220> FEATURE:
<223> OTHER INFORMATION: Human Zif 268

<400> SEQUENCE: 48

Glu Arg Pro Tyr Ala Cys Pro Val Glu Ser Cys Asp Arg Arg Phe Ser
1               5                   10                  15

Arg Ser Asp Glu Leu Thr Arg His Ile Arg Ile His Thr Gly Gln Lys
            20                  25                  30

Pro Phe Gln Cys Arg Ile Cys Met Arg Asn Phe Ser Arg Ser Asp His
        35                  40                  45

Leu Thr Thr His Ile Arg Thr His Thr Gly Glu Lys Pro Phe Ala Cys
    50                  55                  60

Asp Ile Cys Gly Arg Lys Phe Ala Arg Ser Asp Glu Arg Lys Gly His
65                  70                  75                  80

Thr Lys Ile His Leu Arg Gln Lys Asp
                85

<210> SEQ ID NO 49
<211> LENGTH: 434
<212> TYPE: PRT
<213> ORGANISM: Artificial Sequence
<220> FEATURE:
<223> OTHER INFORMATION: Mousified 11-zinc finger modulator 2 mZF-ZF87

<400> SEQUENCE: 49

Met Gly Arg Ile Arg Lys Lys Leu Arg Leu Ala Glu Arg Pro Phe Gln
1               5                   10                  15

Cys Arg Ile Cys Met Arg Asn Phe Ser Gln Ser Ala Asp Leu Thr Arg
            20                  25                  30

His Thr Lys Ile His Thr Gly Ser Glu Arg Pro Phe Gln Cys Arg Ile
        35                  40                  45

Cys Met Arg Asn Phe Ser Gln Ser Ala Asp Leu Thr Arg His Ile Arg
    50                  55                  60

Thr His Thr Gly Glu Lys Pro Phe Ala Cys Asp Ile Cys Gly Arg Lys
65                  70                  75                  80

Phe Ala Gln Ser Ala Asp Leu Thr Arg His Thr Lys Ile His Thr Gly
                85                  90                  95

Ser Glu Arg Pro Phe Gln Cys Arg Ile Cys Met Arg Asn Phe Ser Gln
            100                 105                 110

Ser Ala Asp Leu Thr Arg His Ile Arg Thr His Thr Gly Glu Lys Pro
        115                 120                 125

Phe Ala Cys Asp Ile Cys Gly Arg Lys Phe Ala Gln Ser Ala Asp Leu
    130                 135                 140

Thr Arg His Thr Lys Ile His Leu Arg Gln Lys Asp Gly Gly Gly Gly
145                 150                 155                 160

Ser Gly Gly Gly Ser Gly Gly Gly Ser Gln Leu Val Gly Thr
                165                 170                 175

Ala Glu Arg Pro Phe Gln Cys Arg Ile Cys Met Arg Asn Phe Ser Gln
            180                 185                 190

Ser Ala Asp Leu Thr Arg His Ile Arg Thr His Thr Gly Glu Lys Pro
        195                 200                 205

Phe Ala Cys Asp Ile Cys Gly Arg Lys Phe Ala Gln Ser Ala Asp Leu
    210                 215                 220

Thr Arg His Thr Lys Ile His Thr Gly Ser Glu Arg Pro Phe Gln Cys
225                 230                 235                 240

Arg Ile Cys Met Arg Asn Phe Ser Gln Ser Ala Asp Leu Thr Arg His
                245                 250                 255

Ile Arg Thr His Thr Gly Glu Lys Pro Phe Ala Cys Asp Ile Cys Gly
            260                 265                 270

Arg Lys Phe Ala Gln Ser Ala Asp Leu Thr Arg His Thr Lys Ile His
        275                 280                 285

Thr Gly Ser Glu Arg Pro Phe Gln Cys Arg Ile Cys Met Arg Asn Phe
    290                 295                 300

Ser Gln Ser Ala Asp Leu Thr Arg His Ile Arg Thr His Thr Gly Glu
305                 310                 315                 320

Lys Pro Phe Ala Cys Asp Ile Cys Gly Arg Lys Phe Ala Gln Ser Ala
                325                 330                 335

Asp Leu Thr Arg His Thr Lys Ile His Leu Arg Gln Lys Asp Gly Gly
            340                 345                 350

```
Gly Ser Gly Gly Gly Ser Glu Glu Met Leu Ser Phe Arg Asp Val
            355                 360                 365

Ala Ile Asp Phe Ser Ala Glu Glu Trp Glu Cys Leu Glu Pro Ala Gln
    370                 375                 380

Trp Asn Leu Tyr Arg Asp Val Met Leu Glu Asn Tyr Ser His Leu Val
385                 390                 395                 400

Phe Leu Gly Leu Ala Ser Cys Lys Pro Tyr Leu Val Thr Phe Leu Glu
                405                 410                 415

Gln Arg Gln Glu Pro Ser Val Val Lys Arg Pro Ala Ala Thr Val
            420                 425                 430

His Pro

<210> SEQ ID NO 50
<211> LENGTH: 430
<212> TYPE: PRT
<213> ORGANISM: Artificial Sequence
<220> FEATURE:
<223> OTHER INFORMATION: Mousified 11-zinc finger modulator 1 mZF-ZF87

<400> SEQUENCE: 50

Met Gly Arg Ile Arg Lys Lys Leu Arg Leu Ala Glu Arg Pro Tyr Ala
1               5                   10                  15

Cys Pro Val Glu Ser Cys Asp Arg Arg Phe Ser Gln Ser Gly Asp Leu
            20                  25                  30

Thr Arg His Ile Arg Ile His Thr Gly Ser Gln Lys Pro Phe Gln Cys
        35                  40                  45

Arg Ile Cys Met Arg Asn Phe Ser Gln Ser Gly Asp Leu Thr Arg His
    50                  55                  60

Ile Arg Thr His Thr Gly Glu Lys Pro Phe Ala Cys Asp Ile Cys Gly
65                  70                  75                  80

Arg Lys Phe Ala Gln Ser Gly Asp Arg Lys Arg His Thr Lys Ile His
                85                  90                  95

Thr Gly Ser Gln Lys Pro Phe Gln Cys Arg Ile Cys Met Arg Asn Phe
            100                 105                 110

Ser Gln Ser Gly Asp Leu Thr Arg His Ile Arg Thr His Thr Gly Glu
        115                 120                 125

Lys Pro Phe Ala Cys Asp Ile Cys Gly Arg Lys Phe Ala Gln Ser Gly
    130                 135                 140

Asp Arg Lys Arg His Thr Lys Ile His Leu Arg Gln Lys Asp Gly Gly
145                 150                 155                 160

Gly Gly Ser Gly Gly Gly Ser Gly Gly Gly Ser Gln Lys Pro
                165                 170                 175

Phe Gln Cys Arg Ile Cys Met Arg Asn Phe Ser Gln Ser Gly Asp Leu
            180                 185                 190

Thr Arg His Ile Arg Thr His Thr Gly Glu Lys Pro Phe Ala Cys Asp
        195                 200                 205

Ile Cys Gly Arg Lys Phe Ala Gln Ser Gly Asp Arg Lys Arg His Thr
    210                 215                 220

Lys Ile His Thr Gly Ser Gln Lys Pro Phe Gln Cys Arg Ile Cys Met
225                 230                 235                 240

Arg Asn Phe Ser Gln Ser Gly Asp Leu Thr Arg His Ile Arg Thr His
                245                 250                 255

Thr Gly Glu Lys Pro Phe Ala Cys Asp Ile Cys Gly Arg Lys Phe Ala
            260                 265                 270
```

```
Gln Ser Gly Asp Arg Lys Arg His Thr Lys Ile His Thr Gly Ser Gln
            275                 280                 285
Lys Pro Phe Gln Cys Arg Ile Cys Met Arg Asn Phe Ser Gln Ser Gly
        290                 295                 300
Asp Leu Thr Arg His Ile Arg Thr His Thr Gly Glu Lys Pro Phe Ala
305                 310                 315                 320
Cys Asp Ile Cys Gly Arg Lys Phe Ala Gln Ser Gly Asp Arg Lys Arg
                325                 330                 335
His Thr Lys Ile His Leu Arg Gln Lys Asp Gly Gly Gly Ser Gly Gly
            340                 345                 350
Gly Gly Ser Glu Glu Met Leu Ser Phe Arg Asp Val Ala Ile Asp Phe
        355                 360                 365
Ser Ala Glu Glu Trp Glu Cys Leu Glu Pro Ala Gln Trp Asn Leu Tyr
370                 375                 380
Arg Asp Val Met Leu Glu Asn Tyr Ser His Leu Val Phe Leu Gly Leu
385                 390                 395                 400
Ala Ser Cys Lys Pro Tyr Leu Val Thr Phe Leu Glu Gln Arg Gln Glu
                405                 410                 415
Pro Ser Val Val Lys Arg Pro Ala Ala Ala Thr Val His Pro
            420                 425                 430

<210> SEQ ID NO 51
<211> LENGTH: 430
<212> TYPE: PRT
<213> ORGANISM: Artificial Sequence
<220> FEATURE:
<223> OTHER INFORMATION: Mousified 11-zinc finger modulator 3 mZF-ZF87

<400> SEQUENCE: 51

Met Gly Arg Ile Arg Lys Lys Leu Arg Leu Ala Glu Arg Pro Tyr Ala
1               5                   10                  15
Cys Pro Val Glu Ser Cys Asp Arg Arg Phe Ser Gln Ser Ala Asp Leu
            20                  25                  30
Thr Arg His Ile Arg Ile His Thr Gly Ser Gln Lys Pro Phe Gln Cys
        35                  40                  45
Arg Ile Cys Met Arg Asn Phe Ser Gln Ser Ala Asp Leu Thr Arg His
    50                  55                  60
Ile Arg Thr His Thr Gly Glu Lys Pro Phe Ala Cys Asp Ile Cys Gly
65                  70                  75                  80
Arg Lys Phe Ala Gln Ser Ala Asp Arg Lys Arg His Thr Lys Ile His
                85                  90                  95
Thr Gly Ser Gln Lys Pro Phe Gln Cys Arg Ile Cys Met Arg Asn Phe
            100                 105                 110
Ser Gln Ser Ala Asp Leu Thr Arg His Ile Arg Thr His Thr Gly Glu
        115                 120                 125
Lys Pro Phe Ala Cys Asp Ile Cys Gly Arg Lys Phe Ala Gln Ser Ala
    130                 135                 140
Asp Arg Lys Arg His Thr Lys Ile His Leu Arg Gln Lys Asp Gly Gly
145                 150                 155                 160
Gly Gly Ser Gly Gly Gly Gly Ser Gly Gly Gly Ser Gln Lys Pro
                165                 170                 175
Phe Gln Cys Arg Ile Cys Met Arg Asn Phe Ser Gln Ser Ala Asp Leu
            180                 185                 190
Thr Arg His Ile Arg Thr His Thr Gly Glu Lys Pro Phe Ala Cys Asp
        195                 200                 205
```

```
Ile Cys Gly Arg Lys Phe Ala Gln Ser Ala Asp Lys Arg His Thr
210                 215                 220
Lys Ile His Thr Gly Ser Gln Lys Pro Phe Gln Cys Arg Ile Cys Met
225                 230                 235                 240
Arg Asn Phe Ser Gln Ser Ala Asp Leu Thr Arg His Ile Arg Thr His
                245                 250                 255
Thr Gly Glu Lys Pro Phe Ala Cys Asp Ile Cys Gly Arg Lys Phe Ala
                260                 265                 270
Gln Ser Ala Asp Arg Lys Arg His Thr Lys Ile His Thr Gly Ser Gln
            275                 280                 285
Lys Pro Phe Gln Cys Arg Ile Cys Met Arg Asn Phe Ser Gln Ser Ala
290                 295                 300
Asp Leu Thr Arg His Ile Arg Thr His Thr Gly Glu Lys Pro Phe Ala
305                 310                 315                 320
Cys Asp Ile Cys Gly Arg Lys Phe Ala Gln Ser Ala Asp Arg Lys Arg
                325                 330                 335
His Thr Lys Ile His Leu Arg Gln Lys Asp Gly Gly Ser Gly Gly
            340                 345                 350
Gly Gly Ser Glu Glu Met Leu Ser Phe Arg Asp Val Ala Ile Asp Phe
        355                 360                 365
Ser Ala Glu Glu Trp Glu Cys Leu Glu Pro Ala Gln Trp Asn Leu Tyr
370                 375                 380
Arg Asp Val Met Leu Glu Asn Tyr Ser His Leu Val Phe Leu Gly Leu
385                 390                 395                 400
Ala Ser Cys Lys Pro Tyr Leu Val Thr Phe Leu Glu Gln Arg Gln Glu
                405                 410                 415
Pro Ser Val Val Lys Arg Pro Ala Ala Ala Thr Val His Pro
                420                 425                 430

<210> SEQ ID NO 52
<211> LENGTH: 430
<212> TYPE: PRT
<213> ORGANISM: Artificial Sequence
<220> FEATURE:
<223> OTHER INFORMATION: Mousified 11-zinc finger modulator 4 mZF-ZF87

<400> SEQUENCE: 52

Met Gly Arg Ile Arg Lys Lys Leu Arg Leu Ala Glu Arg Pro Tyr Ala
1               5                   10                  15
Cys Pro Val Glu Ser Cys Asp Arg Arg Phe Ser Gln Ser Ala Asp Leu
                20                  25                  30
Thr Arg His Ile Arg Ile His Thr Gly Ser Gln Lys Pro Phe Gln Cys
            35                  40                  45
Arg Ile Cys Met Arg Asn Phe Ser Gln Ser Gly Asp Leu Thr Arg His
50                  55                  60
Ile Arg Thr His Thr Gly Glu Lys Pro Phe Ala Cys Asp Ile Cys Gly
65                  70                  75                  80
Arg Lys Phe Ala Gln Ser Gly Asp Arg Lys Arg His Thr Lys Ile His
                85                  90                  95
Thr Gly Ser Gln Lys Pro Phe Gln Cys Arg Ile Cys Met Arg Asn Phe
            100                 105                 110
Ser Gln Ser Gly Asp Leu Thr Arg His Ile Arg Thr His Thr Gly Glu
        115                 120                 125
Lys Pro Phe Ala Cys Asp Ile Cys Gly Arg Lys Phe Ala Gln Ser Gly
    130                 135                 140
```

```
Asp Arg Lys Arg His Thr Lys Ile His Leu Arg Gln Lys Asp Gly
145                 150                 155                 160

Gly Gly Ser Gly Gly Gly Ser Gly Gly Gly Ser Gln Lys Pro
            165                 170                 175

Phe Gln Cys Arg Ile Cys Met Arg Asn Phe Ser Gln Ser Gly Asp Leu
            180                 185                 190

Thr Arg His Ile Arg Thr His Thr Gly Glu Lys Pro Phe Ala Cys Asp
            195                 200                 205

Ile Cys Gly Arg Lys Phe Ala Gln Ser Gly Asp Arg Lys Arg His Thr
        210                 215                 220

Lys Ile His Thr Gly Ser Gln Lys Pro Phe Gln Cys Arg Ile Cys Met
225                 230                 235                 240

Arg Asn Phe Ser Gln Ser Gly Asp Leu Thr Arg His Ile Arg Thr His
            245                 250                 255

Thr Gly Glu Lys Pro Phe Ala Cys Asp Ile Cys Gly Arg Lys Phe Ala
            260                 265                 270

Gln Ser Gly Asp Arg Lys Arg His Thr Lys Ile His Thr Gly Ser Gln
        275                 280                 285

Lys Pro Phe Gln Cys Arg Ile Cys Met Arg Asn Phe Ser Gln Ser Gly
290                 295                 300

Asp Leu Thr Arg His Ile Arg Thr His Thr Gly Glu Lys Pro Phe Ala
305                 310                 315                 320

Cys Asp Ile Cys Gly Arg Lys Phe Ala Gln Ser Gly Asp Arg Lys Arg
            325                 330                 335

His Thr Lys Ile His Leu Arg Gln Lys Asp Gly Gly Ser Gly Gly
            340                 345                 350

Gly Gly Ser Glu Glu Met Leu Ser Phe Arg Asp Val Ala Ile Asp Phe
        355                 360                 365

Ser Ala Glu Glu Trp Glu Cys Leu Glu Pro Ala Gln Trp Asn Leu Tyr
370                 375                 380

Arg Asp Val Met Leu Glu Asn Tyr Ser His Leu Val Phe Leu Gly Leu
385                 390                 395                 400

Ala Ser Cys Lys Pro Tyr Leu Val Thr Phe Leu Glu Gln Arg Gln Glu
            405                 410                 415

Pro Ser Val Val Lys Arg Pro Ala Ala Ala Thr Val His Pro
            420                 425                 430

<210> SEQ ID NO 53
<211> LENGTH: 477
<212> TYPE: PRT
<213> ORGANISM: Artificial Sequence
<220> FEATURE:
<223> OTHER INFORMATION: Humanised 11-zinc finger modulator 2 hZF-ZF-
      kox1

<400> SEQUENCE: 53

Met Gly Pro Lys Lys Arg Arg Lys Val Thr Gly Glu Arg Pro Phe Gln
1               5                   10                  15

Cys Arg Ile Cys Met Arg Asn Phe Ser Gln Ser Ala Asp Leu Thr Arg
            20                  25                  30

His Thr Lys Ile His Thr Gly Ser Glu Arg Pro Phe Gln Cys Arg Ile
            35                  40                  45

Cys Met Arg Asn Phe Ser Gln Ser Ala Asp Leu Thr Arg His Ile Arg
        50                  55                  60

Thr His Thr Gly Glu Lys Pro Phe Ala Cys Asp Ile Cys Gly Arg Lys
65                  70                  75                  80
```

```
Phe Ala Gln Ser Ala Asp Leu Thr Arg His Thr Lys Ile His Thr Gly
                85                  90                  95

Ser Glu Arg Pro Phe Gln Cys Arg Ile Cys Met Arg Asn Phe Ser Gln
            100                 105                 110

Ser Ala Asp Leu Thr Arg His Ile Arg Thr His Thr Gly Glu Lys Pro
            115                 120                 125

Phe Ala Cys Asp Ile Cys Gly Arg Lys Phe Ala Gln Ser Ala Asp Leu
130                 135                 140

Thr Arg His Thr Lys Ile His Leu Arg Gln Lys Asp Gly Gly Gly Gly
145                 150                 155                 160

Ser Gly Gly Gly Ser Gly Gly Gly Ser Gln Leu Val Gly Thr
                165                 170                 175

Ala Glu Arg Pro Phe Gln Cys Arg Ile Cys Met Arg Asn Phe Ser Gln
            180                 185                 190

Ser Ala Asp Leu Thr Arg His Ile Arg Thr His Thr Gly Glu Lys Pro
            195                 200                 205

Phe Ala Cys Asp Ile Cys Gly Arg Lys Phe Ala Gln Ser Ala Asp Leu
210                 215                 220

Thr Arg His Thr Lys Ile His Thr Gly Ser Glu Arg Pro Phe Gln Cys
225                 230                 235                 240

Arg Ile Cys Met Arg Asn Phe Ser Gln Ser Ala Asp Leu Thr Arg His
                245                 250                 255

Ile Arg Thr His Thr Gly Glu Lys Pro Phe Ala Cys Asp Ile Cys Gly
                260                 265                 270

Arg Lys Phe Ala Gln Ser Ala Asp Leu Thr Arg His Thr Lys Ile His
            275                 280                 285

Thr Gly Ser Glu Arg Pro Phe Gln Cys Arg Ile Cys Met Arg Asn Phe
290                 295                 300

Ser Gln Ser Ala Asp Leu Thr Arg His Ile Arg Thr His Thr Gly Glu
305                 310                 315                 320

Lys Pro Phe Ala Cys Asp Ile Cys Gly Arg Lys Phe Ala Gln Ser Ala
                325                 330                 335

Asp Leu Thr Arg His Thr Lys Ile His Leu Arg Gln Lys Asp Gly Gly
            340                 345                 350

Gly Gly Ser Gly Gly Gly Ser Ser Leu Ser Pro Gln His Ser Ala
            355                 360                 365

Val Thr Gln Gly Ser Ile Ile Lys Asn Lys Glu Gly Met Asp Ala Lys
370                 375                 380

Ser Leu Thr Ala Trp Ser Arg Thr Leu Val Thr Phe Lys Asp Val Phe
385                 390                 395                 400

Val Asp Phe Thr Arg Glu Glu Trp Lys Leu Leu Asp Thr Ala Gln Gln
                405                 410                 415

Ile Val Tyr Arg Asn Val Met Leu Glu Asn Tyr Lys Asn Leu Val Ser
            420                 425                 430

Leu Gly Tyr Gln Leu Thr Lys Pro Asp Val Ile Leu Arg Leu Glu Lys
            435                 440                 445

Gly Glu Glu Pro Trp Leu Val Glu Arg Glu Ile His Gln Glu Thr His
450                 455                 460

Pro Asp Ser Glu Thr Ala Phe Glu Ile Lys Ser Ser Val
465                 470                 475

<210> SEQ ID NO 54
<211> LENGTH: 473
```

```
<212> TYPE: PRT
<213> ORGANISM: Artificial Sequence
<220> FEATURE:
<223> OTHER INFORMATION: Humanised 11-zinc finger modulator 1 hZF-ZF-kox
      1

<400> SEQUENCE: 54

Met Gly Pro Lys Lys Arg Arg Lys Val Thr Gly Glu Arg Pro Tyr Ala
1               5                   10                  15

Cys Pro Val Glu Ser Cys Asp Arg Arg Phe Ser Gln Ser Gly Asp Leu
            20                  25                  30

Thr Arg His Ile Arg Ile His Thr Gly Ser Gln Lys Pro Phe Gln Cys
        35                  40                  45

Arg Ile Cys Met Arg Asn Phe Ser Gln Ser Gly Asp Leu Thr Arg His
    50                  55                  60

Ile Arg Thr His Thr Gly Glu Lys Pro Phe Ala Cys Asp Ile Cys Gly
65                  70                  75                  80

Arg Lys Phe Ala Gln Ser Gly Asp Arg Lys Arg His Thr Lys Ile His
                85                  90                  95

Thr Gly Ser Gln Lys Pro Phe Gln Cys Arg Ile Cys Met Arg Asn Phe
            100                 105                 110

Ser Gln Ser Gly Asp Leu Thr Arg His Ile Arg Thr His Thr Gly Glu
        115                 120                 125

Lys Pro Phe Ala Cys Asp Ile Cys Gly Arg Lys Phe Ala Gln Ser Gly
    130                 135                 140

Asp Arg Lys Arg His Thr Lys Ile His Leu Arg Gln Lys Asp Gly Gly
145                 150                 155                 160

Gly Gly Ser Gly Gly Gly Ser Gly Gly Gly Ser Gln Lys Pro
                165                 170                 175

Phe Gln Cys Arg Ile Cys Met Arg Asn Phe Ser Gln Ser Gly Asp Leu
            180                 185                 190

Thr Arg His Ile Arg Thr His Thr Gly Glu Lys Pro Phe Ala Cys Asp
        195                 200                 205

Ile Cys Gly Arg Lys Phe Ala Gln Ser Gly Asp Arg Lys Arg His Thr
    210                 215                 220

Lys Ile His Thr Gly Ser Gln Lys Pro Phe Gln Cys Arg Ile Cys Met
225                 230                 235                 240

Arg Asn Phe Ser Gln Ser Gly Asp Leu Thr Arg His Ile Arg Thr His
                245                 250                 255

Thr Gly Glu Lys Pro Phe Ala Cys Asp Ile Cys Gly Arg Lys Phe Ala
            260                 265                 270

Gln Ser Gly Asp Arg Lys Arg His Thr Lys Ile His Thr Gly Ser Gln
        275                 280                 285

Lys Pro Phe Gln Cys Arg Ile Cys Met Arg Asn Phe Ser Gln Ser Gly
    290                 295                 300

Asp Leu Thr Arg His Ile Arg Thr His Thr Gly Glu Lys Pro Phe Ala
305                 310                 315                 320

Cys Asp Ile Cys Gly Arg Lys Phe Ala Gln Ser Gly Asp Arg Lys Arg
                325                 330                 335

His Thr Lys Ile His Leu Arg Gln Lys Asp Gly Gly Gly Gly Ser Gly
            340                 345                 350

Gly Gly Ser Ser Leu Ser Pro Gln His Ser Ala Val Thr Gln Gly
        355                 360                 365

Ser Ile Ile Lys Asn Lys Glu Gly Met Asp Ala Lys Ser Leu Thr Ala
    370                 375                 380
```

Trp Ser Arg Thr Leu Val Thr Phe Lys Asp Val Phe Val Asp Phe Thr
385                 390                 395                 400

Arg Glu Glu Trp Lys Leu Leu Asp Thr Ala Gln Gln Ile Val Tyr Arg
            405                 410                 415

Asn Val Met Leu Glu Asn Tyr Lys Asn Leu Val Ser Leu Gly Tyr Gln
        420                 425                 430

Leu Thr Lys Pro Asp Val Ile Leu Arg Leu Glu Lys Gly Glu Glu Pro
            435                 440                 445

Trp Leu Val Glu Arg Glu Ile His Gln Glu Thr His Pro Asp Ser Glu
    450                 455                 460

Thr Ala Phe Glu Ile Lys Ser Ser Val
465                 470

<210> SEQ ID NO 55
<211> LENGTH: 473
<212> TYPE: PRT
<213> ORGANISM: Artificial Sequence
<220> FEATURE:
<223> OTHER INFORMATION: Humanised 11-zinc finger modulator 3 hZF-ZF-
      kox1

<400> SEQUENCE: 55

Met Gly Pro Lys Lys Arg Arg Lys Val Thr Gly Glu Arg Pro Tyr Ala
1               5                   10                  15

Cys Pro Val Glu Ser Cys Asp Arg Arg Phe Ser Gln Ser Ala Asp Leu
            20                  25                  30

Thr Arg His Ile Arg Ile His Thr Gly Ser Gln Lys Pro Phe Gln Cys
        35                  40                  45

Arg Ile Cys Met Arg Asn Phe Ser Gln Ser Ala Asp Leu Thr Arg His
    50                  55                  60

Ile Arg Thr His Thr Gly Glu Lys Pro Phe Ala Cys Asp Ile Cys Gly
65                  70                  75                  80

Arg Lys Phe Ala Gln Ser Ala Asp Arg Lys Arg His Thr Lys Ile His
                85                  90                  95

Thr Gly Ser Gln Lys Pro Phe Gln Cys Arg Ile Cys Met Arg Asn Phe
            100                 105                 110

Ser Gln Ser Ala Asp Leu Thr Arg His Ile Arg Thr His Thr Gly Glu
        115                 120                 125

Lys Pro Phe Ala Cys Asp Ile Cys Gly Arg Lys Phe Ala Gln Ser Ala
    130                 135                 140

Asp Arg Lys Arg His Thr Lys Ile His Leu Arg Gln Lys Asp Gly Gly
145                 150                 155                 160

Gly Gly Ser Gly Gly Gly Gly Ser Gly Gly Gly Gly Ser Gln Lys Pro
                165                 170                 175

Phe Gln Cys Arg Ile Cys Met Arg Asn Phe Ser Gln Ser Ala Asp Leu
            180                 185                 190

Thr Arg His Ile Arg Thr His Thr Gly Glu Lys Pro Phe Ala Cys Asp
        195                 200                 205

Ile Cys Gly Arg Lys Phe Ala Gln Ser Ala Asp Arg Lys Arg His Thr
    210                 215                 220

Lys Ile His Thr Gly Ser Gln Lys Pro Phe Gln Cys Arg Ile Cys Met
225                 230                 235                 240

Arg Asn Phe Ser Gln Ser Ala Asp Leu Thr Arg His Ile Arg Thr His
                245                 250                 255

Thr Gly Glu Lys Pro Phe Ala Cys Asp Ile Cys Gly Arg Lys Phe Ala

```
              260              265              270
Gln Ser Ala Asp Arg Lys Arg His Thr Lys Ile His Thr Gly Ser Gln
        275              280              285
Lys Pro Phe Gln Cys Arg Ile Cys Met Arg Asn Phe Ser Gln Ser Ala
        290              295              300
Asp Leu Thr Arg His Ile Arg Thr His Thr Gly Glu Lys Pro Phe Ala
305              310              315              320
Cys Asp Ile Cys Gly Arg Lys Phe Ala Gln Ser Ala Asp Arg Lys Arg
                325              330              335
His Thr Lys Ile His Leu Arg Gln Lys Asp Gly Gly Gly Ser Gly
            340              345              350
Gly Gly Gly Ser Ser Leu Ser Pro Gln His Ser Ala Val Thr Gln Gly
        355              360              365
Ser Ile Ile Lys Asn Lys Glu Gly Met Asp Ala Lys Ser Leu Thr Ala
        370              375              380
Trp Ser Arg Thr Leu Val Thr Phe Lys Asp Val Phe Val Asp Phe Thr
385              390              395              400
Arg Glu Glu Trp Lys Leu Leu Asp Thr Ala Gln Gln Ile Val Tyr Arg
                405              410              415
Asn Val Met Leu Glu Asn Tyr Lys Asn Leu Val Ser Leu Gly Tyr Gln
            420              425              430
Leu Thr Lys Pro Asp Val Ile Leu Arg Leu Glu Lys Gly Glu Pro
        435              440              445
Trp Leu Val Glu Arg Glu Ile His Gln Glu Thr His Pro Asp Ser Glu
    450              455              460
Thr Ala Phe Glu Ile Lys Ser Ser Val
465              470

<210> SEQ ID NO 56
<211> LENGTH: 473
<212> TYPE: PRT
<213> ORGANISM: Artificial Sequence
<220> FEATURE:
<223> OTHER INFORMATION: Humanised 11-zinc finger modulator 4 hZF-ZF-
      kox1

<400> SEQUENCE: 56

Met Gly Pro Lys Lys Arg Arg Lys Val Thr Gly Glu Arg Pro Tyr Ala
1               5                   10                  15
Cys Pro Val Glu Ser Cys Asp Arg Arg Phe Ser Gln Ser Ala Asp Leu
            20                  25                  30
Thr Arg His Ile Arg Ile His Thr Gly Ser Gln Lys Pro Phe Gln Cys
        35                  40                  45
Arg Ile Cys Met Arg Asn Phe Ser Gln Ser Gly Asp Leu Thr Arg His
    50                  55                  60
Ile Arg Thr His Thr Gly Glu Lys Pro Phe Ala Cys Asp Ile Cys Gly
65                  70                  75                  80
Arg Lys Phe Ala Gln Ser Gly Asp Arg Lys Arg His Thr Lys Ile His
                85                  90                  95
Thr Gly Ser Gln Lys Pro Phe Gln Cys Arg Ile Cys Met Arg Asn Phe
            100                 105                 110
Ser Gln Ser Gly Asp Leu Thr Arg His Ile Arg Thr His Thr Gly Glu
        115                 120                 125
Lys Pro Phe Ala Cys Asp Ile Cys Gly Arg Lys Phe Ala Gln Ser Gly
    130                 135                 140
```

Asp Arg Lys Arg His Thr Lys Ile His Leu Arg Gln Lys Asp Gly
145                 150                 155                 160

Gly Gly Ser Gly Gly Gly Ser Gly Gly Gly Ser Gln Lys Pro
            165                 170                 175

Phe Gln Cys Arg Ile Cys Met Arg Asn Phe Ser Gln Ser Gly Asp Leu
                180                 185                 190

Thr Arg His Ile Arg Thr His Thr Gly Glu Lys Pro Phe Ala Cys Asp
            195                 200                 205

Ile Cys Gly Arg Lys Phe Ala Gln Ser Gly Asp Arg Lys Arg His Thr
        210                 215                 220

Lys Ile His Thr Gly Ser Gln Lys Pro Phe Gln Cys Arg Ile Cys Met
225                 230                 235                 240

Arg Asn Phe Ser Gln Ser Gly Asp Leu Thr Arg His Ile Arg Thr His
                245                 250                 255

Thr Gly Glu Lys Pro Phe Ala Cys Asp Ile Cys Gly Arg Lys Phe Ala
            260                 265                 270

Gln Ser Gly Asp Arg Lys Arg His Thr Lys Ile His Thr Gly Ser Gln
        275                 280                 285

Lys Pro Phe Gln Cys Arg Ile Cys Met Arg Asn Phe Ser Gln Ser Gly
290                 295                 300

Asp Leu Thr Arg His Ile Arg Thr His Thr Gly Glu Lys Pro Phe Ala
305                 310                 315                 320

Cys Asp Ile Cys Gly Arg Lys Phe Ala Gln Ser Gly Asp Arg Lys Arg
                325                 330                 335

His Thr Lys Ile His Leu Arg Gln Lys Asp Gly Gly Gly Ser Gly
            340                 345                 350

Gly Gly Gly Ser Ser Leu Ser Pro Gln His Ser Ala Val Thr Gln Gly
        355                 360                 365

Ser Ile Ile Lys Asn Lys Glu Gly Met Asp Ala Lys Ser Leu Thr Ala
370                 375                 380

Trp Ser Arg Thr Leu Val Thr Phe Lys Asp Val Phe Val Asp Phe Thr
385                 390                 395                 400

Arg Glu Glu Trp Lys Leu Leu Asp Thr Ala Gln Gln Ile Val Tyr Arg
                405                 410                 415

Asn Val Met Leu Glu Asn Tyr Lys Asn Leu Val Ser Leu Gly Tyr Gln
                420                 425                 430

Leu Thr Lys Pro Asp Val Ile Leu Arg Leu Glu Lys Gly Glu Glu Pro
            435                 440                 445

Trp Leu Val Glu Arg Glu Ile His Gln Glu Thr His Pro Asp Ser Glu
        450                 455                 460

Thr Ala Phe Glu Ile Lys Ser Ser Val
465                 470

<210> SEQ ID NO 57
<211> LENGTH: 1290
<212> TYPE: DNA
<213> ORGANISM: Artificial Sequence
<220> FEATURE:
<223> OTHER INFORMATION: Mousified 11-zinc finger modulator 1 mZF-ZF87

<400> SEQUENCE: 57
atgggccgca ttagaaagaa actcagactc gcagaaagac cttacgcctg tcctgtggaa     60
tcctgtgata gacggttcag ccagagcggg gatctgacaa ggcacatcag aattcatact    120
gggtcccaga agcccttcca gtgccggatc tgtatgcgca ctttagccag tccggagac    180

```
ctcacccgac acatccgaac ccatacaggg gagaagcctt tcgcctgcga catttgtggt    240
cggaaatttg ctcagagcgg cgataggaag agacacacaa aaatccatac tggctcccag    300
aagccattcc agtgccgaat ttgtatgagg aattttctc agagtggcga cctgactcga     360
cacatcagga ctcataccgg cgaaaagccc ttcgcatgcg acatttgtgg aaggaaattt    420
gcccagtctg gggatcggaa gcgccacacc aaaatccatc tcagacagaa ggacggagga    480
ggaggttccg gaggaggagg tagtggcgga ggggttcac agaagccttt ccagtgcaga     540
atctgtatgc ggaactttc acagagcgga gatctgacca gacacatccg gacacatact    600
ggggagaagc cattcgcttg cgacatttgt ggtaggaaat ttgcacagtc tggcgatcga    660
aagaggcaca ccaaaatcca tacaggaagt cagaaacctt tccagtgccg catttgtatg    720
cgaaattttt cccagtctgg tgacctgaca cgccatattc gaacccatac aggggaaaaa    780
cctttcgcct gtgacatttg tggaagaaaa tttgctcaga gcggggatag aaagcggcac    840
actaaaatcc ataccggctc tcagaaacca ttccagtgcc ggatttgtat gcgcaacttt    900
agtcagtcag gcgacctgac cagacacatc agaactcaca ccggagagaa acccttcgca    960
tgtgatatct gtggtcggaa attcgcccag agcggcgatc gcaagcgaca cactaaaatc    1020 caccctccgcc agaaggacgg cggaggatcc ggagggggtg ggtccgaaga gatgctcagt   1080
tttagagatg tcgctattga cttttcagcc gaggaatggg agtgcctgga acctgcccag   1140
tggaacctgt acagggacgt gatgctggag aattatagcc acctggtctt cctgggcctc   1200
gcctcctgca gccctacct cgtgaccttt ctcgaacaga ggcaggagcc aagcgtcgtc    1260
aagagaccag cagcagcaac cgtccatcca                                    1290

<210> SEQ ID NO 58
<211> LENGTH: 1416
<212> TYPE: DNA
<213> ORGANISM: Artificial Sequence
<220> FEATURE:
<223> OTHER INFORMATION: Humanised 11-zinc finger modulator 1 hZF-ZF-
      kox1

<400> SEQUENCE: 58
atgggcccga agaaacgccg taaagtgacc ggcgagcgcc cctacgcctg tcctgtggaa     60
tcctgtgata gacggttcag ccagagcggg gatctgacaa ggcacatcag aattcatact   120
gggtcccaga agcccttcca gtgccggatc tgtatgcgca actttagcca gtccggagac   180
ctcacccgac acatccgaac ccatacaggg gagaagcctt tcgcctgcga catttgtggt   240
cggaaatttg ctcagagcgg cgataggaag agacacacaa aaatccatac tggctcccag   300
aagccattcc agtgccgaat ttgtatgagg aattttctc agagtggcga cctgactcga    360
cacatcagga ctcataccgg cgaaaagccc ttcgcatgcg acatttgtgg aaggaaattt   420
gcccagtctg gggatcggaa gcgccacacc aaaatccatc tcagacagaa ggacggagga   480
ggaggttccg gaggaggagg tagtggcgga ggggttcac agaagccttt ccagtgcaga    540
atctgtatgc ggaactttc acagagcgga gatctgacca gacacatccg gacacatact   600
ggggagaagc cattcgcttg cgacatttgt ggtaggaaat ttgcacagtc tggcgatcga   660
aagaggcaca ccaaaatcca tacaggaagt cagaaacctt tccagtgccg catttgtatg   720
cgaaattttt cccagtctgg tgacctgaca cgccatattc gaacccatac aggggaaaaa   780
cctttcgcct gtgacatttg tggaagaaaa tttgctcaga gcggggatag aaagcggcac   840
actaaaatcc ataccggctc tcagaaacca ttccagtgcc ggatttgtat gcgcaacttt   900
```

```
agtcagtcag gcgacctgac cagacacatc agaactcaca ccggagagaa acccttcgca    960
tgtgatatct gtggtcggaa attcgcccag agcggcgatc gcaagcgaca cactaaaatc   1020
cacctccgcc agaaggacgg cggaggatcc ggaggggtg ggtccagctt gtctcctcag    1080
cactctgctg tcactcaagg aagtatcatc aagaacaagg agggcatgga tgctaagtca   1140
ctaactgcct ggtcccggac actggtgacc ttcaaggatg tatttgtgga cttcaccagg   1200
gaggagtgga agctgctgga cactgctcag cagatcgtgt acagaaatgt gatgctggag   1260
aactataaga acctggtttc cttgggttat cagcttacta agccagatgt gatcctccgg   1320
ttggagaagg gagaagagcc ctggctggtg gagagagaaa ttcaccaaga gacccatcct   1380
gattcagaga ctgcatttga aatcaaatca tcagtt                             1416
```

<210> SEQ ID NO 59
<211> LENGTH: 437
<212> TYPE: PRT
<213> ORGANISM: Artificial Sequence
<220> FEATURE:
<223> OTHER INFORMATION: Humanised 10-zinc finger modulator hZF-ZF-kox1

<400> SEQUENCE: 59

```
Met Gly Pro Lys Lys Arg Arg Lys Val Thr Gly Glu Arg Pro Tyr Ala
1               5                   10                  15

Cys Pro Val Glu Ser Cys Asp Arg Arg Phe Ser Gln Ser Gly Asp Leu
            20                  25                  30

Thr Arg His Ile Arg Ile His Thr Gly Gln Lys Pro Phe Gln Cys Arg
        35                  40                  45

Ile Cys Met Arg Asn Phe Ser Gln Ser Gly Asp Arg Lys Arg His Ile
    50                  55                  60

Arg Thr His Gln Asn Lys Lys Gly Ser His Ile Cys His Ile Gln Gly
65                  70                  75                  80

Cys Gly Lys Val Tyr Gly Gln Ser Gly Asp Leu Thr Arg His Leu Arg
                85                  90                  95

Trp His Thr Gly Glu Arg Pro Phe Met Cys Thr Trp Ser Tyr Cys Gly
            100                 105                 110

Lys Arg Phe Thr Gln Ser Gly Asp Arg Lys Arg His Lys Arg Thr His
        115                 120                 125

Leu Arg Gln Lys Asp Gly Glu Arg Pro Tyr Ala Cys Pro Val Glu Ser
    130                 135                 140

Cys Asp Arg Arg Phe Ser Gln Ser Gly Asp Leu Thr Arg His Ile Arg
145                 150                 155                 160

Ile His Thr Gly Glu Lys Pro Tyr Lys Cys Pro Glu Cys Gly Lys Ser
                165                 170                 175

Phe Ser Gln Ser Gly Asp Arg Lys Arg His Gln Arg Thr His Thr Gly
            180                 185                 190

Ser Glu Arg Pro Phe Met Cys Asn Trp Ser Tyr Cys Gly Lys Arg Phe
        195                 200                 205

Thr Gln Ser Gly Asp Leu Thr Arg His Lys Arg Thr His Thr Gly Glu
    210                 215                 220

Lys Pro Phe Ala Cys Pro Glu Cys Pro Lys Arg Phe Met Gln Ser Gly
225                 230                 235                 240

Asp Arg Lys Arg His Ile Lys Thr His Thr Gly Ser Glu Lys Pro Phe
                245                 250                 255

Gln Cys Arg Ile Cys Met Arg Asn Phe Ser Gln Ser Gly Asp Leu Thr
            260                 265                 270
```

```
Arg His Ile Arg Thr His Thr Gly Glu Arg Pro Phe Ala Cys Asp Ile
            275                 280                 285
Cys Gly Arg Lys Phe Ala Gln Ser Gly Asp Arg Lys Arg His Thr Lys
    290                 295                 300
Ile His Leu Arg Gln Lys Asp Gly Gly Ser Gly Gly Gly Gly Ser
305                 310                 315                 320
Ser Leu Ser Pro Gln His Ser Ala Val Thr Gln Gly Ser Ile Ile Lys
                325                 330                 335
Asn Lys Glu Gly Met Asp Ala Lys Ser Leu Thr Ala Trp Ser Arg Thr
            340                 345                 350
Leu Val Thr Phe Lys Asp Val Phe Val Asp Phe Thr Arg Glu Glu Trp
        355                 360                 365
Lys Leu Leu Asp Thr Ala Gln Gln Ile Val Tyr Arg Asn Val Met Leu
    370                 375                 380
Glu Asn Tyr Lys Asn Leu Val Ser Leu Gly Tyr Gln Leu Thr Lys Pro
385                 390                 395                 400
Asp Val Ile Leu Arg Leu Glu Lys Gly Glu Pro Trp Leu Val Glu
                405                 410                 415
Arg Glu Ile His Gln Glu Thr His Pro Asp Ser Glu Thr Ala Phe Glu
            420                 425                 430
Ile Lys Ser Ser Val
        435

<210> SEQ ID NO 60
<211> LENGTH: 1311
<212> TYPE: DNA
<213> ORGANISM: Artificial Sequence
<220> FEATURE:
<223> OTHER INFORMATION: Humanised 10-zinc finger modulator hZF-ZF-kox1

<400> SEQUENCE: 60
atgggcccga agaaacgccg taaagtgacc ggcgagcgcc cctacgcctg ccctgtggag      60
tcctgcgata gaagattttc ccagagcggc gacctgacca gacatattcg gattcacacc    120
ggccagaagc cattccagtg cagaatctgt atgcggaact tttcccagag cggcgaccgc    180
aagcggcaca ttcgcactca tcagaataag aaagggtctc acatctgcca tattcagggg    240
tgtggcaaag tgtatggaca gagcggcgac ctgacccgac acctgaggtg cataccgga    300 gagaggccct tcatgtgcac atggagttac tgtggcaaga ggttcaccca gagcggcgac    360
cgcaagagac acaaacggac acatctgcga cagaaggacg gagagcgacc atatgcatgc    420
ccagtcgaaa gttgtgatag agattctca cagagcggcg acctgacccg ccacatccga    480
attcataccg gcgagaaacc ttacaagtgc ccagaatgtg aaagagcttt tcccagagc    540 ggcgaccgca gaggcacca gagaacccat acaggcagtg agcggcccett catgtgcaac    600 tggtcatatt gtggaaaaag gtttacccag agcggcgacc tgacccggca caaacgcaca    660
catactggcg agaagccttt cgcttgcccc gaatgtccta gcggtttat gcagagcggc    720 gaccgcaagc ggcacatcaa aacccataca ggaagcgaga agccttttcca gtgccgaatt    780 tgtatgagga ttttttccca gagcggcgac ctgacccgac acatcaggac tcataccggg    840
gaacggccat cgcctgcga catttgtggc agaaaatttg cacagagcgg cgaccgcaag    900
cgacacacca aaatccacct ccgccagaag gacggcggag gatccggagg gggtgggtcc    960
agcttgtctc ctcagcactc tgctgtcact caaggaagta tcatcaagaa caaggagggc   1020
atggatgcta agtcactaac tgcctggtcc cggacactgg tgaccttcaa ggatgtattt   1080
```

-continued

```
gtggacttca ccagggagga gtggaagctg ctggacactg ctcagcagat cgtgtacaga    1140
aatgtgatgc tggagaacta taagaacctg gtttccttgg gttatcagct tactaagcca    1200
gatgtgatcc tccggttgga gaagggagaa gagccctggc tggtggagag agaaattcac    1260
caagagaccc atcctgattc agagactgca tttgaaatca aatcatcagt t             1311
```

<210> SEQ ID NO 61
<211> LENGTH: 500
<212> TYPE: PRT
<213> ORGANISM: Artificial Sequence
<220> FEATURE:
<223> OTHER INFORMATION: Humanised 12-zinc finger modulator hZF-ZF-kox1

<400> SEQUENCE: 61

```
Met Gly Pro Lys Lys Arg Lys Val Thr Gly Glu Arg Pro Tyr Ala
1               5                   10                  15

Cys Pro Val Glu Ser Cys Asp Arg Arg Phe Ser Gln Ser Gly Asp Leu
            20                  25                  30

Thr Arg His Ile Arg Ile His Thr Gly Gln Lys Pro Phe Ala Cys Asp
        35                  40                  45

Ile Cys Gly Arg Lys Phe Ala Gln Ser Gly Asp Arg Lys Arg His Thr
    50                  55                  60

Lys Ile His Thr Gly Ser Gln Lys Pro Phe Gln Cys Arg Ile Cys Met
65                  70                  75                  80

Arg Asn Phe Ser Gln Ser Gly Asp Leu Thr Arg His Ile Arg Thr His
                85                  90                  95

Thr Gly Glu Lys Pro Phe Ala Cys Asp Ile Cys Gly Arg Lys Phe Ala
            100                 105                 110

Gln Ser Gly Asp Arg Lys Arg His Thr Lys Ile His Thr Gly Ser Gln
        115                 120                 125

Lys Pro Phe Gln Cys Arg Ile Cys Met Arg Asn Phe Ser Gln Ser Gly
    130                 135                 140

Asp Leu Thr Arg His Ile Arg Thr His Thr Gly Glu Lys Pro Phe Ala
145                 150                 155                 160

Cys Asp Ile Cys Gly Arg Lys Phe Ala Gln Ser Gly Asp Arg Lys Arg
                165                 170                 175

His Thr Lys Ile His Leu Arg Gln Lys Asp Gly Gly Gly Ser Gly
            180                 185                 190

Gly Gly Gly Ser Gly Gly Gly Ser Gln Lys Pro Phe Gln Cys Arg
        195                 200                 205

Ile Cys Met Arg Asn Phe Ser Gln Ser Gly Asp Leu Thr Arg His Ile
    210                 215                 220

Arg Thr His Thr Gly Glu Lys Pro Phe Ala Cys Asp Ile Cys Gly Arg
225                 230                 235                 240

Lys Phe Ala Gln Ser Gly Asp Arg Lys Arg His Thr Lys Ile His Thr
                245                 250                 255

Gly Ser Gln Lys Pro Phe Gln Cys Arg Ile Cys Met Arg Asn Phe Ser
            260                 265                 270

Gln Ser Gly Asp Leu Thr Arg His Ile Arg Thr His Thr Gly Glu Lys
        275                 280                 285

Pro Phe Ala Cys Asp Ile Cys Gly Arg Lys Phe Ala Gln Ser Gly Asp
    290                 295                 300

Arg Lys Arg His Thr Lys Ile His Thr Gly Ser Gln Lys Pro Phe Gln
305                 310                 315                 320

Cys Arg Ile Cys Met Arg Asn Phe Ser Gln Ser Gly Asp Leu Thr Arg
```

```
                 325                 330                 335
His Ile Arg Thr His Thr Gly Glu Lys Pro Phe Ala Cys Asp Ile Cys
        340                 345                 350

Gly Arg Lys Phe Ala Gln Ser Gly Asp Arg Lys Arg His Thr Lys Ile
        355                 360                 365

His Leu Arg Gln Lys Asp Gly Gly Ser Gly Gly Gly Ser Ser
370                 375                 380

Leu Ser Pro Gln His Ser Ala Val Thr Gln Gly Ser Ile Ile Lys Asn
385                 390                 395                 400

Lys Glu Gly Met Asp Ala Lys Ser Leu Thr Ala Trp Ser Arg Thr Leu
                405                 410                 415

Val Thr Phe Lys Asp Val Phe Val Asp Phe Thr Arg Glu Glu Trp Lys
                420                 425                 430

Leu Leu Asp Thr Ala Gln Gln Ile Val Tyr Arg Asn Val Met Leu Glu
                435                 440                 445

Asn Tyr Lys Asn Leu Val Ser Leu Gly Tyr Gln Leu Thr Lys Pro Asp
450                 455                 460

Val Ile Leu Arg Leu Glu Lys Gly Glu Glu Pro Trp Leu Val Glu Arg
465                 470                 475                 480

Glu Ile His Gln Glu Thr His Pro Asp Ser Glu Thr Ala Phe Glu Ile
                485                 490                 495

Lys Ser Ser Val
        500

<210> SEQ ID NO 62
<211> LENGTH: 1500
<212> TYPE: DNA
<213> ORGANISM: Artificial Sequence
<220> FEATURE:
<223> OTHER INFORMATION: Humanised 12-zinc finger modulator hZF-ZF-kox1

<400> SEQUENCE: 62
atgggcccga agaaacgccg taaagtgacc ggcgagcgcc cctacgcctg tcctgtggaa      60
tcctgtgata gacggttcag ccagagcggg gatctgacaa ggcacatcag aattcatact    120
gggcagaagc ccttcgcctg cgacatttgt ggtcggaaat ttgctcagag cggcgatagg    180
aagagacaca caaaaatcca tactggctcc cagaagccat tccagtgccg gatctgtatg    240
cgcaacttta gccagtccgg agacctcacc cgacacatcc gaacccatac aggggagaag    300
cctttcgcct gcgacatttg tggtcggaaa tttgctcaga gcggcgatag gaagagacac    360
acaaaaatcc atactggctc ccagaagcca ttccagtgcc gaatttgtat gaggaatttt    420
tctcagagtg gcgacctgac tcgacacatc aggactcata ccggcgaaaa gcccttcgca    480
tgcgacattt gtggaaggaa atttgcccag tctggggatc ggaagcgcca caccaaaatc    540
catctcagac agaaggacgg aggaggaggt tccggaggag aggtagtgg cggagggggt    600 tcacagaagc ctttccagtg cagaatctgt atgcggaact tttcacagag cggagatctg    660
accagacaca tccggacaca tactggggag aagccattcg cttgcgacat tgtggtagg    720 aaatttgcac agtctggcga tcgaaagagg cacaccaaaa tccatacagg aagtcagaaa    780
cctttccagt gccgcatttg tatgcgaaat ttttcccagt ctggtgacct gacacgccat    840
attcgaaccc atacagggga aaaccctttc gcctgtgaca tttgtggaag aaaatttgct    900
cagagcgggg atagaaagcg gcacactaaa atccataccg gctctcagaa accattccag    960
tgccggattt gtatgcgcaa ctttagtcag tcaggcgacc tgaccagaca catcagaact   1020
```

-continued

```
cacaccggag agaaacccct cgcatgtgat atctgtggtc ggaaattcgc ccagagcggc    1080
gatcgcaagc gacacactaa aatccacctc cgccagaagg acggcggagg atccggaggg    1140
ggtgggtcca gcttgtctcc tcagcactct gctgtcactc aaggaagtat catcaagaac    1200
aaggagggca tggatgctaa gtcactaact gcctggtccc ggacactggt gaccttcaag    1260
gatgtatttg tggacttcac caggggaggag tggaagctgc tggacactgc tcagcagatc    1320
gtgtacagaa atgtgatgct ggagaactat aagaacctgg tttccttggg ttatcagctt    1380
actaagccag atgtgatcct ccggttggag aagggagaag agccctggct ggtggagaga    1440
gaaattcacc aagagaccca tcctgattca gagactgcat ttgaaatcaa atcatcagtt    1500
```

<210> SEQ ID NO 63
<211> LENGTH: 690
<212> TYPE: PRT
<213> ORGANISM: Artificial Sequence
<220> FEATURE:
<223> OTHER INFORMATION: Humanised 18-zinc finger modulator hZF-ZF-kox1

<400> SEQUENCE: 63

```
Met Gly Pro Lys Lys Arg Arg Lys Val Thr Gly Glu Arg Pro Tyr Ala
1               5                   10                  15

Cys Pro Val Glu Ser Cys Asp Arg Arg Phe Ser Gln Ser Gly Asp Leu
            20                  25                  30

Thr Arg His Ile Arg Ile His Thr Gly Gln Lys Pro Phe Ala Cys Asp
        35                  40                  45

Ile Cys Gly Arg Lys Phe Ala Gln Ser Gly Asp Arg Lys Arg His Thr
    50                  55                  60

Lys Ile His Thr Gly Ser Gln Lys Pro Phe Gln Cys Arg Ile Cys Met
65                  70                  75                  80

Arg Asn Phe Ser Gln Ser Gly Asp Leu Thr Arg His Ile Arg Thr His
                85                  90                  95

Thr Gly Glu Lys Pro Phe Ala Cys Asp Ile Cys Gly Arg Lys Phe Ala
            100                 105                 110

Gln Ser Gly Asp Arg Lys Arg His Thr Lys Ile His Thr Gly Ser Gln
        115                 120                 125

Lys Pro Phe Gln Cys Arg Ile Cys Met Arg Asn Phe Ser Gln Ser Gly
    130                 135                 140

Asp Leu Thr Arg His Ile Arg Thr His Thr Gly Glu Lys Pro Phe Ala
145                 150                 155                 160

Cys Asp Ile Cys Gly Arg Lys Phe Ala Gln Ser Gly Asp Arg Lys Arg
                165                 170                 175

His Thr Lys Ile His Leu Arg Gln Lys Asp Gly Gly Gly Ser Gly
            180                 185                 190

Gly Gly Gly Ser Gly Gly Gly Ser Gln Lys Pro Tyr Ala Cys Pro
        195                 200                 205

Val Glu Ser Cys Asp Arg Arg Phe Ser Gln Ser Gly Asp Leu Thr Arg
    210                 215                 220

His Ile Arg Ile His Thr Gly Gln Lys Pro Phe Ala Cys Asp Ile Cys
225                 230                 235                 240

Gly Arg Lys Phe Ala Gln Ser Gly Asp Arg Lys Arg His Thr Lys Ile
                245                 250                 255

His Thr Gly Ser Gln Lys Pro Phe Gln Cys Arg Ile Cys Met Arg Asn
            260                 265                 270

Phe Ser Gln Ser Gly Asp Leu Thr Arg His Ile Arg Thr His Thr Gly
        275                 280                 285
```

```
Glu Lys Pro Phe Ala Cys Asp Ile Cys Gly Arg Lys Phe Ala Gln Ser
    290             295                 300
Gly Asp Arg Lys Arg His Thr Lys Ile His Thr Gly Ser Gln Lys Pro
305             310                 315                 320
Phe Gln Cys Arg Ile Cys Met Arg Asn Phe Ser Gln Ser Gly Asp Leu
                325                 330                 335
Thr Arg His Ile Arg Thr His Thr Gly Glu Lys Pro Phe Ala Cys Asp
            340                 345                 350
Ile Cys Gly Arg Lys Phe Ala Gln Ser Gly Asp Arg Lys Arg His Thr
        355                 360                 365
Lys Ile His Leu Arg Gln Lys Asp Gly Gly Gly Ser Gly Gly Gly
    370                 375                 380
Gly Ser Gly Gly Gly Gly Ser Gln Lys Pro Phe Gln Cys Arg Ile Cys
385             390                 395                 400
Met Arg Asn Phe Ser Gln Ser Gly Asp Leu Thr Arg His Ile Arg Thr
                405                 410                 415
His Thr Gly Glu Lys Pro Phe Ala Cys Asp Ile Cys Gly Arg Lys Phe
            420                 425                 430
Ala Gln Ser Gly Asp Arg Lys Arg His Thr Lys Ile His Thr Gly Ser
        435                 440                 445
Gln Lys Pro Phe Gln Cys Arg Ile Cys Met Arg Asn Phe Ser Gln Ser
    450                 455                 460
Gly Asp Leu Thr Arg His Ile Arg Thr His Thr Gly Glu Lys Pro Phe
465             470                 475                 480
Ala Cys Asp Ile Cys Gly Arg Lys Phe Ala Gln Ser Gly Asp Arg Lys
                485                 490                 495
Arg His Thr Lys Ile His Thr Gly Ser Gln Lys Pro Phe Gln Cys Arg
            500                 505                 510
Ile Cys Met Arg Asn Phe Ser Gln Ser Gly Asp Leu Thr Arg His Ile
        515                 520                 525
Arg Thr His Thr Gly Glu Lys Pro Phe Ala Cys Asp Ile Cys Gly Arg
    530                 535                 540
Lys Phe Ala Gln Ser Gly Asp Arg Lys Arg His Thr Lys Ile His Leu
545             550                 555                 560
Arg Gln Lys Asp Gly Gly Gly Ser Gly Gly Gly Gly Ser Ser Leu Ser
                565                 570                 575
Pro Gln His Ser Ala Val Thr Gln Gly Ser Ile Ile Lys Asn Lys Glu
            580                 585                 590
Gly Met Asp Ala Lys Ser Leu Thr Ala Trp Ser Arg Thr Leu Val Thr
        595                 600                 605
Phe Lys Asp Val Phe Val Asp Phe Thr Arg Glu Glu Trp Lys Leu Leu
    610                 615                 620
Asp Thr Ala Gln Gln Ile Val Tyr Arg Asn Val Met Leu Glu Asn Tyr
625             630                 635                 640
Lys Asn Leu Val Ser Leu Gly Tyr Gln Leu Thr Lys Pro Asp Val Ile
                645                 650                 655
Leu Arg Leu Glu Lys Gly Glu Glu Pro Trp Leu Val Glu Arg Glu Ile
            660                 665                 670
His Gln Glu Thr His Pro Asp Ser Glu Thr Ala Phe Glu Ile Lys Ser
        675                 680                 685
Ser Val
    690
```

<210> SEQ ID NO 64
<211> LENGTH: 2070
<212> TYPE: DNA
<213> ORGANISM: Artificial Sequence
<220> FEATURE:
<223> OTHER INFORMATION: Humanised 18-zinc finger modulator hZF-ZF-kox1

<400> SEQUENCE: 64

```
atgggcccga agaaacgccg taaagtgacc ggcgagcgcc cctacgcctg tcctgtggaa      60
tcctgtgata gacggttcag ccagagcggg gatctgacaa ggcacatcag aattcatact     120
gggcagaagc ccttcgcctg cgacatttgt ggtcggaaat ttgctcagag cggcgatagg     180
aagagacaca caaaaatcca tactggctcc cagaagccat tccagtgccg gatctgtatg     240
cgcaacttta gccagtccgg agacctcacc cgacacatcc gaacccatac aggggagaag     300
cctttcgcct gcgacatttg tggtcggaaa tttgctcaga gcggcgatag gaagagacac     360
acaaaaatcc atactggctc ccagaagcca ttccagtgcc gaatttgtat gaggaatttt     420
tctcagagtg gcgacctgac tgacacatc aggactcata ccggcgaaaa gcccttcgca     480
tgcgacattt gtggaaggaa atttgcccag tctgggatc ggaagcgcca caccaaaatc     540
catctcagac agaaggacgg aggaggaggt tccggaggag gaggtagtgg cggaggggt     600
tcacagaagc cttacgcctg tcctgtggaa tcctgtgata gacggttcag ccagagcggg     660
gatctgacaa ggcacatcag aattcatact gggcagaagc ccttcgcctg cgacatttgt     720
ggtcggaaat ttgctcagag cggcgatagg aagagacaca caaaaatcca tactggctcc     780
cagaagccat tccagtgccg gatctgtatg cgcaacttta gccagtccgg agacctcacc     840
cgacacatcc gaacccatac aggggagaag cctttcgcct gcgacatttg tggtcggaaa     900
tttgctcaga gcggcgatag gaagagacac acaaaaatcc atactggctc ccagaagcca     960
ttccagtgcc gaatttgtat gaggaatttt tctcagagtg gcgacctgac tgacacatc    1020
aggactcata ccggcgaaaa gcccttcgca tgcgacattt gtggaaggaa atttgcccag    1080
tctgggatc ggaagcgcca caccaaaatc catctcagac agaaggacgg aggaggaggt    1140
tccggaggag gaggtagtgg cggaggggt tcacagaagc cttccagtg cagaatctgt    1200
atgcggaact tttcacagag cggagatctg accagacaca tccggacaca tactggggag    1260
aagccattcg cttgcgacat ttgtggtagg aaatttgcac agtctggcga tcgaaagagg    1320
cacaccaaaa tccatacagg aagtcagaaa cctttccagt gccgcatttg tatgcgaaat    1380
tttcccagt ctggtgacct gacacgccat attcgaaccc atacagggga aaaacctttc    1440
gcctgtgaca tttgtggaag aaaatttgct cagagcgggg atagaaagcg gcacactaaa    1500
atccataccg gctctcagaa accattccag tgccggattt gtatgcgcaa ctttagtcag    1560
tcaggcgacc tgaccagaca catcagaact cacaccggag agaaaccctt cgcatgtgat    1620
atctgtggtc ggaaattcgc ccagagcggc gatcgcaagc gacacactaa aatccacctc    1680
cgccagaagg acgcggagg atccggaggg ggtgggtcca gcttgtctcc tcagcactct    1740
gctgtcactc aaggaagtat catcaagaac aaggagggca tggatgctaa gtcactaact    1800
gcctggtccc ggacactggt gaccttcaag gatgtatttg tggacttcac cagggaggag    1860
tggaagctgc tggacactgc tcagcagatc gtgtacagaa atgtgatgct ggagaactat    1920
aagaacctgg tttccttggg ttatcagctt actaagccag atgtgatcct ccggttggag    1980
aagggagaag agccctggct ggtggagaga gaaattcacc aagagaccca tcctgattca    2040
gagactgcat ttgaaatcaa atcatcagtt                                    2070
```

```
<210> SEQ ID NO 65
<211> LENGTH: 5
<212> TYPE: PRT
<213> ORGANISM: Artificial Sequence
<220> FEATURE:
<223> OTHER INFORMATION: Linker

<400> SEQUENCE: 65

Thr Gly Gln Lys Pro
1               5

<210> SEQ ID NO 66
<211> LENGTH: 5
<212> TYPE: PRT
<213> ORGANISM: Artificial Sequence
<220> FEATURE:
<223> OTHER INFORMATION: Linker

<400> SEQUENCE: 66

Thr Gly Glu Arg Pro
1               5

<210> SEQ ID NO 67
<211> LENGTH: 12
<212> TYPE: DNA
<213> ORGANISM: Artificial Sequence
<220> FEATURE:
<223> OTHER INFORMATION: Dodecamer repeat sequence

<400> SEQUENCE: 67
ccccgccccg cg                                                              12

<210> SEQ ID NO 68
<211> LENGTH: 509
<212> TYPE: PRT
<213> ORGANISM: Artificial Sequence
<220> FEATURE:
<223> OTHER INFORMATION: ZF11-Kox-1

<400> SEQUENCE: 68

Met Ala Asp Tyr Lys Asp His Asp Gly Asp Tyr Lys Asp His Asp Ile
1               5                   10                  15

Asp Tyr Lys Asp Asp Asp Asp Lys Pro Lys Lys Lys Arg Lys Val Thr
                20                  25                  30

Gly Ala Glu Arg Pro Phe Gln Cys Arg Ile Cys Met Arg Asn Phe Ser
            35                  40                  45

Gln Arg Ala Thr Leu Gln Arg His Thr Lys Ile His Thr Gly Ser Glu
        50                  55                  60

Arg Pro Phe Gln Cys Arg Ile Cys Met Arg Asn Phe Ser Gln Arg Ala
65                  70                  75                  80

Thr Leu Gln Arg His Ile Arg Thr His Thr Gly Glu Lys Pro Phe Ala
                85                  90                  95

Cys Asp Ile Cys Gly Arg Lys Phe Ala Gln Arg Ala Thr Leu Gln Arg
                100                 105                 110

His Thr Lys Ile His Thr Gly Ser Glu Arg Pro Phe Gln Cys Arg Ile
            115                 120                 125

Cys Met Arg Asn Phe Ser Gln Arg Ala Thr Leu Gln Arg His Ile Arg
        130                 135                 140

Thr His Thr Gly Glu Lys Pro Phe Ala Cys Asp Ile Cys Gly Arg Lys
145                 150                 155                 160
```

```
Phe Ala Gln Arg Ala Thr Leu Gln Arg His Thr Lys Ile His Leu Arg
                165                 170                 175
Gln Lys Asp Gly Gly Gly Ser Gly Gly Gly Ser Gly Gly Gly
            180                 185                 190
Gly Ser Gln Leu Val Gly Thr Ala Glu Arg Pro Phe Gln Cys Arg Ile
        195                 200                 205
Cys Met Arg Asn Phe Ser Gln Arg Ala Thr Leu Gln Arg His Ile Arg
    210                 215                 220
Thr His Thr Gly Glu Lys Pro Phe Ala Cys Asp Ile Cys Gly Arg Lys
225                 230                 235                 240
Phe Ala Gln Arg Ala Thr Leu Gln Arg His Thr Lys Ile His Thr Gly
                245                 250                 255
Ser Glu Arg Pro Phe Gln Cys Arg Ile Cys Met Arg Asn Phe Ser Gln
            260                 265                 270
Arg Ala Thr Leu Gln Arg His Ile Arg Thr His Thr Gly Glu Lys Pro
        275                 280                 285
Phe Ala Cys Asp Ile Cys Gly Arg Lys Phe Ala Gln Arg Ala Thr Leu
    290                 295                 300
Gln Arg His Thr Lys Ile His Thr Gly Ser Glu Arg Pro Phe Gln Cys
305                 310                 315                 320
Arg Ile Cys Met Arg Asn Phe Ser Gln Arg Ala Thr Leu Gln Arg His
                325                 330                 335
Ile Arg Thr His Thr Gly Glu Lys Pro Phe Ala Cys Asp Ile Cys Gly
            340                 345                 350
Arg Lys Phe Ala Gln Arg Ala Thr Leu Gln Arg His Thr Lys Ile His
        355                 360                 365
Leu Arg Gln Lys Asp Gly Gly Gly Ser Gly Gly Gly Ser Gly
370                 375                 380
Gly Gly Ser Gln Leu Val Ser Ser Leu Ser Pro Gln His Ser Ala
385                 390                 395                 400
Val Thr Gln Gly Ser Ile Ile Lys Asn Lys Glu Gly Met Asp Ala Lys
                405                 410                 415
Ser Leu Thr Ala Trp Ser Arg Thr Leu Val Thr Phe Lys Asp Val Phe
            420                 425                 430
Val Asp Phe Thr Arg Glu Glu Trp Lys Leu Leu Asp Thr Ala Gln Gln
        435                 440                 445
Ile Val Tyr Arg Asn Val Met Leu Glu Asn Tyr Lys Asn Leu Val Ser
    450                 455                 460
Leu Gly Tyr Gln Leu Thr Lys Pro Asp Val Ile Leu Arg Leu Glu Lys
465                 470                 475                 480
Gly Glu Glu Pro Trp Leu Val Glu Arg Glu Ile His Gln Glu Thr His
                485                 490                 495
Pro Asp Ser Glu Thr Ala Phe Glu Ile Lys Ser Ser Val
            500                 505
```

<210> SEQ ID NO 69
<211> LENGTH: 7
<212> TYPE: PRT
<213> ORGANISM: Artificial Sequence
<220> FEATURE:
<223> OTHER INFORMATION: Recognition sequence

<400> SEQUENCE: 69

```
Gln Arg Ala Thr Leu Gln Arg
1               5
```

```
<210> SEQ ID NO 70
<211> LENGTH: 19
<212> TYPE: DNA
<213> ORGANISM: Artificial Sequence
<220> FEATURE:
<223> OTHER INFORMATION: Primer

<400> SEQUENCE: 70
gtggaagctg ctggacact                                              19

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
aacgtaaagt gaccggggcc g                                           21

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
ggtccgaaga gatgctcagt                                             20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
caggaagacc aggtggctat                                             20

<210> SEQ ID NO 74
<211> LENGTH: 18
<212> TYPE: DNA
<213> ORGANISM: Artificial Sequence
<220> FEATURE:
<223> OTHER INFORMATION: Primer

<400> SEQUENCE: 74
gctgcaccga ccgtgagt                                               18

<210> SEQ ID NO 75
<211> LENGTH: 18
<212> TYPE: DNA
<213> ORGANISM: Artificial Sequence
<220> FEATURE:
<223> OTHER INFORMATION: Primer

<400> SEQUENCE: 75
cgcaggctgc agggttac                                               18

<210> SEQ ID NO 76
<211> LENGTH: 20
<212> TYPE: DNA
<213> ORGANISM: Artificial Sequence
<220> FEATURE:
<223> OTHER INFORMATION: Primer
```

```
<400> SEQUENCE: 76
cagatgtcag aatggtggct                                              20

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
gccttggaag attagaatcc a                                            21

<210> SEQ ID NO 78
<211> LENGTH: 21
<212> TYPE: DNA
<213> ORGANISM: Artificial Sequence
<220> FEATURE:
<223> OTHER INFORMATION: Primer

<400> SEQUENCE: 78
cacctgcctc cacctcatgg c                                            21

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
atgctccttg ggggccctgg                                              20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
atcccaatgc aaaggagttc                                              20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
ctgctgatga cccaccatag                                              20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
acttcgtgca agaaatgctg                                              20

<210> SEQ ID NO 83
```

```
<211> LENGTH: 20
<212> TYPE: DNA
<213> ORGANISM: Artificial Sequence
<220> FEATURE:
<223> OTHER INFORMATION: Primer

<400> SEQUENCE: 83
gctcatagct cttggctcct                                               20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
ggttaagcag tacagcccca                                               20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
agaggtcctt ttcaccagca                                               20

<210> SEQ ID NO 86
<211> LENGTH: 21
<212> TYPE: DNA
<213> ORGANISM: Artificial Sequence
<220> FEATURE:
<223> OTHER INFORMATION: Primer

<400> SEQUENCE: 86
gcttctttgc agctccttcg t                                             21

<210> SEQ ID NO 87
<211> LENGTH: 17
<212> TYPE: DNA
<213> ORGANISM: Artificial Sequence
<220> FEATURE:
<223> OTHER INFORMATION: Primer

<400> SEQUENCE: 87
ccagcgcagc gatatcg                                                  17

<210> SEQ ID NO 88
<211> LENGTH: 22
<212> TYPE: DNA
<213> ORGANISM: Artificial Sequence
<220> FEATURE:
<223> OTHER INFORMATION: Primer

<400> SEQUENCE: 88
ccaccgacat gggcacaatg ca                                            22

<210> SEQ ID NO 89
<211> LENGTH: 22
<212> TYPE: DNA
<213> ORGANISM: Artificial Sequence
<220> FEATURE:
<223> OTHER INFORMATION: Primer

<400> SEQUENCE: 89
```

```
atgggcaaag gtggttgcag gg                                              22
```

<210> SEQ ID NO 90
<211> LENGTH: 108
<212> TYPE: PRT
<213> ORGANISM: Artificial Sequence
<220> FEATURE:
<223> OTHER INFORMATION: ZF4xHunt

<400> SEQUENCE: 90

```
Phe Gln Cys Arg Ile Cys Met Arg Asn Phe Ser Gln Arg Ala Thr Leu
1               5                   10                  15

Gln Arg His Ile Arg Thr His Thr Gly Glu Lys Pro Phe Ala Cys Asp
            20                  25                  30

Ile Cys Gly Arg Lys Phe Ala Gln Arg Ala Thr Leu Gln Arg His Thr
        35                  40                  45

Lys Ile His Thr Gly Ser Glu Arg Pro Phe Gln Cys Arg Ile Cys Met
    50                  55                  60

Arg Asn Phe Ser Gln Arg Ala Thr Leu Gln Arg His Ile Arg Thr His
65                  70                  75                  80

Thr Gly Glu Lys Pro Phe Ala Cys Asp Ile Cys Gly Arg Lys Phe Ala
                85                  90                  95

Gln Arg Ala Thr Leu Gln Arg His Thr Lys Ile His
            100                 105
```

<210> SEQ ID NO 91
<211> LENGTH: 165
<212> TYPE: PRT
<213> ORGANISM: Artificial Sequence
<220> FEATURE:
<223> OTHER INFORMATION: ZF6xHunt

<400> SEQUENCE: 91

```
Phe Gln Cys Arg Ile Cys Met Arg Asn Phe Ser Gln Arg Ala Thr Leu
1               5                   10                  15

Gln Arg His Ile Arg Thr His Thr Gly Glu Lys Pro Phe Ala Cys Asp
            20                  25                  30

Ile Cys Gly Arg Lys Phe Ala Gln Arg Ala Thr Leu Gln Arg His Thr
        35                  40                  45

Lys Ile His Thr Gly Ser Glu Arg Pro Phe Gln Cys Arg Ile Cys Met
    50                  55                  60

Arg Asn Phe Ser Gln Arg Ala Thr Leu Gln Arg His Ile Arg Thr His
65                  70                  75                  80

Thr Gly Glu Lys Pro Phe Ala Cys Asp Ile Cys Gly Arg Lys Phe Ala
                85                  90                  95

Gln Arg Ala Thr Leu Gln Arg His Thr Lys Ile His Thr Gly Ser Glu
            100                 105                 110

Arg Pro Phe Gln Cys Arg Ile Cys Met Arg Asn Phe Ser Gln Arg Ala
        115                 120                 125

Thr Leu Gln Arg His Ile Arg Thr His Thr Gly Glu Lys Pro Phe Ala
    130                 135                 140

Cys Asp Ile Cys Gly Arg Lys Phe Ala Gln Arg Ala Thr Leu Gln Arg
145                 150                 155                 160

His Thr Lys Ile His
                165
```

<210> SEQ ID NO 92

```
<211> LENGTH: 331
<212> TYPE: PRT
<213> ORGANISM: Artificial Sequence
<220> FEATURE:
<223> OTHER INFORMATION: ZF11xHunt

<400> SEQUENCE: 92

Phe Gln Cys Arg Ile Cys Met Arg Asn Phe Ser Gln Arg Ala Thr Leu
1               5                   10                  15

Gln Arg His Thr Lys Ile His Thr Gly Ser Glu Arg Pro Phe Gln Cys
            20                  25                  30

Arg Ile Cys Met Arg Asn Phe Ser Gln Arg Ala Thr Leu Gln Arg His
        35                  40                  45

Ile Arg Thr His Thr Gly Glu Lys Pro Phe Ala Cys Asp Ile Cys Gly
    50                  55                  60

Arg Lys Phe Ala Gln Arg Ala Thr Leu Gln Arg His Thr Lys Ile His
65                  70                  75                  80

Thr Gly Ser Glu Arg Pro Phe Gln Cys Arg Ile Cys Met Arg Asn Phe
                85                  90                  95

Ser Gln Arg Ala Thr Leu Gln Arg His Ile Arg Thr His Thr Gly Glu
            100                 105                 110

Lys Pro Phe Ala Cys Asp Ile Cys Gly Arg Lys Phe Ala Gln Arg Ala
        115                 120                 125

Thr Leu Gln Arg His Thr Lys Ile His Leu Arg Gln Lys Asp Gly Gly
    130                 135                 140

Gly Gly Ser Gly Gly Gly Ser Gly Gly Gly Ser Gln Leu Val
145                 150                 155                 160

Gly Thr Ala Glu Arg Pro Phe Gln Cys Arg Ile Cys Met Arg Asn Phe
                165                 170                 175

Ser Gln Arg Ala Thr Leu Gln Arg His Ile Arg Thr His Thr Gly Glu
            180                 185                 190

Lys Pro Phe Ala Cys Asp Ile Cys Gly Arg Lys Phe Ala Gln Arg Ala
        195                 200                 205

Thr Leu Gln Arg His Thr Lys Ile His Thr Gly Ser Glu Arg Pro Phe
    210                 215                 220

Gln Cys Arg Ile Cys Met Arg Asn Phe Ser Gln Arg Ala Thr Leu Gln
225                 230                 235                 240

Arg His Ile Arg Thr His Thr Gly Glu Lys Pro Phe Ala Cys Asp Ile
                245                 250                 255

Cys Gly Arg Lys Phe Ala Gln Arg Ala Thr Leu Gln Arg His Thr Lys
            260                 265                 270

Ile His Thr Gly Ser Glu Arg Pro Phe Gln Cys Arg Ile Cys Met Arg
        275                 280                 285

Asn Phe Ser Gln Arg Ala Thr Leu Gln Arg His Ile Arg Thr His Thr
    290                 295                 300

Gly Glu Lys Pro Phe Ala Cys Asp Ile Cys Gly Arg Lys Phe Ala Gln
305                 310                 315                 320

Arg Ala Thr Leu Gln Arg His Thr Lys Ile His
                325                 330

<210> SEQ ID NO 93
<211> LENGTH: 359
<212> TYPE: PRT
<213> ORGANISM: Artificial Sequence
<220> FEATURE:
<223> OTHER INFORMATION: ZF12xHunt
```

<400> SEQUENCE: 93

```
Phe Gln Cys Arg Ile Cys Met Arg Asn Phe Ser Gln Arg Ala Thr Leu
1               5                   10                  15
Gln Arg His Ile Arg Thr His Thr Gly Glu Lys Pro Phe Ala Cys Asp
            20                  25                  30
Ile Cys Gly Arg Lys Phe Ala Gln Arg Ala Thr Leu Gln Arg His Thr
        35                  40                  45
Lys Ile His Thr Gly Ser Glu Arg Pro Phe Gln Cys Arg Ile Cys Met
    50                  55                  60
Arg Asn Phe Ser Gln Arg Ala Thr Leu Gln Arg His Ile Arg Thr His
65                  70                  75                  80
Thr Gly Glu Lys Pro Phe Ala Cys Asp Ile Cys Gly Arg Lys Phe Ala
                85                  90                  95
Gln Arg Ala Thr Leu Gln Arg His Thr Lys Ile His Thr Gly Ser Glu
            100                 105                 110
Arg Pro Phe Gln Cys Arg Ile Cys Met Arg Asn Phe Ser Gln Arg Ala
        115                 120                 125
Thr Leu Gln Arg His Ile Arg Thr His Thr Gly Glu Lys Pro Phe Ala
    130                 135                 140
Cys Asp Ile Cys Gly Arg Lys Phe Ala Gln Arg Ala Thr Leu Gln Arg
145                 150                 155                 160
His Thr Lys Ile His Leu Arg Gln Lys Asp Gly Gly Gly Ser Gly
                165                 170                 175
Gly Gly Gly Ser Gly Gly Gly Ser Gln Leu Val Gly Thr Ala Glu
            180                 185                 190
Arg Pro Phe Gln Cys Arg Ile Cys Met Arg Asn Phe Ser Gln Arg Ala
        195                 200                 205
Thr Leu Gln Arg His Ile Arg Thr His Thr Gly Glu Lys Pro Phe Ala
    210                 215                 220
Cys Asp Ile Cys Gly Arg Lys Phe Ala Gln Arg Ala Thr Leu Gln Arg
225                 230                 235                 240
His Thr Lys Ile His Thr Gly Ser Glu Arg Pro Phe Gln Cys Arg Ile
                245                 250                 255
Cys Met Arg Asn Phe Ser Gln Arg Ala Thr Leu Gln Arg His Ile Arg
            260                 265                 270
Thr His Thr Gly Glu Lys Pro Phe Ala Cys Asp Ile Cys Gly Arg Lys
        275                 280                 285
Phe Ala Gln Arg Ala Thr Leu Gln Arg His Thr Lys Ile His Thr Gly
    290                 295                 300
Ser Glu Arg Pro Phe Gln Cys Arg Ile Cys Met Arg Asn Phe Ser Gln
305                 310                 315                 320
Arg Ala Thr Leu Gln Arg His Ile Arg Thr His Thr Gly Glu Lys Pro
                325                 330                 335
Phe Ala Cys Asp Ile Cys Gly Arg Lys Phe Ala Gln Arg Ala Thr Leu
            340                 345                 350
Gln Arg His Thr Lys Ile His
        355
```

<210> SEQ ID NO 94
<211> LENGTH: 528
<212> TYPE: PRT
<213> ORGANISM: Artificial Sequence
<220> FEATURE:
<223> OTHER INFORMATION: ZF18xHunt

<400> SEQUENCE: 94

| | | | | | | | | | | | | | | |
|---|---|---|---|---|---|---|---|---|---|---|---|---|---|---|
|Phe|Gln|Cys|Arg|Ile|Cys|Met|Arg|Asn|Phe|Ser|Gln|Arg|Ala|Thr|Leu
1| | | |5| | | | |10| | | | |15|

Gln Arg His Ile Arg Thr His Thr Gly Glu Lys Pro Phe Ala Cys Asp
          20                  25                  30

Ile Cys Gly Arg Lys Phe Ala Gln Arg Ala Thr Leu Gln Arg His Thr
          35                  40                  45

Lys Ile His Thr Gly Ser Glu Arg Pro Phe Gln Cys Arg Ile Cys Met
    50                  55                      60

Arg Asn Phe Ser Gln Arg Ala Thr Leu Gln Arg His Ile Arg Thr His
65                  70                  75                  80

Thr Gly Glu Lys Pro Phe Ala Cys Asp Ile Cys Gly Arg Lys Phe Ala
                85                  90                  95

Gln Arg Ala Thr Leu Gln Arg His Thr Lys Ile His Thr Gly Ser Glu
            100                 105                 110

Arg Pro Phe Gln Cys Arg Ile Cys Met Arg Asn Phe Ser Gln Arg Ala
        115                 120                 125

Thr Leu Gln Arg His Ile Arg Thr His Thr Gly Glu Lys Pro Phe Ala
    130                 135                 140

Cys Asp Ile Cys Gly Arg Lys Phe Ala Gln Arg Ala Thr Leu Gln Arg
145                 150                 155                 160

His Thr Lys Ile His Leu Arg Gln Lys Asp Gly Gly Ser Gln Leu
                165                 170                 175

Val Gly Thr Ala Glu Arg Pro Phe Gln Cys Arg Ile Cys Met Arg Asn
        180                 185                 190

Phe Ser Gln Arg Ala Thr Leu Gln Arg His Ile Arg Thr His Thr Gly
        195                 200                 205

Glu Lys Pro Phe Ala Cys Asp Ile Cys Gly Arg Lys Phe Ala Gln Arg
    210                 215                 220

Ala Thr Leu Gln Arg His Thr Lys Ile His Thr Gly Ser Glu Arg Pro
225                 230                 235                 240

Phe Gln Cys Arg Ile Cys Met Arg Asn Phe Ser Gln Arg Ala Thr Leu
            245                 250                 255

Gln Arg His Ile Arg Thr His Thr Gly Glu Lys Pro Phe Ala Cys Asp
            260                 265                 270

Ile Cys Gly Arg Lys Phe Ala Gln Arg Ala Thr Leu Gln Arg His Thr
        275                 280                 285

Lys Ile His Thr Gly Ser Glu Arg Pro Phe Gln Cys Arg Ile Cys Met
    290                 295                 300

Arg Asn Phe Ser Gln Arg Ala Thr Leu Gln Arg His Ile Arg Thr His
305                 310                 315                 320

Thr Gly Glu Lys Pro Phe Ala Cys Asp Ile Cys Gly Arg Lys Phe Ala
                325                 330                 335

Gln Arg Ala Thr Leu Gln Arg His Thr Lys Ile His Leu Arg Gln Lys
            340                 345                 350

Asp Gly Gly Gly Ser Gly Thr Ala Glu Arg Pro Phe Gln Cys Arg Ile
        355                 360                 365

Cys Met Arg Asn Phe Ser Gln Arg Ala Thr Leu Gln Arg His Ile Arg
    370                 375                 380

Thr His Thr Gly Glu Lys Pro Phe Ala Cys Asp Ile Cys Gly Arg Lys
385                 390                 395                 400

Phe Ala Gln Arg Ala Thr Leu Gln Arg His Thr Lys Ile His Thr Gly
            405                 410                 415

```
Ser Glu Arg Pro Phe Gln Cys Arg Ile Cys Met Arg Asn Phe Ser Gln
        420                 425                 430
Arg Ala Thr Leu Gln Arg His Ile Arg Thr His Thr Gly Glu Lys Pro
            435                 440                 445
Phe Ala Cys Asp Ile Cys Gly Arg Lys Phe Ala Gln Arg Ala Thr Leu
    450                 455                 460
Gln Arg His Thr Lys Ile His Thr Gly Ser Glu Arg Pro Phe Gln Cys
465                 470                 475                 480
Arg Ile Cys Met Arg Asn Phe Ser Gln Arg Ala Thr Leu Gln Arg His
                485                 490                 495
Ile Arg Thr His Thr Gly Glu Lys Pro Phe Ala Cys Asp Ile Cys Gly
            500                 505                 510
Arg Lys Phe Ala Gln Arg Ala Thr Leu Gln Arg His Thr Lys Ile His
        515                 520                 525

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
cctgaagttc atctgcacca                                         20

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
aagtcgtgct gcttcatgtg                                         20

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
agatgctgcg gaagaagaag                                         20

<210> SEQ ID NO 98
<211> LENGTH: 19
<212> TYPE: DNA
<213> ORGANISM: Artificial Sequence
<220> FEATURE:
<223> OTHER INFORMATION: Primer

<400> SEQUENCE: 98
ggtaccgtcg actgcagaa                                          19

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
```
ctttgctttc cttggtcagg					20

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
tatccaacac ttcgtggggt					20

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
gtctccctcc gatctggata					20

<210> SEQ ID NO 102
<211> LENGTH: 20
<212> TYPE: DNA
<213> ORGANISM: Artificial Sequence
<220> FEATURE:
<223> OTHER INFORMATION: Primer

<400> SEQUENCE: 102
cacacttcca gggctgtaga					20

<210> SEQ ID NO 103
<211> LENGTH: 20
<212> TYPE: DNA
<213> ORGANISM: Artificial Sequence
<220> FEATURE:
<223> OTHER INFORMATION: Primer

<400> SEQUENCE: 103
ccagcaccgt agagaggatt					20

<210> SEQ ID NO 104
<211> LENGTH: 19
<212> TYPE: DNA
<213> ORGANISM: Artificial Sequence
<220> FEATURE:
<223> OTHER INFORMATION: Primer

<400> SEQUENCE: 104
agccctgtcc aaacacaaa					19

<210> SEQ ID NO 105
<211> LENGTH: 20
<212> TYPE: DNA
<213> ORGANISM: Artificial Sequence
<220> FEATURE:
<223> OTHER INFORMATION: Primer

<400> SEQUENCE: 105
gacgcagctg agcaagttag					20

<210> SEQ ID NO 106
<211> LENGTH: 20
<212> TYPE: DNA

```
<213> ORGANISM: Artificial Sequence
<220> FEATURE:
<223> OTHER INFORMATION: Primer

<400> SEQUENCE: 106
gaaggaacgt gggttgaact                                                  20

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
agagcttcgg aagagacgag                                                  20

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
actcccaagt gctcctgaac                                                  20

<210> SEQ ID NO 109
<211> LENGTH: 20
<212> TYPE: DNA
<213> ORGANISM: Artificial Sequence
<220> FEATURE:
<223> OTHER INFORMATION: Primer

<400> SEQUENCE: 109
aactgtgtgg ctcactctgg                                                  20

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
tgggaagatg ttaccgttga                                                  20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
gggaactaca ccctcctgaa                                                  20

<210> SEQ ID NO 112
<211> LENGTH: 20
<212> TYPE: DNA
<213> ORGANISM: Artificial Sequence
<220> FEATURE:
<223> OTHER INFORMATION: Primer

<400> SEQUENCE: 112
cgctgcttct tcttcctctt                                                  20
```

```
<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
acgccgaata taatcccaag                                               20

<210> SEQ ID NO 114
<211> LENGTH: 20
<212> TYPE: DNA
<213> ORGANISM: Artificial Sequence
<220> FEATURE:
<223> OTHER INFORMATION: Primer

<400> SEQUENCE: 114
cttcactctt ggctcctgtg                                               20

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
cagatgtcag aatggtggct                                               20

<210> SEQ ID NO 116
<211> LENGTH: 21
<212> TYPE: DNA
<213> ORGANISM: Artificial Sequence
<220> FEATURE:
<223> OTHER INFORMATION: Primer

<400> SEQUENCE: 116
gccttggaag attagaatcc a                                             21

<210> SEQ ID NO 117
<211> LENGTH: 21
<212> TYPE: DNA
<213> ORGANISM: Artificial Sequence
<220> FEATURE:
<223> OTHER INFORMATION: Primer

<400> SEQUENCE: 117
cacctgcctc cacctcatgg c                                             21

<210> SEQ ID NO 118
<211> LENGTH: 20
<212> TYPE: DNA
<213> ORGANISM: Artificial Sequence
<220> FEATURE:
<223> OTHER INFORMATION: Primer

<400> SEQUENCE: 118
atgctccttg ggggcctgg                                                20

<210> SEQ ID NO 119
<211> LENGTH: 20
<212> TYPE: DNA
<213> ORGANISM: Artificial Sequence
<220> FEATURE:
```

<223> OTHER INFORMATION: Primer

<400> SEQUENCE: 119
tgtggagaga atcgaggaga                                           20

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
cagccctgtc caaatacaaa                                           20

<210> SEQ ID NO 121
<211> LENGTH: 20
<212> TYPE: DNA
<213> ORGANISM: Artificial Sequence
<220> FEATURE:
<223> OTHER INFORMATION: Primer

<400> SEQUENCE: 121
atcccaatgc aaaggagttc                                           20

<210> SEQ ID NO 122
<211> LENGTH: 20
<212> TYPE: DNA
<213> ORGANISM: Artificial Sequence
<220> FEATURE:
<223> OTHER INFORMATION: Primer

<400> SEQUENCE: 122
ctgctgatga cccaccatag                                           20

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
acctcgcact attcttggct                                           20

<210> SEQ ID NO 124
<211> LENGTH: 20
<212> TYPE: DNA
<213> ORGANISM: Artificial Sequence
<220> FEATURE:
<223> OTHER INFORMATION: Primer

<400> SEQUENCE: 124
tgcatctgtt ggaccttgat                                           20

<210> SEQ ID NO 125
<211> LENGTH: 20
<212> TYPE: DNA
<213> ORGANISM: Artificial Sequence
<220> FEATURE:
<223> OTHER INFORMATION: Primer

<400> SEQUENCE: 125
tgcccgtgtt cctcaccgga                                           20

```
<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
gcgcggagac agtggttgct                                               20

<210> SEQ ID NO 127
<211> LENGTH: 20
<212> TYPE: DNA
<213> ORGANISM: Artificial Sequence
<220> FEATURE:
<223> OTHER INFORMATION: Primer

<400> SEQUENCE: 127
cactggcaat agcaaaggaa                                               20

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
ttcttgagcg agttcaccac                                               20

<210> SEQ ID NO 129
<211> LENGTH: 20
<212> TYPE: DNA
<213> ORGANISM: Artificial Sequence
<220> FEATURE:
<223> OTHER INFORMATION: Primer

<400> SEQUENCE: 129
acttcgtgca agaaatgctg                                               20

<210> SEQ ID NO 130
<211> LENGTH: 20
<212> TYPE: DNA
<213> ORGANISM: Artificial Sequence
<220> FEATURE:
<223> OTHER INFORMATION: Primer

<400> SEQUENCE: 130
gctcatagct cttggctcct                                               20

<210> SEQ ID NO 131
<211> LENGTH: 20
<212> TYPE: DNA
<213> ORGANISM: Artificial Sequence
<220> FEATURE:
<223> OTHER INFORMATION: Primer

<400> SEQUENCE: 131
tcctggcttt gaggagccga                                               20

<210> SEQ ID NO 132
<211> LENGTH: 22
<212> TYPE: DNA
<213> ORGANISM: Artificial Sequence
<220> FEATURE:
<223> OTHER INFORMATION: Primer
```

```
<400> SEQUENCE: 132
ccacagcaca gctctgcagc at                                              22

<210> SEQ ID NO 133
<211> LENGTH: 20
<212> TYPE: DNA
<213> ORGANISM: Artificial Sequence
<220> FEATURE:
<223> OTHER INFORMATION: Primer

<400> SEQUENCE: 133
gggggctcaa gcaggcatgg                                                 20

<210> SEQ ID NO 134
<211> LENGTH: 20
<212> TYPE: DNA
<213> ORGANISM: Artificial Sequence
<220> FEATURE:
<223> OTHER INFORMATION: Primer

<400> SEQUENCE: 134
gggagccagc ctccgagtca                                                 20

<210> SEQ ID NO 135
<211> LENGTH: 20
<212> TYPE: DNA
<213> ORGANISM: Artificial Sequence
<220> FEATURE:
<223> OTHER INFORMATION: Primer

<400> SEQUENCE: 135
cagatgtcag aatggtggct                                                 20

<210> SEQ ID NO 136
<211> LENGTH: 21
<212> TYPE: DNA
<213> ORGANISM: Artificial Sequence
<220> FEATURE:
<223> OTHER INFORMATION: Primer

<400> SEQUENCE: 136
gccttggaag attagaatcc a                                               21

<210> SEQ ID NO 137
<211> LENGTH: 20
<212> TYPE: DNA
<213> ORGANISM: Artificial Sequence
<220> FEATURE:
<223> OTHER INFORMATION: Primer

<400> SEQUENCE: 137
ggttaagcag tacagcccca                                                 20

<210> SEQ ID NO 138
<211> LENGTH: 20
<212> TYPE: DNA
<213> ORGANISM: Artificial Sequence
<220> FEATURE:
<223> OTHER INFORMATION: Primer

<400> SEQUENCE: 138
agaggtcctt ttcaccagca                                                 20

<210> SEQ ID NO 139
<211> LENGTH: 16
```

```
<212> TYPE: DNA
<213> ORGANISM: Artificial Sequence
<220> FEATURE:
<223> OTHER INFORMATION: Primer

<400> SEQUENCE: 139
gtaaaacgac ggccag                                                         16

<210> SEQ ID NO 140
<211> LENGTH: 17
<212> TYPE: DNA
<213> ORGANISM: Artificial Sequence
<220> FEATURE:
<223> OTHER INFORMATION: Primer

<400> SEQUENCE: 140
caggaaacag ctatgac                                                        17

<210> SEQ ID NO 141
<211> LENGTH: 292
<212> TYPE: PRT
<213> ORGANISM: Artificial Sequence
<220> FEATURE:
<223> OTHER INFORMATION: ZF10xHunt

<400> SEQUENCE: 141

Tyr Ala Cys Pro Val Glu Ser Cys Asp Arg Phe Ser Gln Arg Ala
1               5                   10                  15

Thr Leu Thr Arg His Ile Arg Ile His Thr Gly Gln Lys Pro Phe Gln
            20                  25                  30

Cys Arg Ile Cys Met Arg Asn Phe Ser Gln Arg Ala Thr Leu Ser Arg
        35                  40                  45

His Ile Arg Thr His Gln Asn Lys Lys Gly Ser His Ile Cys His Ile
    50                  55                  60

Gln Gly Cys Gly Lys Val Tyr Gly Gln Arg Ala Thr Leu Gln Arg His
65                  70                  75                  80

Leu Arg Trp His Thr Gly Glu Arg Pro Phe Met Cys Thr Trp Ser Tyr
                85                  90                  95

Cys Gly Lys Arg Phe Thr Gln Arg Ala Thr Leu Gln Arg His Lys Arg
            100                 105                 110

Thr His Leu Arg Gln Lys Asp Gly Glu Arg Pro Tyr Ala Cys Pro Val
        115                 120                 125

Glu Ser Cys Asp Arg Arg Phe Ser Gln Arg Ala Thr Leu Ser Arg His
    130                 135                 140

Ile Arg Ile His Thr Gly Glu Lys Pro Tyr Lys Cys Pro Glu Cys Gly
145                 150                 155                 160

Lys Ser Phe Ser Gln Arg Ala Thr Leu Gln Arg His Gln Arg Thr His
                165                 170                 175

Thr Gly Ser Glu Arg Pro Phe Met Cys Asn Trp Ser Tyr Cys Gly Lys
            180                 185                 190

Arg Phe Thr Gln Arg Ala Thr Leu Thr Arg His Lys Arg Thr His Thr
        195                 200                 205

Gly Glu Lys Pro Phe Ala Cys Pro Glu Cys Pro Lys Arg Phe Met Gln
    210                 215                 220

Arg Ala Thr Leu Gln Arg His Ile Lys Thr His Thr Gly Ser Glu Lys
225                 230                 235                 240

Pro Phe Gln Cys Arg Ile Cys Met Arg Asn Phe Ser Gln Arg Ala Thr
                245                 250                 255
```

Leu Gln Arg His Ile Arg Thr His Thr Gly Glu Arg Pro Phe Ala Cys
            260                 265                 270

Asp Ile Cys Gly Arg Lys Phe Ala Gln Arg Ala Thr Leu Gln Arg His
        275                 280                 285

Thr Lys Ile His
    290

<210> SEQ ID NO 142
<211> LENGTH: 132
<212> TYPE: PRT
<213> ORGANISM: Artificial Sequence
<220> FEATURE:
<223> OTHER INFORMATION: ZNF10xHunt C-terminal linker and repressor
      domain

<400> SEQUENCE: 142

Leu Arg Gln Lys Asp Ala Pro Lys Lys Lys Arg Lys Val Gly Gly Ser
1               5                   10                  15

Leu Ser Pro Gln His Ser Ala Val Thr Gln Gly Ser Ile Ile Lys Asn
            20                  25                  30

Lys Glu Gly Met Asp Ala Lys Ser Leu Thr Ala Trp Ser Arg Thr Leu
        35                  40                  45

Val Thr Phe Lys Asp Val Phe Val Asp Phe Thr Arg Glu Glu Trp Lys
    50                  55                  60

Leu Leu Asp Thr Ala Gln Gln Ile Val Tyr Arg Asn Val Met Leu Glu
65                  70                  75                  80

Asn Tyr Lys Asn Leu Val Ser Leu Gly Tyr Gln Leu Thr Lys Pro Asp
                85                  90                  95

Val Ile Leu Arg Leu Glu Lys Gly Glu Glu Pro Trp Leu Val Glu Arg
            100                 105                 110

Glu Ile His Gln Glu Thr His Pro Asp Ser Glu Thr Ala Phe Glu Ile
        115                 120                 125

Lys Ser Ser Val
    130

<210> SEQ ID NO 143
<211> LENGTH: 2095
<212> TYPE: DNA
<213> ORGANISM: Artificial Sequence
<220> FEATURE:
<223> OTHER INFORMATION: Mouse hsp90ab1 promoter 2k plus exon I 95 bp
      (mouse NCBI 15516 NC_000083.6)

<400> SEQUENCE: 143
agtacactcc tgtccccatt ctactttcag aacaggaatg ccctgggtt tagtgacccc      60 attattcaca gagaccttca ttttcctgtc catgaaatat acagtagc tttcaaccat     120 tcagaggcca aggagaggta gtcagtgctg tttgtgaact agggaatcca ggattggtgg    180
gtcttaggga aacactaccc tggagctaaa tgtccagccc agggatcagc taggctcctt    240
ttgctgagag ggtttgagtg ttgaagtttc tggtttcaga ttaggaatca atgcaacacc    300
ctagggcctt ctgagcaatc ctacccagtg tctcctcata tattgatttc tttatgggct    360
tcacacacac acacacacac acacacacac acacacacag aattaaggag               420
aggctaacag acagtgcagg atgggatgat aacagacgaa gtagacagag gcaaggagaa    480
agcaactact gtttaacaat gaatgcacat tagacagact gcaggcaagc accgggaaca    540
aaggtgtggg cggtggtgtg gggacacaag ccagcatgag ctaagatagc agagcactga    600
gtgcccatcc tctactggag ggctcatcag tccaacaagc ttccagatgc agccttggaa    660

```
aaaggcaagg ctagattgcc agctgaagga catggcaggc cacctttaga acagaggcac    720
tggcacaact tggttttctg ctcctggaa ctgggccaac ctgtgaccag caccttcatg    780
cggatgccta gaactccagc ttctctgaaa agactgggac ctgctcctct ctaggtccaa    840
agagctgcat gcagtaggga agaggctaga gaagcgaaac cagcttgaga aacagcttgt    900
gctcacatag ggagggcgca cgtacccgcg cgctgtgtac gtgggagacc ggggaggctg    960
aggggtgggg agtgttctac ccagtagcgc aagctgctag ctcggttctc tgttcactag   1020
aaggtgtccg cagtcactca cccccacagc ccccgtgccc tgtgaccgat ccaggtcagc   1080
tatccctccc tctgcgctcc actccccac tgttatgtgg gcctcttagg ccacgcgtg    1140 gagggtcgtt caaccctggc ccacggtagg cagacttggg gaaaatttct cccagggta   1200 agatcaaggt aggggaaaaa aaaaaaaaaa aaaagccacc cagccaagcg cgacgaaga    1260 cactgcccccc gccgcagcag gggaggtgga gcctaggggg gaggggtgga gaccgccgag   1320
acaggcctag aaactgctgg aagaaatcgc agcaccaccg ctgctgatcc ttccgccgca   1380
ggccgccaaa gagtccctac cagcccaggc ccgtgcccct cccctcgggg aaagcggctc   1440
ccagcctgaa gctgtgctgt acccgggagg gtggggatgg gggaatcggg ggcctcctta   1500
aagttggaca aggaatttat catccttttc tcttgatgtg cgatttgtag ggaacattct   1560
agtaagatcg ggtctggaaa tggcagccga gttggccacc tccattctct ttcagtcccc   1620
tgagttctgg actcttgggg ggtgggggggg tggaagcgcc taccttgagt tttctgaggc   1680
agtccgtagg gtattcgccc gcagatacat ccctaattgc atatgcatgc tccctgctca   1740
tcttgagggg ggacatgtcc tactcctgca gaaatggggg atgtgcaaaa cgatattgaa   1800
ttggccttga ctcaggaacc aggcccgggg tcccgctcct ccccgccccc tccacgatct   1860
gctaccatga cgtcaaggtg ggcgggcggc ggcaggtgcg tggcccgcag ccactccttt   1920
aaggcggagg gatccaaggg cggggcccgg gctgtgcttc gccttatata gggcggtcgg   1980
gggcgttcgg gagctctctt gagtcacccc cgcgcagcct aggcttgccg tgcgagtcgg   2040
acttggtccg ggcccaccac cctgctctgt actactactc ggctttcccg tcaag         2095
```

<210> SEQ ID NO 144
<211> LENGTH: 2179
<212> TYPE: DNA
<213> ORGANISM: Artificial Sequence
<220> FEATURE:
<223> OTHER INFORMATION: Human hsp90ab1promoter 2k plus exon 1 179bp
    (human NCBI 3326 NC_000006.12)

<400> SEQUENCE: 144

```
gcctggctag gcatggtcct aagactgctc cctttcccaa gctgagctga gggcctctgc      60
ggcttctccc atcctcctat ggttcacact tggctgctgc agcctccagt gggttaaggg    120
ctcccagtcc tgtgtatgca tctctgcatc cccaggatct ccacacagtg gaggcttagt    180
gagtgtcaat gagtggaaaa cgatggagct tgtggacaca ggtaggcggt ctcctgaaag    240
gcttcctgga agagaaagtg gaatttcttt tttttttttc tttttttgaga cagagtctca    300 ctgtgtcgct caggctggag tgcagtggcg tgatctcggc tcacggcaac ctctgccgcc    360
cgggttcaag tgattctcct gcttcagcct cccaagtagc ggggactata ggcgcgctac    420
cacgcccggc taattttgt attttagta gagacaaggt ttcaccgag tggccaggct      480 ggtcttgaac tcctgacctg gtgatccgct ggactcggcc tcccaaagtg ctggaattac    540
aggcatgagc caccgcgccc agccccctt tttttttttt ttttttttg agacggagtt     600
```

-continued

```
tctcttttgt tgcccaggct ggagtgcaat ggcatggtct cagctcactg cagcctctgc    660
ctccagagtt caagcaatct tcctgcctca gcctcccaag tagctgggat tacaggcatg    720
tgccaccacg cccagctaat ttttagtaga gacgaggttt ttcaccatgt tggccaggct    780
ggttgtgaac tactgacctc gggtgatcca cccacctcgg ccttccaaag tgctgggatt    840
acaggtatga gccactgtgc ccagcagaga agtggaatt tctatgctgg tgtaacattt    900
gagattttcc catttagaaa gtcttcagga agccgtcgag tcttgacaca gaaaggatcc    960
agctcagggg aagcccatcc acaggagtga ttcctgcttt ggatttaggt cctaggggtg   1020
agatcacatc cctgctccat ttctggagca gaaagggagc tagtgcagca aggactctga   1080
gtagacgggc cttgggagtc actgaagcca cttccctgtt gacagaatgt gcacactgac   1140
tttcatccgc tcacaggaga gtgagagttt gtgaatgctc tctgtgaact ggggagcaga   1200
tttttaatga gctctgctta aaggagagg acacgttaag ggatcacgct cccactggtt   1260
tgcggttttg gtcaggaata gagcacccaa cgcccttct tatagacttc tcccagccat   1320 aggcttttg cagaccataa tgaaagggag aaaggatatc caatcgggat ggtgatggca   1380
ggcatggcga gtggacagg gacaaagaag aggaaagcaa gggacaccct ttgttctttg   1440
gtattcaaca catgaacaaa acttgttaac gaatcgtaga ctgggtaaca acagggctgg   1500
tgagggagga cgatgtgggt ggctgtgggg aaactcttcc caagcatccc aggggtgggc   1560
caggaagggg agcagatgga catctacagg gcacagagca gggagtggct attctctcct   1620
ggaggggttg tgggtccagc aggctttcgg atgaggcctt ggaaaggcaa ggacagcttg   1680
ccaactggag ggcaggcaaa acggctgagc caggccagac acggcagctc actgccagg   1740 ggcatggcct aggggctctg gtgccaaggc tgaaggggaa caacttggcc agccgctctg   1800
tggccggcat cgtcacgcgg cctccaagag ctccggctgc cctgcactgg ttcccagaga   1860 ctcccctcctt cccaggtcca aatgctgca ggagcgaagt gggcggaaaa aaagcgaacc   1920
agcttgagaa agggcttgac gtgcctgcgt agggagggcg catgtccccg tgctccgtgt   1980
acgtggcggc cgcaggggct agaggggggt cccccccgca ggtactccac tctcagtctg   2040
caaaagtgta cgcccgcaga gccgccccag gtgcctgggg gttgtgtgat tgacgcgggg   2100
aaggaggggt cagccgatcc ctccccaacc ctccatccca tccctgagga ttgggctggt   2160
acccgcgtct ctcggacag                                                 2179
```

<210> SEQ ID NO 145
<211> LENGTH: 20121
<212> TYPE: DNA
<213> ORGANISM: Artificial Sequence
<220> FEATURE:
<223> OTHER INFORMATION: Mouse Hsp90ab1 - 20kb to 100b

<400> SEQUENCE: 145

```
ctcttgagtc ctcttgagtc gggtgtccct tgaatatgct tcttccttac aggactagcc     60
cactggtgct gttatctcct cttgagagt gaggcacagg gcagcatgtc aagggtttgg    120
ttaggagctc tgggagcacg atgctagctt tccaaatttc ccttcaaagc cactgtcaga    180
cacgggaaga ggatagttag tggccttgga ctgagaaagg aactgggggt ggggggggga    240
agaaaggaac attctggaac tggaggtcaa ggaaaggaac ttgctgtgga gaagtctgtg    300
tccctcccac agttatgaaa tatattcctg gagaactcag gaagccccta ggcagcagct    360
ggaaaggcgt agaggctggc tccagcagag gctggctcca gcagaggctg gctccagcag    420
```

-continued

| | |
|---|---|
| aggctggagg gagtcccgat tactctagga agcagtctgc gaagggaagg ccctccctgc | 480 |
| cacagtcttg attgggtgat ggggtggggg cacccaggag gggagagtgc aggctcatgg | 540 |
| caggcctcag gagacctgtg ttccttacag ggtctgtttg ctctctcact ctttctccct | 600 |
| ttttcccctc tgctctgtct cctccccttt gcctgctctg tcactgttgt cactgtccct | 660 |
| gacccctttt ctcttttctg tcttctttga ctgtctttcc ctgcctctca atcatccgtc | 720 |
| ctcctcctcc tcctcgattg ctccccaccc ttcggtttcc aagcttataa actgcttctg | 780 |
| ctgctggata aaaatagcgg tggcagcggc caggctggca gccaggtgca gcccaatcag | 840 |
| gcagagagac gacaggaagg ccttcctggg gccaaaggcc agatggggct gagttgagtg | 900 |
| gtcctgagtc tgcagaggct tcccttgcct actctgtgtc cagctctacc ccccccccc | 960 |
| aagagaaagg cccagggcag tgtggaagca gagccagaca gggctcgata ttcctttacc | 1020 |
| cccagcaaga gccagaggga gggagctgcc agccaggcac agccgagaac actggagcca | 1080 |
| tgacaaccag tcaccagcct caggacaggt actgggtggc caaggggtgt gacggagggt | 1140 |
| ggttgcaggg agggggagc cggtctggag atctggggag tgagtctcta gggtaagggt | 1200 |
| gggagggagg gaggtgcggt gtttgggact tgagggaggg gacctcagga ctaactgtgt | 1260 |
| tcccagcctg gtggttctga gtcagttctg catgggtag ggtggagaac atgcatgccc | 1320 |
| tggctgggtg ctggctagca tgcccgcagg gctaggtgag cagtaggtcc ctattggagt | 1380 |
| gtctcagtct ttccactgtt atgcgcagct agacagcagc ttccagctcc tcccaccatc | 1440 |
| actgtgggga gacacttggc tgcttccctc attccagaac acatctggca ggactacccc | 1500 |
| tgtccctggg ggtcgccctt gcatgacctc agcccacgct gctctctggc ctgacccttc | 1560 |
| cagccttcta gctccggagc ttgggatctt cctcaagcta gttaaggtcc ggaatgcgtg | 1620 |
| ctaggatgga aaaggagctt gagtctagtc cttcagaggg gctgaggctt gtggaagttt | 1680 |
| atgaagccat gatacactct ttccagatgg cccctctgtc ctgttgggtc tctgaacctc | 1740 |
| tcacggctcc cctgcccacc attttcctct tgtgctatgt aactaggccc attctgactg | 1800 |
| gagagttagc tgcatctttc tgggaccatt tctccatcct gtaaagtctg gtgagaacac | 1860 |
| cagccttctg tgactgtttt ctgagggaa gaattgtcat tgtcattgta ggttccagct | 1920 |
| tcctgcctcc tttccttccc aggctgcctg gtgccctggc ctcttcaaca atctacccat | 1980 |
| ttcactgctg cctggctcag cagctcttct ctgacctcct gtccttgtat aaccttccct | 2040 |
| cggaatttta ccttccatct gagcctttga accaagcctt gagcatcttg acctcaaagg | 2100 |
| gaatggatga gggctttgaa ggctgtggtg tggccatggc ttagactggc gaatttggtt | 2160 |
| gctcttctgg ctgtcccatt tcaggcttgc aagaggcctg ttccactgag ttgggtctct | 2220 |
| gctaccatct ctgtgcagcc tgtagatgcc ggctaagggg aaggtatttt accaggcata | 2280 |
| ggcaactgta atggaaggga ccagggccac taagcttaca ggcaaagact gtccgaagtc | 2340 |
| atgctcagaa ccagatggca gccataagtc ctaatctatc tgccctgccg taggtagttt | 2400 |
| ggactataaa actggttctg tctgtctaat atctaataag ggaaaaaaaa attctatagc | 2460 |
| tctctacttc ctagtcccca cccctaccc ccagccatgt gacccactgg gtctagaatt | 2520 |
| gtctgggtgt tgtttttga cctcaagagt tcttgagaga actggcgttc ccgcttagac | 2580 |
| agcttaacta cttccagctg gtgtggtggg gctggggctt gtgcccactg cccttaccc | 2640 |
| gcccaccttt aacagaggtt ccaacaccag ctctggaagt gtgggtcatc acactgcttc | 2700 |
| cccgatcacc cagcccctg aaccttctag gacttgggaa caaggttct gtctcccgtg | 2760 |
| tcattcagaa ctgccaccag cccttttcct tcaacccatc ttacagcctg tcctgtaccc | 2820 |

```
aggacctaca catccctcac acctctgcag gagggcgcct acttgtggat acacacagct    2880
gggaccgctg ggtagacggg agggagggga ggtgggctga ctgatcactt tgcctttttc    2940
ctacgcaggt ataaggcagt atggcttatc ttctttgtgc tgggcctggg gacactgctc    3000
ccctggaatt tttttatgac cgcaaccaag gtgaggttgg agtgggggtc aggtactagg    3060
ctccagagga catgttcctt aggctttcaa ggcctggttc tgtgcctctg gcacagaga    3120 gggacagagg tcccaacact caacctctgc aaaccccaca gtatttcaca aaccgcctgg    3180
acgtgtccca gaatgtgtcc tcggacactg atcaatcatg cgaaagcacc aaggccttgg    3240
ctgaccccac agtggccttg ccagcccgga gttctctcag tgccatcttc aacaatgtca    3300
tgaccctgtg tgccatgctg cccttgctgg tcttcacctg cctcaactcg tttctgcatc    3360
agcggtgagc ctccccgtcc atgatgccca gccagctcct gcttcctcag ccccaggctg    3420
acccttcctg acaccccacc accaccacca ccctgcctc tcctaggatc tctcaatctg    3480
ttcggatctt gggcagcctg ctggcaatcc tgctggtatt ccttgtcact gccgccctgg    3540
tgaaggtgga gatggatgct ctgatcttct tgtcatcac catgatcaag attgtgctca    3600
tcaattgtaa tcgggagggg acgggatgga cagccatggg cctgggttga atcagggtg    3660 ggggtggttc aggttaaagc ttcctgggaa gccctgattg ccagcctctg ctgacaagct    3720
gtctttgcta ctccccagca tttggtgcca ttttgcaagc cagccttttt ggtctggcag    3780
gtgtcctgcc agccaactac acagccccca tcatgagtgg ccagggcctg gctggcttct    3840
tcacctctgt cgccatgatc tgtgccattg ccagtgagtc caactgcgcg cgcactgccc    3900
tgctttgctg gttgtgggga ggcagggtag ggtgatttgg aagggtggag cgtatctgag    3960
cttgtgcact gtctgcgcca ggtggttctg agctgtcaga aagcgccttt ggctacttca    4020
tcacagcctg tgcagttgtc attttggcca tcctgtgcta cctggctctg cctcggacgg    4080
tgagcaaatg ggggggatttg gggaggcctc ggggtttcaa agcaagggtg tctggaaact    4140
aaaggatggc aagctcggat gcctagagct gccctgactc tacttacttc tcccatctcc    4200
cttgctgaac aggaattcta tcgccattac ctgcagctca accttgcggg gcctgcagag    4260
caggagacca agttggatct cataagtaaa ggtcttaatt actaaaggaa gtctggtagg    4320
gcggtaggat gggagtggga gggttgtggg catgttgtgt taactggcag ctgggagcca    4380
aaggaggaca ctcgggccgt gagtgggtag ggagagggga aaagaggggt gagccaggga    4440
agatagcgca gatgccttgc agggtcttgg cgtgttgctc ggttggtaag agtgggtgca    4500
caaaggcctg agtttgattc ctgcactggg caaggtggtg cacatgtaac cttagcgttt    4560
gggaaggaga ggcaggagga ctgtattcaa ggtcatcctt ggctatacag tgagttcaag    4620
gccagcctga cctacatgac atcttgatga agaaagaagg gaaacttggg tcaccctgaa    4680
tgtctcgggc attcggacag aggtcagcgg cttcagaggg aacagagaat gacaggagcc    4740
tcctggggga agggtcagtc cccaggggct cgagtcaagg gttattaggg tagaactgcg    4800
gactagccag ttaagggagg tgcccacctc cagctcattc tacctgttgt tctgtcctcc    4860
ccaaaactta aagatccttt tacaacctct caccegacag gagaggagcc aaaaggaaga    4920
agagaggaat ctggggtgcc aggccccaac tctccaccca caacagaaa ccagtctatc    4980 aaagccatac ttaagagtgt acgtgggccc ggggtgtcct gcctaccctt cctcacccttt    5040 ctttctcctt ttgctgtttc taccttatac cacttccctt tctgatctaa gactgggctt    5100
tctcctgtct tcctatgaat gctgtgtgtg tgtctgtctg tctgtctgtc tgtctgtgag    5160
```

```
atttaaaaaa aaaagattta tttatttatt atacataagt acattgtagt tgtcttcaga    5220
caccacagaa gagggcaaca gatctcatta cagatggttg tgagccacca tgtaattgct    5280
gggaattgaa ctcaggacct tcaaaagagc agtccgtgct tttaactgct gagccatctc    5340
tccagcccca tctctgagat ttatttattt atttatttat ttatttattt atttattgtt    5400
ttttcaagaa cagggttttg atgtagccct ggttgtcttg gaactcactc tgtagaccag    5460
gctggccttg aactcagaga tcagcctgcc tctgcctcct gagttctggg attaaaaagg    5520
ggtatggtac cagtgtctgg ctctttggtc ttttgtacac agagccatga caacctaggg    5580
ccctgtatga atctctcttc tcttctctct ctccagatct gtgtcccggc tctgtctgtc    5640
tgcttcatct tcacggttac cattgggttg ttccctgctg tgactgctga ggtggaatcc    5700
agcatcgcag gcacaagtcc ctggagtatg tgtgtcccTT gcccctccc agccccccc    5760
cccagccccc gcacttccct cctaggacgg attcacccag agtctaaagt ggaatcatgg    5820
gtggggtatg ggcaacctct ggggctccct ctgcccagct ggatctacac gggcctacta    5880
gacaccctgc cattggatgg aaacctctga ggcagaatga agagtcctag gcccagagag    5940
ggccagttgc taagtcttaa gtctctttcc tagaaagcta cttcattccc gtggcctgtt    6000
tcttgaattt caatgtcttt gactggctag gccggagcct cactgctgtc tgcatgtggg    6060
tgagtacagc atgggcggca gggctgtggg gttcaggtgt ccagctgagg ccaagaggga    6120
acccaagaaa gtatggtggc tgcagtgtgg ctctgtgact gatagagggc ttgctagcat    6180
gcatggcccc tgggtcccat ctgtaaaact gcaagaaggg aaaatggagg gggtggggca    6240
gtggctcaac aggttaagag cactgactgc tcttccagag atcctgagtt caattcccag    6300
cagccacaac ggtggctcac aaccatctgt aatgggatct gatgccctct tctggtgcat    6360
ctgaagacag ctaccagtgt actcatcaaa acaaaaaac ctgcaagaag gaaaaaatac    6420
cgtgtactac tcataactta tgtgtaactc tgtgtacaag ttcattcgtt tgtttatctg    6480
tctgtagagg cagggtctct gtgtgttgct atctgggaat ttactctgta gaccaggctg    6540
gcctggaact cagatctctt tactccctgc ttcccaagtg catgtgccac cagctaagac    6600
tttcaaatta tgtgtgtgtg catgtgaatg caatgcccac agaggccaga agagggcacc    6660
agatcccctg gagctggagt tagaggagct tgtgaggact ggaaactaaa cctgggtctt    6720
ccgcaagagc aggactctta actattgagc cattcctggc ccatgcgtac agttcttagg    6780
tgtgtagcct ggcagaggtg tgcatgtcat ggctcccacc tagatggaaa gatacatctc    6840
gacatatcat aggcaccact gcgccccTag caatcagcac ccccaaaggc acccaggcct    6900
agtggtttta tccaagtccc caggggcccc aggagaccgg gaggactgac atgcgtgctg    6960
aagccttgcc tgtgtccgca gcctggccag gatagccgct ggctgccggt tttggtcgcc    7020
tcgaggattg tgtttattcc cctgctgatg ctctgcaacg tgaaggctcg ccactgcggc    7080
gcgcagcggc accacttcgt ctttaagcat gacgcctggt tcatcgcctt catggctgcc    7140
tttgccttct ccaatggcta cctcgccagc ctctgcatgt gcttcgggcc caagtgagtc    7200
gggccatgag gggatttggt gacatcaggc aggacttaca gggagatggc agtaggagag    7260
tccctcccca tctcatagct gcacggagtt ggagttgctg gggggtttta aggggcagtg    7320
gaggtaaggg cttgctaatg tgctcctgct gagctgtgtg ggaagggatt aagacagggt    7380
ggaggatggt ccctagacac agtctcccaa gaagtgggct gggattggga gtgttggaag    7440
gtttgggggt gggggacag ggctgggctc agcttgccta agattaccct gcctttcctt    7500
ttaggaaagt caaaccagct gaggcggaga cagcaggaaa catcatgtcc ttctttctgt    7560
```

```
gtctgggcct ggctctggga gctgtgttgt ccttcttgtt aagggcactt gtgtgaccct    7620
gtggggacag aagaactaca ctgcctgctt cctgctcact ccttccctg ccagggacga    7680 gcaggggtcg agaggggctg ttcttctagc tgacttctgc tttcctctgg actgtgcttc    7740
gcccagctgt ccaggagcca gcgatggcct gcgggtggac ttggaattca gggtcagaat    7800
ggcaagggct caatggcctc tgactgacag ctccgactga tgcccgctta ctccaagcac    7860
aagagactcc agggccaaga gagatctgtc cgcctgccta tcacaggata gggcggaggc    7920
ggatggctga ttggtgtcgt gtgacctgat gtccctcccc ttgcccttct tccttctgtg    7980
cctgttccat gtccccagcc cttgtcattt tactgccttt tttatactga cagaaaccag    8040
gtgccttcag aggccatctg attaaataaa cattttttt ctccatagct ctgtgcatcc    8100
ttccaaggtt taactaactc cttggagagg agagaaggct ggcagcctga gtctaggttt    8160
ctgcaatgac ccaagcctgg gcctgggtat aaggggagg atgcagtcct tcagtctcag    8220
aggggctgca gcgcccccta ctggggacac agggaagaga caggcctgga gccaagacgc    8280
cacccagact gtggcccaga tttagaaaga tgtagcccga gtggtcttca cattccataa    8340
gtacctgaag gtgccttga accgcttcct atgtgctggt actgcagctg tgtaccacca    8400
tgtcctggat ctagggatca agtccagggc tttgtgcatg ctaggcaagc gctctgctag    8460
ccgagctatg ccccagcccc tcttctcat ttcaagggcc tggaaatgga ggcagctttg    8520
tcttccccgc taccttcccc tcccccacca cgctgtcctc agctcctgga atgaactctg    8580
ccaaactggc cagccccacc cccagctcct ggccatactc ccacatccct gggcaggaaa    8640
aggctgaggc ctgggctctc ccttaccttg gctccaggcc ctgacaccaa agcccaggct    8700
gccagacttc ctggagaaca acgggcctat gtgtcctcat gttggcgttg gacctccccg    8760
ttcttcagcc atactgtggt ctgaggaagg gtgtgttggt atgggatgtg agactcctc    8820 ggtggagggg gcgctgatgc tccagctcag gactgactgg aactgagagg aacactctgg    8880
tcctaagtgc cccttgtccc cagccctggg agacagaagc ttttgccccg ccccatctcc    8940
caagccccct cccccaaggc tgcatgttct ctcatcctct accagctgat ggctacaggg    9000
gtggccctac tgttgggact tcctttttc acagaaattt catttaaact agtggttctc    9060
aaacttccta gtgcttcaac acttttaaca cagttcctca tggggtgagc cccaaccata    9120
aaattatttt cgttgctgtt tcataactgc aattctgctg ctgttatgag tcgttctata    9180
aatatctgtt ttcccatggt cttgggtgac ccctgtgaaa gggtccttag acccaccccca    9240 aaggggtcac aatccacagg tggagaactg atttaaacaa aggcttcaga ctttcgtgag    9300
aagtagtgta ttttcttttg ttttgtttt tttattgag acagagtttc tctctaacct    9360
tggctgtcct ggaactctat atatagatca tgctggcctt aaactcagag atccacctgc    9420
ctctgcttcc tgagtgctgg gatttaaagg tgtatacaac catagcctgg ttgtttttca    9480 attcttttc ttcttcttct tttttttt ttaaaattaa tgtgcattgg tgttttgct    9540 tacatatatg tctgtgtcag agcatctgac cctctgggac tggagttaaa gacagttgtg    9600
agctgccacg tggctcctgg gaattgaacc caggttcct ggaagagcag ccaatgctct    9660
taaccactga gccatccctc cctccattcc ccagttgctt gttatcaatc cttactaagg    9720
tcaagcttgg tggtgggttg gaggttaaac gcatcactgt accaagcacg ggtgtccatg    9780
actagtttgt caaaactgca tacatgcctc agcagtggta gctcacacct ttaatgctgt    9840
cgcttgggag gcagaggcag gcagatctgt gagttcaagg ctgttctggt ggtctacagt    9900
```

```
tcaagttcca ggaaagcagg gctatacaga gaaaccatgt ttcaaacaac caaaccaatc    9960
aaccaacaaa caccccccagc atacatctgc tctgttagaa atggccttcc tatgctatct   10020
ggttcaaact gcctgttccc taactaggag gcaagctaaa aaatacaaac aaagtctctc   10080
ctgcttgccc ttagctccaa tgacttgact tcctcctcgt actgaaattc acgagaggtt   10140
tagcagcttt cttttcaac actggtagcc tctggggaac ccgaattttt ttcccaaact    10200
ctaacttcct acctcagtc tggctcctgg gttccctcta atccacccc gtgtgtggcc     10260 acaaggaact ggtgagagtg taattactca ttttccaaag atttatttta tgtatgtgag   10320
tacactgtag ctgtcctcag acataccaga agagggcacc agaccccact acagatgctt   10380
gtgagccacc ttgtggttgc tgagagttga actcaggacc tctgggagag cagtcagtgt   10440
tctcaccgct gagccatctc tccagccctc ccctttcccc gccctccccc cttttttga    10500 gtcagttttt ctgtgtagcc ctgactgtct tggaacttgc tctctagaga tcctcctgtc   10560
tctgcctcct gagcactagg aagtaaggta tgtgccaccg ctgtcctgcc tgtaactact   10620
tttttactgg tcttagcttt tccgaagagt gttgaagatt cagcaagatg gctgtgcatc   10680
ctggctggca tggtactcac tatggctact ctcccgaggg ctaggattga ggcatggcac   10740
catcacaagg gaattttgt gcagtgatta caagggtgtc tctcccttcc ccaaagttcc    10800
ctgatgtttg actctctacc attggcttgt gaaagtctct ccccgttctg cgccctaggg   10860
cgttggtgat atgacttatc tcctgtcaca ctttgagctg aaagtgctcc ctggttccta   10920
ggggtgatct gaagatattc atgagcatgt gacgcttgtc aagtttaccc catctcatgt   10980
cccacccacc tatgtggtga cattcattgc ttgaatgtcc ttgaatgtta gtaggctctt   11040
aactctggca ctgacctgaa tgggtgtcgg aggggggcat ttatgattct gccaccagtg   11100
ttgaagaaaa tatctggaat ataatcgttt tctcccaaag tctttttaaa aaaaaaaaac   11160
aattttatgt acattggtgt tttgcttgca tatacatcta gttgcagaca gttgtgaact   11220
accatgtggg tcctgggaat tgaacccagg tgctctgtaa gaggagccag tgctcttaag   11280
aaccactgag atctctcttc agcctcccc acctcaaact cttctaatgc atagccttgt    11340
ccctgagtaa ctacactgat ggcttctgac cacaagtgag ctctgtaggc accaccttga   11400
aggtcaagga gagtcaggac ccactgcagg ttacttcctc ctcctgggag ggagggaagc   11460
ttgagcaagg gactgccagg tatccttcct gccacaatgt tgtacatcac ttcctgacgt   11520
ctctggtctc tgttcaaagc agtctactga actgctgttt tctggatggc tgccactgat   11580
gtaaaagtcc tttactgtgt gggtcaatat ggtgaagatt gcagagcacc cccttgtggt   11640
cataatccac cactgcaatt gagcagacca gtgactgcaa ggatgtctgc ttttccggt    11700 gtttacatga gaagactggt aaattctacc tttgtttaaa aacctctagg tatagaaagg   11760
aggagatgtg aaaacaaggg tacaaggaag tggagagaca ggagaacctc aattctcacc   11820
taaactaaat tgttcgtaga attaagttga tagcaactag gaatggatgt gagcagagaa   11880
ctgtgctgtc tggctgtgca aacaggaaag tgtgacggca ggagattggc cagaatgatg   11940
tcacagctag gctggcagtc catacaggtc cctggggacc gtagtgttcc tagggtggga   12000
atggccagag tcctcaactc cttaacccat cgatgactgt gttctagcca ggctagaaaa   12060
acaggcttac cctgtttgtt ttcatggtgt gcccattcag ccctctaccc ctcccggtag   12120
tcccgagcac gcggctttct gggtcctagc tgtggggaag tgctaagtgt ggatcagcag   12180
ggcccgagac agcagcacgc tcttccttgg ccttttcagg gggtagggcc acttggcttg   12240
aattcagacc cacagagtca tctgtcttgg gcccagctgt tcaaaccagg aaaagccatt   12300
```

```
ctctgtggct ccggtttctc gccagggagt gggaacatcg ggcaggctct gctaagggaa   12360
ttaaaccacg tgcctagagt tggtacaggg taagaagata ctatttattt atttatttat   12420
ttatttattt atttattaga gttggtacag ggtaagaaga tactatttat ttatttattt   12480
atttattggt ttttcgagac agggtttctc cgtgtagccc tggctgtcct gaaactcact   12540
ctgtagacca ggctggcctc aaactcagaa atctgcctgc ctttgcctcc caaatgctgg   12600
gattaaaggt gtgcaccacc actgaacagc aagaagatac tcttaatgct gctgccccgt   12660
aaggtcccct ggtaaccagg atgagtctcg gcatcctggg gtggtccacc taagctacct   12720
gctcccctcc cccacacctc tgggcgctgg gagcttgaga accaagccat acttacctag   12780
ttacctcttc cagtgtggat tactgcttgg gctcttgctg tcagtcagtc agctaggaat   12840
cccaagactt tggagacggg atgcaccctg ggtttgggt aggggctgct ggagctaagc   12900
aaagtatgtg atgtcacagg ttccctgccc cccacctcaa tgggagcacc ttctccactt   12960
gcttgtgagg aagtcagact gtgggaccta taccactgca cctcgtgccc aggtcacctt   13020
acaccaggta ctcagagtct ctcatgtgta aagcagggaa ggtaacaggt ggagagccac   13080
agagatcatg aatgactcag ctctcccata gctggggact gggactcctc gatgcgtgcc   13140
tggtttactc tggaaaacag aaaggctaaa ggatgaaaaa gggattctgt aggcaggcat   13200
gacgatgcgg tgcgtgcctt taatcccagg actcaggaag cagaggcagg gggatttctg   13260
tgagtttgag gccagcctgg tctaacagag ttgagttcga ggacagccaa ggaaggctac   13320
actgtgaaac cctgactcaa aacaaaaaca aacaacagc aacaaaaaga ttctgtcagt   13380
aaactacagt ggaacgaaag gcttgggtcc ttgatgtgta tctctgccac ccagtcccag   13440
agctaaggac acaggcacag agcacagcaa acagagatcc agtcagctga dacccgtgtg   13500
cagaaaggga gtcgccagtg cctggggcag aacaggaggc aggcagaacc caggacaggt   13560
tgtgtgtatg gcgccagcct gcccctcccc tgaccagtca ggtccagaat aaattctgtt   13620
caggctactc tttagtttcc cttgaagggg ctgggagcac tggaggtcaa gtctgagagg   13680
actgtggtag aagagaaggc agggctggtt agttagttac ataccttaga gacacaggtc   13740
ttcagaacac ggaaaaatgg tcccgagtgt gttaatgggg taccctgatg aggtcccgtt   13800
tacattttga gatagggtc agtcacaaat cctgtccttt tttttttttt ttttggtttt   13860
tcgagacagg gtttctctgt gtagccctgg ctgtcctggc attcactttg tagaccaggc   13920
tggcctggaa ctcagaaatg cctctgcctc ccgagggctg ggattaaagg catgcgccac   13980
cacgcccggc tctcttttta catttctctt ttaatcctgt ccctttttata accattctgc   14040 ctttagcgat tctgttcttg tccataactt tagctatcgg cttggttagg cctgggtctt   14100
caatccaaat ccagtctgga tcgcccctc ccatccctct gcctgttgga tagctgtttt   14160
tgtcttgttt ttatgatttg cttattatgt atacagtgtt ctgcctgcat gtacacatgc   14220
aagtcagaag agggcgccag atctcattac agatggtcat gagccaccat gtggttgttg   14280
gggattgaac tcaggacctc tggaagagca gatagtgctc ttaacctctg ggctggcctt   14340
gaactcagaa atcctcctgc ctctaccctcc cgagtgctgg gattaaaggc gtgcgccacc   14400
actgcctggc ccctgagctt tacttgagca tactaagtgc atagaacctc cagcccactt   14460
gggcccttaa caacccaagg atgaacctgg gtggcctaag gaaacagaca ggcttaggac   14520
ccatggagtc agggtagtac acagctctgc tctcagaaga ttaaaaaga aaaaaaaaa   14580 aaagccaggt gactcccagt gacctagaaa ggaagccctt caggaaggga ggagtgtggg   14640
```

```
cacagaaagc agccctgcag gctggggctg ggttataaaa ggctgcgggt gccatgctga    14700
gctctatcct gaagagtggg aaaggcccct agagacagcc ttaaaacccc ctaggcctgg    14760
aggggcctga gtcccagtag taggctgcaa ccaccattgt tcctaagata gggtttatac    14820
ttgatccggc agaagctgtt ggagagtggc cagctaacac agctcgtaac aggtcactac    14880
ttgccgctgc tgggcccac gcttggttat ctacaccctg taggcaaaga attctcctta     14940
caattggtag tgaattgggg gtaaaatcaa ctccttcact ctccacacct tgctttttt      15000 tctttgtttt taaccatttt ccccaatgtt gtccagacta ctctgcttca gtgtccagaa    15060
tgctgggaca aacaaatgcc accattcctg agttaaagat agtgtattga taagggaaaa    15120
tgttacattt gaattttagc ccctataaag ttttgaatgt gccttgccag cctgcctgtg    15180
cgttgtgtac acataatacc tttgggggca ggagaggtga atatttctct agaactggag    15240
ttacaggtag ttgtgagcca caccccacac cccggctctg ggaatcttac ccccatcttc    15300
tgcaggagca agtgttgttt ttttttttt ttttttttt tttgagacag agtctctgta      15360
tagccctggc tgtcctggaa ctcctttgta gaccaggctg gcctcaaact caggaatctg    15420
cctgcgtctg cctcccaagt gctgggatta aaggcgtgcg ccaccatgct cggcaagaca    15480
gagtctttgt atgtagtcct cgatgtcctg gaacttacca tgtagacgaa gctggcctca    15540
cactcagaga cccaccctcc tttgcctcct gggtgctggc atcaaaggtg cttacaacca    15600
ccccgagcct gtctacaggt gtcttgcttc catgtgtgtg tgccatgtgt gctccggaag    15660
ggcagccagt gattttagcc cctgattcat ctctctagcc ccatcatcgt ttttttttt     15720 tgtttgttta tttattttat tttattttt tgttttcga gacagggttt ctctgtgtag      15780
ccctggctgt cctggaactc actctgtaga ccaggctggc ctcgaactca gaaatcctcc    15840
tgcctctgcc tccgagtgc tgggattaaa ggcgtgcgcc accactgccc ggcatcatcg     15900
ttgttttaag gcagggtctc actccataga ccaggctagc ctgcagaaca ctgcatagcc    15960
taggctgccc tggaactcat ggtaatcctc tacccaaat tctaaatgcc ggaaaagtaa     16020
atatgagcta ctaaacccag actcgagact atgaatattt gaaaattttc tgggtaagcg    16080
tgagaagata aattacctag ccattgggtt tactaaatca agcctgataa gtgccttatt    16140
aaaaaaggca aacggaaagg tggagggacg gctcagcggt taagaccaca tactgctctt    16200
gcagaggacc cagcctttat tttttattt tttatttttt ttgttttttt ttttttgaga    16260 cagggttct ctgtatagct ctggctgtcg taactcactc tgtagatcag gctggcctag    16320
aactcaaatc ggcctgcctc tgcctcccta gtgctgggat taaaggcatg tgctaccact    16380
gcccggcttg gacccagcct ttagttccca gctcccacat ccacctggaa ctccatatct    16440
gacctttggc atcacatgca catacacata attgagaata aaataaatac tatgggggctg   16500 gagagatggc tccgtggtta agaacactgg ctgttgttct tccagaggac ctgggttgaa    16560
ttcctggcac ccacatgggg gctcagaacc atttgtaatt tccaattccg ggggatctga    16620
agaccttcat ctgacctctg tgggtaccag gttagcatac agggtgtact tacatacatg    16680
cagccaaaat actacacata gtgtatgtgt gtacatgcct ttaaaatgca acacagctga    16740
tatggtgata catgtattgt gatcagaaat aggaggatga gaagcaggcg gatttctgag    16800
tttgaggcca gcctggtcta caaagtgagt accaggacag ccagggctat agagagaaac    16860
cctgtctcga aaacaaaac aaacaaaaaa agaaatagga ggatgagaag ttcaaggtca     16920
aaccaggcac tggaggcaca tgcctttaat cccagcattt gggagactaa ggcaggctga    16980
tttctgagtt caaggccagc ctggtctata aagttccagg acacagagaa accctgcaaa    17040
```

```
aaaaaaaaaa aaaaaaaaaa aaaaaaaaaa aagaaagaaa taccataaaa actaatattc  17100
attattaaac gttcgtgtgt gcgtatttcc tggaggagct ggagttacag tggctgtgag  17160
ctggcagagg tgcccgggtg gaacttcggc cctcaagacc agttagtgct ggaccttctc  17220
tctaaccccc aggccttta taaaaaggaa tcttatcatc ttatcacccg ggtgtgaagg  17280
tgcgccttca atcccagcac tctggaggta gtgacacacc tactccaaca aggccatact  17340
tcctaatagt gccactccct aggcatatac aaaccatcac ccccccccc caaaaagag  17400 aacttatctt gtgtgtgtgt gtgtgtgtgt gtaagtatgg cacaaggac acaatcaatg  17460 cacatgaaga agtccaagga caacttgagg agtcagtttg tccctttcac catgggatct  17520
gtcatcaaat tgaggtctgg gctgtcctgc ttggaggacc agggtaaatg cttttaccca  17580
tggagtgagt catcgtgctc cctagccctc ctcctccttg gttgttgaga tagagtctgt  17640
tagtataacc cttagctggt ctggtaccat gtacttggaa ttacaagcat cctcttgtct  17700
caaccaccct aatactgaca cagacatgtg ctgccacagc aaggtaaaag gtatctctag  17760
gttgatataa aatgattttt ccactttatg caacaggatt tcactcctag cccacgctgg  17820
cctgtaatac gcgctcctct cctctcctcc gagctgggat cgaagctgtg ccccccaccc  17880
ccatgcctgg tgcccgttcc ccaactgaga acgtcccagg aagctgctgt ggagccttgg  17940
tcctgtcatt gctggggac agccaaaggg aaactgcaga ggagaggttc ctggcctgct  18000
tcagactagg gttccagcaa gagagagtac actcctgtcc ccattctact ttcagaacag  18060
gaatggccct gggtttagtg acccccattat tcacagagac cttcattttc ctgtccatga  18120
aatatacaga gtagctttca accattcaga ggccaaggag aggtagtcag tgctgtttgt  18180
gaactaggga atccaggatt ggtgggtctt agggaaacac taccctggag ctaaatgtcc  18240
agcccaggga tcagctaggc tccttttgct gagagggttt gagtgttgaa gtttctggtt  18300
tcagattagg aatcaatgca acaccctagg gccttctgag caatcctacc cagtgtctcc  18360
tcatatattg atttctttat gggcttcaca cacacacaca cacacacaca cacacacaca  18420
cacacacaca cacagaatta aggagaggct aacagacagt gcaggatggg atgataacag  18480
acgaagtaga cagaggcaag gagaaagcaa ctactgttta acaatgaatg cacattagac  18540
agactgcagg caagcaccgg gaacaaaggt gtgggcggtg gtgtggggac acaagccagc  18600
atgagctaag atagcagagc actgagtgcc catcctctac tggagggctc atcagtccaa  18660
caagcttcca gatgcagcct tggaaaaagg caaggctaga ttgccagctg aaggacatgg  18720
caggccacct ttagaacaga ggcactggca caacttggtt ttctggctcc tggaactggg  18780
ccaacctgtg accagcacct tcatgcggat gcctagaact ccagcttctc tgaaaagact  18840
gggacctgct cctctctagg tccaaagagc tgcatgcagt agggaagagg ctagagaagc  18900
gaaaccagct tgagaaacag cttgtgctca cataggagg gcgcacgtac ccgcgcgctg  18960
tgtacgtggg agaccgggga ggctgagggg tggggagtgt tctacccagt agcgcaagct  19020
gctagctcgg ttctctgttc actagaaggt gtccgcagtc actcaccccc acagccccg   19080 tgccctgtga ccgatccagg tcagctatcc ctccctctgc gctccactcc cccactgtta  19140
tgtgggcctc ttagggccac gcgtggaggg tcgttcaacc ctggcccacg gtaggcagac  19200
ttggggaaaa tttcttccca gggtaagatc aaggtagggg aaaaaaaaa aaaaaaaag   19260 ccacccagcc aagcggcgac gaagacactg ccccgccgc agcaggggag gtggagccta  19320 gggggaggg gtggagaccg ccgagacagg cctagaaact gctggaagaa atcgcagcac  19380
```

| | | | | |
|---|---|---|---|---|
| caccgctgct | gatccttccg | ccgcaggccg | ccaaagagtc | cctaccagcc caggcccgtg | 19440 |
| cccctcccct | cggggaaagc | ggctcccagc | ctgaagctgt | gctgtacccg ggagggtggg | 19500 |
| gatgggggaa | tcgggggcct | ccttaaagtt | ggacaaggaa | tttatcatcc tttctcttg | 19560 |
| atgtgcgatt | tgtagggaac | attctagtaa | gatcgggtct | ggaaatgcca gccgagttgg | 19620 |
| ccacctccat | tctctttcag | tcccctgagt | tctggactct | tgggggtgg ggggtggaa | 19680 |
| gcgcctacct | tgagttttct | gaggcagtcc | gtagggtatt | cgcccgcaga tacatcccta | 19740 |
| attgcatatg | catgctccct | gctcatcttg | agggggaca | tgtcctactc ctgcagaaat | 19800 |
| gggggatgtg | caaaacgata | ttgaattggc | cttgactcag | gaaccaggcc cggggtcccg | 19860 |
| ctcctccccg | cccctccac | gatctgctac | catgacgtca | aggtgggcgg gcggcggcag | 19920 |
| gtgcgtggcc | cgcagccact | cctttaaggc | ggagggatcc | aagggcgggg cccgggctgt | 19980 |
| gcttcgcctt | atatagggcg | gtcggggcg | ttcgggagct | ctcttgagtc accccgcgc | 20040 |
| agcctaggct | tgccgtgcga | gtcggacttg | gtccgggccc | accaccctgc tctgtactac | 20100 |
| tactcggctt | tcccgtcaag | g | | | 20121 |

<210> SEQ ID NO 146
<211> LENGTH: 1813
<212> TYPE: DNA
<213> ORGANISM: Artificial Sequence
<220> FEATURE:
<223> OTHER INFORMATION: Synthetic mouse 1.8kb hsp90ab1 promoter - enhancer design

<400> SEQUENCE: 146

| | | | | |
|---|---|---|---|---|
| gctagcaaca | ccctagggcc | ttctgagcaa | tcctacccag | tgtctcctca tatattgatt | 60 |
| tctttatggg | cttcacacac | acacacacac | acacacacac | acacacacac | 120 |
| agaattaagg | agaggctaac | agacagtgca | ggatgggatg | ataacagacg aagtagacag | 180 |
| aggcaaggag | aaagcaacta | ctgtttaaca | atgaatgcac | attagacaga ctgcaggcaa | 240 |
| gcaccgggaa | caaaggtgtg | ggcggtggtg | tggggacaca | agccagcatg agctaagata | 300 |
| gcagagcact | gagtgcccat | cctctactgg | agggctcatc | agtccaacaa gcttccagat | 360 |
| gcagccttgg | aaaaaggcaa | ggctagattg | ccagctgaag | gacatggcag gccacccttta | 420 |
| gaacagaggc | actggcacaa | cttggttttc | tggctcctgg | aactgggcca acctgtgacc | 480 |
| agcaccttca | tgcggatgcc | tagaactcca | gcttctctga | aaagactggg acctgctcct | 540 |
| ctctaggtcc | aaagagctgc | atgcagtagg | gaagaggcta | gagaagcgaa accagcttga | 600 |
| gaaacagctt | gtgctcacat | agggagggcg | cacgtacccg | cgcgctgtgt acgtgggaga | 660 |
| ccggggaggc | tgaggggtgg | ggagtgttct | acccagtagc | gcaagctgat agctcggttc | 720 |
| tctgttcact | agaaggtgtc | cgcagtcact | cacccccaca | gccccgtgc cctgtgaccg | 780 |
| atccaggtca | gctatccctc | cctctgcgct | ccactccccc | actgttatgt gggcctctta | 840 |
| gggccacgcg | tggagggtcg | ttcaaccctg | gcccacggta | ggcagacttg gggaaaattt | 900 |
| cttcccaggg | taagatcaag | gtaggggaaa | aaaaaaaaa | aaaaagcca cccagccaag | 960 |
| cggcgacgaa | gacactgccc | ccgccgcagc | agggaggtg | gagcctaggg gggaggggtg | 1020 |
| gagaccgcca | agacaggcct | agaaactgct | ggaagaaatc | gcagcaccac cgctgctgat | 1080 |
| ccttccgccg | caggccgcca | aagagtccct | accagccag | gccgtgccc ctcccctcgg | 1140 |
| ggaaagcggc | tccagcctg | aagctgtgct | gtacccggga | gggtgggat ggggaatcg | 1200 |
| ggggcctcct | taaagttgga | caaggaattt | atcatccttt | tctcttgatg tgcgatttgt | 1260 |

-continued

| | |
|---|---|
| agggaacatt ctagtaagat cgggtctgga aatggcagcc gagttggcca cctccattct | 1320 |
| ctttcagtcc cctgagttct ggactcttgg ggggtggggg ggtggaagcg cctaccttga | 1380 |
| gttttctgag gcagtccgta gggtattcgc ccgcagatac atccctaatt gcatatgcat | 1440 |
| gctccctgct catcttgagg ggggacatgt cctactcctg cagaaatggg ggatgtgcaa | 1500 |
| aacgatattg aattggcctt gactcaggaa ccaggcccgg ggtcccgctc ctccccgccc | 1560 |
| cctccacgat ctgctaccat gacgtcaagg tgggcgggcg gcggcaggtg cgtgccccgc | 1620 |
| agccactcct ttaaggcgga gggatccaag ggcggggccc gggctgtgct tcgcctttata | 1680 |
| tagggcggtc gggggcgttc gggagctctc ttgagtcacc cccgcgcagc ctaggcttgc | 1740 |
| cgtgcgagtc ggacttggtc cgggcccacc accctgctct gtactactac tcggctttcc | 1800 |
| cgtcaaggct agc | 1813 |

<210> SEQ ID NO 147
<211> LENGTH: 1813
<212> TYPE: DNA
<213> ORGANISM: Artificial Sequence
<220> FEATURE:
<223> OTHER INFORMATION: Synthetic human 1.8kb hsp90ab1 promoter-
      enhancer design

<400> SEQUENCE: 147

| | |
|---|---|
| gctagcctgc ttcagcctcc caagtagcgg ggactatagg cgcgctacca cgcccggcta | 60 |
| attttttgtat tttagtagaga acaaggtttt caccagagtg gccaggctgg tcttgaactc | 120 |
| ctgacctggt gatccgctgg actcggcctc ccaaagtgct ggaattacag gcatgagcca | 180 |
| ccgcgcccag cccccttttt tttttttttt tttttttgag acggagtttc tcttttgttg | 240 |
| cccaggctgg agtgcaatgg catggtctca gctcactgca gcctctgcct ccagagttca | 300 |
| agcaatcttc ctgcctcagc ctcccaagta gctgggatta caggcatgtg ccaccacgcc | 360 |
| cagctaattt ttagtagaga cgaggttttt caccatgttg gccaggctgg ttgtgaacta | 420 |
| ctgacctcgg gtgatccacc cacctcggcc ttccaaagtg ctgggattac aggtatgagc | 480 |
| cactgtgccc agcagagaaa gtggaatttc tatgctggtg taacatttga gattttccca | 540 |
| tttagaaagt cttcaggaag ccgtcgagtc ttgacacaga aaggatccag ctcagggaa | 600 |
| gcccatccac aggagtgatt cctgctttgg atttaggtcc taggggtgag atcacatccc | 660 |
| tgctccattt ctggagcaga aagggagcta gtgcagcaag gactctgagt agacgggcct | 720 |
| tgggagtcac tgaagccact tccctgttga cagaatgtgc acactgactt tcatccgctc | 780 |
| acaggagagt gagagtttgt gaatgctctc tgtgaactgg ggagcagatt tttaatgagc | 840 |
| tctgcttaga aggagaggac acgttaaggg atcacgctcc cactggtttg cggttttggt | 900 |
| caggaataga gcacccaacg ccccttctta tagacttctc ccagccatag cttttttgca | 960 |
| gaccataatg aaagggagaa aggatatcca atcgggatgg tgatggcagg catggcgaag | 1020 |
| tggacaggga caaagaagag gaaagcaagg gacacccttt gttctttggt attcaacaca | 1080 |
| tgaacaaaac ttgttaacga atcgtagact gggtaacaac agggctggtg agggaggacg | 1140 |
| atgtgggtgg ctgtgtgggaa actcttccca agcatcccag gggtgggcca ggaaggggag | 1200 |
| cagatggaca tctacagggc acagagcagg gagtggctat tctctcctgg aggggttgtg | 1260 |
| ggtccagcag gctttcggat gaggccttgg aaaggcaagg acagcttgcc aactggaggg | 1320 |
| caggcaaaac ggctgagcca ggccagacac ggcagctcac tggccagggg catggcctag | 1380 |
| gggctctggt gccaaggctg aaggggaaca acttggccag ccgctctgtg gccggcatcg | 1440 |

```
tcacgcggcc tccaagagct ccggctgccc tgcactggtt cccagagact ccctccttcc    1500
caggtccaaa tggctgcagg agcgaagtgg gcggaaaaaa agcgaaccag cttgagaaag    1560
ggcttgacgt gcctgcgtag ggagggcgca tgtccccgtg ctccgtgtac gtggcggccg    1620
caggggctag aggggggtcc ccccgcagg  tactccactc tcagtctgca aaagtgtacg    1680
cccgcagagc cgccccaggt gcctgggtgt tgtgtgattg acgcggggaa ggagggg tca   1740 gccgatccct ccccaacccct ccatcccatc cctgaggatt gggctggtac ccgcgtctct   1800
cggacaggct agc                                                       1813
```

<210> SEQ ID NO 148
<211> LENGTH: 1813
<212> TYPE: DNA
<213> ORGANISM: Artificial Sequence
<220> FEATURE:
<223> OTHER INFORMATION: Synthetic human 1.8kb eno2 (pNSE) promoter - enhancer design

<400> SEQUENCE: 148

```
gctagccata ccttgaacgc ctggacaagg aattctatga ggaggaggaa cgggctgagg      60
ctgatgtgat tcgacagagg ctgaaggaag aaaaggagca ggagcctgag ccccagcgtg     120
acctggaacc cgaacagtca ttgatctagc agcagttcta gcctctaaag atagtaagga    180
agcctgcagg gaggcagtgg gaggaggcca agggctgggc aggtagggga agaggcaaga    240
ggggaagctg ctgcagaagg aggtgggaga ggaaagcatc agacaagcag gaccc ttaaa   300 gagaggaggg ttaggagtca gggagaggaa aagggaccca aggggcctgg gaccagctga    360
gaaagactta ggaggccaga agagtaagtg aaaagaattg gggtggcagg cagaggagtt    420 ggtgggggggt ggggcagcca tacctgacac agagtgaagt cggctaggaa aggacaggtg   480
tgggtgcatg gtaggggctg caggggaaag ttggtggtgt atgcagctgg acctaggaga    540
gaagcaggag aggaagatcc agcacaaaaa atctgaagct aaaaacagga cacagagatg    600
ggggaagaaa agagggcaga gtgaggcaaa aagagactga agagatgagg gtggccgcca    660
ggcactttag ataggggaga ggctttattt acctctgttt gtttttttttt ttttttttttt  720 ttttttttttg cgaggtagtc ttgcttagtc tccaggctgg agtgcagtgg cacaatctca   780
gctcactgca acttccacct cctgggttca gcaattctc  ctgcctcagc ctcccgagta    840
gctgggacta caggcgcatg caaccgcgcc tggctaattt ttgtattttt agtagaaacg    900
gggtttcacc acgttagcca ggatggtctg gatctcctga cctcgtgatc tgcccgcctc    960
cgccttccaa agtgctggga ttacaggggt gagccacagc gcctggtccc tatttacttc   1020
tgtcttctac ctccaggaga tcaaagacgc tggccttcag acctgatcag actcccaggg   1080
gcagccacca catgtatgac agagaacaga ggatgcctgt ttttgcccca aagctggaaa   1140
ttcatcacaa cctgaggccc aggatctgct ctgtgccggt cctctgggca gtgtggggtg   1200
cagaatgggg tgcctaggcc tgagcgttgc ctggagccta gccggggggc cgccctcggg   1260
caggcgtggg tgagagccaa gaccgcgtgg gccgcggggt gctggtagga gtggttggag   1320
agacttgcga aggcggctgg ggtgttcgga tttccaataa agaaacagag tgatgctcct   1380
gtgtctgacc gggtttgtga gacattgagg ctgtcttggg cttcactggc agtgtgggcc   1440
ttcgtacccg ggctacaggg gtgcggctct gcctgttact gtcgagtggg tcgggccgtg   1500
ggtatgagcg cttgtgtgcg ctggggccag gtcgtgggtg cccccaccct tccccatcc    1560 tcctcccttc cccactccac cctcgtcggt ccccaaccc  gcgctcgtac gtgcgcctcc   1620
```

```
gccggcagct cctgactcat cgggggctcc gggtcacatg cgcccgcgcg gccctatagg      1680
cgcctcctcc gcccgccgcc cgggagccgc agccgccgcc gccactgcca ctcccgctct      1740
ctcagcgccg ccgtcgccac cgccaccgcc accgccacta ccaccgtctg agtctgcagt      1800
cccgagggct agc                                                        1813
```

<210> SEQ ID NO 149
<211> LENGTH: 1801
<212> TYPE: DNA
<213> ORGANISM: Artificial Sequence
<220> FEATURE:
<223> OTHER INFORMATION: Synthetic mouse 1.8kb hsp90ab1 promoter-
      enhancer design - without flanking restriction sites

<400> SEQUENCE: 149

```
aacaccctag ggccttctga gcaatcctac ccagtgtctc ctcatatatt gatttcttta        60
tgggcttcac acacacacac acacacacac acacacacac acacacacac acacagaatt       120
aaggagaggc taacagacag tgcaggatgg gatgataaca gacgaagtag acagaggcaa       180
ggagaaagca actactgttt aacaatgaat gcacattaga cagactgcag gcaagcaccg       240
ggaacaaagg tgtgggcggt ggtgtgggga cacaagccag catgagctaa gatagcagag       300
cactgagtgc ccatcctcta ctggagggct catcagtcca acaagcttcc agatgcagcc       360
ttggaaaaag gcaaggctag attgccagct gaaggacatg gcaggccacc tttagaacag       420
aggcactggc acaacttggt tttctggctc ctggaactgg gccaacctgt gaccagcacc       480
ttcatgcgga tgcctagaac tccagcttct ctgaaaagac tgggacctgc tcctctctag       540
gtccaaagag ctgcatgcag tagggaagag gctagagaag cgaaaccagc ttgagaaaca       600
gcttgtgctc acatagggag ggcgcacgta cccgcgcgct gtgtacgtgg agaccgggg       660 aggctgaggg gtggggagtg ttctacccag tagcgcaagc tgctagctcg gttctctgtt       720
cactagaagg tgtccgcagt cactcacccc cacagccccc gtgccctgtg accgatccag       780
gtcagctatc cctccctctg cgctccactc ccccactgtt atgtgggcct cttagggcca       840
cgcgtggagg gtcgttcaac cctggcccac ggtaggcaga cttggggaaa atttcttccc       900
agggtaagat caaggtaggg gaaaaaaaaa aaaaaaaaa gccacccagc caagcggcga       960
cgaagacact gcccccgccg cagcagggga ggtggagcct aggggggagg ggtggagacc      1020
gccgagacag gcctagaaac tgctggaaga aatcgcagca ccaccgctgc tgatccttcc      1080
gccgcaggcc gccaaagagt ccctaccagc ccaggcccgt gcccctcccc tcggggaaag      1140
cggctcccag cctgaagctg tgctgtaccc gggagggtgg ggatggggga atcggggcc       1200 tccttaaagt tggacaagga atttatcatc cttttctctt gatgtgcgat ttgtagggaa      1260
cattctagta agatcgggtc tggaaatggc agccgagttg gccacctcca ttctctttca      1320
gtcccctgag ttctggactc ttgggggtg ggggggtgga agcgcctacc ttgagttttc       1380
tgaggcagtc cgtagggtat tcgcccgcag atacatccct aattgcatat gcatgctccc      1440
tgctcatctt gagggggggac atgtcctact cctgcagaaa tggggatgt gcaaaacgat       1500 attgaattgg ccttgactca ggaaccaggc ccggggtccc gctcctcccc gcccctcca       1560 cgatctgcta ccatgacgtc aaggtggcg ggcggcggca ggtgcgtggc ccgcagccac       1620
tcctttaagg cggagggatc caagggcggg gcccgggctg tgcttcgcct tatatagggc      1680 ggtcggggc gttcgggagc tctcttgagt caccccgcg cagcctaggc ttgccgtgcg        1740
agtcggactt ggtccgggcc caccaccctg ctctgtacta ctactcggct ttcccgtcaa      1800
```

| g | 1801 |

<210> SEQ ID NO 150
<211> LENGTH: 1801
<212> TYPE: DNA
<213> ORGANISM: Artificial Sequence
<220> FEATURE:
<223> OTHER INFORMATION: Synthetic human 1.8kb hsp90ab1 promoter - enhancer design - without flanking restriction sites

<400> SEQUENCE: 150

| ctgcttcagc ctcccaagta gcggggacta taggcgcgct accacgcccg gctaatttttt | 60 |
| gtattttttag tagagacaag gtttcaccag agtggccagg ctggtcttga actcctgacc | 120 |
| tggtgatccg ctggactcgg cctcccaaag tgctggaatt acaggcatga gccaccgcgc | 180 |
| ccagcccct tttttttttt tttttttttt tgagacggag tttctctttt gttgcccagg | 240 |
| ctggagtgca atggcatggt ctcagctcac tgcagcctct gcctccagag ttcaagcaat | 300 |
| cttcctgcct cagcctccca gtagctggga ttacaggca tgtgccacca cgcccagcta | 360 |
| attttttagta gagacgaggt ttttcaccat gttggccagg ctggttgtga actactgacc | 420 |
| tcgggtgatc cacccacctc ggccttccaa agtgctggga ttacaggtat gagccactgt | 480 |
| gcccagcaga gaaagtggaa tttctatgct ggtgtaacat ttgagatttt cccatttaga | 540 |
| aagtcttcag gaagccgtcg agtcttgaca cagaaaggat ccagctcagg ggaagcccat | 600 |
| ccacaggagt gattcctgct ttggatttag gtcctagggg tgagatcaca tccctgctcc | 660 |
| atttctggag cagaaaggga gctagtcag caaggactct gagtagacgg gccttgggag | 720 |
| tcactgaagc cacttccctg ttgacagaat gtgcacactg actttcatcc gctcacagga | 780 |
| gagtgagagt ttgtgaatgc tctctgtgaa ctggggagca gatttttaat gagctctgct | 840 |
| tagaaggaga ggacacgtta agggatcacg ctcccactgg tttgcggttt tggtcaggaa | 900 |
| tagagcaccc aacgcccctt cttatagact tctcccagcc ataggctttt tgcagaccat | 960 |
| aatgaaaggg agaaaggata tccaatcggg atggtgatgg caggcatggc gaagtggaca | 1020 |
| gggacaaaga agaggaaagc aagggacacc ctttgttctt tggtattcaa cacatgaaca | 1080 |
| aaacttgtta acgaatcgta gactgggtaa caacagggct ggtgagggag gacgatgtgg | 1140 |
| gtggctgtgg ggaaactctt cccaagcatc ccaggggtgg gccaggaagg ggagcagatg | 1200 |
| gacatctaca gggcacagag cagggagtgg ctattctctc ctggaggggt tgtgggtcca | 1260 |
| gcaggctttc ggatgaggcc ttggaaaggc aaggacagct tgccaactgg agggcaggca | 1320 |
| aaacggctga gccaggccag acacggcagc tcactggcca ggggcatggc ctaggggctc | 1380 |
| tggtgccaag gctgaagggg aacaacttgg ccagccgctc tgtggccggc atcgtcacgc | 1440 |
| ggcctccaag agctccggct gccctgcact ggttcccaga gactccctcc ttcccaggtc | 1500 |
| caaatggctg caggagcgaa gtgggcggaa aaaagcgaa ccagcttgag aaagggcttg | 1560 |
| acgtgcctgc gtagggaggg cgcatgtccc cgtgctccgt gtacgtggcg gccgcagggg | 1620 |
| ctagaggggg gtccccccg caggtactcc actctcagtc tgcaaaagtg tacgcccgca | 1680 |
| gagccgcccc aggtgcctgg gtgttgtgtg attgacgcgg ggaaggaggg gtcagccgat | 1740 |
| ccctccccaa ccctccatcc catccctgag gattgggctg gtaccgcgt ctctcggaca | 1800 |
| g | 1801 |

<210> SEQ ID NO 151
<211> LENGTH: 1801
<212> TYPE: DNA

<213> ORGANISM: Artificial Sequence
<220> FEATURE:
<223> OTHER INFORMATION: Synthetic human 1.8 kb eno2 (pNSE) promoter - enhancer design - without flanking restriction sites

<400> SEQUENCE: 151

| | | | | | |
|---|---|---|---|---|---|
| cataccttga | acgcctggac | aaggaattct | atgaggagga | ggaacgggct | gaggctgatg | 60 |
| tgattcgaca | gaggctgaag | gaagaaaagg | agcaggagcc | tgagcccag | cgtgacctgg | 120 |
| aacccgaaca | gtcattgatc | tagcagcagt | tctagcctct | aaagatagta | aggaagcctg | 180 |
| cagggaggca | gtgggaggag | gccaagggct | gggcaggtag | gggaagaggc | aagaggggaa | 240 |
| gctgctgcag | aaggaggtgg | gagaggaaag | catcagacaa | gcaggaccct | taaagagagg | 300 |
| agggttagga | gtcagggaga | ggaaaaggga | cccaaggggc | ctgggaccag | ctgagaaaga | 360 |
| cttaggaggc | cagaagagta | agtgaaaaga | attggggtgg | caggcagagg | agttggtggg | 420 |
| gggtggggca | gccatacctg | acacagagtg | aagtcggcta | ggaaaggaca | ggtgtgggtg | 480 |
| catggtaggg | gctgcagggg | aaagttggtg | gtgtatgcag | ctggacctag | gagagaagca | 540 |
| ggagaggaag | atccagcaca | aaaaatctga | agctaaaaac | aggacacaga | gatgggggaa | 600 |
| gaaaagaggg | cagagtgagg | caaaaagaga | ctgaagagat | gagggtggcc | gccaggcact | 660 |
| ttagataggg | gagaggcttt | atttacctct | gtttgttttt | tttttttttt | tttttttttt | 720 |
| tttgcgaggt | agtcttgctt | agtctccagg | ctggagtgca | gtggcacaat | ctcagctcac | 780 |
| tgcaacttcc | acctcctggg | ttcaagcaat | tctcctgcct | cagcctcccg | agtagctggg | 840 |
| actacaggcg | catgcaaccg | cgcctggcta | attttttgtat | ttttagtaga | acgggtttt | 900 |
| caccacgtta | gccaggatgg | tctggatctc | ctgacctcgt | gatctgcccg | cctccgcctt | 960 |
| ccaaagtgct | gggattacag | gggtgagcca | cagcgcctgg | tccctattta | cttctgtctt | 1020 |
| ctacctccag | gagatcaaag | acgctggcct | tcagacctga | tcagactccc | aggggcagcc | 1080 |
| accacatgta | tgacagagaa | cagaggatgc | ctgtttttgc | cccaaagctg | gaaattcatc | 1140 |
| acaacctgag | gcccaggatc | tgctctgtgc | cggtcctctg | ggcagtgtgg | ggtgcagaat | 1200 |
| ggggtgccta | ggcctgagcg | ttgcctggag | cctaggccgg | gggccgccct | cgggcaggcg | 1260 |
| tgggtgagag | ccaagaccgc | gtgggccgcg | gggtgctggt | aggagtggtt | ggagagactt | 1320 |
| gcgaaggcgg | ctggggtgtt | cggatttcca | ataaagaaac | agagtgatgc | tcctgtgtct | 1380 |
| gaccgggttt | gtgagacatt | gaggctgtct | tgggcttcac | tggcagtgtg | ggccttcgta | 1440 |
| cccgggctac | aggggtgcgg | ctctgcctgt | tactgtcgag | tgggtcgggc | cgtgggtatg | 1500 |
| agcgcttgtg | tgcgctgggg | ccaggtcgtg | ggtgccccca | cccttccccc | atcctcctcc | 1560 |
| cttccccact | ccaccctcgt | cggtccccca | acccgcgctc | gtacgtgcgc | ctccgccggc | 1620 |
| agctcctgac | tcatcggggg | ctccgggtca | catgcgcccg | cgcggcccta | taggcgcctc | 1680 |
| ctccgcccgc | cgcccgggag | ccgcagccgc | cgccgccact | gccactcccg | ctctctcagc | 1740 |
| gccgccgtcg | ccaccgccac | cgccaccgcc | actaccaccg | tctgagtctg | cagtcccgag | 1800 |
| g | | | | | | 1801 |

<210> SEQ ID NO 152
<211> LENGTH: 1808
<212> TYPE: DNA
<213> ORGANISM: Artificial Sequence
<220> FEATURE:
<223> OTHER INFORMATION: Synthetic rat 1.8 kb eno2 (pNSE) promoter-enhancer design

<400> SEQUENCE: 152

```
gctagcctcc tctgctcgcc caatccttcc aaccccctat ggtggtatgg ctgacacaga    60
aaatgtctgc tcctgtatgg gacatttgcc cctcttctcc aaatataaga caggatgagg   120
cctagctttt gctgctccaa agttttaaaa gaacacattg cacggcattt agggactcta   180
aagggtggag gaggaatgag ggaattgcat catgccaagg ctggtcctca tccatcactg   240
cttccagggc ccagagtggc ttccaggagg tattcttaca aaggaagccc gatctgtagc   300
taacactcag agcccatttt cctgcgttaa cccctcccga cctcatatac aggagtaaca   360
tgatcagtga cctgggggag ctggccaaac tgcgggacct gcccaagctg agggccttgg   420
tgctgctgga caacccctgt gccgatgaga ctgactaccg ccaggaggcc ctggtgcaga   480
tggcacacct agagcgccta gacaaagagt actatgagga cgaggaccgg gcagaagctg   540
aggagatccg acagaggctg aaggaggaac aggagcaaga actcgacccg gaccaagaca   600
tggaaccgta cctcccgcca acttagtggc acctctagcc tgcagggaca gtaaaggtga   660
tggcaggaag gcagccccg gaggtcaaag gctgggcacg cggaggagga ggccagagtc   720
agaggctgcg ggtatctcag atatgaagga agatgagag aggctcagga agaggtaaga   780
aaagacacaa gagaccagag aagggagaag aattagagag ggaggcagag gaccgctgtc   840
tctacagaca tagctggtag agactgggag gaagggatga accctgagcg catgaaggga   900
aggaggtggc tggtggtata tggaggatgt agctgggcca gggaaaagat cctgcactaa   960
aaatctgaag ctaaaaataa caggacacgg ggtggagagg cgaaaggagg gcagagtgag  1020
gcagagagac tgagaggcct ggggatgtgg gcattccggt agggcacaca gttcacttgt  1080
cttctctttt tccaggaggc caaagatgct gacctcaaga actcataata ccccagtggg  1140
gaccaccgca ttcatagccc tgttacaaga agtgggagat gttccttttt gtcccagact  1200
ggaaatccgt tacatcccga ggctcaggtt ctgtggtggt catctctgtg tggcttgttc  1260
tgtgggccta cctaaagtcc taagcacagc tctcaagcag atccgaggcg actaagatgc  1320
tagtaggggt tgtctggaga gaagagccga ggaggtgggc tgtgatggat cagttcagct  1380
ttcaaataaa aaggcgtttt tatattctgt gtcgagttcg tgaaccctg tggtgggctt  1440 ctccatctgt ctgggttagt acctgccact atactggaat aaggggacgc ctgcttccct  1500
cgagttggct ggacaaggtt atgagcatcc gtgtacttat ggggttgcca gcttggtcct  1560
ggatcgcccg ggcccttccc ccacccgttc ggttccccac caccaccgc gctcgtacgt  1620 gcgtctccgc ctgcagctct tgactcatcg gggcccccg ggtcacatgc gctcgctcgg  1680
ctctataggc gccgccccct gcccacccc cgcccgcgct gggagccgca gccgccgcca  1740
ctcctgctct ctctgcgccg ccgccgtcac caccgccacc gccaccggct gagtctgcag  1800
tcgctagc                                                         1808
```

<210> SEQ ID NO 153
<211> LENGTH: 1796
<212> TYPE: DNA
<213> ORGANISM: Artificial Sequence
<220> FEATURE:
<223> OTHER INFORMATION: Synthetic rat 1.8 kb eno2 (pNSE) promoter-
      enhancer design - without flanking restriction sites

<400> SEQUENCE: 153

```
ctcctctgct cgcccaatcc ttccaacccc ctatggtggt atggctgaca cagaaaatgt    60
ctgctcctgt atgggacatt tgcccctctt ctccaaatat aagacaggat gaggcctagc   120
ttttgctgct ccaaagtttt aaaagaacac attgcacggc atttagggac tctaaagggt   180
```

```
ggaggaggaa tgagggaatt gcatcatgcc aaggctggtc ctcatccatc actgcttcca     240
gggcccagag tggcttccag gaggtattct tacaaaggaa gcccgatctg tagctaacac     300
tcagagccca ttttcctgcg ttaacccctc ccgacctcat atacaggagt aacatgatca     360
gtgacctggg ggagctggcc aaactgcggg acctgcccaa gctgagggcc ttggtgctgc     420
tggacaaccc ctgtgccgat gagactgact accgccagga ggccctggtg cagatggcac     480
acctagagcg cctagacaaa gagtactatg aggacgagga ccgggcagaa gctgaggaga     540
tccgacagag gctgaaggag aacaggagc aagaactcga cccggaccaa gacatggaac      600
cgtacctccc gccaacttag tggcacctct agcctgcagg acagtaaag gtgatggcag       660 gaaggcagcc cccggaggtc aaaggctggg cacgcgggag gagaggccag agtcagaggc     720
tgcgggtatc tcagatatga aggaaagatg agagaggctc aggaagaggt aagaaaagac     780
acaagagacc agagaaggga gaagaattag agagggaggc agaggaccgc tgtctctaca     840
gacatagctg gtagagactg ggaggaaggg atgaaccctg agcgcatgaa gggaaggagg     900
tggctggtgg tatatggagg atgtagctgg gccagggaaa agatcctgca ctaaaaatct     960
gaagctaaaa ataacaggac acggggtgga gaggcgaaag gagggcagag tgaggcagag    1020
agactgagag gcctggggat gtgggcattc cggtagggca cacagttcac ttgtcttctc    1080 ttttccagg aggccaaaga tgctgacctc aagaactcat aatacccag tggggaccac      1140 cgcattcata gccctgttac aagaagtggg agatgttcct ttttgtccca gactggaaat    1200
ccgttacatc ccgaggctca ggttctgtgg tggtcatctc tgtgtggctt gttctgtggg    1260
cctacctaaa gtcctaagca cagctctcaa gcagatccga ggcgactaag atgctagtag    1320
gggttgtctg gagagaagag ccgaggaggt gggctgtgat ggatcagttc agctttcaaa    1380
taaaaaggcg tttttatatt ctgtgtcgag ttcgtgaacc cctgtggtgg gcttctccat    1440
ctgtctgggt tagtacctgc cactatactg gaataagggg acgcctgctt ccctcgagtt    1500
ggctggacaa ggttatgagc atccgtgtac ttatggggtt gccagcttgg tcctggatcg    1560
cccgggccct tccccacc gttcggttcc ccaccaccac ccgcgctcgt acgtgcgtct      1620
ccgcctgcag ctcttgactc atcggggccc ccgggtcac atgcgctcgc tcggctctat    1680
aggcgccgcc ccctgcccac cccccgcccg cgctgggagc cgcagccgcc gccactcctg    1740
ctctctctgc gccgccgccg tcaccaccgc caccgccacc ggctgagtct gcagtc        1796
```

<210> SEQ ID NO 154
<211> LENGTH: 304
<212> TYPE: DNA
<213> ORGANISM: Artificial Sequence
<220> FEATURE:
<223> OTHER INFORMATION: Predicted promoter / enhancer region 1 - mouse Hsp90ab1

<400> SEQUENCE: 154

```
ggagggaga gtgcaggctc atggcaggcc tcaggagacc tgtgttcctt acagggtctg      60
tttgctctct cactctttct ccctttttcc cctctgctct gtctcctccc ctttgcctgc    120
tctgtcactg ttgtcactgt ccctgacccc ttttctcttt tctgtcttct ttgactgtct    180
ttccctgcct ctcaatcatc cgtcctcctc ctcctcctcg attgctcccc acccttcggt    240
ttccaagctt ataaactgct tctgctgctg gataaaaata gcggtggcag cggccaggct    300
ggca                                                                 304
```

```
<210> SEQ ID NO 155
<211> LENGTH: 305
<212> TYPE: DNA
<213> ORGANISM: Artificial Sequence
<220> FEATURE:
<223> OTHER INFORMATION: Predicted promoter / enhancer region 2 - Mouse
      Hsp90ab1

<400> SEQUENCE: 155
tgccagactt cctggagaac aacgggccta tgtgtcctca tgttggcgtt ggacctcccc      60
gttcttcagc catactgtgg tctgaggaag ggtgtgttgg tatgggatgt gagactccct     120
cggtggaggg ggcgctgatg ctccagctca ggactgactg gaactgagag gaacactctg     180
gtcctaagtg ccccttgtcc ccagccctgg gagacagaag cttttgcccc gccccatctc     240
ccaagccccc tcccccaagg ctgcatgttc tctcatcctc taccagctga tggctacagg     300
ggtgg                                                                  305

<210> SEQ ID NO 156
<211> LENGTH: 312
<212> TYPE: DNA
<213> ORGANISM: Artificial Sequence
<220> FEATURE:
<223> OTHER INFORMATION: Predicted promoter / enhancer region 3 - Mouse
      Hsp90ab1

<400> SEQUENCE: 156
gatccacctg cctctgcttc ctgagtgctg ggatttaaag gtgtatacaa ccatagcctg      60
ggttgttttc aattcttttt cttcttcttc tttttttttt tttaaaatta atgtgcattg     120 gtgttttgc ttacatatat gtctgtgtca gagcatctga ccctctggga ctggagttaa      180
agacagttgt gagctgccac gtggctcctg ggaattgaac ccaggtttcc tggaagagca     240
gccaatgctc ttaaccactg agccatccct cctccattc cccagttgct tgttatcaat      300
ccttactaag gt                                                          312

<210> SEQ ID NO 157
<211> LENGTH: 455
<212> TYPE: DNA
<213> ORGANISM: Artificial Sequence
<220> FEATURE:
<223> OTHER INFORMATION: Predicted promoter / enhancer region 4 - Mouse
      Hsp90ab1

<400> SEQUENCE: 157
tggaagagca gatagtgctc ttaacctctg ggctggcctt gaactcagaa atcctcctgc      60
ctctacctcc cgagtgctgg gattaaaggc gtgcgccacc actgcctggc ccctgagctt     120
tacttgagca tactaagtgc atagaacctc cagcccactt gggcccttaa caacccaagg     180
atgaacctgg gtggcctaag gaaacagaca ggcttaggac ccatggagtc agggtagtac     240
acagctctgc tctcagaaga ttaaaaaaga aaaaaaaaa aaagccaggt gactcccagt      300
gacctagaaa ggaagccctt caggaaggga ggagtgtggg cacagaaagc agccctgcag     360
gctggggctg ggttataaaa ggctgcgggt gccatgctga gctctatcct gaagagtggg     420 aaaggccct agagacagcc ttaaaacccc ctagg                                  455

<210> SEQ ID NO 158
<211> LENGTH: 455
<212> TYPE: DNA
<213> ORGANISM: Artificial Sequence
<220> FEATURE:
<223> OTHER INFORMATION: Predicted promoter / enhancer region 5 - Mouse
```

Hsp90ab1

<400> SEQUENCE: 158

| ggatgagaag ttcaaggtca aaccaggcac tggaggcaca tgcctttaat cccagcattt | 60 |
| gggagactaa ggcaggctga tttctgagtt caaggccagc ctggtctata aagttccagg | 120 |
| acacagagaa accctgcaaa aaaaaaaaaa aaaaaaaaaa aaaaaaaaaa aagaaagaaa | 180 |
| taccataaaa actaatattc attattaaac gttcgtgtgt gcgtatttcc tggaggagct | 240 |
| ggagttacag tggctgtgag ctggcagagg tgcccgggtg gaacttcggc cctcaagacc | 300 |
| agttagtgct ggaccttctc tctaaccccc aggcctttta taaaaaggaa tcttatcatc | 360 |
| ttatcacccg ggtgtgaagg tgcgccttca atcccagcac tctggaggta gtgacacacc | 420 |
| tactccaaca aggccatact tcctaatagt gccac | 455 |

<210> SEQ ID NO 159
<211> LENGTH: 293
<212> TYPE: DNA
<213> ORGANISM: Artificial Sequence
<220> FEATURE:
<223> OTHER INFORMATION: Predicted promoter / enhancer region 6 - Mouse Hsp90ab1

<400> SEQUENCE: 159

| ccacctccat tctctttcag tcccctgagt tctggactct tgggggtgg ggggtggaa | 60 |
| gcgcctacct tgagttttct gaggcagtcc gtagggtatt cgcccgcaga tacatcccta | 120 |
| attgcatatg catgctccct gctcatcttg agggggaca tgtcctactc ctgcagaaat | 180 |
| gggggatgtg caaaacgata ttgaattggc cttgactcag gaaccaggcc cggggtcccg | 240 |
| ctcctccccg cccctccac gatctgctac catgacgtca aggtgggcgg gcg | 293 |

<210> SEQ ID NO 160
<211> LENGTH: 274
<212> TYPE: DNA
<213> ORGANISM: Artificial Sequence
<220> FEATURE:
<223> OTHER INFORMATION: Predicted promoter / enhancer region 7 - Mouse Hsp90ab1

<400> SEQUENCE: 160

| ctaattgcat atgcatgctc cctgctcatc ttgaggggg acatgtccta ctcctgcaga | 60 |
| aatggggat gtgcaaaacg atattgaatt ggccttgact caggaaccag gcccggggtc | 120 |
| ccgctcctcc ccgcccccctc cacgatctgc taccatgacg tcaaggtggg cgggcggcgg | 180 |
| caggtgcgtg gcccgcagcc actcctttaa ggcggaggga tccaagggcg ggcccgggc | 240 |
| tgtgcttcgc cttatatagg gcggtcgggg gcgt | 274 |

<210> SEQ ID NO 161
<211> LENGTH: 3
<212> TYPE: DNA
<213> ORGANISM: Artificial Sequence
<220> FEATURE:
<223> OTHER INFORMATION: Recognition sequence
<220> FEATURE:
<221> NAME/KEY: misc_feature
<222> LOCATION: (3)..(3)
<223> OTHER INFORMATION: a or t
<220> FEATURE:
<221> NAME/KEY: misc_feature
<222> LOCATION: (1)..(3)
<223> OTHER INFORMATION: Repeat unit

<400> SEQUENCE: 161 gcw                                                                             3

<210> SEQ ID NO 162
<211> LENGTH: 3
<212> TYPE: DNA
<213> ORGANISM: Artificial Sequence
<220> FEATURE:
<223> OTHER INFORMATION: CAG-repeat
<220> FEATURE:
<221> NAME/KEY: misc_feature
<222> LOCATION: (1)..(3)
<223> OTHER INFORMATION: Repeat unit

<400> SEQUENCE: 162 cag                                                                             3

<210> SEQ ID NO 163
<211> LENGTH: 3
<212> TYPE: DNA
<213> ORGANISM: Artificial Sequence
<220> FEATURE:
<223> OTHER INFORMATION: CAG-repeat
<220> FEATURE:
<221> NAME/KEY: misc_feature
<222> LOCATION: (1)..(3)
<223> OTHER INFORMATION: Repeat unit

<400> SEQUENCE: 163 agc                                                                             3

<210> SEQ ID NO 164
<211> LENGTH: 3
<212> TYPE: DNA
<213> ORGANISM: Artificial Sequence
<220> FEATURE:
<223> OTHER INFORMATION: CAG-repeat
<220> FEATURE:
<221> NAME/KEY: misc_feature
<222> LOCATION: (1)..(3)
<223> OTHER INFORMATION: Repeat unit

<400> SEQUENCE: 164 agc                                                                             3

<210> SEQ ID NO 165
<211> LENGTH: 3
<212> TYPE: DNA
<213> ORGANISM: Artificial Sequence
<220> FEATURE:
<223> OTHER INFORMATION: CTG-repeat
<220> FEATURE:
<221> NAME/KEY: misc_feature
<222> LOCATION: (1)..(3)
<223> OTHER INFORMATION: Repeat unit

<400> SEQUENCE: 165 ctg                                                                             3

<210> SEQ ID NO 166
<211> LENGTH: 3
<212> TYPE: DNA
<213> ORGANISM: Artificial Sequence
<220> FEATURE:
<223> OTHER INFORMATION: CTG-repeat
<220> FEATURE:
<221> NAME/KEY: misc_feature
<222> LOCATION: (1)..(3)
<223> OTHER INFORMATION: Repeat unit

```
<400> SEQUENCE: 166 tgc                                                                        3

<210> SEQ ID NO 167
<211> LENGTH: 3
<212> TYPE: DNA
<213> ORGANISM: Artificial Sequence
<220> FEATURE:
<223> OTHER INFORMATION: CTG-repeat
<220> FEATURE:
<221> NAME/KEY: misc_feature
<222> LOCATION: (1)..(3)
<223> OTHER INFORMATION: Repeat unit

<400> SEQUENCE: 167 gct                                                                        3

<210> SEQ ID NO 168
<211> LENGTH: 9
<212> TYPE: DNA
<213> ORGANISM: Artificial Sequence
<220> FEATURE:
<223> OTHER INFORMATION: Zif268 binding sequence

<400> SEQUENCE: 168 gcgtgggcg                                                                  9

<210> SEQ ID NO 169
<211> LENGTH: 3
<212> TYPE: DNA
<213> ORGANISM: Artificial Sequence
<220> FEATURE:
<223> OTHER INFORMATION: GNT/A-repeat
<220> FEATURE:
<221> NAME/KEY: misc_feature
<222> LOCATION: (1)..(3)
<223> OTHER INFORMATION: Repeat unit
<220> FEATURE:
<221> NAME/KEY: misc_feature
<222> LOCATION: (2)..(2)
<223> OTHER INFORMATION: a or g or c or t
<220> FEATURE:
<221> NAME/KEY: misc_feature
<222> LOCATION: (3)..(3)
<223> OTHER INFORMATION: a or t

<400> SEQUENCE: 169 gnw                                                                        3

<210> SEQ ID NO 170
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
agcagcagca gcagcagcag cagcagcagc agcagc                                   36

<210> SEQ ID NO 171
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
```
cagcagcagc agcag                                                    15

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
cagcagcagc agcagcagca g                                             21

<210> SEQ ID NO 173
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cagcagcagc agcagcagca gcagcagcag cagcagcag                          39

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
gcagcagcag cagcagca                                                 18

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gcagctgcag ctgcagct                                                 18

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
dagdagdagd agdagdagda g                                             21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177

```
csgcsgcsgc sgcsgcsgcs g                                          21
```

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178

```
cahcahcahc ahcahcahca h                                          21
```

<210> SEQ ID NO 179
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179

```
agcagcagca gcagcagcag cagcagcagc agc                             33
```

<210> SEQ ID NO 180
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180

```
gctgctgctg ctgctgctgc tgctgctgct gctgct                          36
```

<210> SEQ ID NO 181
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181

```
gctgctgctg ctgctgctgc tgctgctgct gct                             33
```

<210> SEQ ID NO 182
<211> LENGTH: 10
<212> TYPE: DNA
<213> ORGANISM: Artificial Sequence
<220> FEATURE:
<223> OTHER INFORMATION: Predicted Trasciptional Promoter Binding Site

<400> SEQUENCE: 182

```
gccccgcccc                                                       10
```

<210> SEQ ID NO 183
<211> LENGTH: 10
<212> TYPE: DNA
<213> ORGANISM: Artificial Sequence
<220> FEATURE:
<223> OTHER INFORMATION: Predicted Trasciptional Promoter Binding Site

<400> SEQUENCE: 183

```
ggggcggggc                                                       10
```

```
<210> SEQ ID NO 184
<211> LENGTH: 11
<212> TYPE: DNA
<213> ORGANISM: Artificial Sequence
<220> FEATURE:
<223> OTHER INFORMATION: Predicted Trasciptional Promoter Binding Site

<400> SEQUENCE: 184
gccccctccc c                                                                11

<210> SEQ ID NO 185
<211> LENGTH: 10
<212> TYPE: DNA
<213> ORGANISM: Artificial Sequence
<220> FEATURE:
<223> OTHER INFORMATION: Predicted Trasciptional Promoter Binding Site

<400> SEQUENCE: 185 gggggaggggg                                                                 10

<210> SEQ ID NO 186
<211> LENGTH: 9
<212> TYPE: DNA
<213> ORGANISM: Artificial Sequence
<220> FEATURE:
<223> OTHER INFORMATION: Predicted Trasciptional Promoter Binding Site

<400> SEQUENCE: 186 ccctccccc                                                                   9

<210> SEQ ID NO 187
<211> LENGTH: 10
<212> TYPE: DNA
<213> ORGANISM: Artificial Sequence
<220> FEATURE:
<223> OTHER INFORMATION: Predicted Trasciptional Promoter Binding Site

<400> SEQUENCE: 187
ccccaccccc                                                                  10

<210> SEQ ID NO 188
<211> LENGTH: 10
<212> TYPE: DNA
<213> ORGANISM: Artificial Sequence
<220> FEATURE:
<223> OTHER INFORMATION: Predicted Trasciptional Promoter Binding Site

<400> SEQUENCE: 188
gggggtgggg                                                                  10
```

What is claimed is:

1. An isolated nucleic acid encoding a polypeptide, the polypeptide comprising a zinc finger peptide having 8, 9, 10, 11 or 12 zinc finger domains and which binds to a CAG- and/or a CTG-trinucleotide repeat sequence; wherein the zinc finger peptide comprising the sequence:

N'-[(Formula 4)-$L_3$]$_{n0}$-{[(Formula 6)-$L_2$-(Formula 6)-$L_3$]$_{n1}$-[(Formula 6)-$L_2$-(Formula 6)-$X_L$]}$_{n2}$-[(Formula 4)-$L_2$-(Formula 6)-$L_3$]$_{n3}$-[(Formula 6)-$L_2$-(Formula 6)]-C', wherein n0, n1, n2 and n3 are integers representing the number of times that the corresponding sequence within square brackets is repeated, and wherein n0 is 0 or 1, n1 is 1 or 2, n2 is 1, and n3 is 2, $L_2$ is -TGEKP-(SEQ ID NO: 6), $L_3$ is selected from the group consisting of -TGSERP-(SEQ ID NO: 10) and -TGSQKP-(SEQ ID NO: 16), and $X_L$ is selected from the group consisting of the amino acid sequences of SEQ ID NOs: 21, 22, 23 and 24;

Formula 4 is a zinc finger domain of the sequence $X_2$ C $X_{2\ or\ 4}$ C $X_5$ $X^{-1}$ $X^{+1}$ $X^{+2}$ $X^{+3}$ $X^{+4}$ $X^{+5}$ $X^{+6}$ H $X_{3\ or\ 4\ or\ 5}$H/C and Formula 6 is a zinc finger domain of the sequence $X_2$ C $X_2$ C $X_5$ $X^{-1}$ $X^{+1}$ $X^{+2}$ $X^{+3}$ $X^{+4}$ $X^{+5}$ $X^{+6}$ H $X_3$ H, wherein X is any amino acid unless otherwise defined, the numbers in subscript indicate the numbers of residues represented by X at that position, and the number in superscript indicates the position of the amino acid in the recognition sequence of the zinc finger domain;

and wherein:

(i) the zinc finger domains of the zinc finger peptide collectively have recognition sequences $X^{-1}$ $X^{+1}$ $X^{+2}$ $X^{+3}$ $X^{+4}$ $X^{+5}$ $X^{+6}$ selected from and including both members of a group consisting of the amino acid sequences of SEQ ID NOs: 2 and 5; or
(ii) the zinc finger domains of the zinc finger peptide collectively have recognition sequences $X^{-1}$ $X^{+1}$ $X^{+2}$ $X^{+3}$ $X^{+4}$ $X^{+5}$ $X^{+6}$ selected from and including both members of a group consisting of the amino acid sequences of SEQ ID NOs: 3 and 4; or
(iii) the zinc finger domains of the zinc finger peptide collectively have recognition sequences $X^{-1}$ $X^{+1}$ $X^{+2}$ $X^{+3}$ $X^{+4}$ $X^{+5}$ $X^{+6}$ selected from and including all members of a group consisting of the amino acid sequences of SEQ ID NOs: 2, 3 and 4.

2. The nucleic acid according to claim 1, wherein the zinc finger peptide has 11 zinc finger domains and wherein the recognition sequences $X^{-1}$ $X^{+1}$ $X^{+2}$ $X^{+3}$ $X^{+4}$ $X^{+5}$ $X^{+6}$ include both the amino acid sequences of SEQ ID NOs: 2 and 5; or wherein the recognition sequences $X^{-1}$ $X^{+1}$ $X^{+2}$ $X^{+3}$ $X^{+4}$ $X^{+5}$ $X^{+6}$ include both the amino acid sequences of SEQ ID NOs: 3 and 4.

3. The nucleic acid according to claim 1, wherein $L_3$ is -TGSQKP-(SEQ ID NO: 16).

4. The nucleic acid according to claim 1, wherein all of the zinc finger domains are defined according to Formula 6.

5. The nucleic acid according to claim 1, wherein the polypeptide comprises the human Kruppel-associated box (KRAB) repressor domain from Kox-1 according to the amino acid sequence of SEQ ID NO: 39, or the mouse KRAB repressor domain from ZF87 according to the amino acid sequence of SEQ ID NO: 40.

6. The nucleic acid according to claim 1, wherein the polypeptide comprises the nuclear localisation signal sequence according to the amino acid sequence of SEQ ID NO: 37 or SEQ ID NO: 38.

7. The nucleic acid according to claim 1, wherein the zinc finger peptide has a sequence selected from the group consisting of the amino acid sequences of SEQ ID NOs: 29, 33 and 35.

8. The nucleic acid according to claim 1, wherein the polypeptide comprises a sequence selected from the group consisting of the amino acid sequences of SEQ ID NOs: 51, 52, 54, 55 and 56.

9. The nucleic acid according to claim 1, wherein the polypeptide comprising a zinc finger peptide having 10, 11 or 12 zinc finger domains.

10. An adeno-associated virus (AAV) vector comprising a nucleic acid expression construct capable of expressing a polypeptide, the polypeptide comprising a zinc finger peptide having 8, 9, 10, 11, or 12 zinc finger domains and which binds to a CAG- and/or CTG-trinucleotide repeat sequence; wherein the zinc finger peptide comprising the sequence:

N'-[(Formula 4)-$L_3$]$_{n0}$-{[(Formula 6)-$L_2$-(Formula 6)-$L_3$]$_{n1}$-[(Formula 6)-$L_2$-(Formula 6)-$X_L$]}$_{n2}$-[(Formula 4)-$L_2$-(Formula 6)-$L_3$]$_{n3}$-[(Formula 6)-$L_2$-(Formula 6)]-C', wherein n0, n1, n2 and n3 are integers representing the number of times that the corresponding sequence within square brackets is repeated, and wherein n0 is 0 or 1, n1 is 1 or 2, n2 is 1, and n3 is 2, $L_2$ is -TGEKP-(SEQ ID NO: 6), $L_3$ is selected from the group consisting of -TGSERP-(SEQ ID NO: 10) and -TGSQKP-(SEQ ID NO: 16), and $X_L$ is selected from the group consisting of the amino acid sequences of SEQ ID NOs: 21, 22, 23 and 24;

Formula 4 is a zinc finger domain of the sequence $X_2$ C $X_{2\ or\ 4}$ C $X_5$ $X^{-1}$ $X^{+1}$ $X^{+2}$ $X^{+3}$ $X^{+4}$ $X^{+5}$ $X^{+6}$ H $X_{3\ or\ 4\ or\ 5}$H/C and Formula 6 is a zinc finger domain of the sequence $X_2$ C $X_2$ C $X_5$ $X^{-1}$ $X^{+1}$ $X^{+2}$ $X^{+3}$ $X^{+4}$ $X^{+5}$ $X^{+6}$ H $X_3$ H, wherein X is any amino acid unless otherwise defined, the numbers in subscript indicate the numbers of residues represented by X at that position, and the number in superscript indicates the position of the amino acid in the recognition sequence of the zinc finger domain;

and wherein:
(i) the zinc finger domains the zinc finger peptide collectively have recognition sequences $X^{-1}$ $X^{+1}$ $X^{+2}$ $X^{+3}$ $X^{+4}$ $X^{+5}$ $X^{+6}$ selected from and including both members of a group consisting of the amino acid sequences of SEQ ID NOs: 2 and 5;
(ii) the zinc finger domains of the zinc finger peptide collectively have recognition sequences $X^{-1}$ $X^{+1}$ $X^{+2}$ $X^{+3}$ $X^{+4}$ $X^{+5}$ $X^{+6}$ selected from and including both members of a group consisting of the amino acid sequences of SEQ ID NOs: 3 and 4; or
(iii) the zinc finger domains of the zinc finger peptide collectively have recognition sequences $X^{-1}$ $X^{+1}$ $X^{+2}$ $X^{+3}$ $X^{+4}$ $X^{+5}$ $X^{+6}$ selected from and including all members of a group consisting of the amino acid sequences of SEQ ID NOs: 2, 3 and 4.

11. The adeno-associated virus (AAV) vector according to claim 10, wherein the zinc finger peptide has 11 zinc finger domains and wherein the recognition sequences $X^{-1}$ $X^{+1}$ $X^{+2}$ $X^{+3}$ $X^{+4}$ $X^{+5}$ $X^{+6}$ include both the amino acid sequences of SEQ ID NOs: 2 and 5; or wherein the recognition sequences $X^{-1}$ $X^{+1}$ $X^{+2}$ $X^{+3}$ $X^{+4}$ $X^{+5}$ $X^{+6}$ include both the amino acid sequences of SEQ ID NOs: 3 and 4; and wherein the polypeptide comprises the human KRAB repressor domain from Kox-1 according to the amino acid sequence of SEQ ID NO: 39, or the mouse KRAB repressor domain from ZF87 according to the amino acid sequence of SEQ ID NO: 40 arranged C-terminal to the zinc finger peptide.

12. The adeno-associated virus (AAV) vector according to claim 10, wherein the zinc finger peptide has a sequence selected from the group consisting of the amino acid sequences of SEQ ID Nos: 29, 33 and 35.

13. The adeno-associated virus (AAV) according to claim 10, wherein the polypeptide comprises a sequence selected from the group consisting of the amino acid sequences of SEQ ID NOs: 51, 52, 54, 55 and 56.

14. The AAV vector according to claim 10, the polypeptide comprising a zinc finger peptide having 10, 11, or 12 zinc finger domains.

15. A polypeptide comprising a zinc finger peptide, the zinc finger peptide having 8, 9, 10, 11 or 12 zinc finger domains and which binds to CAG- and/or CTG-trinucleotide repeat sequence; wherein the zinc finger peptide comprising the sequence:

N'-[(Formula 4)-$L_3$]$_{n0}$-{[(Formula 6)-$L_2$-(Formula 6)-$L_3$]$_{n1}$-[(Formula 6)-$L_2$-(Formula 6)-$X_L$]}$_{n2}$-[(Formula 4)-$L_2$-(Formula 6)-$L_3$]$_{n3}$-[(Formula 6)-$L_2$-(Formula 6)]-C', wherein n0, n1, n2 and n3 are integers representing the number of times that the corresponding sequence within square brackets is repeated, and wherein n0 is 0 or 1, n1 is 1 or 2, n2 is 1, n3 is 2, $L_2$ is -TGEKP-(SEQ ID NO: 6), $L_3$ is selected from the group consisting of -TGSERP-(SEQ ID NO: 10) and -TGSQKP-(SEQ ID NO: 16), and $X_L$ is selected from the group consisting of the amino acid sequences of SEQ ID NOs: 21, 22, 23 and 24;

Formula 4 is a zinc finger domain of the sequence $X_2$ C $X_{2\ or\ 4}$ C $X_5$ $X^{-1}$ $X^{+1}$ $X^{+2}$ $X^{+3}$ $X^{+4}$ $X^{+5}$ $X^{+6}$ H $X_{3\ or\ 4\ or\ 5}$H/C and Formula 6 is a zinc finger domain of the sequence $X_2 \, C \, X_2 \, C \, X_5 \, X^{-1} \, X^{+1} \, X^{+2} \, X^{+3} \, X^{+4} \, X^{+5} \, X^{+6} \, H \, X_3 \, H$, wherein X is any amino acid unless otherwise defined, the numbers in subscript indicate the numbers of residues represented by X at that position, and the number in superscript indicates the position of the amino acid in the recognition sequence of the zinc finger domain;

and wherein:
(i) the zinc finger domains of the zinc finger peptide collectively have recognition sequences $X^{-1} \, X^{+1} \, X^{+2} \, X^{+3} \, X^{+4} \, X^{+5} \, X^{+6}$ selected from and including both members of a group consisting of the amino acid sequences of SEQ ID NOs: 2 and 5; or
(ii) the zinc finger domains of the zinc finger peptide collectively have recognition sequences $X^{-1} \, X^{+1} \, X^{+2} \, X^{+3} \, X^{+4} \, X^{+5} \, X^{+6}$ selected from and including both members of a group consisting of the amino acid sequences of SEQ ID NOs: 3 and 4; or
(iii) the zinc finger domains of the zinc finger peptide collectively have recognition sequences $X^{-1} \, X^{+1} \, X^{+2} \, X^{+3} \, X^{+4} \, X^{+5} \, X^{+6}$ selected from and including all members of a group consisting of the amino acid sequences of SEQ ID NOs: 2, 3 and 4.

16. The polypeptide according to claim 15, wherein the zinc finger peptide has 11 zinc finger domains, wherein $L_3$ is -TGSQKP-(SEQ ID NO: 16); and wherein $X_L$ is the amino acid sequence of SEQ ID NO: 24.

17. The polypeptide according to claim 15 which comprises a peptide sequence having at least 95% identity to a peptide sequence selected from any of the amino acid sequences of SEQ ID NOs: 33, 35, 49, 50, 51, 52, 54, 55 and 56.

18. The polypeptide according to claim 15, wherein the zinc finger peptide has 10, 11 or 12 zinc finger domains.

* * * * *